(12) United States Patent
Chen et al.

(10) Patent No.: US 7,892,795 B2
(45) Date of Patent: Feb. 22, 2011

(54) METHODS AND COMPOSITIONS FOR DETECTING BK VIRUS

(75) Inventors: Fan Chen, Fullerton, CA (US); Lilly I. Kong, Covina, CA (US); Jules Chen, Walnut, CA (US); Mehrdad Jannatipour, Oceanside, CA (US)

(73) Assignee: Focus Diagnostics, Inc., Herndon, VA (US)

( * ) Notice: Subject to any disclaimer, the term of this patent is extended or adjusted under 35 U.S.C. 154(b) by 750 days.

(21) Appl. No.: 11/246,904

(22) Filed: Oct. 6, 2005

(65) Prior Publication Data

US 2007/0031825 A1     Feb. 8, 2007

Related U.S. Application Data

(60) Provisional application No. 60/705,217, filed on Aug. 2, 2005.

(51) Int. Cl.
| | |
|---|---|
| C12P 19/34 | (2006.01) |
| C12Q 1/68 | (2006.01) |
| C07H 21/02 | (2006.01) |
| C07H 21/04 | (2006.01) |

(52) U.S. Cl. ..................... 435/91.2; 435/6; 536/24.33; 536/23.1

(58) Field of Classification Search ............... None
See application file for complete search history.

(56) References Cited

U.S. PATENT DOCUMENTS

| | | | |
|---|---|---|---|
| 5,213,796 A | | 5/1993 | Garcea et al. |
| 5,541,308 A | * | 7/1996 | Hogan et al. ............ 536/23.1 |
| 6,605,602 B1 | | 8/2003 | Vats |

FOREIGN PATENT DOCUMENTS

| | | |
|---|---|---|
| WO | WO 92/19774 | 11/1992 |
| WO | WO-01/66148 | 9/2001 |
| WO | WO-2007/130519 | 11/2007 |

OTHER PUBLICATIONS

GenBank Accession No. AY628224 (NCBI Jun. 22, 2004).*
Del Valle et al. Apr. 2004 Journal of Virology vol. 78 p. 3462.*
Stoner et al. American Journal of Kidney Diseases 2002 vol. 39 p. 1102.*
Whiley et al. Journal of Clincal Microbiolgoy 2001 vol. 39 p. 4357.*
MacKenzie et al. Leukemia 2001 vol. 15 p. 415.*
Anna Marta Degener, et al., Identification of a New Control Region in the Genome of the DDP Stain of BK Virus Isolated from PBMC. J Medical Virology 58:413 (1999).
Stoner et al., BK Virus Regulatory Region Rearrangements in Brain and Cerebrospinal Fluid from a Leukemia Patient with Tubulointerstitial Nephritis and Meningoencephalitis. American J of Kidney Diseases. 33:1102 (2002).
Watzinger et al., Real-Time Quantitative PCR Assays for Detection and Monitoring of Pathogenic Human Viruses in Immunosuppressed Pediatric Patients. Journal of Clinical Microbiology, 42(11):5189-5198 (2004).
Schatzl et al, Detection by PCR of human polyomaviruses BK and JC in immunocompromised individuals and partial sequencing of control regions, J. of Medical Virology, 42(2):138-145, 1994.
Search Report dated Nov. 10, 2009 for EP Application No. 06788689. 5.
Vanchiere et al, Detection of BK virus and simian virus 40 in the urine of healthy children, J. of Medical Virology, 74(3):447-454, 2005.
Yang et al, BK Virus DNA Complete Nucleotide Sequence of a Human Tumor Virus, Science, 206:456-462, 1979.
J Bergallo, et al, Detection and typing of BKV, JCV, and SV40 by multiplex nested polymerase chain reaction, Molecular Biotech, (2007), 35:243-252.
Communication pursuant to Article 94(3) EPC dated Dec. 1, 2010 in EP application 06788689.
McNees, et al, Specific and quantitative detection of human polyomaviruses BKV, JCV, and SV40 by real time PCR, J Clin Virol, (2005), 34:52-62.

* cited by examiner

*Primary Examiner*—Sarae Bausch
*Assistant Examiner*—Katherine Salmon
(74) *Attorney, Agent, or Firm*—Foley & Lardner LLP

(57) ABSTRACT

The invention provides methods and compositions for rapid, sensitive, and highly specific nucleic acid-based (e.g., DNA based) detection of a BK virus in a sample. In general, the methods involve detecting a target nucleic acid having a target sequence of a conserved region of BK viral genomes. The invention also features compositions, including primers, probes, and kits, for use in the methods of the invention.

30 Claims, 54 Drawing Sheets

```
Consensus  #1    .TCACA.GAATTGCA.AG.AGAACAGA.AGATT.TTTAG.GACTC..TTGGCTAGTAGATTTTTGGA.GAAAC.ACCTGGAC.ATTGTAAATGCCCC..T.AAC
Majority         CTCACAAGAATTGCAAAGAAGAACAGAACAGAGATTTTTAGAGACTCCTTGGCTAGTAGATTTTTGGAGGAGGAAACTACCTGGACAATTGTAAATGCCCCTATAAAC ay628224         CTCACAAGAATTGCAAAGAAGAACAGAACAGAGATTTTTAGAGACTCCTTGGCTAGTAGATTTTTGGAGGAGGAAACTACCTGGACAATTGTAAATGCCCCTATGAAC   1241
ay628225         CTCACAAGAATTGCAAAGAAGAACAGAACAGAGATTTTTAGAGACTCCTTGGCTAGTAGATTTTTGGAGGAGGAAACTACCTGGACAATTGTAAATGCCCCTATGAAC   1241
ay628226         CTCACAAGAATTGCAAAGAAGAACAGAACAGAGATTTTTAGAGACTCCTTGGCTAGTAGATTTTTGGAGGAGGAAACTACCTGGACAATTGTAAATGCCCCTATGAAC   1241
ay628227         CTCACAAGAATTGCAAAGAAGAACAGAACAGAGATTTTTAGAGACTCCTTGGCTAGTAGATTTTTGGAGGAGGAAACTACCTGGACAATTGTAAATGCCCCTATGAAC   1241
ay628228         CTCACAAGAATTGCAAAGAAGAACAGAACAGAGATTTTTAGAGACTCCTTGGCTAGTAGATTTTTGGAGGAGGAAACTACCTGGACAATTGTAAATGCCCCTATGAAC   1241
ay628229         CTCACAAGAATTGCAAAGAAGAACAGAACAGAGATTTTTAGAGACTCCTTGGCTAGTAGATTTTTGGAGGAGGAAACTACCTGGACAATTGTAAATGCCCCTATGAAC   1241
ay628230         CTCACAAGAATTGCAAAGAAGAACAGAACAGAGATTTTTAGAGACTCCTTGGCTAGTAGATTTTTGGAGGAGGAAACTACCTGGACAATTGTAAATGCCCCTATGAAC   1241
ay628231         CTCACAAGAATTGCAAAGAAGAACAGAACAGAGATTTTTAGAGACTCCTTGGCTAGTAGATTTTTGGAGGAGGAAACTACCTGGACAATTGTAAATGCCCCTATGAAC   1241
ay628232         CTCACAAGAATTGCAAAGAAGAACAGAACAGAGATTTTTAGAGACTCCTTGGCTAGTAGATTTTTGGAGGAGGAAACTACCTGGACAATTGTAAATGCCCCTATGAAC   1241
ay628233         CTCACAAGAATTGCAAAGAAGAACAGAACAGAGATTTTTAGAGACTCCTTGGCTAGTAGATTTTTGGAGGAGGAAACTACCTGGACAATTGTAAATGCCCCTATGAAC   1241
ay628234         CTCACAAGAATTGCAAAGAAGAACAGAACAGAGATTTTTAGAGACTCCTTGGCTAGTAGATTT'TTGGAGGAGGAAACTACCTGGACAATTGTAAATGCCCCTATGAAC   1192
ay628235         CTCACAAGAATTGCAAAGAAGAACAGAACAGAGATTTTTAGAGACTCCTTGGCTAGTAGATTTTTGGAGGAGGAAACTACCTGGACAATTGTAAATGCCCCTATGAAC   1241
ay628236         CTCACAAGAATTGCAAAGAAGAACAGAACAGAGATTTTTAGAGACTCCTTGGCTAGTAGATTTTTGGAGGAGGAAACTACCTGGACAATTGTAAATGCCCCTATGAAC   1241
ay628237         CTCACAAGAATTGCAAAGAAGAACAGAACAGAGATTTTTAGAGACTCCTTGGCTAGTAGATTTTTGGAGGAGGAAACTACCTGGACAATTGTAAATGCCCCTATGAAC   1229
ay628238         CTCACAAGAATTGCAAAGGAGAAGAACAGAACAGAGATCTTTAGGGACTCTTTGGCTAGTAGATCTTTTGGAAGAAGAACCACCTGGACAATTGTAAATGCCCCATAAAC   1232
m23122           TTCACAAGAATTGCAAAGAAGAACAGAACAGAGATTTTTAGAGACTCCTTGGCTAGTAGATTTTTGGAGGAGGAAACTACCTGGACAATTGTAAATGCCCCTATAAAC   1208
nc_001538        CTCACAAGAATTGCAGAGAAGAACAGAACAGAGATTTTTAGAGACTCCTTGGCTAGTAGATTTTTGGAGGAGGAAACTACCTGGACAATTGTAAATGCCCCTATAAAC   1253
v01108           CTCACAGAATTGCAGAGAAGAACAGAACAGAGATTTTTAGAGACTCCTTGGCTAGTAGATTTTTGGAGGAGGAAACTACCTGGACAATTGTAAATGCCCCTGTAAAC   1253
v01109           CTCACAAGAATTGCAAAGAAGAACAGAACAGAGATTTTTAGAGACTCCTTGGCTAGTAGATTTTTGGAGGAGGAAACTACCTGGACAATTGTAAATGCCCCTATAAAC   1045
Focus2           CTCACAAGAATTGCAAAGAAGAACAGAACAGAGATTTTTAGAGACTCCTTGGCTAGTAGATTTTTGGAGGAGGAAACTACCATTGACAATTGTAAATGCCCCTATAAAC   1241
Focus4           CTCACAAGAATTGCAAAGAAGAACAGAACAGAGATTTTTAGAGACTCCTTGGCTAGTAGATTTTTGGAGGAGGAAACTACCATTGACAATTGTAAATGCCCCTATAAAC   1241
Focus9           CTCACAAGAATTGCAAAGAAGAACAGAACAGAGATTTTTAGAGACTCCTTGGCTAGTAGATTTTTGGAGGAGGAAACTACCTGGACAATTGTAAATGCCCCTGTAAAC   1290
Focus11          CTCACAGGAATTGCAGAGAAGAACAGAACAGAGATTCTTAGAGACTCCTTGGCTAGTAGATTTTTGGAGGAGGAAACTACCTGGACAATTGTAAATGCCCCTGTAAAC   1243
Focus13          CTCACAAGAATTGCAAAGAAGAACAGAACAGAGATTCTTAGAGACTCCTTGGCTAGTAGATTTTTGGAGGAGGAAACTACCTGGACAATTGTAAATGCCCCTATAAAC   1242
Focus14          CTCACAAGAATTGCAAAGAAGAACAGAACAGAGATTTTTAGAGACTCCTTGGCTAGTAGATTTTTGGAGGAGGAAACTACCTGGACAATTGTAAATGCCCCTATAAAC   1240
Focus18          TTCACAAGAATTGCAAAGAAGAACAGAACAGAGATTCTTAGAGACTCCTTGGCTAGTAGATTTTTGGAGGAGGAAACTACCGGACCAATTGTAAATGCCCCTGTAAAC   1243
Focus19          TTCACAAGAATTGCAAAGAAGAACAGAACAGAGATTTTTAGAGACTCCTTGGCTAGTAGATTTTTGGAGGAGGAAACTACCTGGACAATTGTAAATGCCCCTATAAAC   1241
Focus23          CTCACAAGAATTGCAGAGAAGAACAGAACAGAGATTTTTAGAGACTCCTTGGCTAGTAGATTTTTGGAGGAGGAAACTACCTGGACAATTGTAAATGCCCCTATAAAC   1241
Focus29          CTCACAAGAATTGCAGAGAAGAACAGAACAGAGATTTTTAGAGACTCCTTGGCTAGTAGATTTTTGGAGGAGGAAACTACCATTGACAATTGTAAATGCCCCTATAAAC   1242
Focus30          CTCACAAGAATTGCAGAGAAGAACAGAACAGAGATTTTTAGAGACTCCTTGGCTAGTAGATTTTTGGAGGAGGAAACTACCTGGACAATTGTAAATGCCCCTATAAAC   1241
Focus31          CTCACAGGAATTGCAGAGAAGAACAGAACAGAGATTTTTAGAGACTCCTTGGCTAGTAGATTTTTGGAGGAGGAAACTACCATTGACAATTGTAAATGCCCCTATAAAC   1242
Focus32          CTCACAGGAATTGCAGAGAAGAACAGAACAGAGATTTTTAGAGACTCCTTGGCTAGTAGATTTTTGGAGGAGGAAACTACCTGGACAATTGTAAATGCCCCTATAAAC   1205
```

```
Consensus #1    C.CT.CC.AA..T.AATGAGGA.CTAACCTGTGG.AAT.TACT.ATGTGGAGGCTGT.AC.GTA.AAACAGAGGT.A.TGGAATAACTAG.ATGC.TAA
Majority        CCCTCCCCAATTTAAATGAGGACCTAACCTGTGGAAATCTACTGATGTGGAGGCTGTAACTGTACAAACAGAGGTCATTGAATAACTAGCATGCTTAA
ay628224        CCCTCCCCAATTTAAATGAGGACCTAACCTGTGGAAATCTACTGATGTGGAGGCTGTAACTGTACAAACAGAGGTCATTGAATAACTAGCATGCTTAA 1934
ay628225        CCCTCCCCAATTTAAATGAGGACCTAACCTGTGGAAATCTACTGATGTGGAGGCTGTAACTGTACAAACAGAGGTCATTGAATAACTAGCATGCTTAA 1934
ay628226        CCCTCCCCAATTTAAATGAGGACCTAACCTGTGGAAATCTACTGATGTGGAGGCTGTAACTGTACAAACAGAGGTCATTGAATAACTAGCATGCTTAA 1934
ay628227        CCCTCCCCAATTTAAATGAGGACCTAACCTGTGGAAATCTACTGATGTGGAGGCTGTAACTGTACAAACAGAGGTCATTGAATAACTAGCATGCTTAA 1934
ay628228        CCCTCCCCAATTTAAATGAGGAATCTAACCTGTGGAAATCTACTGATGTGGAGGCTGTAACTGTACAAACAGAGGTCATTGAATAACTAGCATGCTTAA 1934
ay628229        CCCTCCCCAATTTAAATGAGGACCTAACCTGTGGAAATCTACTGATGTGGAGGCTGTAACTGTACAAACAGAGGTCATTGAATAACTAGCATGCTTAA 1934
ay628230        CCCTCCCCAATTTAAATGAGGACCTAACCTGTGGAAATCTACTGATGTGGAGGCTGTAACTGTACAAACAGAGGTCATTGAATAACTAGCATGCCTAA 1934
ay628231        CCCTCCCCAATTTAAATGAGGACCTAACCTGTGGAAATCTACTGATGTGGAGGCTGTAACTGTACAAACAGAGGTCATTGAATAACTAGCATGCTTAA 1934
ay628232        CCCTCCCCAATTTAAATGAGGACCTAACCTGTGGAAATCTACTGATGTGGAGGCTGTAACTGTACAAACAGAGGTCATTGAATAACTAGCATGCTTAA 1934
ay628233        CCCTCCCCAATTTAAATGAGGACCTAACCTGTGGAAATCTACTGATGTGGAGGCTGTACTGTACAAACAGAGGTCATTGAATAACTAGCATGCTTAA 1934
ay628234        CCCTCCCCAATTTAAATGAGGACCTAACCTGTGGAAATCTACTGATGTGGAGGCTGTAACAGTACAAACAGAGGTCATTGAATAACTAGCATGCTTAA 1885
ay628235        CCCTCCCCAATTTAAATGAGGACCTAACCTGTGGAAATCTACTGATGTGGAGGCTGTAACAGTACAAACAGAGGTCATTGAATAACTAGCATGCTTAA 1934
ay628236        CCCTCCCCAATTTAAATGAGGACCTAACCTGTGGAAATCTACTGATGTGGAGGCTGTAACTGTACAAACAGAGGTCATTGAATAACTAGCATGCTTAA 1934
ay628237        CCCTCCCCAATTTAAATGAGGACCTAACCTGTGGAAATCTACTGATGTGGAGGCTGTAACTGTACAAACAGAGGTCATTGAATAACTAGCATGCTTAA 1922
ay628238        CCCTCCCCAATTTAAATGAGGACCTAACCTGTGGAAATCTACTAATGTGGAGGCTGTAACTGTACAAAACAGAGGTTATTGAATAACTAGCATGCTTAA 1925
m23122          CACTGCCAACCTAAATGAGGACCTAACCTGTGGAAATCTACTGATGTGGAGGCTGTAACTGTACAAACAGAGGTCATTGAATAACTAGCATGCTTAA 1901
nc_001538       CCCTCCCCAATTTAAATGAGGACCTAACCTGTGGAAATCTACTGATGTGGAGGCTGTAACTGTACAAACAGAGGTTATTGAATAACTAGCATGCTTAA 1946
v01108          CCCTCCCCAATTTAAATGAGGACCTAACCTGTGGAAATCTACTGATGTGGAGGCTGTAACTGTACAAACAGAGGTTATTGAATAACTAGCATGCTTAA 1946
v01109          CCCTCCCCAATTTAAATGAGGACCTAACCTGTGGAAATCTACTGATGTGGAGGCTGTAACTGTACAAACAGAGGTTATTGAATAACTAGCATGCTTAA 1738
Focus2          CCCTCCCCAATTTAAATGAGGACCTAACCTGTGGAAATCTACTGATGTGGAGGCTGTAACTGTACAGTAGTACAAACAGAGGTTATTGAATAACTAGCATGCTTAA 1940
Focus4          CCCTCCCCAATTTAAATGAGGACCTAACCTGTGGAAATCTACTGATGTGGAGGCTGTAACTGTACAGTAGTACAAACAGAGGTTATTGAATAACTAGCATGCTTAA 1940
Focus9          CCCTCCCCAATTTGAATGAGGATCTAACCTGTGGAAATCTACTAATGTGGAGGCTGTGACTGTAAGTAGTACAAACAGAGGTTATTGAATAACTAGTATGCTTAA 1989
Focus11         CACTACCTAATTTGAATGAGGATCTAACCTGTGGAAATCTACTAATGTGGAGGCTGTGACTGTAAGTAGTACAAACAGAGGTTATTGAATAACTAGTATGCTTAA 1942
Focus13         CCCTCCCCAATTTAAATGAGGACCTAACCTGTGGAAATCTACTGATGTGGAGGCTGTAACTGTACAGTAGTACAAACAGAGGTTATTGAATAACTAGCATGCTTAA 1942
Focus14         CCCTCCCCAATTTAAATGAGGACCTAACCTGTGGAAATCTACTGATGTGGAGGCTGTAACTGTACAGTAGTACAAACAGAGGTTATTGAATAACTAGCATGCTTAA 1939
Focus18         CACTACCTAATTTGAATGAGGATCTAACCTGTGGAAATCTACTAATGTGGAGGCTGTGACTGTGTAAAAACAGAGGTTATTGAATAACTAGCATGCTTAA 1942
Focus19         CCCTCCCCAATTTAAATGAGGACCTAACCTGTGGAAATCTACTGATGTGGAGGCTGTGACTGTAAATGTACAAACAGAGGTTATTGAATAACTAGTATGCTTAA 1942
Focus23         CCCTCCCCAATTTAAATGAGGACCTAACCTGTGGAAATCTACTGATGTGGAGGCTGTAACTGTACAAACAGAGGTTATTGAATAACTAGCATGCTTAA 1940
Focus29         CCCTCCCCAATTTAAATGAGGACCTAACCTGTGGAAATCTACTGATGTGGAGGCTGTAACTGTACAAACAGAGGTTATTGAATAACTAGCATGCTTAA 1940
Focus30         CCCTCCCCAATTTAAATGAGGACCTAACCTGTGTGGAAATCTACTGATGTGGAGGCTGTAACTGTAACAGTACAAACAGAGGTTATTGAATAACTAGCATGCTTAA 1941
Focus31         CCCTCCCCAATTTAAATGAGGACCTAACCTGTGGAAATCTACTGATGTGGAGGCTGTAACAGTACAAACAGAGGTTATTGAATAACTAGCATGCTTAA 1940
Focus32         CCCTGCCCAATTTAAATGAGGACCTAACCTGTGGAAATTTACTGATGTGGAGGCTGTAACTGTAACTGTACAAACAGAGGTTATTGAATAACTAGCATGCTTAA 1904
```

FIG. 1T

| | |
|---|---|
| Consensus #1 | CCTTCA.GCAGGGTC..CA.AAAGT.CATGA..ATGGTGGAGG.AAACCT.T.C.AGGCAG.AATTT.CACTT.TTTGCTGT.GGTGG.GA.CCCTTGGAA |
| Majority | CCTTCATGCAGGGTCACAAAAAGTGCATGAGCATGGTGGAGGTAAACCTAAACCTATTCAAGGCAGTAAATTTCACTTCTTTGCTCTTTGCTGTTGGTGGTGGAGACCCCTTGGAA 2034 |
| ay628224 | CCTTCACGCAGGGTCACAAAAAGTGCATGAGCATGGTGGAGGTAAACCTATTCAAGGCAGTAAATTTCACTTCTTTGCTCTTTGCTGTTGGTGGTGGAGACCCCTTGGAA 2034 |
| ay628225 | CCTTCATGCAGGGTCACAAAAAGTGCATGAGCATGGTGGAGGTAAACCTATTCGAGGCAGTAAATTTCACTTCTTTGCTCTTTGCTGTTGGTGGTGGAGACCCCTTGGAA 2034 |
| ay628226 | CCTTCATGCAGGGTCACAAAAAGTGCATGAGCATGGTGGAGGTAAACCTATTCAAGGCAGTAAATTCACTTCTTTGCTCTTTGCTGTTGGTGGTGGAGACCCCTTGGAA 2034 |
| ay628227 | CCTTCATGCAGGGTCACAAAAAGTGCATGAGCATGGTGGAGGTAAACCTATTCAAGGCAGTAAATTTCACTTCTTTGCTCTTTGCTGTTGGTGGTGGAGACCCCTTGGAA 2034 |
| ay628228 | CCTTCATGCAGGGTCACAAAAAGTGCATGAGCATGGTGGAGGTAAACCTATTCAAGGCAGTAAATTTCACTTCTTTGCTCTTTGCTGTTGGTGGTGGAGACCCCTTGGAA 2034 |
| ay628229 | CCTTCATGCAGGGTCACAAAAAGTGCATGAGCATGGTGGAGGTAAACCTATTCAAGGCAGTAAATTTCACTTCTTTGCTCTTTGCTGTTGGTGGTGGAGACCCCTTGGAA 2034 |
| ay628230 | CCTTCATGCAGGGTCACAAAAAGTGCATGAGCATGGTGGAGGTAAACCTATTCAAGGCAGTAAATTTCACTTCTTTGCTCTTTGCTGTTGGTGGTGGAGACCCCTTGGAA 2034 |
| ay628231 | CCTTCATGCAGGGTCACAAAAAGTGCATGAGCATGGTGGAGGTAAACCTATTCAAGGCAGTAAATTTCACTTCTTTGCTCTTTGCTGTTGGTGGTGGAGACCCCTTGGAA 2034 |
| ay628232 | CCTTCATGCAGGGTCACAAAAAGTGCATGAGCATGGTGGAGGTAAACCTATTCAAGGCAGTAAATTTCACTTCTTTGCTCTTTGCTGTTGGTGGTGGAGACCCCTTGGAA 2034 |
| ay628233 | CCTTCATGCAGGGTCACAAAAAGTGCATGAGCATGGTGGAGGTAAACCTATTCAAGGCAGTAAATTTCACTTCTTTGCTCTTTGCTGTTGGTGGTGGAGACCCCTTGGAA 2034 |
| ay628234 | CCTTCATGCAGGGTCACAAAAAGTGCATGAGCATGGTGGAGGTAAACCTATTCAAGGCAGTAAATTTCACTTCTTTTGCTCTTTTGCTGTTGGTGGTGGAGACCCCTTGGAA 1985 |
| ay628235 | CCTTCATGCAGGGTCACAAAAAGTGCATGAGCATGGTGGAGGTAAACCTATTCAAGGCAGTAAATTTCACTTCTTTGCTCTTTGCTGTTGGTGGTGGAGACCCCTTGGAA 2034 |
| ay628236 | CCTTCATGCAGGGTCACAAAAAGTGCATGAGCATGGTGGAGGTAAACCTATTCAAGGCAGTAAATTTCACTTCTTTGCTCTTTGCTGTTGGTGGTGGAGACCCCTTGGAA 2034 |
| ay628237 | CCTTCATGCAGGGTCACAAAAAGTGCATGAGCATGGTGGAGGTAAACCTATTCAAGGCAGTAAATTTCACTTCTTTGCTCTTTGCTGTTGGTGGTGGAGATCCCTTGGAA 2022 |
| ay628238 | CCTTCATGCAGGGTCACAAAAAGTGCATGAGCATGGTGGAGGTAAACCTATTCAAGGCAGTAAATTTCCACTTCTTTGCTCTTTGCTGTTGGTGGTGGAGACCCCTTGGAA 2025 |
| m23122 | CCTTCATGCAGGGTCCCAAAAAGTGCATGAGAATGGTGGAGGTAAACCTGTCCAAGGCAGTAAATTTCCACTTTTTGCTCTTTTGCTGTGGGTGGTAGTGGAGACCCTTGGAA 2001 |
| nc_001538 | CCTTCATGCAGGGTCACAAAAAGTGCATGAGCATGGTGGAGGTAAACCTATTCAAGGCAGTAAATTTCCACTTCTTTGCTCTTTGCTGTTGGTGGTAGTGGAGAACCCTTGGAA 2046 |
| v01108 | CCTTCATGCAGGGTCACAAAAAGTGCATGAGCATGGTGGAGGTAAACCTATTCAAGGCAGTAAATTTCCACTTCTTTGCTCTTTGCTGTTGGTGGTAGTGGAGAACCCTTGGAA 2046 |
| v01109 | CCTTCATGCAGGGTCACAAAAAGTGCATGAGCATGGTGGAGGTAAACCTATTCAAGGCAGTAAATTTCCACTTCTTTGCTCTTTGCTGTTGGTGGTGGAGACCCCTTGGAA 1838 |
| Focus2 | CCTTCATGCAGGGTCACAAAAAGTGCATGAGCATGGTGGAGGTAAACCTATTCAAGGCAGTAAATTTCCACTTCTTTGCTCTTTGCTGTTGGTGGTGGAGACCCCTTGGAA 2040 |
| Focus4 | CCTTCATGCAGGGTCACAAAAAGTGCATGAGCATGAAAATGGTGGAGGTAAACCTATTCAAGGCAGTAAATTTCCACTTTTTGCTCTTTTGCTGTTGGTGGTGGAGACCCCTTGGAA 2089 |
| Focus9 | CCTTCATGCAGGGTCACAAAAAGTGCATGAGCATGGTGGAGGTAAACCTATTCAAGGCAGCAATTAATTTCCACTTCTTTGCTCTTTGCTGTTGGTGGGTGGAGACCCCTTGGAA 2042 |
| Focus11 | CCTTCATGCAGGGTCACAAAAAGTGCATGAGCATGGTGGAGGTAAACCTATTCAAGGCAGTAAATTTCCACTTCTTTGCTCTTTGCTGTTGGTGGTGGAGACCCCTTGGAA 2042 |
| Focus13 | CCTTCATGCAGGGTCACAAAAAGTGCATGAGCATGGTGGAGGTAAACCTATTCAAGGCAGTAAATTTCCACTTCTTTGCTCTTTGCTGTTGGTGGTGGAGACCCCTTGGAA 2039 |
| Focus14 | CCTTCATGCAGGGTCACAAAAAGTGCATGAGCATGGTGGAGGTAAACCTATTCAAGGCAGTAAATTTCCACTTTTTCACTTTTTGCTCTTTTGCTGTTGGTGGGTGGAGACCCCTTGGAA 2042 |
| Focus18 | CCTTCATGCAGGGTCACAGAAAGTGCATGAGCATGAAAATGGTGGAGGTAAACCTATTCAAGGCAGCAATTAATTTCCACTTCTTTGCTCTTTGCTGTTGGTGGTGGAGACCCCTTGGAA 2040 |
| Focus19 | CCTTCATGCAGGGTCACAGAAAGTGCATGAGCATGAAAATGGTGGAGGTAAACCTATTCAAGGAGAAAAACCTATTAATTTCCACTTCTTTGCTCTTTGCTGTTGGTGGTGGAGACCCCTTGGAA 2040 |
| Focus23 | CCTTCATGCAGGGTCACAAAAAGTGCATGAGCATGGTGGAGGTAAACCTATTCAAGGCAGTAAATTTCCACTTCTTTTGCTCTTTTGCTGTTGGTGGTGGAGACCCCTTGGAA 2041 |
| Focus29 | CCTTCATGCAGGGTCACAAAAAGTGCATGAGCATGGTGGAGGTAAACCTATTCAAGGCAGTAAATTTCCACTTCTTTTGCTCTTTTGCTGTTGGTGGTGGAGACCCCTTGGAA 2040 |
| Focus30 | CCTTCATGCAGGGTCACAAAAAGTGCATGAGCATGGTGGAGGTAAACCTATTCAAGGCAGTAAATTTCCACTTCTTTTGCTCTTTTGCTGTTGGTGGTGGAGACCCCTTGGAA 2041 |
| Focus31 | CCTTCATGCAGGGTCACAAAAAGTGCATGAGCATGGTGGAGGTAAACCTATTCAAGGCAGTAAATTTCCACTTCTTTTGCTCTTTTGCTGTTGGTGGTGGAGACCCCTTGGAA 2041 |
| Focus32 | CCTTCATGCAGGGTCACAAAAAGTGCATGAGCATGGTGGAGGAAAAAACCTATTCAAGGCAGTAAATTTCCACTTCTTGCTCTTCTTTGCTGTTGGTGGTGGAGACCCCTTGGAA 2004 |

```
Consensus #1 TG.AGG.TATCTAC.CTTTT.TTAGCTAA.ACTGTATC.ACTGCTTGCTGACAAAT...TTTTT..T.TTTACTTTCTGCAAA.AT..TAGCATTTGCA.
Majority     TGAAGGGTATCTACTCTTTTTTTAGCTAAAACTGTATCTACTGCTTGCTGACAAATACTTTTTTGATTTTTACTTTCTGCAAAAAATAGTAGCATTTGCAA
ay628224     TGAAGGGTATCTACTCTTTTTTTAGCTAAAACTGTATCTACTGCTTGCTGACAAATACTTTTTTGATTTTTACTTTCTGCAAAAAATAGTAGCATTTGCAA 3830
ay628225     TGAAGGGTATCTACTCTTTTTTTAGCTAAAACTGTATCTACTGCTTGCTGACAAATACTTTTTTGATTTTTACTTTCTGCAAAAAATAGTAGCATTTGCAA 3830
ay628226     TGAAGGGTATCTACTCTTTTTTTAGCTAAAACTGTATCTACTGCTTGCTGACAAATACTTTTTTGATTTTTACTTTCTGCAAAAAATAGTAGCATTTGCAA 3830
ay628227     TGAAGGGTATCTACTCTTTTTTTAGCTAAAACTGTATCTACTGCTTGCTGACAAATACTTTTTTGATTTTTACTTTCTGCAAAAAATAGTAGCATTTGCAA 3830
ay628228     TGAAGGGTATCTACTCTTTTTTTAGCTAAAACTGTATCTACTGCTTGCTGACAAATACTTTTTTGATTTTTACTTTCTGCAAAAAATAGTAGCATTTGCAA 3830
ay628229     TGAAGGGTATCTACTCTTTTTTTAGCTAAAACTGTATCTACTGCTTGCTGACAAATACTTTTTTGATCTTTACTTTCTGCAAAAAATAGTAGCATTTGCAA 3830
ay628230     TGAAGGGTATCTACTCTTTTTTTAGCTAAAACTGTATCTACTGCTTGCTGACAAATACTTTTTTGATTTTTACTTTCTGCAAAAAATAGTAGCATTTGCAA 3830
ay628231     TGAAGGGTATCTACTCTTTTTTTAGCTAAAACTGTATCTACTGCTTGCTGACAAATACTTTTTTGATTTTTACTTTCTGCAAAAAATAGTAGCATTTGCAA 3830
ay628232     TGAAGGGTATCTACTCTTTTTTTAGCTAAAACTGTATCTACTGCTTGCTGACAAATACTTTTTTGATTTTTACTTTCTGCAAAAAATAGTAGCATTTGCAA 3830
ay628233     TGAAGGGTATCTACTCTTTTTTTAGCTAAAACTGTATCTACTGCTTGCTGACAAATACTTTTTTGATTTTTACTTTCTGCAAAAAATAGTAGCATTTGCAA 3830
ay628234     TGGAGGCTATCTACTCTTTTTTTAGCTAAAACTGTATCTACTGCTTGCTGACAAATACTTTTTTGATTTTTACTTTCTGCAAAGATAGTAGCATTTGCAA 3781
ay628235     TGAAGGCTATCTACTCTTTTTTTAGCTAAAACTGTATCTACTGCTTGCTGACAAATACTTTTTTGATTTTTACTTTCTGCAAAGATAGTAGCATTTGCAA 3830
ay628236     TGAAGGCTATCTACTCTTTTTTTAGCTAAAACTGTATCTACTGCTTGCTGACAAATGCTTTTTTGATTTTTACTTTCTGCAAAGATAGTAGCATTTGCAC 3830
ay628237     TGAAGGGTATCTACTCTTTTTTTAGCTAAAACTGTATCTACTGCTTGCTGACAAATACTTTTTTGATTTTTACTTTCTGCAAAAAATAGTAGCATTTGCAA 3818
ay628238     TGAAGGGTATCTACTCTTTTTTTAGCTAAAACTGTATCTACTGCTTGCTGACAAATACTTTTTTGATTTTTACTTTCTGCAAAAAATAGTAGCATTTGCAA 3821
m23122       TGAAGGGTATCTACTCTTTTTTTAGCTAATACTGTATCTACTGCTTGCTGACAAATACTTTTTTGATTTTTACTTTCTGCAAAAAATAATAGCATTTGCAA 3785
nc_001538    TGAAGGGTATCTACTCTTTTTTTAGCTAAAACTGTATCTACTGCTTGCTGACAAATACTTTTTTGATTTTTACTTTCTGCAAAAAATAATAGCATTTGCAA 3842
v01108       TGAAGGGTATCTACTCTTTTTTTAGCTAAAACTGTATCTACTGCTTGCTGACAAATACTTTTTTGATTTTTACTTTCTGCAAAAAATAATAGCATTTGCAA 3842
v01109       TGAAGGGTATCTACTCTTTTTTTAGCTAAAACTGTATCTACTGCTTGCTGACAAATAACTTTTTTGTTTTTACTTTCTGCAAAAAATAATAGCATTTGCAA 3634
Focus2       TGAAGGGTATCTACTCTTTTTTTAGCTAAAACTGTATCTACTGCTTGCTGACAAATACTTTTTTGATTTTTACTTTCTGCAAAGATAATAGCATTTGCAA 3836
Focus4       TGAAGGCTATCTACTCTTTTTTTAGCTAAAACTGTATCTACTGCTTGCTGACAAATACTTTTTTGATTTTTACTTTCTGCAAAGATAGTAGCATTTGCAA 3836
Focus9       TGAAGGCTATCTACTCTTTTTTTAGCTAAAACTGTATCTACTGCTTGCTGACAAATACTTTTTTGATTTTTACTTTCTGCAAATATAGTAGCATTTGCAA 3885
Focus11      TGGAGGGTATCTACCCTTTTTTTAGCTAACACTGTATCCACTGCTTGCTGACAAATACTTTTTTGATTTTTACTTTCTGCAAAAAATGGTAGCATTTGCAA 3841
Focus13      TGAAGGCTATCTACTCTTTTTTTAGCTAAAACTGTATCTACTGCTTGCTGACAAATACTTTTTTGATTTTTACTTTCTGCAAAGATAGTAGCATTTGCAA 3838
Focus14      TGAAGGCTATCTACTCTTTTTTTAGCTAAAACTGTATCTACTGCTTGCTGACAAATACTTTTTTGATTTTTACTTTCTGCAAAGATAGTAGCATTTGCAA 3835
Focus18      TGGAGGGTATCTACCCTTTTTTTAGCTAACACTGTATCCACTGCTTGCTGACAAATACTTTTTTGATTTTTACTTTCTGCAAAAAATGGTAGCATTTGCAA 3842
Focus19      TGAAGGGTATCTACTCTTTTTTTAGCTAAAACTGTATCTACTGCTTGCTGACAAATACTTTTTTGATTTTTACTTTCTGCAAAAAATAGTAGCATTTGCAA 3836
Focus23      TGAAGGGTATCTACTCTTTTTTTAGCTAAAACTGTATCTACTGCTTGCTGACAAATACTTTTTTGATTTTTACTTTCTGCAAAGATAATAGCATTTGCAA 3836
Focus29      TGAAGGCTATCTACTCTTTTTTTAGCTAAAACTGTATCTACTGCTTGCTGACAAATACTTTTTTGATTTTTACTTTCTGCAAAGATAGTAGCATTTGCAA 3837
Focus30      TGAAGGCTATCTACTCTTTTTTTAGCTAAAACTGTATCTACTGCTTGCTGACAAATACTTTTTTGATTTTTACTTTCTGCAAAGATAGTAGCATTTGCAA 3836
Focus31      TGAAGGCTATCTACTCTTTTTTTAGCTAAAACTGTATCTACTGCTTGCTGACAAATACTTTTTTGATTTTTACTTTCTGCAAAGATAGTAGCATTTGCAA 3837
Focus32      TGAAGGGTATCTACTCTTTTCTTAGCTAAAACTGTATCTACTGCTTGCTGACAAATACTTTTTTGATTTTTACTTTCTGCAAAGATAATAGCATTTGCAA 3800
```

```
Consensus #1  ..CA.T..AT.C..GT.GC...CT.T..CA.....A.....CTT.....T.CTTAAA..TTTTCT..TTAA..G.....AT.T...C.G.CA...C.T.C
Majority      AGCAGTCAATGCA-GTAGCAATCTAT-CCAAACCAAGGGCTCTT-----TTCTTAAAAATTTTCTATTTAAATGCCTTAATCTAAGCTGACATAGCATGC
ay628224      AGCAGTCAATGCA-GTAGCAATCTAT-CCAAACCAAGGGCTCTT-----TTCTTAAAAATTTTCTATTTAAATGCCTTAATCTAAGCTGACATAGCATGC 4810
ay628225      AGCAGTCAATGCA-GTAGCAATCTAT-CCAAACCAAGGGCTCTT-----TTCTTAAAAATTTTCTATTTAAATGCCTTAATCTAAGCTGACATAGCATGC 4810
ay628226      AGCAGTCAATGCA-GTAGCAATCTAT-CCAAACCAAGGGCTCTT-----TTCTTAAAAATTTTCTATTTAAATGCCTTAATCTAAGCTGACATAGCATGC 4810
ay628227      AGCAGTCAATGCA-GTAGCAATCTAT-CCAAACCAAGGGCTCTT-----TTCTTAAAAATTTTCTATTTAAATGCCTTAATCTAAGCTGACATAGCATGC 4810
ay628228      AGCAGTCAATGCA-GTAGCAATCTAT-CCAAACCAAGGGCTCTT-----TTCTTAAAAATTTTCTATTTAAATGCCTTAATCTAAGCTGACATAGCATGC 4810
ay628229      AGCAGTCAATGCA-GTAGCAATCTAT-CCAAACCAAGGGCTCTT-----TTCTTAAAAATTTTCTATTTAAATGCCTTAATCTAAGCTGACATAGCATGC 4810
ay628230      AGCAGTCAATGCA-GTAGCAATCTAT-CCAAACCAAGGGCTCTT-----TTCTTAAAAATTTTCTATTTAAATGCCTTAATCTAAGCTGACATAGCATGC 4810
ay628231      AGCAGTCAATGCA-GTAGCAATCTAT-CCAAACCAAGGGCTCTT-----TTCTTAAAAATTTTCTATTTAAATGCCTTAATCTAAGCTGACATAGCATGC 4810
ay628232      AGCAGTCAATGCA-GTAGCAATCTAT-CCAAACCAAGGGCTCTT-----TTCTTAAAAATTTTCTATTTAAATGCCTTAATCTAAGCTGACATAGCATGC 4810
ay628233      AGCAGTCAATGCA-GTAGCAATCTAT-CCAAACCAAGGGCTCTT-----TTCTTAAAAATTTTCTATTTAAATGCCTTAATCTAAGCTGACATAGCATGC 4810
ay628234      AGCAGTCAATGCA-GTAGCAATCTAT-CCAAACCAAGGGCTCTT-----TTCTTAAAAATTTTCTATTTAAATGCCTTAATCTAAGCTGACATAGCATGC 4761
ay628235      AGCAGTCAATGCA-GTAGCAATCTAT-CCAAACCAAGGGCTCTT-----TTCTTAAAAATTTTCTATTTAAATGCCTTAATCTAAGCTGACATAGCATGC 4810
ay628236      AGCAGTCAATGCA-GTAGCAATCTAT-CCAAACCAAGGGCTCTT-----TTCTTAAAAATTTTCTATTTAAATGCCTTAATCTAAGCTGACATAGCATGC 4810
ay628237      AGCAGTCAATGCA-GTAGCAATCTAT-CCAAACCAAGGGCTCTT-----TTCTTAAAAATTTTCTATTTAAATGCCTTAATCTAAGCTGACATAGCATGC 4798
ay628238      AGCAGTCAATGCA-GTAGCAATCTAT-CCAAACCAAGGGCTCTT-----TTCTTAAAAATTTTCTATTTAAATGCCTTAATCTAAGCTGACATAGCATGC 4801
m23122        AGCAATCAATGCA-GTAGCAATCTAT-CCAAACCAATGGCTCTT-----TTCTTAAAAATTTTCTATTTAAATGCCTTAATCTTAGCTGACATAGCATGC 4767
nc_001538     AGCAGTCAATGCA-GTAGCAATCTAT-CCAAACCAAGGGCTCTT-----TTCTTAAAAATTTTCTATTTAAATGCCTTAATCTAAGCTGACATAGCATGC 4822
v01108        AGCAGTCAATGCA-GTAGCAATCTAT-CCAAACCAAGGGCTCTT-----TTCTTAAAAATTTTCTATTTAAATGCCTTAATCTAAGCTGACATAGCATGC 4822
v01109        TTCATTTTATCCTCGTCGCCCCCTTTGTCAGGGTGAAATTCCTTACACTTCCTTAAAGCTTTTCTCATTAAGGGAA--GATTTCCCCAGGCAGCTCTTTC 4623
Focus2        AGCAGTCAATGCA-GTAGCAATCTAT-CCAAACCAAGGGCTCTT-----TTCTTAAAAATTTTCTATTTAAATGCCTTAATCTAAGCTGACATAGCATGC 4816
Focus4        AGCAGTCAATGCA-GTAGCAATCTAT-CCAAACCAAGGGCTCTT-----TTCTTAAAAATTTTCTATTTAAATGCCTTAATCTAAGCTGACATAGCATGC 4816
Focus9        AGCAGTCAATGCA-GTAGCAATCTAT-CCAAACCAAGGGCTCTT-----TTCTTAAAAATTTTCTATTTAAATGCCTTAATCTAAGCTGACATAGCATGC 4865
Focus11       AGCAGTCAATGCA-GTAGCAATCTAT-CCAAACCAAGGGCTCTT-----TTCTTAAAAATTTTCTATTTAAATGTCTTAATCTTAGCTGACACAGCATGC 4823
Focus13       AGCAGTCAATGCA-GTAGCAATCTAT-CCAAACCAAGGGCTCTT-----TTCTTAAAAATTTTCTATTTAAATGCCTTAATCTAAGCTGACATAGCATGC 4818
Focus14       AGCAGTCAATGCA-GTAGCAATCTAT-CCAAACCAAGGGCTCTT-----TTCTTAAAAATTTTCTATTTAAATGCCTTAATCTAAGCTGACATAGCATGC 4815
Focus18       AGCAGTCAATGCA-GTAGCAATCTAT-CCAAACCAAGGGCTCTT-----TTCTTAAAAATTTTCTATTTAAATGTCTTAATCTTAGCTGACACAGCATGC 4822
Focus19       AGCAGTCAATGCA-GTAGCAATCTAT-CCAAACCAAGGGCTCTT-----TTCTTAAAAATTTTCTATTTAAATGCCTTAATCTAAGCTGACATAGCATGC 4816
Focus23       AGCAGTCAATGCA-GTAGCAATCTAT-CCAAACCAAGGGCTCTT-----TTCTTAAAAATTTTCTATTTAAATGCCTTAATCTAAGCTGACATAGCATGC 4816
Focus29       AGCAGTCAATGCA-GTAGCAATCTAT-CCAAACCAAGGGCTCTT-----TTCTTAAAAATTTTCTATTTAAATGCCTTAATCTAAGCTGACATAGCATGC 4817
Focus30       AGCAGTCAATGCA-GTAGCAATCTAT-CCAAACCAAGGGCTCTT-----TTCTTAAAAATTTTCTATTTAAATGCCTTAATCTAAGCTGACATAGCATGC 4816
Focus31       AGCAGTCAATGCA-GTAGCAATCTAT-CCAAACCAAGGGCTCTT-----TTCTTAAAAATTTTCTATTTAAATGCCTTAATCTAAGCTGACATAGCATGC 4817
Focus32       AGCAGTCAATGCA-GTAGCAATCTAT-CCAAACCAAGGGCTCTT-----TTCTTAAAAATTTTCTATTTAAATGCCTTAATCTAAGCTGACATAGCATGC 4780
```

| | | | |
|---|---|---|---|
| Consensus #1 | ...AA.AG....A......CC.T..A.TC...C.T....A...A.T..A.CCA. | | |
| Majority | -CTAAAAGGTCCATGAGCTCCATGGATTCTTCCCTGTTAA-GCACTTTATCCAT | | |
| ay628224 | -CTAAAAGGTCCATGAGCTCCATGGATTCTTCCCTGTTAA-GCACTTTATCCAT | (SEQ ID NO.:21) | 5141 |
| ay628225 | -CTAAAAGGTCCATGAGCTCCATGGATTCTTCCCTGTTAA-GCACTTTATCCAT | (SEQ ID NO.:22) | 5141 |
| ay628226 | -CTAAAAGGTCCATGAGCTCCATGGATTCTTCCCTGTTAA-GCACTTTATCCAT | (SEQ ID NO.:23) | 5141 |
| ay628227 | -CTAAAAGGTCCATGAGCTCCATGGATTCTTCCCTGTTAA-GCACTTTATCCAT | (SEQ ID NO.:24) | 5141 |
| ay628228 | -CTAAAAGGTCCATGAGCTCCATGGATTCTTCCCTGTTAA-GCACTTTATCCAT | (SEQ ID NO.:25) | 5141 |
| ay628229 | -CTAAAAGGTCCATGAGCTCCATGGATTCTTCCCTGTTAA-GCACTTTATCCAT | (SEQ ID NO.:26) | 5141 |
| ay628230 | -CTAAAAGGTCCATGAGCTCCATGGATTCTTCCCTGTTAA-GCACTTTATCCAT | (SEQ ID NO.:27) | 5141 |
| ay628231 | -CTAAAAGGTCCATGAGCTCCATGGATTCTTCCCTGTTAA-GCACTTTATCCAT | (SEQ ID NO.:28) | 5141 |
| ay628232 | -CTAAAAGGTCCATGAGCTCCATGGATTCTTCCCTGTTAA-GCACTTTATCCAT | (SEQ ID NO.:29) | 5141 |
| ay628233 | -CTAAAAGGTCCATGAGCTCCATGGATTCTTCCCTGTTAA-GCACTTTATCCAT | (SEQ ID NO.:30) | 5141 |
| ay628234 | -CCAAAAGGTCCATGAGCTCCATGGATTCTTCCCTGTTAA-GCACTTTATCCAT | (SEQ ID NO.:31) | 5141 |
| ay628235 | -CCAAAAGGTCCATGAGCTCCATGGATTCTTCCCTGTTAA-GCACTTTATCCAT | (SEQ ID NO.:32) | 5141 |
| ay628236 | -CCAAAAGGTCCATGAGCTCCATGGATTCTTCCCTGTTAA-GCACTTTATCCAT | (SEQ ID NO.:33) | 5092 |
| ay628237 | -CCAAAAGGTCCATGAGCTCCATGGATTCTTCCCTGTTAA-GCACTTTATCCAT | (SEQ ID NO.:34) | 5141 |
| ay628238 | -CTAAAAGGTCCATGAGCTCCATGGATTCTTCCCTGTTAA-GCACTTTATCCAT | (SEQ ID NO.:35) | 5141 |
| m23122 | -CTAAAAGGTCCATGAGCTCCATGGATTCTTCCCTGTTAA-GCACTTTATCCAT | (SEQ ID NO.:36) | 5129 |
| nc_001538 | -CTAAAAGGTCCATGAGCTCCATGGATTCTTCCCTGTTTA-AGACTTTATCCAT | (SEQ ID NO.:37) | 5132 |
| v01108 | -CTAAAAGGTCCATGAGCTCCATGGATTCTTCCCTGTTAA-GAACTTTATCCAT | (SEQ ID NO.:38) | 5098 |
| v01109 | -CTAAAAGGTCCATGAGCTCCATGGATTCTTCCCTGTTAA-GAACTTTATCCAT | (SEQ ID NO.:39) | 5153 |
| Focus2 | GTTAATAGTGAAACCCCGCCCCTAAAATCTCTTACCATGGAATGCAGCAA | (SEQ ID NO.:40) | 5153 |
| Focus4 | -CTAAAAGGTCCATGAGCTCCATGGATTCTTCCCTGTTAA-GCACTTTATCCAT | (SEQ ID NO.:41) | 4963 |
| Focus9 | -CCAAAAGGTCCATGAGCTCCATGGATTCTTCCCTGTTAA-GCACTTTATCCAT | (SEQ ID NO.:42) | 5147 |
| Focus11 | -CCAAAAGGTCCATGAGCTCCATGGATTCTTCCCTGTTAA-GCACTTTATCCAT | (SEQ ID NO.:43) | 5147 |
| Focus13 | -CCAAAAGGTCCATGAGCTCCATGGATTCCTCCCTGTTAA-GCACTTTATCCAT | (SEQ ID NO.:44) | 5196 |
| Focus14 | -CTAAAAGGTCCATGAGCTCCATGGATTCTTCCCTGTTTA-GAACTTTATCCAT | (SEQ ID NO.:45) | 5154 |
| Focus18 | -CCAAAAGGTCCATGAGCTCCATGGATTCTTCCCTGTTAA-GCACTTTATCCAT | (SEQ ID NO.:46) | 5149 |
| Focus19 | -CCAAAAGGTCCATGAGCTCCATGGATTCTTCCCTGTTAA-GCACTTTATCCAT | (SEQ ID NO.:47) | 5146 |
| Focus23 | -CTAAAAGGTCCATGAGCTCCATGGATTCTTCCCTGTTTA-GCACTTTATCCAT | (SEQ ID NO.:48) | 5153 |
| Focus29 | -CTAAAAGGTCCATGAGCTCCATGGATTCTTCCCTGTTAA-GCACTTTATCCAT | (SEQ ID NO.:49) | 5147 |
| Focus30 | -CCAAAAGGTCCATGAGCTCCATGGATTCTTCCCTGTTAA-GCACTTTATCCAT | (SEQ ID NO.:50) | 5147 |
| Focus31 | -CCAAAAGGTCCATGAGCTCCATGGATTCTTCCCTGTTAA-GCACTTTATCCAT | (SEQ ID NO.:51) | 5148 |
| Focus32 | -CTAAAAGGTCCATGAGCTCCATGGATTCTTCCCTGTTAA-GCACTTTATCCAT | (SEQ ID NO.:52) | 5147 |
| | -CCAAAAGGTCCATGAGCTCCATGGATTCTTCCCTGTTAA-GCACTTTATCCAT | (SEQ ID NO.:53) | 5148 |
| | -CTAAAAGGTCCATGAGCTCCATGGATTCTTCCCTGTTAA-GCACTTTATCCAT | (SEQ ID NO.:54) | 5111 |

FIG. 1AAA

METHODS AND COMPOSITIONS FOR DETECTING BK VIRUS

CROSS-REFERENCE

This application claims the benefit of U.S. Provisional Application No. 60/705,217, filed Aug. 2, 2005, which application is incorporated herein by reference in its entirety.

FIELD OF THE INVENTION

The invention relates to detection of BK viruses.

BACKGROUND OF THE INVENTION

Human polyomavirus type BK (BK virus) is a non-enveloped virus with a circular, double-stranded-DNA genome of about 5,300 bp. BK virus was first recognized as a member of the polyomavirus family in 1971, after isolation from the urine of a renal-transplant recipient. Subsequent studies documented a worldwide rate of seroprevalence in adults of more than 80 percent. Typically, primary infection with the BK virus occurs during childhood by the respiratory route, followed by latency of the virus in the urogenital tract. Asymptomatic reactivation and intermittent shedding of virus in the urine occur spontaneously in immunocompetent persons but are more frequent among those with altered cellular immunity, such as pregnant women, patients with cancer who are receiving chemotherapy, HIV-1 infected individuals and recipients of renal or other allografts. Overt clinical disease from BK virus infection is rare and is clearly linked to the degree of immunosuppression.

BK-virus associated nephropathy has become an increasingly recognized cause of renal dysfunction in renal transplant patients. According to retrospective studies, BK virus nephropathy develops in 1 to 5 percent of renal-transplant recipients, with loss of allograft function occurring in as many as 45 percent of the affected patients. Although BK virus-specific antiviral therapy is not available, in some cases, BK virus replication may be controlled by reducing the level of maintenance immunosuppression. Recent evidence suggests that detection of BK virus DNA closely follows the course of BK virus nephropathy and may serve as a noninvasive tool for diagnosis and monitoring. Therefore, quantification of BK virus load in renal transplant patients would be useful both for diagnosing BK virus nephropathy and for monitoring the response to therapy, i.e., reduction in immunosuppression. In addition, BK virus has been implicated in other diseases, such as prostate cancer.

Accordingly, there remains a need for the development of reliable diagnostic tests to detect BK virus with a sensitivity that allows detection of low titers of virus, as well as for detection of different BK virus genotypes. In addition, there remains a need for a reliable diagnostic test to distinguish between BK virus and other polyoma viruses, such as JC virus. Such assays are critical to prevent transmission of the virus through blood and plasma derivatives or by close personal contact. The present invention addresses these needs.

LITERATURE

Literature of interest includes:
U.S. Pat. Nos. 5,213,796; 6,605,602; WO 92/19774; Watzinger et al., Journal of Clinical Microbiology, 42(11):5189-5198 (2004); Anna Marta Degener, et al., J Medical Virology 58:413 (1999); and Stoner et al., American J of Kidney Diseases. 33:1102 (2002).

SUMMARY OF THE INVENTION

The invention provides methods and compositions for rapid, sensitive, and highly specific nucleic acid-based (e.g., DNA based) detection of a BK virus in a sample. In general, the methods involve detecting a target nucleic acid having a target sequence of conserved regions of BK viral genome. The invention also features compositions, including primers, probes, and kits, for use in the methods of the invention.

An advantage of the invention is that it provides for detection of BK virus while avoiding detection of viruses that are closely related genetically. Thus, the invention decreases the incidence of false positives.

Another advantage of the invention is that it decreases the incidence of false negative results that can result from failure to detect genetic variants of the BK virus (e.g., BK viruses of different genotype or strain).

Still another advantage is that the invention encompasses embodiments that require detection of only a relatively short target sequence. This can be particularly advantageous where the assay uses amplification-based technology, such as real-time PCR.

The present invention can be developed into assays or manufactured into kits to be use in reference laboratories or hospitals for the diagnostics of BK virus. The assay can also be utilized in the development and clinical trials of therapeutic drugs for treating diseases caused by BKV infection.

These and other advantages will be readily apparent to the ordinarily skilled artisan upon reading the present specification.

BRIEF DESCRIPTION OF THE DRAWINGS

Figure 1A:
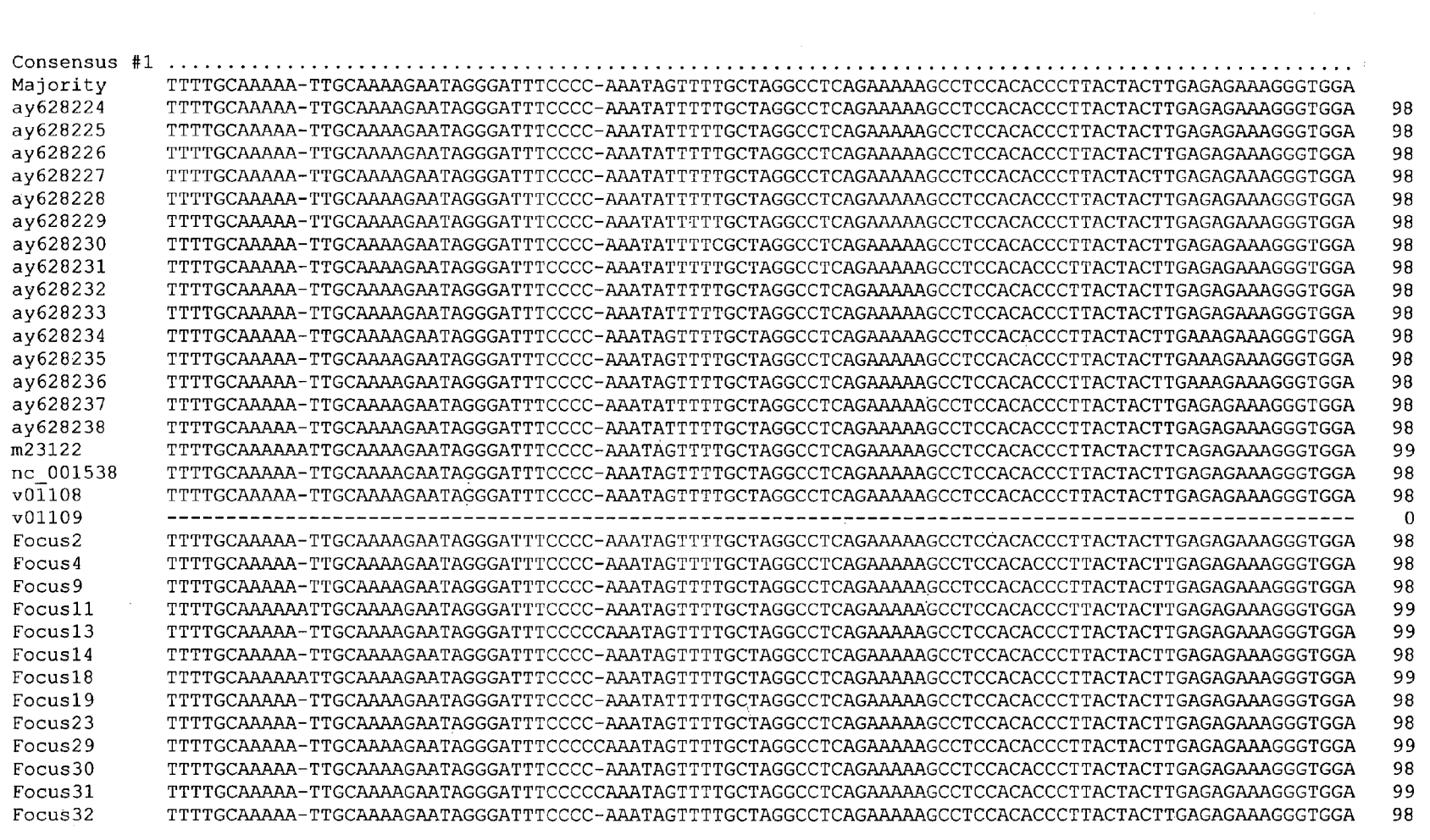
Figure 1B:
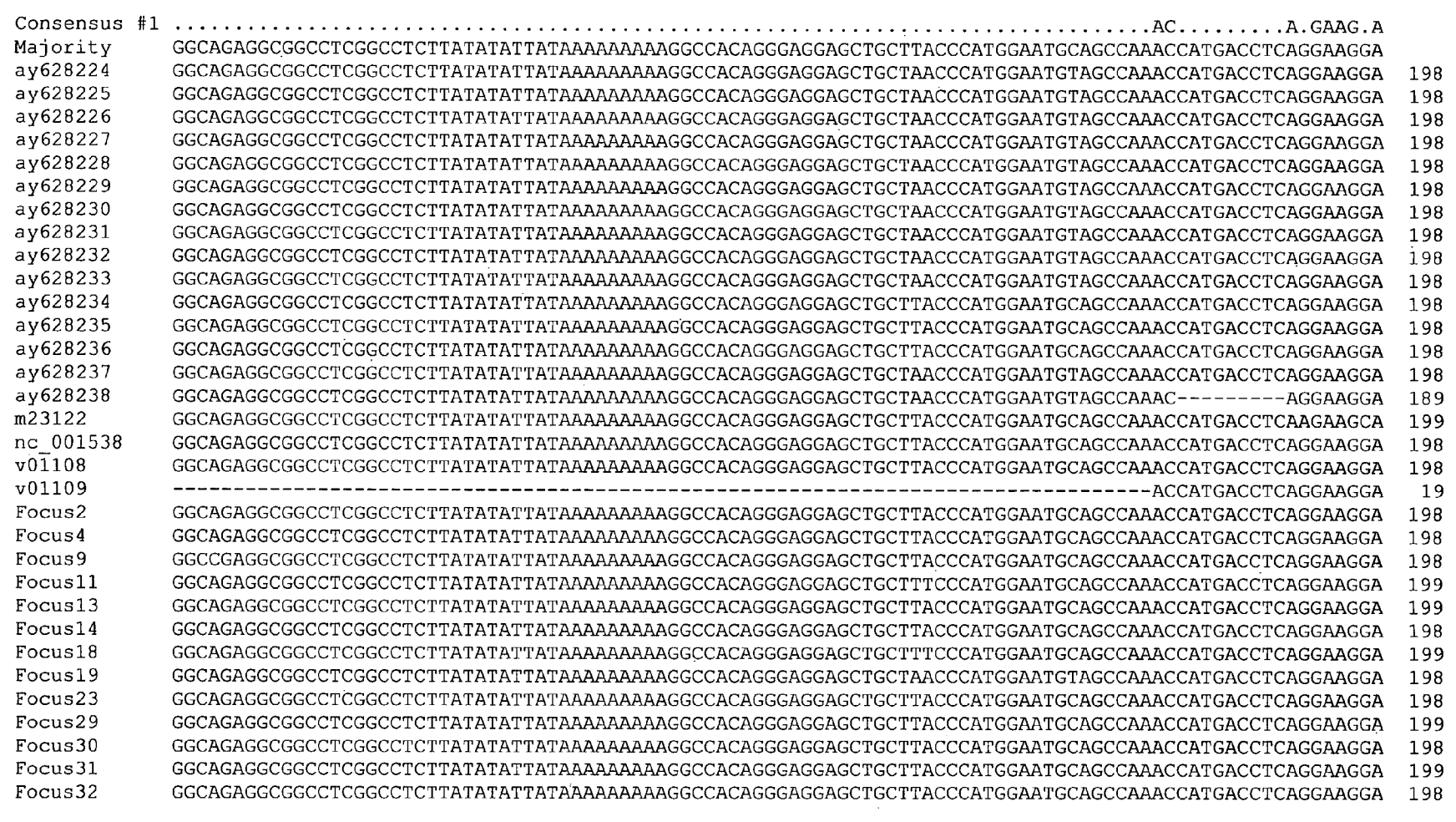
Figure 1C:
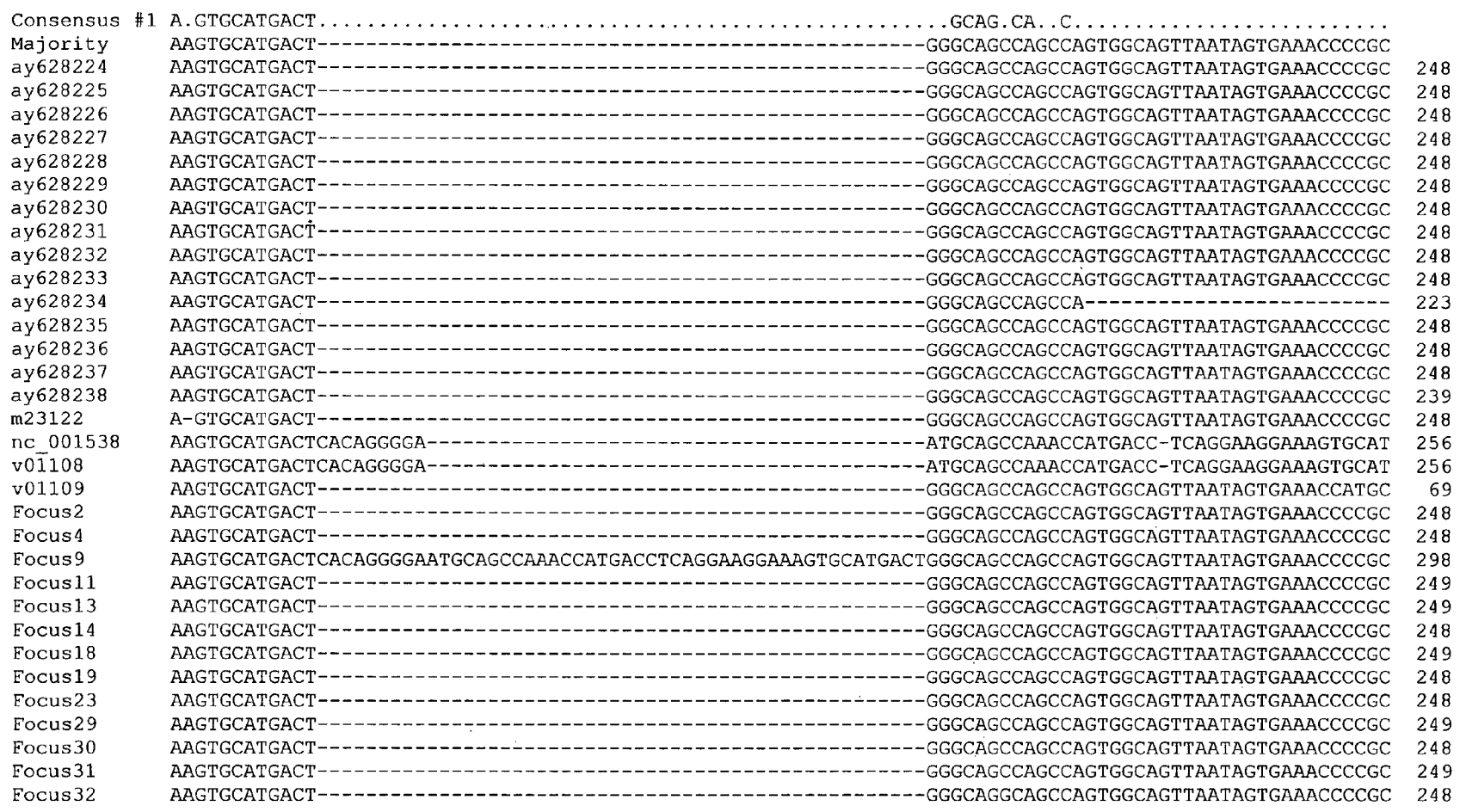
Figure 1D:
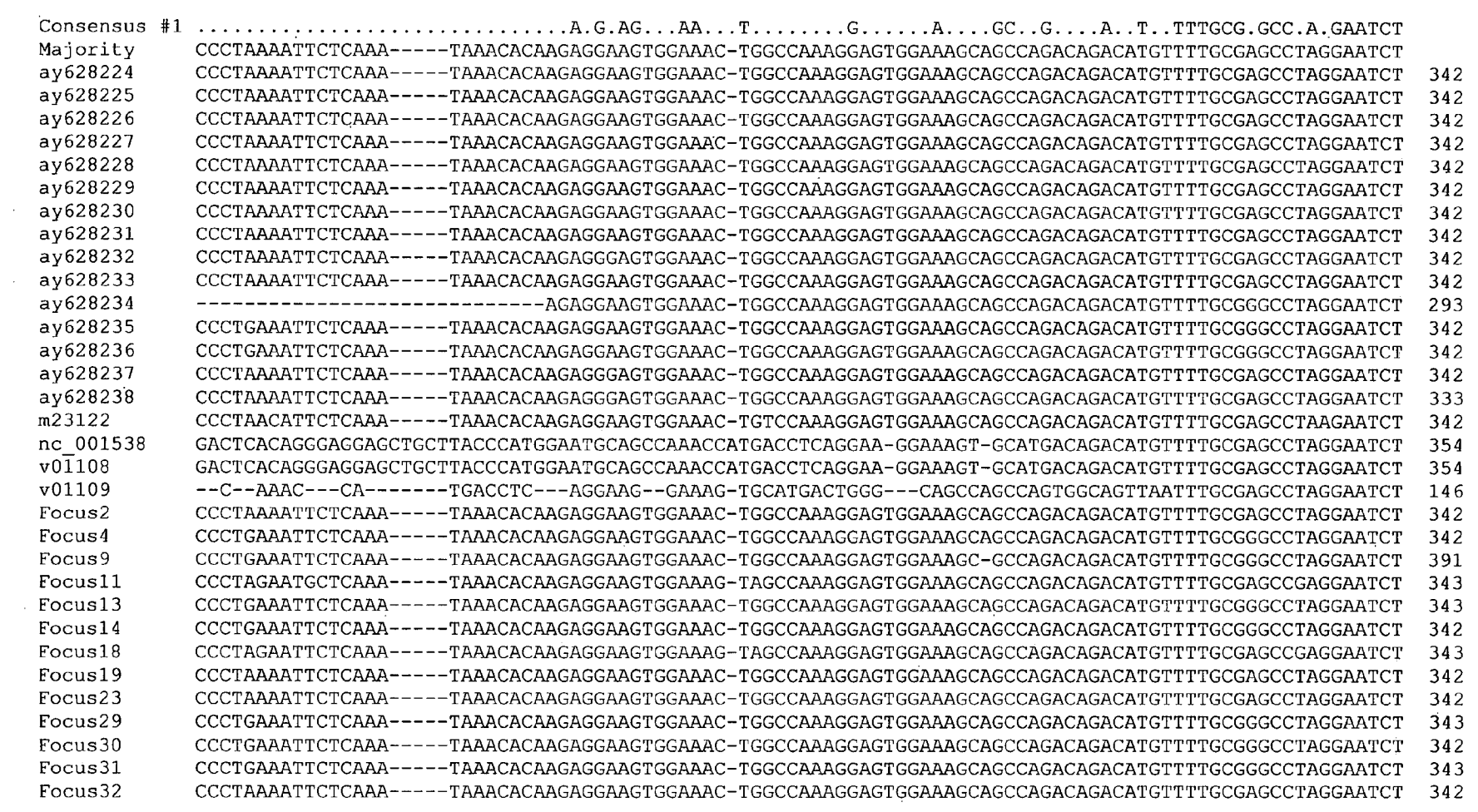
Figure 1E:
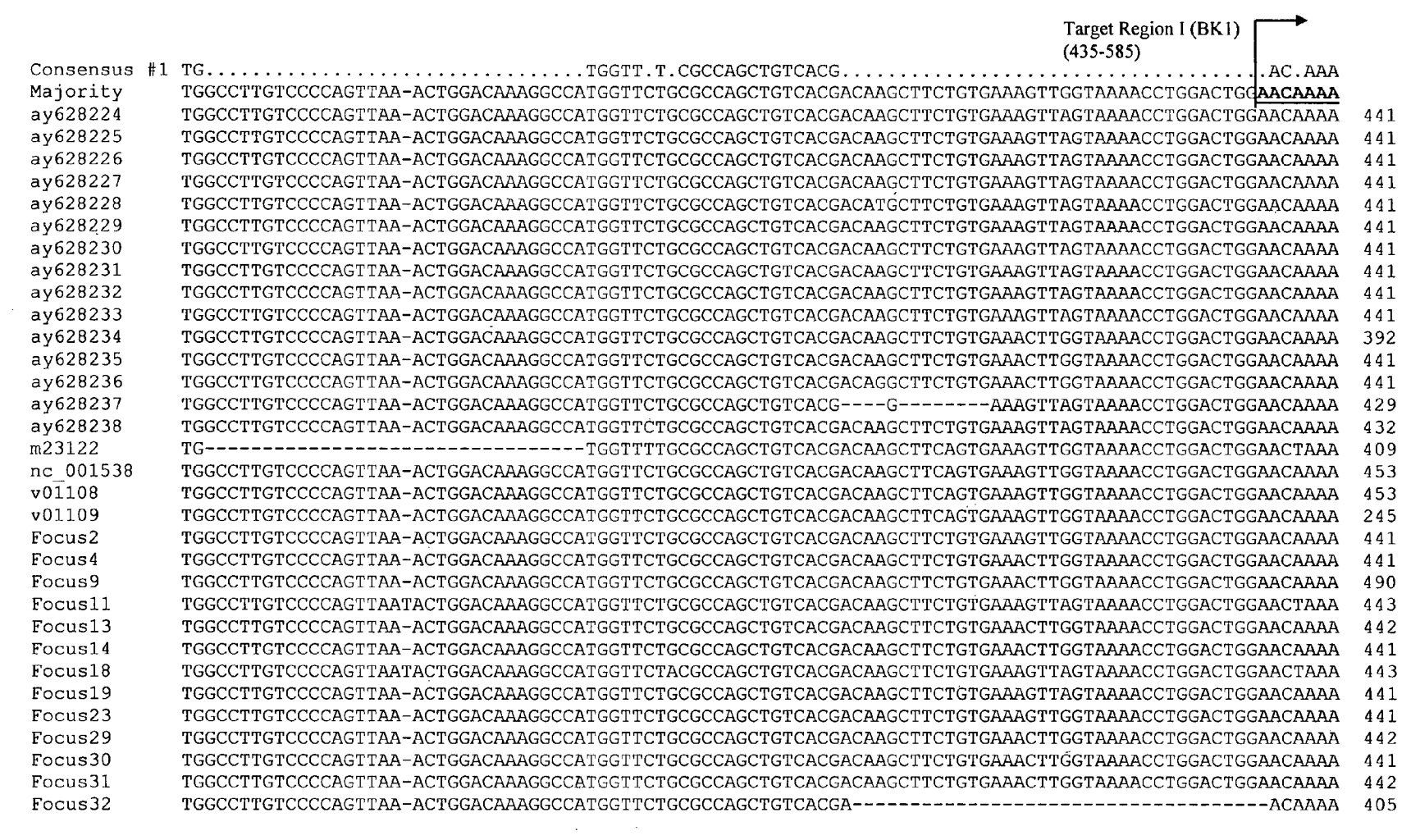
Figure 1F:
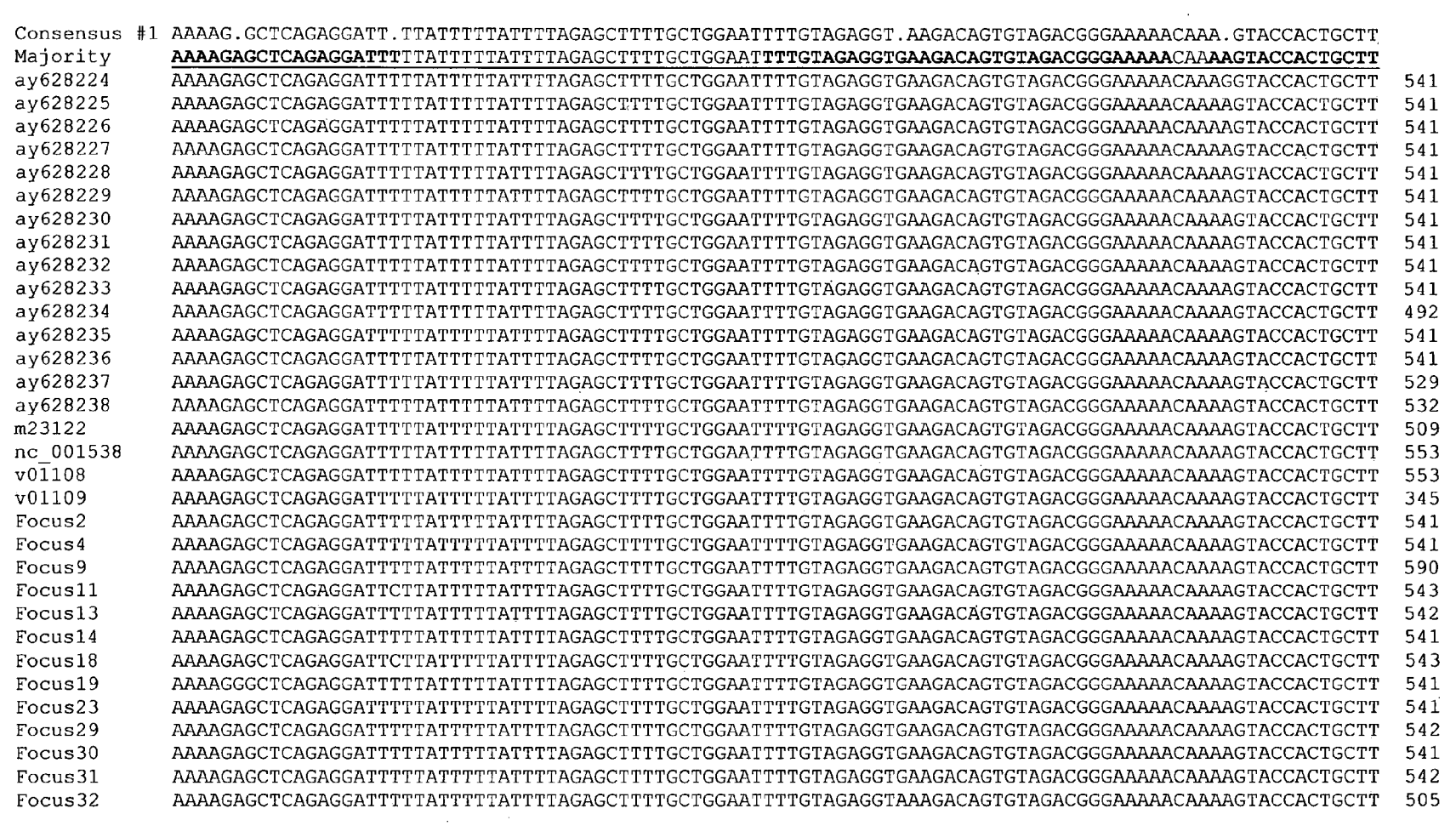
Figure 1G:
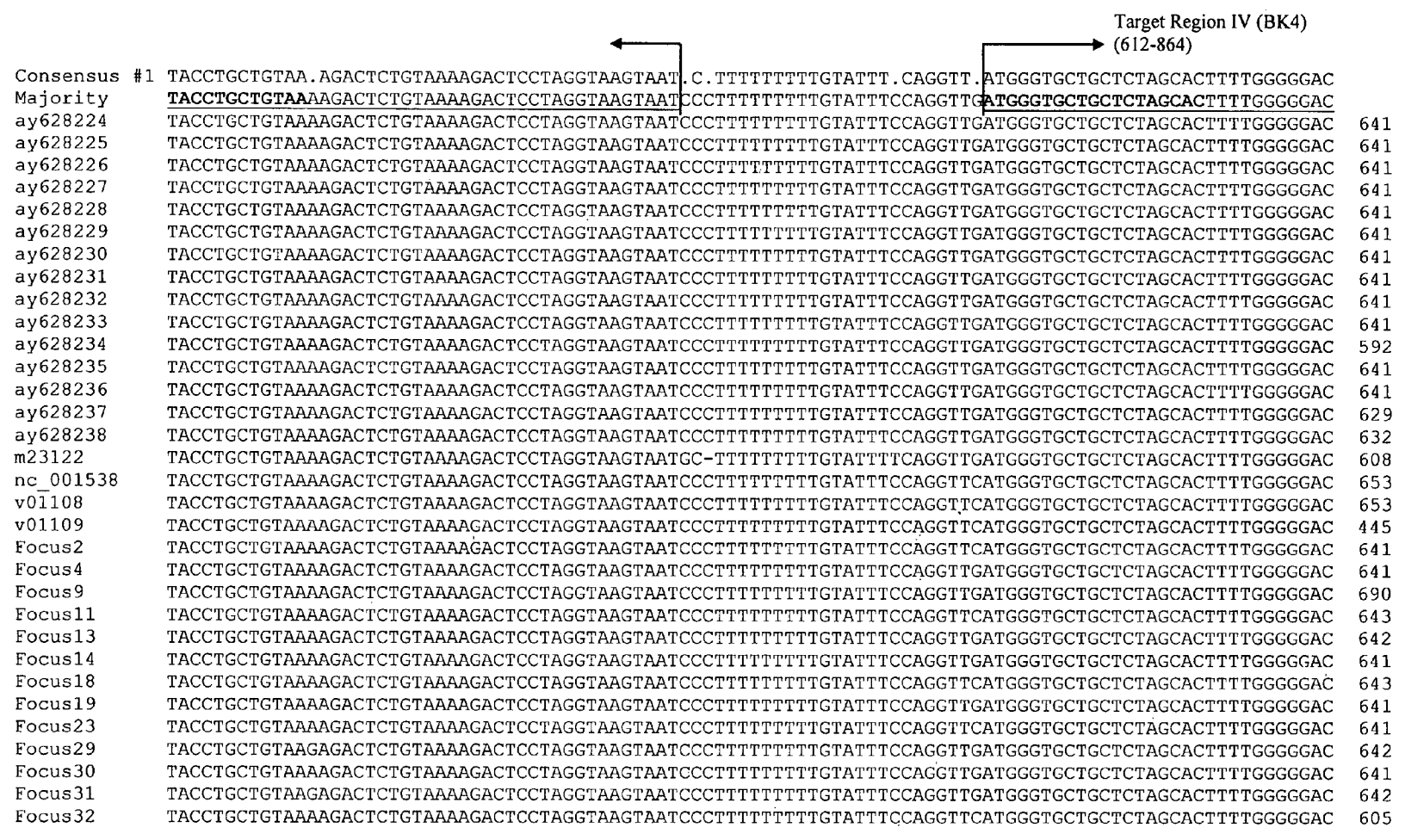
Figure 1H:
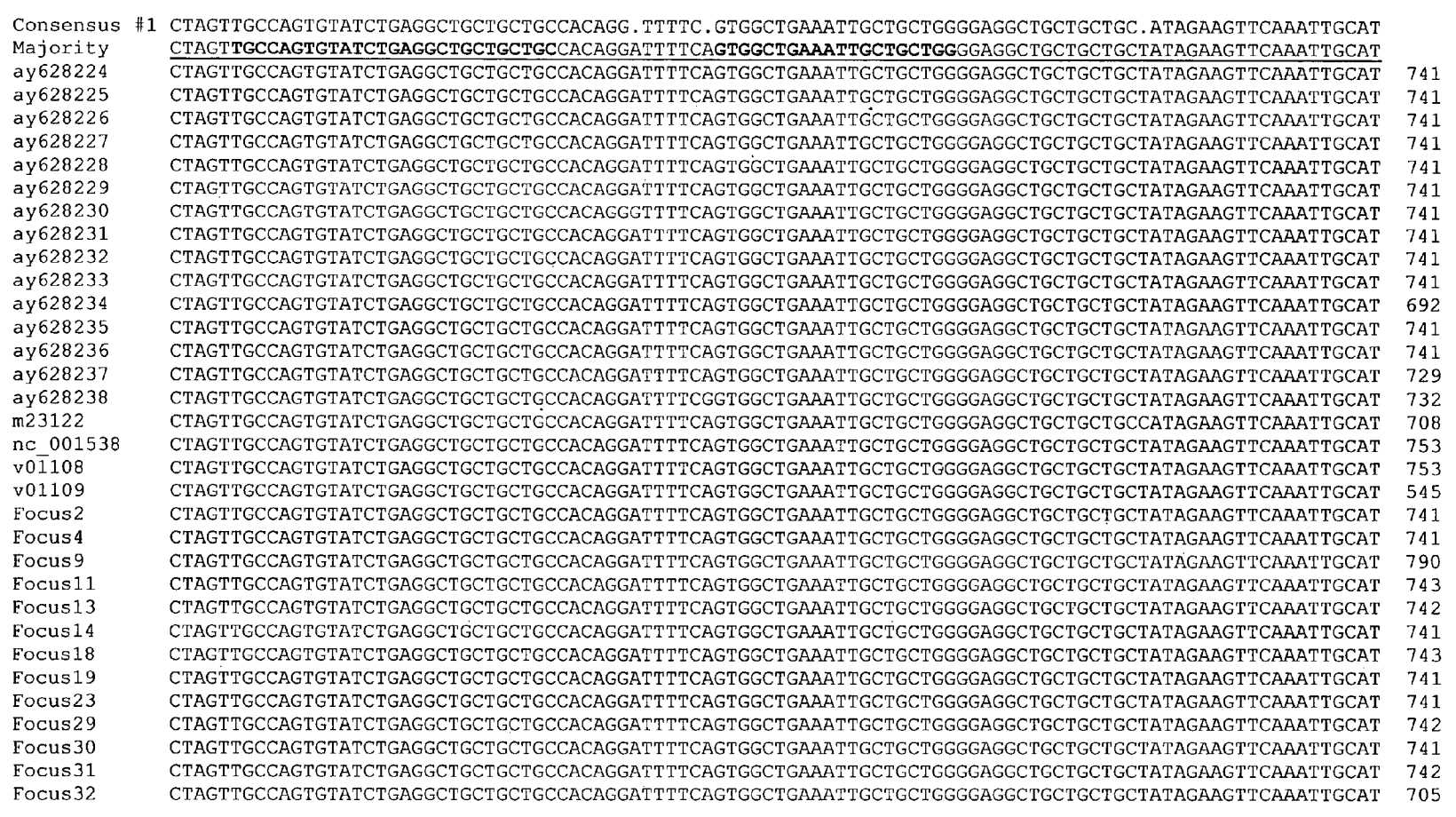
Figure 1I:
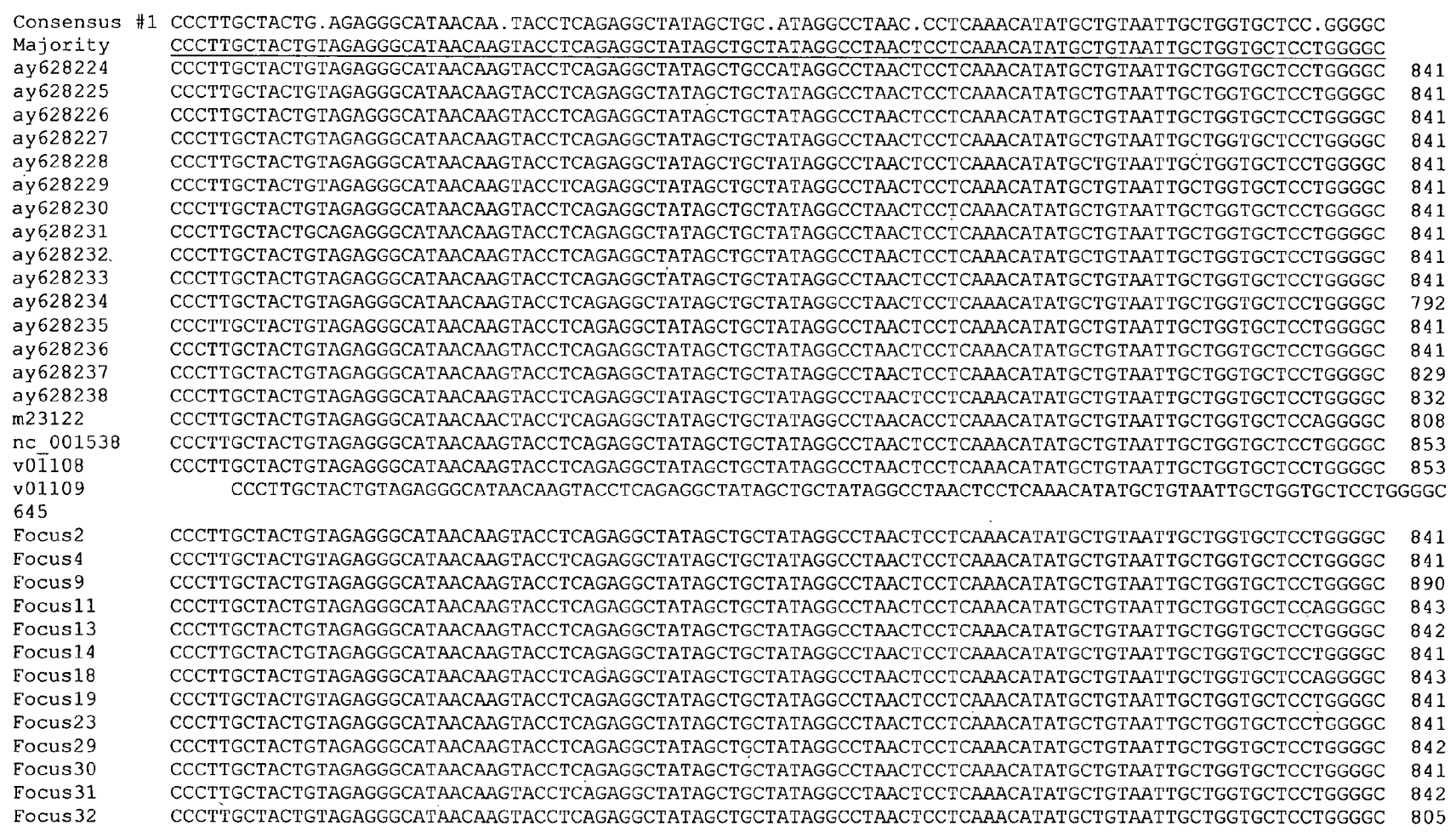
Figure 1J:
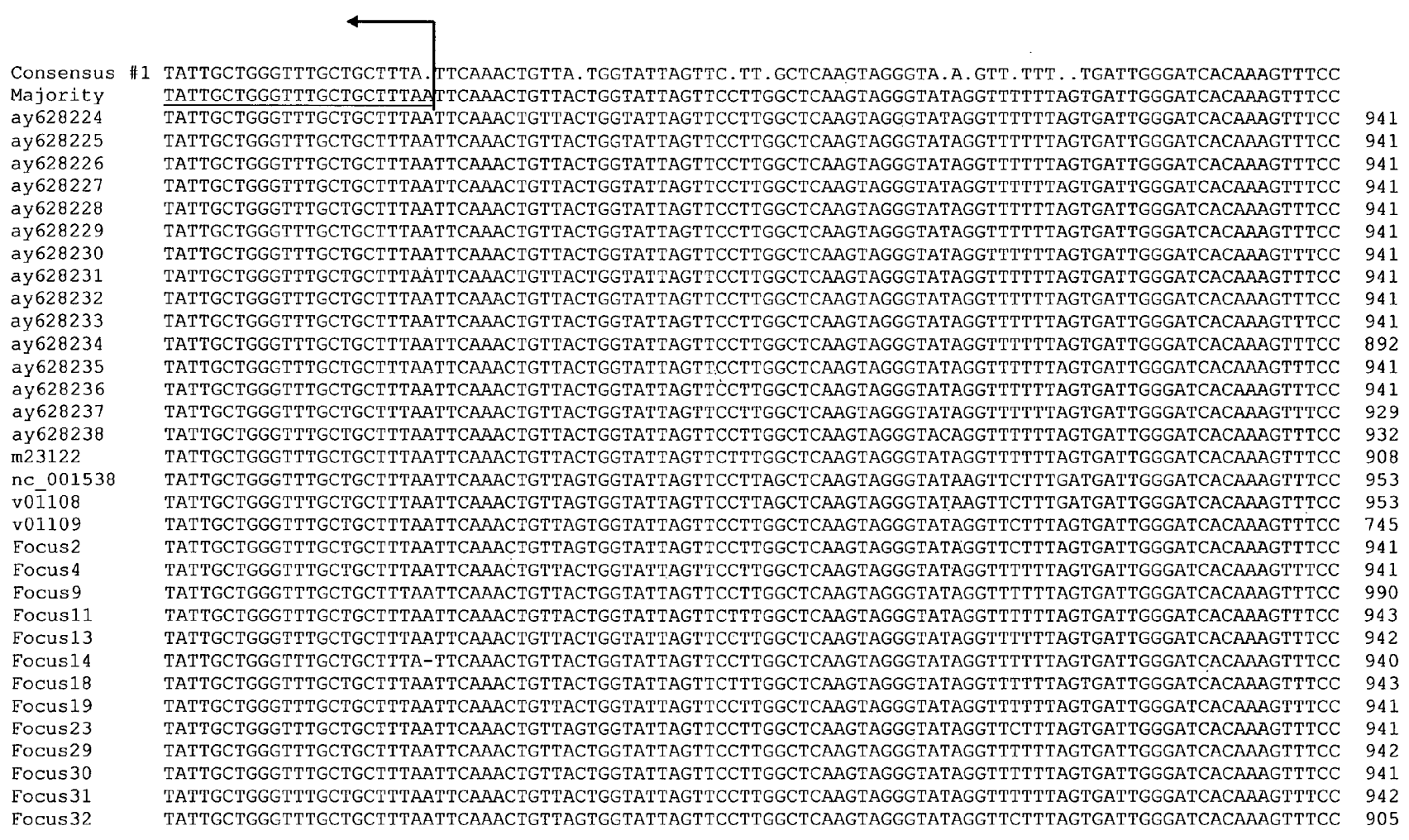
Figure 1K:
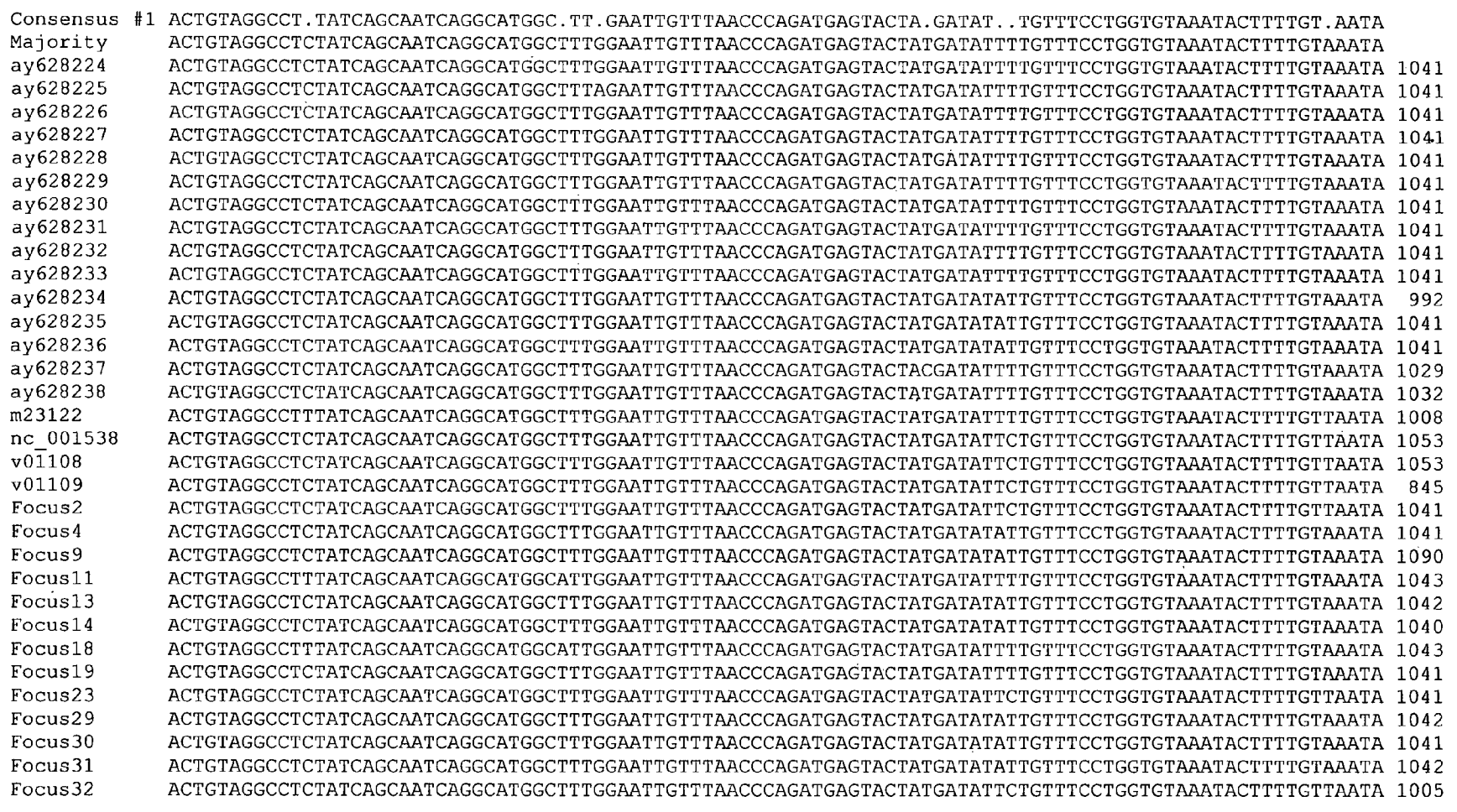
Figure 1L:
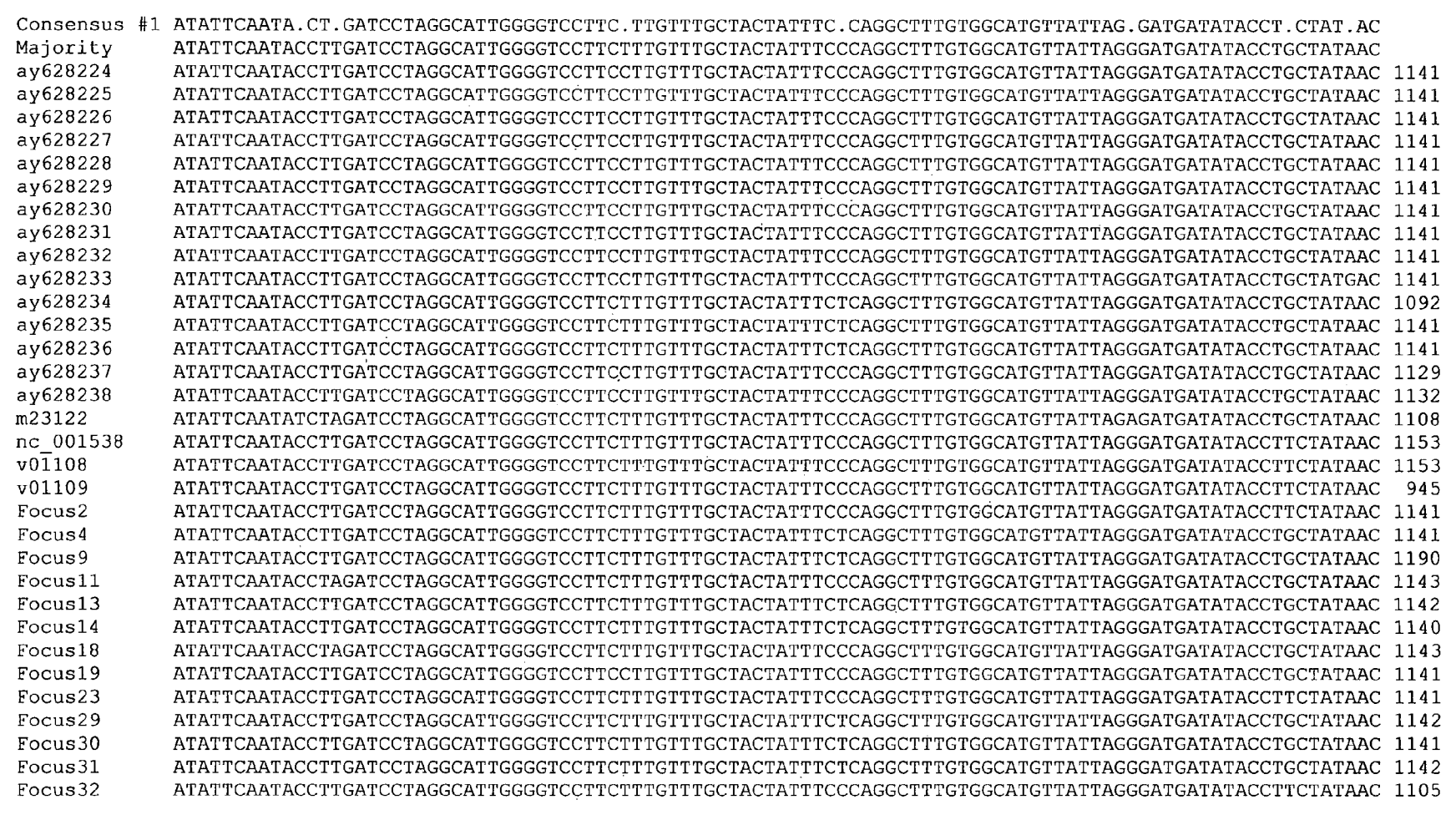
Figure 1N:
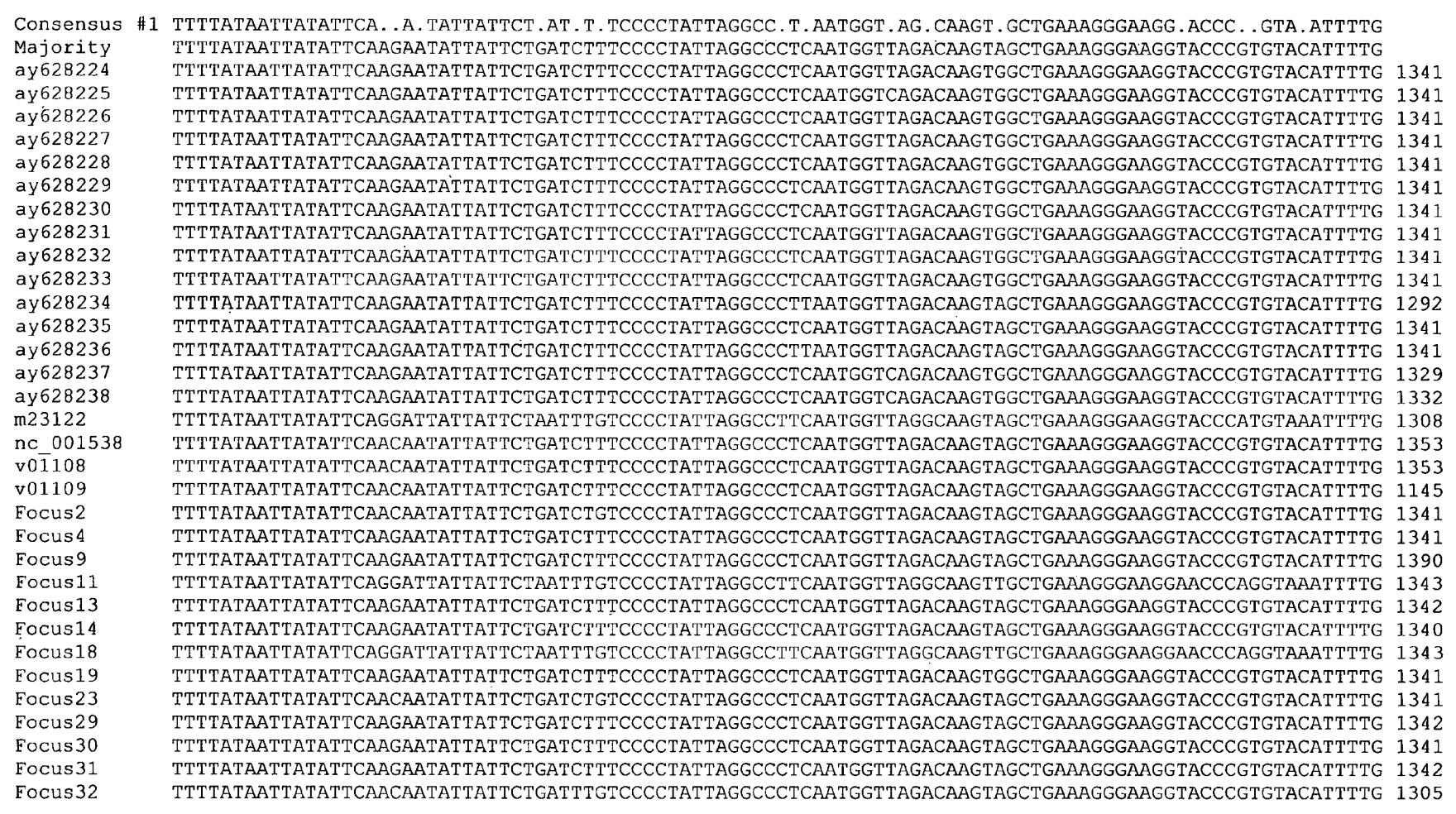
Figure 1P:
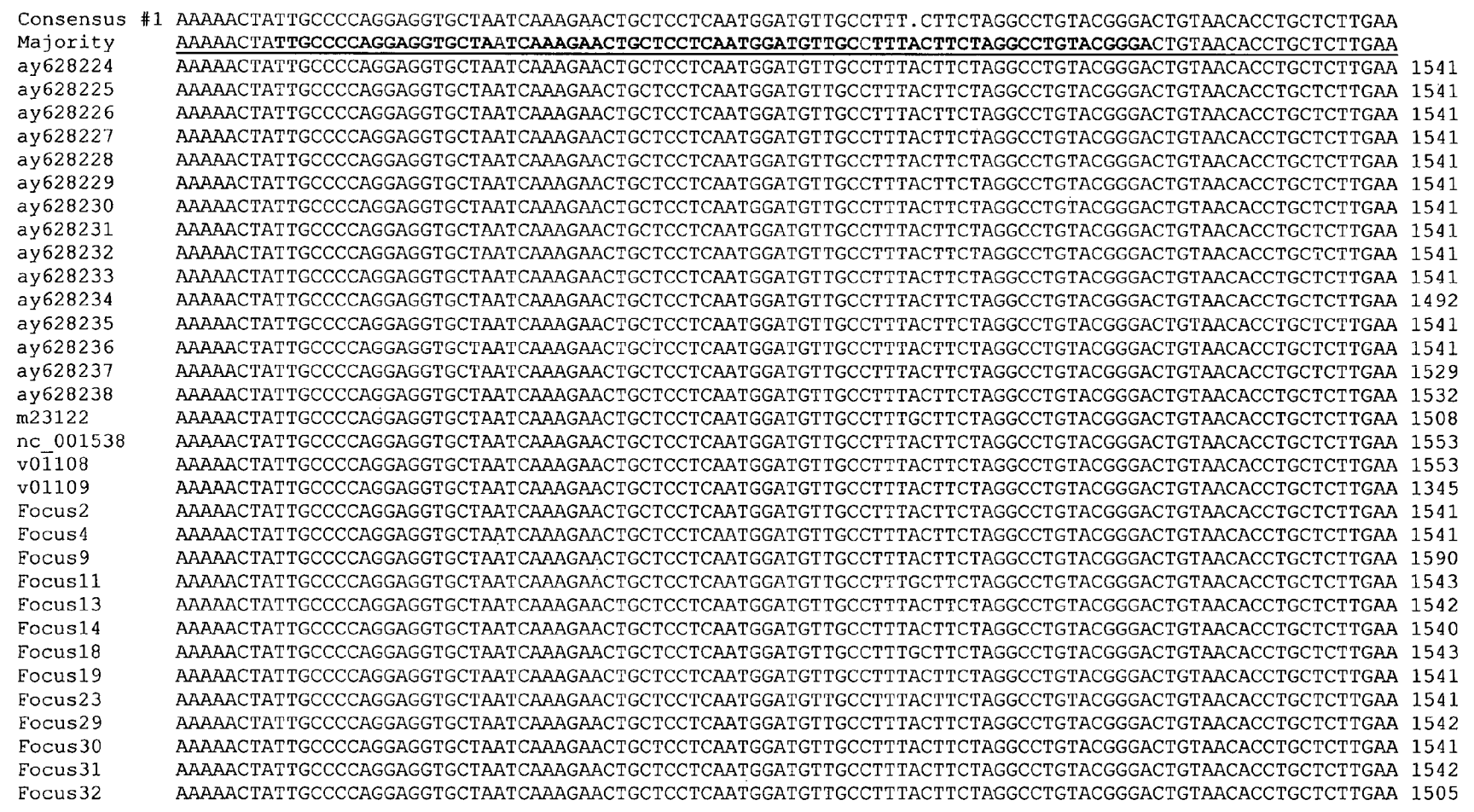
Figure 1Q:
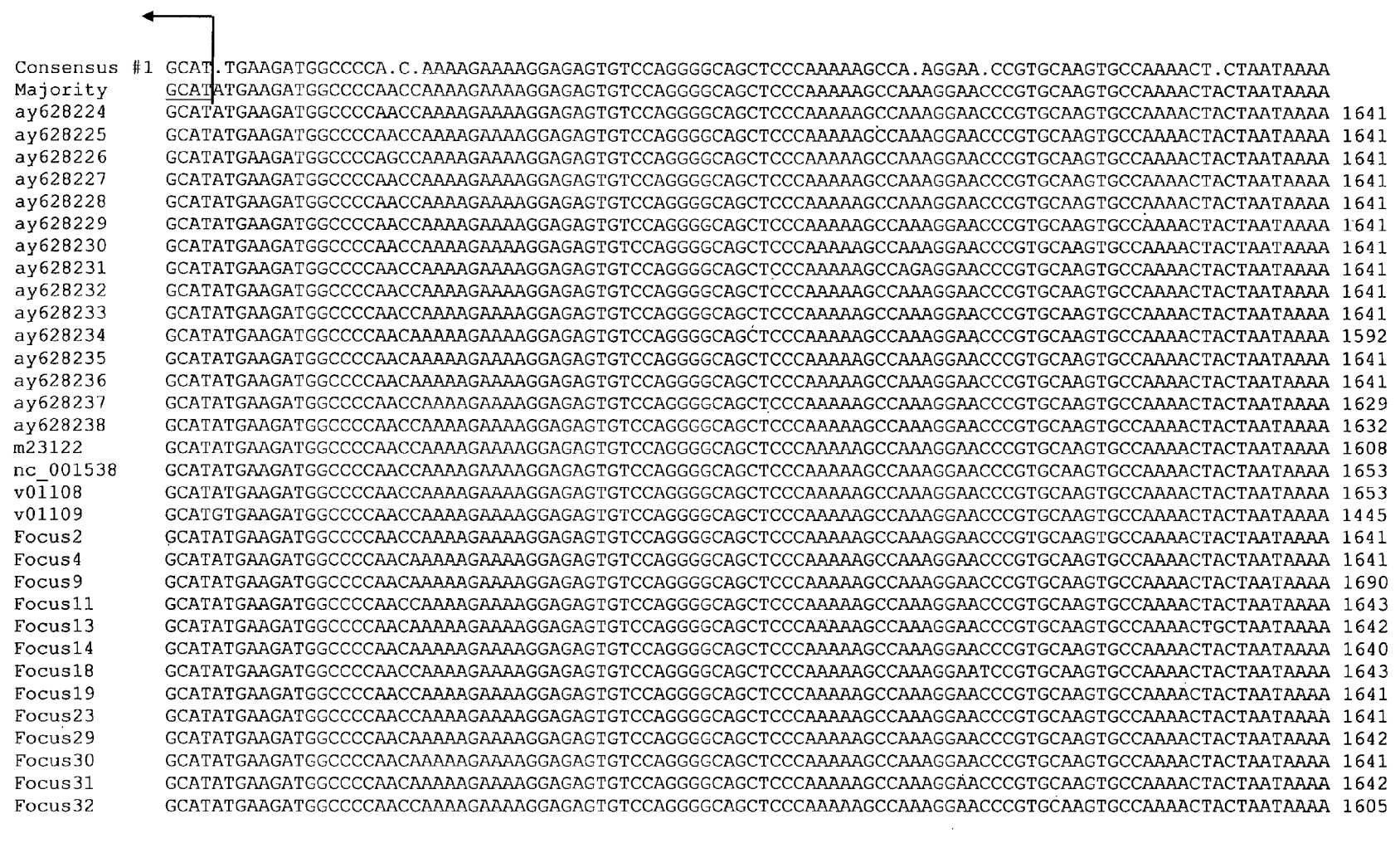
Figure 1R:
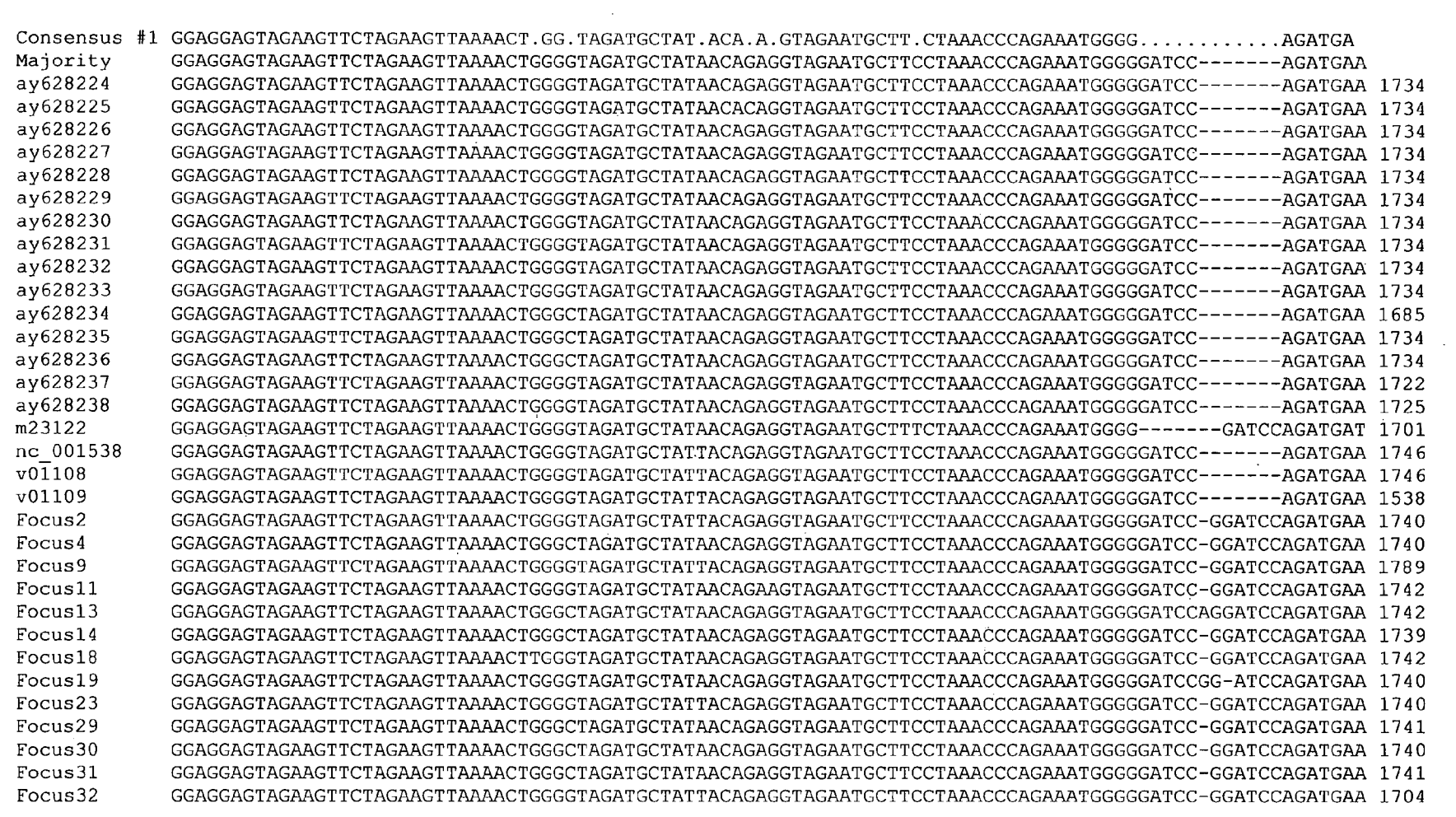
Figure 1S:
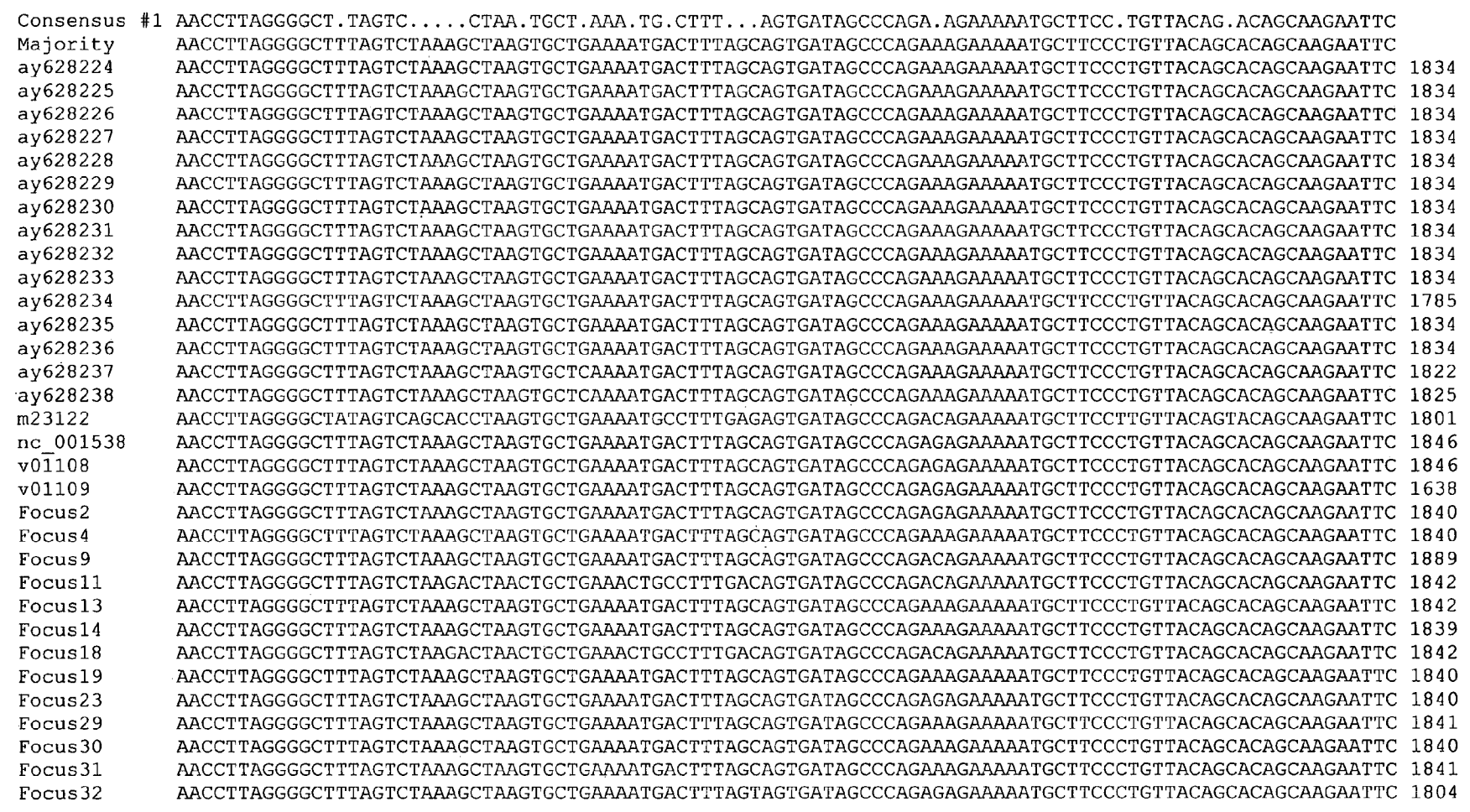
Figure 1V:
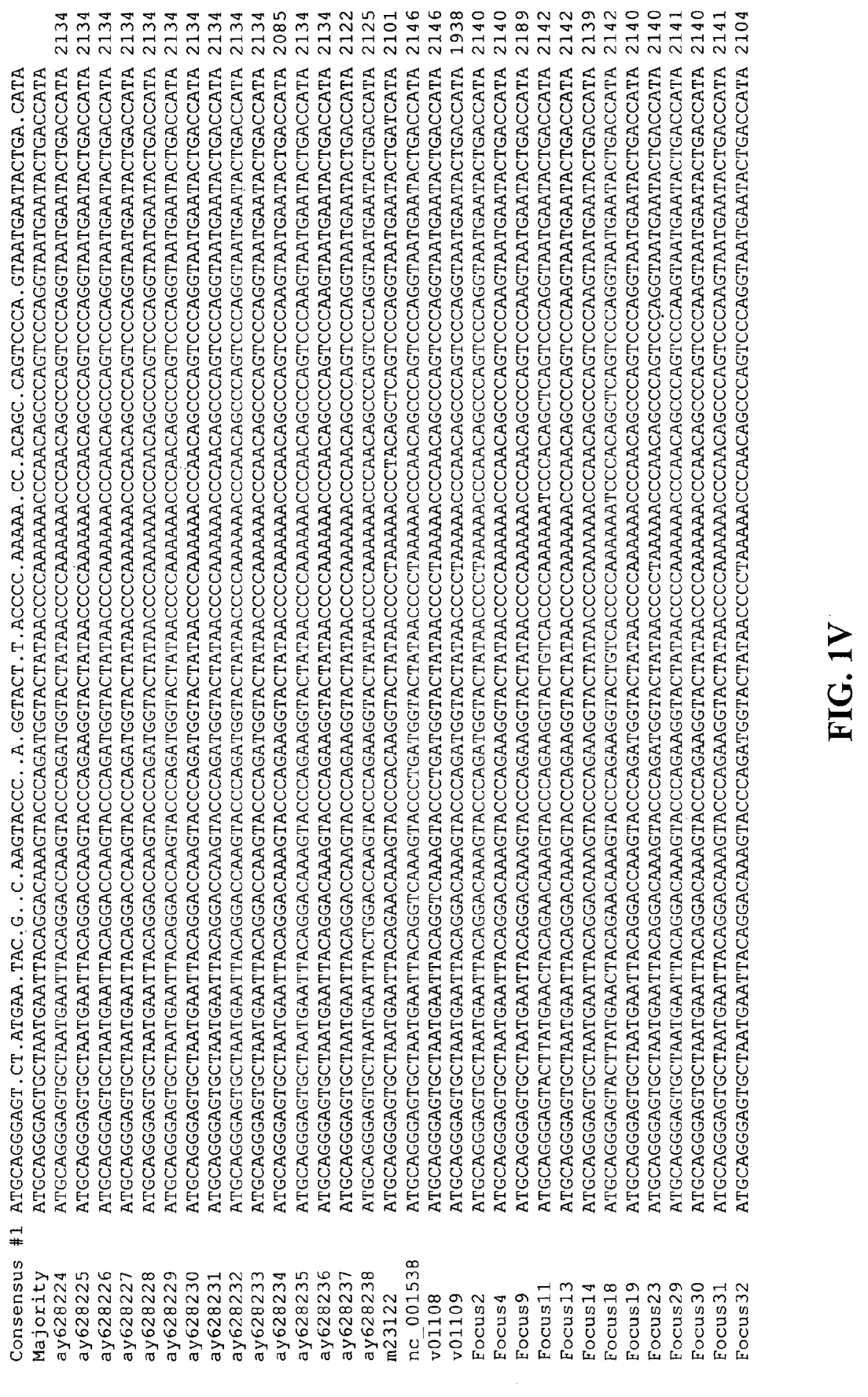
Figure 1W:
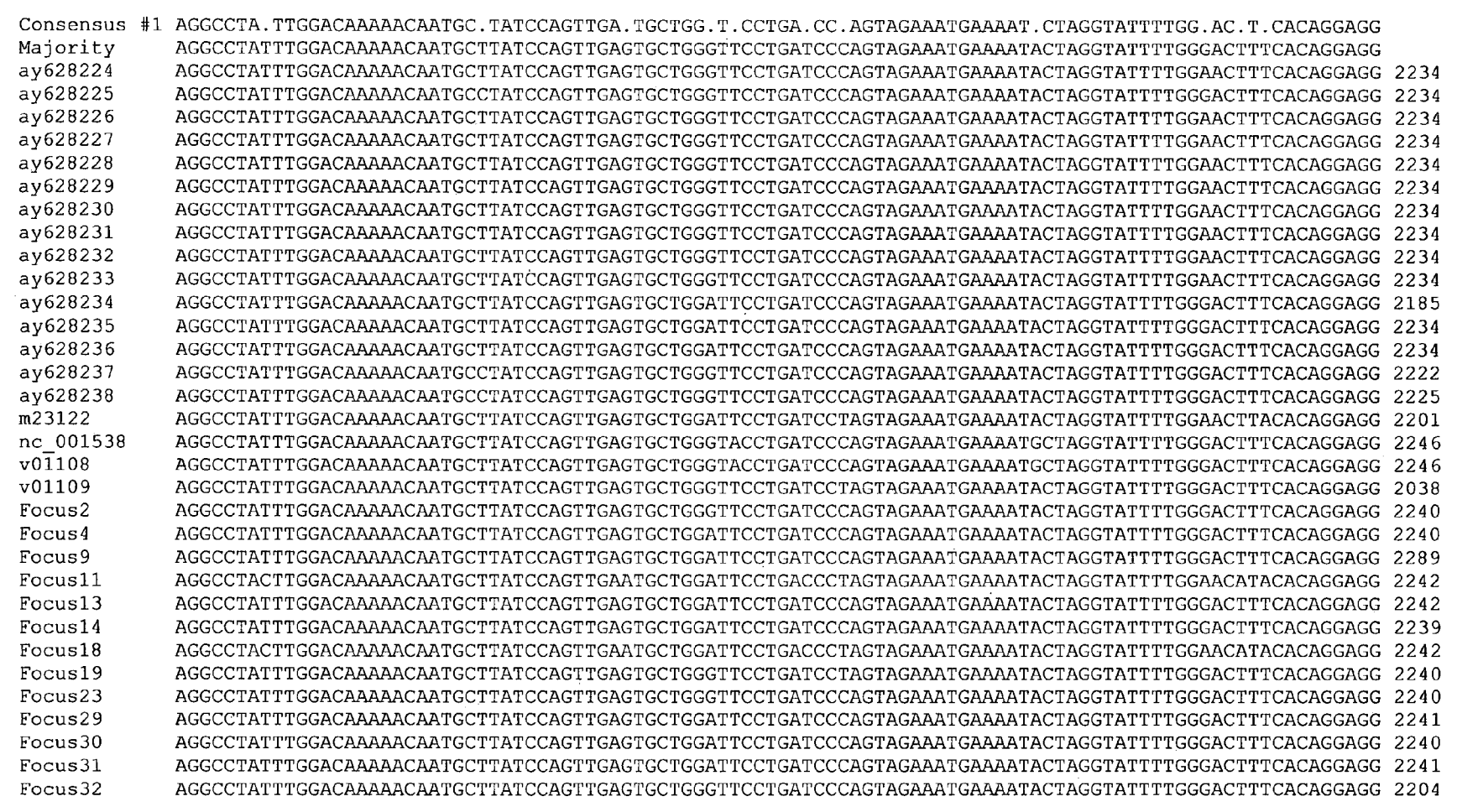
Figure 1X:
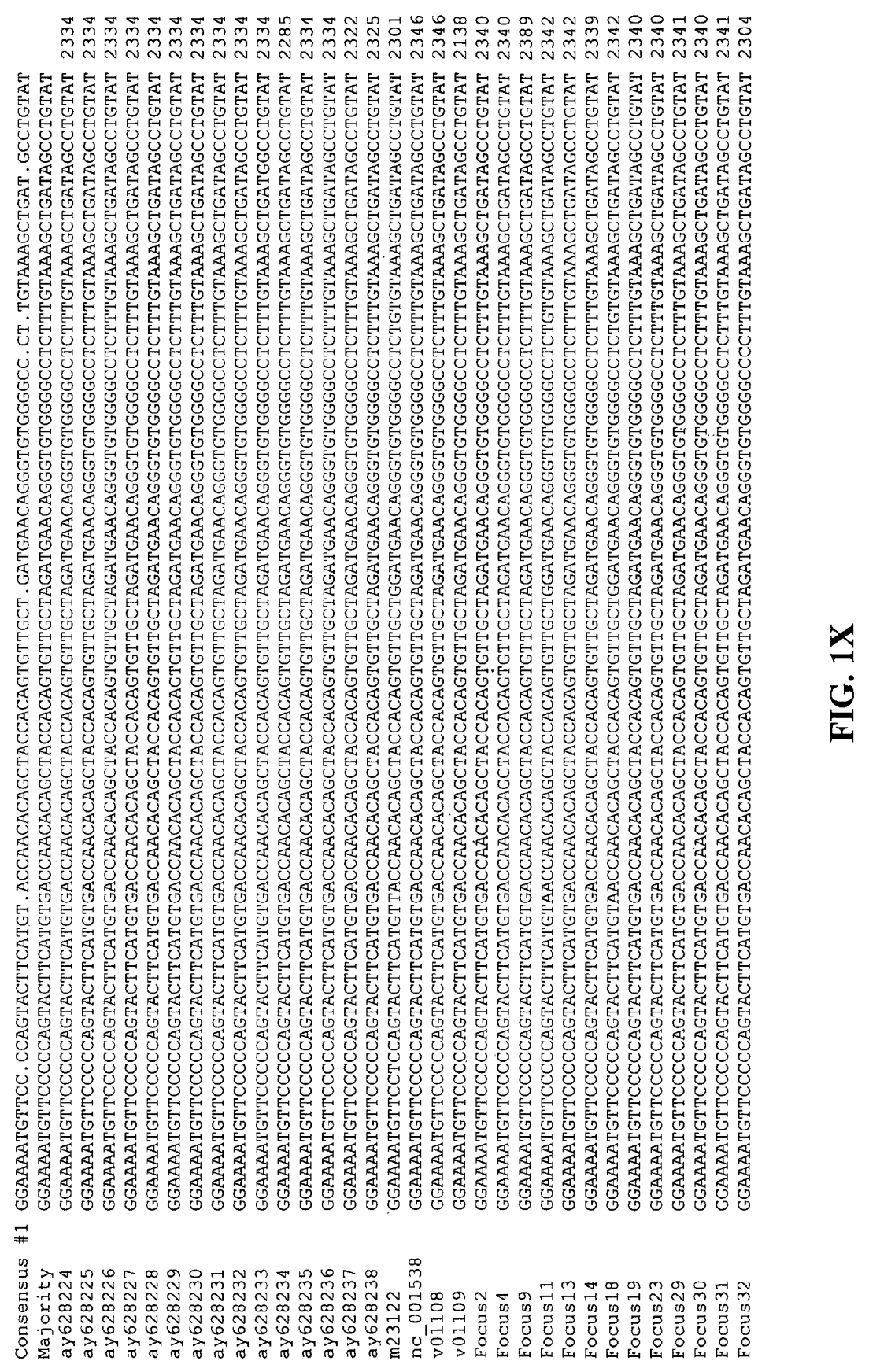
Figure 1Y:
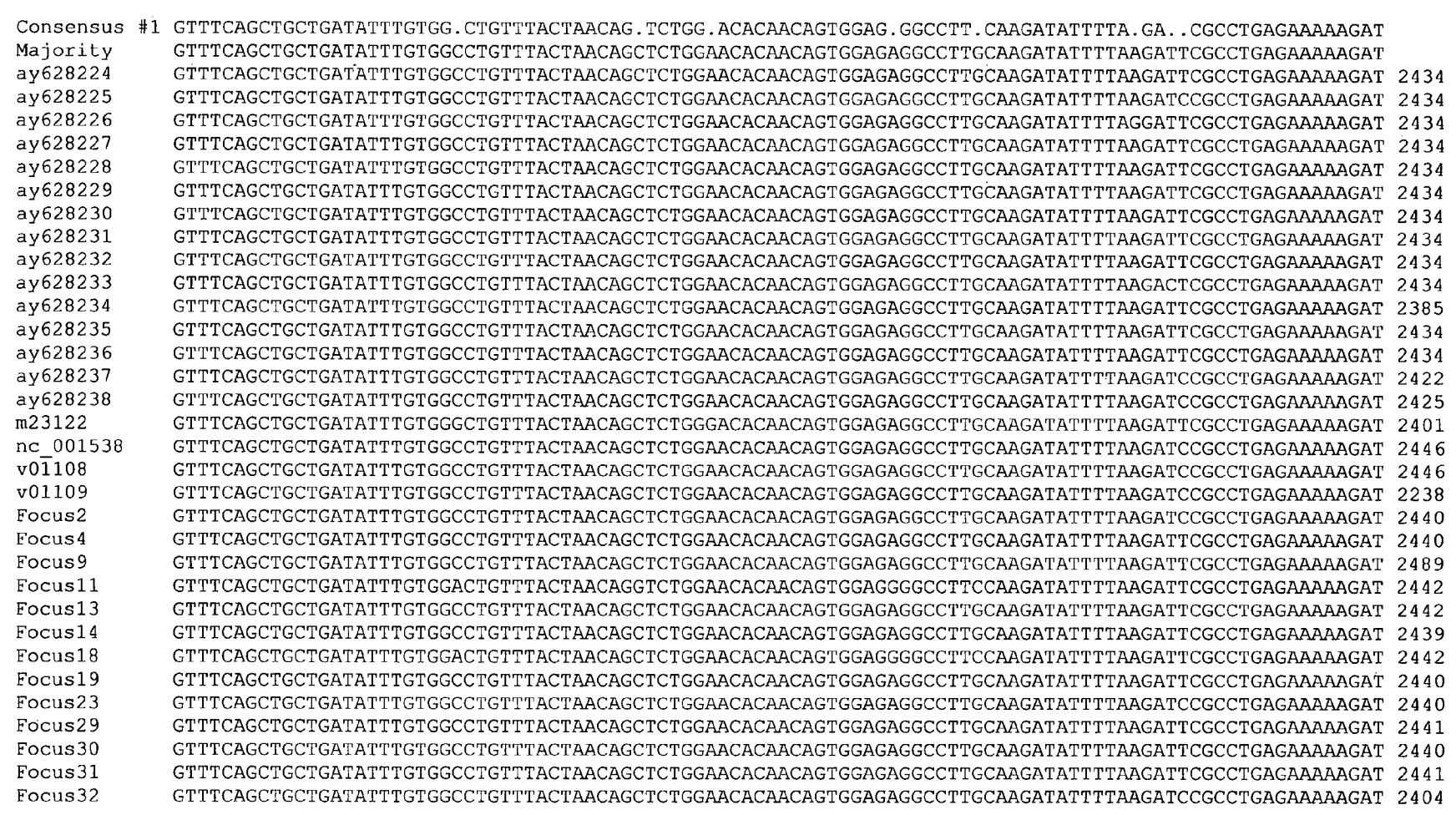
Figure 1Z:
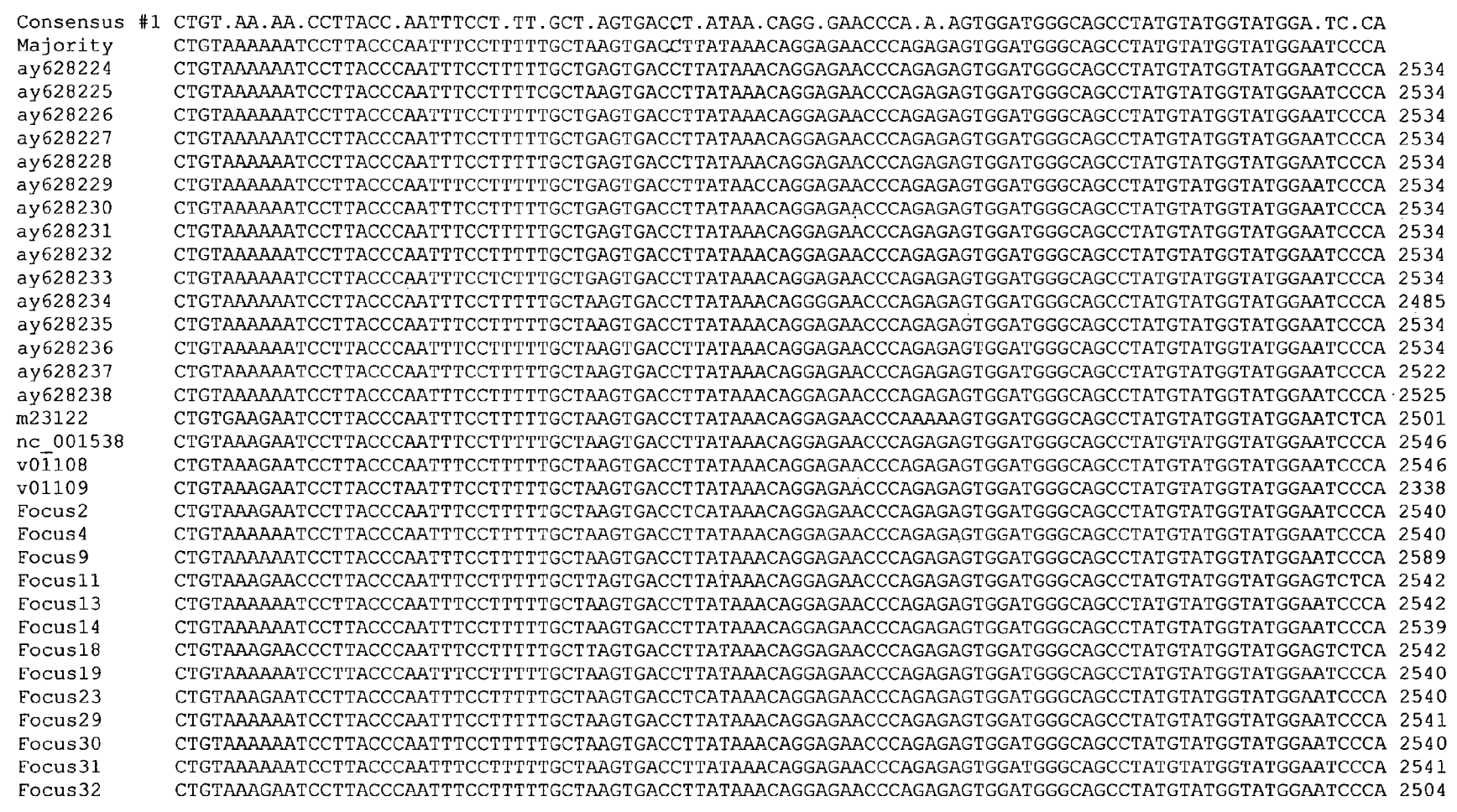

FIG. 1A-FIG. 1AAA shows the alignment of the nucleic acid sequences of the 32 BK virus genotypes. The target nucleic acid regions for detection of BK virus (BKV) according to the invention, which regions are designated as BK1, BK2, BK3, BK4, and BK5 (also referred to herein as Target Regions I, II, III, IV and V, respectively) as denoted in underline typeface and start and end arrows.

Figure 2:
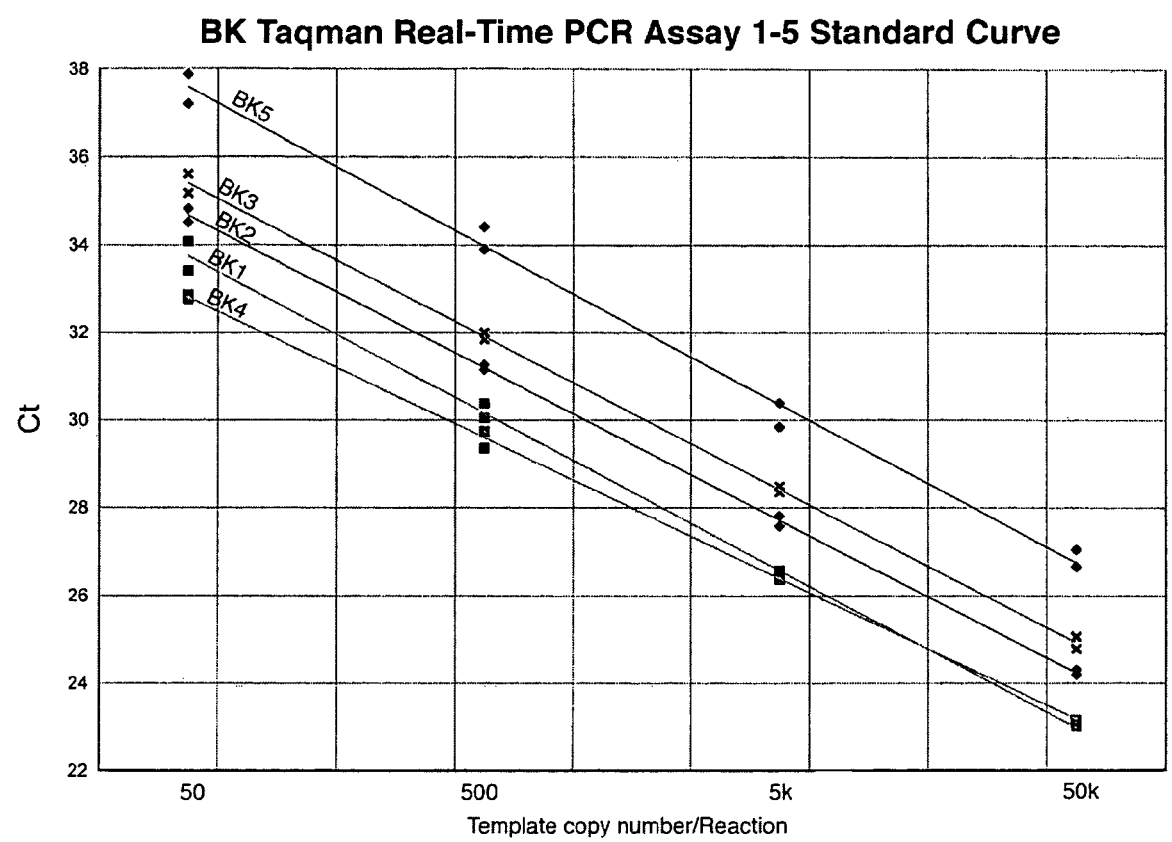

The numbering system on the right side of the figure represents the sequence numbering for each of the genotypes according to the respective GenBank Accession Numbers for each genotype or the numbering for a sequenced genome. All references to sequences numbering herein are based on the sequence numbering for GenBank Accession No. AY628224, unless stated otherwise. Exemplary primers and probes within the Target Regions I-V suitable for use in the methods of the invention are indicated by bold typeface. Probes suitable for use in the invention include any sequence positioned within the sequence of an amplification product that would be produced using two selected primers.

FIG. 2 is a graph showing the standard curves for the Taqman real-time assay for each of BK1, BK2, BK3, BK4, and BK5. Template concentrations ranged from 50 copies per reaction to 50,000 per reaction. All assays were performed in duplicate. For the BK1 assay: slope=−3.58, intercept=43.428, and $R^2$=0.997. For the BK2 assay: slope=−3.48, intercept=44.053, $R^2$=0.999. For the BK3 assay: slope=−3.49, intercept=44.819, $R^2$=0.999. For the BK4 assay: slope=−3.21, intercept=41.466, $R^2$=0.999. For the BK5 assay: slope=−3.61, intercept=47.324, $R^2$=0.994.

Definitions

The terms "BK virus" or "BKV" as used herein refer to a virus from the polyomavirus family that has been associated with nephropathy and renal dysfunction. BK virus is a small non-enveloped virus whose genome includes a circular, double-stranded-DNA molecule around 5,300 bp.

The terms "polynucleotide," "oligonucleotide," "nucleic acid" and "nucleic acid molecule" are used interchangeably herein to include a polymeric form of nucleotides, either ribonucleotides or deoxyribonucleotides. This term refers only to the primary structure of the molecule. Thus, the terms include triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA.

Unless specifically indicated otherwise, there is no intended distinction in length between the terms "polynucleotide," "oligonucleotide," "nucleic acid" and "nucleic acid molecule" and these terms will be used interchangeably. These terms refer only to the primary structure of the molecule. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. In particular, DNA is deoxyribonucleic acid.

Throughout the specification, abbreviations are used to refer to nucleotides (also referred to as bases), including abbreviations that refer to multiple nucleotides. As used herein, G=guanine, A=adenine, T=thymine, C=cytosine, and U=uracil. In addition, R=a purine nucleotide (A or G); Y=a pyrimidine nucleotide (A or T (U)); S=C or G; W=A or T (U); M=A or C; K=G or T (U); V=A, C or G; andN=an y nucleotide (A, T (U), C, or G). Nucleotides can be referred to throughout using lower or upper case letters. It is also understood that nucleotides sequences provided for DNA in the specification also represent nucleotide sequences for RNA, where T is substituted by U.

The terms "deoxyribonucleic acid" and "DNA" as used herein mean a polymer composed of deoxyribonucleotides.

The terms "ribonucleic acid" and "RNA" as used herein refer to a polymer composed of ribonucleotides. Where sequences of a nucleic acid are provided using nucleotides of a DNA sequence, it is understood that such sequences encompass complementary DNA sequences and further also encompass RNA sequences based on the given DNA sequence or its complement, where uracil (U) replaces thymine (T) in the DNA sequence or its complement.

Two nucleotide sequences are "complementary" to one another when those molecules share base pair organization homology. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G, and C of one sequence is then aligned with a T(U), A, C, and G, respectively, of the other sequence. RNA sequences can also include complementary G=U or U=G base pairs. Thus, two sequences need not have perfect homology to be "complementary" under the invention. Usually two sequences are sufficiently complementary when at least about 85% (preferably at least about 90%, and most preferably at least about 95%) of the nucleotides share base pair organization over a defined length of the molecule.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified. The term "isolated" encompasses instances in which the recited material is unaccompanied by at least some of the material with which it is normally associated in its natural state, preferably constituting at least about 0.5%, more preferably at least about 5% by weight of the total protein in a given sample. For example, the term "isolated" with respect to a polynucleotide generally refers to a nucleic acid molecule devoid, in whole or part, of sequences normally associated with it in nature; or a sequence, as it exists in nature, but having heterologous sequences in association therewith; or a molecule disassociated from the chromosome.

"Purified" as used herein means that the recited material comprises at least about 75% by weight of the total material, with at least about 80% being preferred, and at least about 96% being particularly preferred. As used herein, the term "substantially pure" refers to a compound that is removed from its natural environment and is at least 60% free, preferably 75% free, and most preferably 90% free from other components with which it is naturally associated.

A polynucleotide "derived from" or "specific for" a designated sequence, such as a target sequence of a target nucleic acid, refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding to, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived or specific for. Polynucleotides that are derived from" or "specific for" a designated sequence include polynucleotides that are in a sense or an antisense orientations relative to the original polynucleotide.

"Homology" refers to the percent similarity between two polynucleotide or two polypeptide moieties. Two DNA, or two polypeptide sequences are "substantially homologous" to each other when the sequences exhibit at least about 50%, preferably at least about 75%, more preferably at least about 80%, at least about 85%, preferably at least about 90%, and most preferably at least about 95% or at least about 98% sequence similarity over a defined length of the molecules. As used herein, substantially homologous also refers to sequences showing complete Identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100.

Readily available computer programs can be used to aid in the analysis of homology and identity, such as Lasergene from DNASTAR, Inc., and ALIGN, Dayhoff, M. O. in Atlas of Protein Sequence and Structure M. O. Dayhoff ed., 5 Suppl. 3:353-358, National biomedical Research Foundation, Washington, D.C., which adapts the local homology algorithm of Smith and Waterman Advances in Appl. Math. 2:482-489, 1981 for peptide analysis. Programs for determining nucleotide sequence homology are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent homology of a particular nucleotide sequence to a reference sequence can be determined using the homology algorithm of Smith and Waterman with a default scoring table and a gap penalty of six nucleotide positions.

Another method of establishing percent homology in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence homology." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=0; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the internet on a website sponsored by the National Center for Biotechnology Information (NCBI) and the National Library of Medicine (see the world wide website at ncbi.nlm.gov/cgi-bin/BLAST).

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

"Recombinant" as used herein to describe a nucleic acid molecule refers to a polynucleotide of genomic, cDNA, mammalian, bacterial, viral, semisynthetic, synthetic or other origin which, by virtue of its origin, manipulation, or both is not associated with all or a portion of the polynucleotide with which it is associated in nature. The term "recombinant" as used with respect to a protein or polypeptide means a polypeptide produced by expression of a recombinant polynucleotide.

A "control element" refers to a polynucleotide sequence which aids in the transcription and/or translation of a nucleotide sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for or facilitate the transcription and translation of a coding sequence in a host cell.

A "DNA-dependent DNA polymerase" is an enzyme that synthesizes a complementary DNA copy from a DNA template. Examples include DNA polymerase I from E. coli and bacteriophage T7 DNA polymerase. All known DNA-dependent DNA polymerases require a complementary primer to initiate synthesis. Under suitable conditions, a DNA-dependent DNA polymerase may synthesize a complementary DNA copy from an RNA template.

As used herein, the term "target nucleic acid region" or "target nucleic acid" or "target molecules" refers to a nucleic acid molecule with a "target sequence" to be detected (e.g., by amplification). The target nucleic acid may be either single-stranded or double-stranded and may or may not include other sequences besides the target sequence (e.g., the target nucleic acid may or may not include nucleic acid sequences upstream or 5' flanking sequence, may or may not include downstream or 3' flanking sequence, and in some embodiments may not include either upstream (5') or downstream (3') nucleic acid sequence relative to the target sequence. Where detection is by amplification, these other sequences in addition to the target sequence may or may not be amplified with the target sequence.

The term "target sequence" or "target nucleic acid sequence" refers to the particular nucleotide sequence of the target nucleic acid to be detected (e.g., through amplification). The target sequence may include a probe-hybridizing region contained within the target molecule with which a probe will form a stable hybrid under desired conditions. The "target sequence" may also include the complexing sequences to which the oligonucleotide primers complex and be extended using the target sequence as a template. Where the target nucleic acid is single-stranded, the term "target sequence" also refers to the sequence complementary to the "target sequence" as present in the target nucleic acid. If the "target nucleic acid" is originally double-stranded, the term "target sequence" refers to both the plus (+) and minus (−) strands. The invention also contemplates target regions having the full-length of the sequences provided herein, as well as fragments or subsequences of such target regions, and complementary sequences thereof. The terms "fragment" and "subsequence" are used interchangeably in this context. Moreover, where sequences of a "target sequence" are provided herein, it is understood that the sequence may be either DNA or RNA. Thus where a DNA sequence is provided, the RNA sequence is also contemplated and is readily provided by substituting "T" of the DNA sequence with "U" to provide the RNA sequence.

The term "primer" or "oligonucleotide primer" as used herein, refers to an oligonucleotide which acts to initiate synthesis of a complementary nucleic acid strand when placed under conditions in which synthesis of a primer extension product is induced, e.g., in the presence of nucleotides and a polymerization-inducing agent such as a DNA or RNA polymerase and at suitable temperature, pH, metal concentration, and salt concentration. Primers are generally of a length compatible with its use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. If double-stranded, the primer is usually first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

As used herein, the term "probe" or "oligonucleotide probe", used interchangeable herein, refers to a structure comprised of a polynucleotide, as defined above, that contains a nucleic acid sequence complementary to a nucleic acid sequence present in the target nucleic acid analyte (e.g., a nucleic acid amplification product). The polynucleotide regions of probes may be composed of DNA, and/or RNA, and/or synthetic nucleotide analogs. Probes are generally of a length compatible with its use in specific detection of all or a portion of a target sequence of a target nucleic acid, and are usually are in the range of between 8 to 100 nucleotides in length, such as 8 to 75, 10 to 74, 12 to 72, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. The typical probe is in the range of between 10-50 nucleotides long, such as 15-45, 18-40, 20-30, 21-28, 22-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Probes contemplated herein include probes that include a detectable label. For example, when an "oligonucleotide probe" is to be used in a 5' nuclease assay, such as the TaqMan™ assay, the probe includes at least one fluorescer and at least one quencher which is digested by the 5' endonuclease activity of a polymerase used in the reaction in order to detect any amplified target oligonucleotide sequences. In this context, the oligonucleotide probe will have a sufficient number of phosphodiester linkages adjacent to its 5' end so that the 5' to 3' nuclease activity employed can efficiently degrade the bound probe to separate the fluorescers and quenchers. When an oligonucleotide probe is used in the TMA technique, it will be suitably labeled, as described below.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens) and the like. The term "fluorescer" refers to a substance or a portion thereof which is capable of exhibiting fluorescence in the detectable range.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

The term "stringent conditions" refers to conditions under which a primer will hybridize preferentially to, or specifically bind to, its complementary binding partner, and to a lesser extent to, or not at all to, other sequences. Put another way, the term "stringent hybridization conditions" as used herein refers to conditions that are compatible to produce duplexes on an array surface between complementary binding members, e.g., between probes and complementary targets in a sample, e.g., duplexes of nucleic acid probes, such as DNA probes, and their corresponding nucleic acid targets that are present in the sample, e.g., their corresponding MRNA analytes present in the sample.

As used herein, the term "binding pair" refers to first and second molecules that specifically bind to each other, such as complementary polynucleotide pairs capable of forming nucleic acid duplexes. "Specific binding" of the first member of the binding pair to the second member of the binding pair in a sample is evidenced by the binding of the first member to the second member, or vice versa, with greater affinity and specificity than to other components in the sample. The binding between the members of the binding pair is typically noncovalent.

By "selectively bind" is meant that the molecule binds preferentially to the target of interest or binds with greater affinity to the target than to other molecules. For example, a DNA molecule will bind to a substantially complementary sequence and not to unrelated sequences.

A "stringent hybridization" and "stringent hybridization wash conditions" in the context of nucleic acid hybridization (e.g., as in array, Southern or Northern hybridizations) are sequence dependent, and are different under different environmental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO$_4$, 7% sodium dodecyl sulfate (SDS), 1 mnM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions that set forth the conditions which determine whether a nucleic acid is specifically hybridized to a probe. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C. In instances wherein the nucleic acid molecules are deoxyoligonucleotides ("oligos"), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos). See Sambrook, Ausubel, or Tijssen (cited below) for detailed descriptions of equivalent hybridization and wash conditions and for reagents and buffers, e.g., SSC buffers and equivalent reagents and conditions.

Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

The "melting temperature" or "Tm" of double-stranded DNA is defined as the temperature at which half of the helical structure of DNA is lost due to heating or other dissociation of the hydrogen bonding between base pairs, for example, by acid or alkali treatment, or the like. The $T_m$ of a DNA molecule depends on its length and on its base composition. DNA molecules rich in GC base pairs have a higher $T_m$ than those having an abundance of AT base pairs. Separated complementary strands of DNA spontaneously reassociate or anneal to form duplex DNA when the temperature is lowered below the $T_m$. The highest rate of nucleic acid hybridization occurs approximately 25.degree. C. below the $T_m$. The $T_m$ may be estimated using the following relationship: $T_m=69.3+0.41$ (GC) % (Marmur et al. (1962) J. Mol. Biol. 5:109-118).

As used herein, a "biological sample" refers to a sample of tissue or fluid isolated from a subject, which in the context of the invention generally refers to samples suspected of containing nucleic acid and/or viral particles of BK virus, which samples, after optional processing, can be analyzed in an in vitro assay. Typical samples of interest include, but are not necessarily limited to, respiratory secretions (e.g., samples obtained from fluids or tissue of nasal passages, lung, and the like), blood, plasma, serum, blood cells, cerebrospinal fluid, fecal matter, urine, tears, saliva, milk, organs, biopsies, and secretions of the intestinal and respiratory tracts. Samples also include samples of in vitro cell culture constituents including but not limited to conditioned media resulting from the growth of cells and tissues in culture medium, e.g., recombinant cells, and cell components.

The term "assessing" includes any form of measurement, and includes determining if an element is present or not. The terms "determining", "measuring", "evaluating", "assessing" and "assaying" are used interchangeably and includes quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

In the context of the methods involving nucleic acid-based amplification of a target sequence, the term "reference range" refers to a range of $C_T$ (threshold cycle) values from BK virus-negative specimens representative of results that are deemed to indicate that the sample (e.g., a patient specimen) is BK virus-negative.

In the context of the methods involving nucleic acid-based amplification of a target sequence, the term "reportable range" refers to a range of $C_T$ values generated by BK virus-positive specimens that are representative of results to be reported as BK virus-positive patient specimens.

"Analytical specificity" as used herein refers to the ability of a detection system to specifically detect the target virus and not detect other related viruses, or pathogenic or commensal flora found in the specimen types being validated. For example, "analytical specificity" in reference to assays using BK virus primers and a probe refers to the ability of this detection system to specifically amplify and detect the target virus and not detect other related viruses, or pathogenic or commensal flora found in the specimen types being validated.

"Analytical sensitivity" in the context of the methods involving nucleic acid-based amplification of a target sequence refers to the lowest measurable amount of BK virus target DNA that can be detected for each specimen type validated.

"Precision" refers to the ability of an assay to reproducibly generate the same or comparable result for a given sample.

"Accuracy" refers to the ability of an assay to correctly detect a target molecule in a blinded panel containing both positive and negative specimens.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to a "oligonucleotide primer" includes a plurality of such primers and reference to "primer" includes reference to one or more the primers and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The practice of the present invention will employ, unless otherwise indicated, conventional methods of chemistry, biochemistry, recombinant DNA techniques and virology, within the skill of the art. Such techniques are explained fully in the literature. See, e.g., Fundamental Virology, 2nd Edition, vol. I & II (B. N. Fields and D. M. Knipe, eds.); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Oligonucleotide Synthesis (N. Gait, ed., 1984); A Practical Guide to Molecular Cloning (1984).

The invention will now be described in more detail.

DETAILED DESCRIPTION OF THE INVENTION

The invention is based on the discovery of consensus target nucleic acid regions within the BK virus (BKV) genome that include target nucleic acid sequences (also referred to herein as target sequences) for detection of BKV in a sample, particularly a biological sample, with specificity and sensitivity. In particular the detection of one or more target nucleic acid sequence regions allows for detection of BKV in a sample, in general, while also being able to discriminate between, for example, BKV and JC virus (JCV) and/or BKV and SV40. The specificity and simplicity of these assays facilitate rapid, reliable and inexpensive assays for detection of BKV in general. The subject invention finds use in a variety of different applications, including research, medical, drug development and diagnostic applications.

In general, the subject methods provide for detection of BKV in a sample, such as a biological sample, by detection of a target nucleic acid region of the BKV genome. Five such target nucleic acid regions are described herein, termed as Target Regions I-V as designated in FIG. 1.

In some embodiments, the subject methods provide for detection of any BKV isolates, in a sample, such a biological sample. In such embodiments, the subject methods detect a target nucleic acid region, or fragment thereof, by using primers and probe that correspond to sequences within the target region. Exemplary primers within the Target Regions I-V suitable for use in the methods of the invention are provided in Table 1. Probes suitable for use in the invention include any sequence positioned within the sequence of an amplification product that would be produced using selected primers. A probe suitable for use with such an embodiment is selected such that it corresponds to a region that shares a nucleotide sequence between the different BKV isolates to be detected.

We note that the sequences provided herein, and particularly the consensus sequences are provided as DNA sequences. It is understood that the DNA sequences provided may be single stranded or double stranded, and as such the description of the DNA sequences below is intended to also provide the complementary sequence as well.

The compositions and methods of the invention will now be described in more detail.

Target Nucleic Acid Regions

Target nucleic acid sequence regions were identified by alignment of various BKV isolate genomes. The present invention provides for identification of BKV in a sample, such as a biological sample, by detecting one or more target nucleic acid region or a portion thereof. In general, detection is by nucleic acid amplification, which in some embodiments is followed by detection of the amplification product using a hybridization probe. The target nucleic acid regions are described in further detail below.

It will be appreciated that since BKV contains a double-stranded DNA genome from which RNA is generated during viral replication, the primers and probes described herein encompass those having the nucleic acid sequence described herein, as well as primers and probes having the complement of such nucleic acid sequences.

Furthermore, it will be understood that primer pairs useful in the invention include a first primer having a sequence that is the same or similar to that of the BKV sequence provided herein, and a second primer having a sequence that is complementary to the BKV sequence provided herein to provide for amplification of a BKV target nucleic acid region described herein or a fragment thereof (e.g., the first primer is a "forward" primer and the second primer is a "reverse" primer). It will be further understood that primer pairs useful in the invention also include a first primer having a sequence that is complementary to that of the BKV sequence provided herein, and a second primer having a sequence that is the same or similar to the BKV sequence provided herein to provide for amplification of an BKV target nucleic acid region described herein or a fragment thereof (e.g., the first primer is a "reverse" primer and the second primer is a "forward" primer).

It also will be understood that the nucleic acid sequence of probes described herein can be the same or similar to that of the BKV sequence provided or a complement thereof. In addition, primers described herein can also be used as probes, e.g., to detect an amplification product.

Target Region I (BK1)

In one embodiment, the invention provides for detection of BKV in a sample, such as a biological sample, by detection of target nucleic acid sequence region I (FIG. 1, Target Region I (also referred to as BK1), alignment position 435-585 based on numbering of GenBank Accession No. AY628224) as follows:

```
AACAAAAAAAAGAGCTCAGAGGATTTTTATTTTTAT (SEQ ID NO:01)
TTTAGAGCTTTTGCTGGAATTTTGTAGAGGTGAAGA
CAGTGTAGACGGGAAAAACAAAGGTACCACTGCTTT
ACCTGCTGTAAAAGACTCTGTAAAAGACTCCTAGGT
AAGTAAT
``` or a complement thereof, or a fragment thereof, wherein the 5' and 3' end of the nucleic acid is contained within SEQ ID NO:01. This conserved sequence in BKV genome is shown in the alignment of in FIG. 1. In one embodiment of particular interest, the target region is a subsequence of Target Region I, such as

```
AACAAAAAAAAGAGCTCAGAGGATTTTTATTTTTAT (SEQ ID NO:55)
TTTAGAGCTTTTGCTGGAATTTTGTAGAGGTGAAGA
CAGTGTAGACGGGAAAAACAAAAGTACCACTGCTTT
ACCTGCTGTAA
``` or a complement thereof, or a fragment thereof.

Exemplary nucleic acid sequences suitable for design of primers for amplification of a Target Region I nucleic acid, and suitable for use in the methods of the invention, are indicated by underlined typeface in FIG. 1. Suitable sequences for primers for amplification of Target Region I nucleic acid correspond to nucleotides 1-26 and 94-119 of the nucleotide sequence of SEQ ID NO:01, or a complement thereof.

Probes suitable for use in the invention can be designed from any sequence positioned within the sequence of an amplification product that would be produced using two selected primers. Suitable sequences for use as a probe for detection of Target Region I nucleic acid correspond to nucleotides 57-90 of the nucleotide sequence of SEQ ID NO:01, or a complement thereof.

In one embodiment, detection of target region I nucleic acid involves production of an amplification product of at least 151, at least 145, at least 140, at least 135, at least 130, at least 125 at least 120, at least 115, at least 110, at least 105, at least 100, at least 95, at least 90, at least 85, at least 80, at least 75, at least 70, at least 65, at least 60, at least 55, at least 50, at least 45, at least 40, at least 35, at least 30, at least 28, at least 26, at least 24, at least 22, at least 20 consecutive nucleotides of SEQ ID NO:01.

The methods of the invention can involve detection of target region I nucleic acid either alone or in combination with detection of one or more of target regions II-V as described herein. For example, the methods of the invention can involve detection of target region I (BK1) and target region II (BK2); target region I (BK1) and target region III (BK3); target region I (BK1) and target region IV (BK4); target region I (BK1) and target region V (BK5); target region I (BK1), target region II (BK2), and target region III (BK3); target region I (BK1), target region IV (BK4), and target region V (BK5); target region I (BK1), target region III (BK3), and target region V (BK5) and the like. It will be understood that detection of all combination of target regions I-V are contemplates by the present methods.

Exemplary primers and probes are discussed in greater detail below.

Target Region II (BK2)

In one embodiment, the invention provides for detection of BKV in a sample, such as a biological sample, by detection of target nucleic acid sequence region I (FIG. 1, Target Region II (also referred to as BK2), alignment position 1418-1545 based on numbering of GenBank Accession No. AY628224) as follows:

```
TGTACATTCAGGAGAGTTTATAGAAAAAACTATTGC (SEQ ID NO:02)
CCCAGGAGGTGCTAATCAAAGAACTGCTCCTCAATG
GATGTTGCCTTTACTTCTAGGCCTGTACGGGACTGT
AACACCTGCTCTTGAAGCAT
``` or a complement thereof, or a fragment thereof, wherein the 5' and 3' end of the nucleic acid is contained within SEQ ID NO:02. This conserved sequence as found in the BKV genome is illustrated in the alignment of FIG. 1. In one embodiment of particular interest, the target region is a subsequence of Target Region II, such as:

```
TTGCCCCAGGAGGTGCTAATCAAAGAACTGCTCCTC (SEQ ID NO:56)
AATGGATGTTGCCTTTACTTCTAGGCCTGTACGGGA
``` or a complement thereof, or a fragment thereof.

Exemplary nucleic acid sequences suitable for design of primers for amplification of a Target Region II nucleic acid, and suitable for use in the methods of the invention, are indicated by underlined typeface in FIG. 1. Suitable sequences for primers for amplification of Target Region II nucleic acid correspond to nucleotides 33-50 and 82-104 of the nucleotide sequence of SEQ ID NO:02, or a complement thereof.

Probes suitable for use in the invention can be designed from any sequence positioned within the sequence of an amplification product that would be produced using two selected primers. Suitable sequences for use as a probe for detection of Target Region II nucleic acid correspond to nucleotides 52-80 of the nucleotide sequence of SEQ ID NO:02, or a complement thereof.

In one embodiment, detection of target region II nucleic acid involves production of an amplification product of at least 128, at least 120, at least 110, at least 100, at least 90, at least 80, at least 75, at least 70, at least 65, at least 60, at least 55, at least 50, at least at least 45, 40, at least 35, at least 30, at least 28, at least 26, at least 24, at least 22, at least 20 consecutive nucleotides of SEQ ID NO:02.

The methods of the invention can involve detection of target region II nucleic acid either alone or in combination with detection of one or more of target regions I and III-V as described herein. For example, the methods of the invention can involve detection of target region II (BK2) and target region I (BK1); target region II (BK2) and target region III (BK3); target region II (BK2) and target region IV (BK4); target region II (BK2) and target region V (BK5); target region I (BK1), target region II (BK2), and target region III (BK3); target region II (BK2), target region IV (BK4), and target region V (BK5); or target region II (BK2), target region III (BK3), and target region V (BK5) and the like. It will be understood that detection of all combination of target regions I-V are contemplates by the present methods.

Exemplary primers and probes are discussed in greater detail below.

Target Region III (BK3)

In another embodiment, the invention provides for detection of BJKV in a sample, such as a biological sample, by detection of target nucleic acid sequence region III (FIG. 1, Target Region III (also referred to as BK3), alignment position 4097-4560 based on numbering of GenBank Accession No. AY628224) as follows:

```
AGTAAGTATTCCTTATTAACACCCTTACAAATTAAA  (SEQ ID NO:03)
AAACTAAAGGTACACAGCTTTTGACAGAAATTATTA
ATTGCAGAAACTCTATGTCTATGTGGAGTTAAAAAG
AATATAATATTATGCCCAGCACACATGTGTCTACTA
ATGAAAGTTACAGAATATTTTTCCATAAGTTTTTTA
TACAGAATTTGAGCTTTTTCTTTAGTAGTATACACA
GCAAAGCAGGCAAGGGTTCTATTACTAAATACAGCT
TGACTAAGAAACTGGTGTAGATCAGAGGGAAAGTCT
TTAGGGTCTTCTACCTTTCTCTTTTTCTTGGGTGGT
GTGGAGTGTTGAGAATCTGCTGTTGCTTCTTCATCA
CTGGCAAACATATCTTCATGGCAAAATAAATCTTCA
TCCCATTTTTCATTAAAGGAGCTCCACCAGGACTCC
CACTCTTCTGTTCCATAGGTTGGCACCTATAA
``` or a complement thereof, or a fragment thereof, wherein the 5' and 3' end of the nucleic acid is contained within SEQ ID NO:03. This conserved sequence in the BKV genome is shown in the alignment of the three genomes in FIG. 1. In one embodiment of particular interest, the target region is a subsequence of Target Region III, such as:

```
GGAAAGTCTTTAGGGTCTTCTACCTTTCTCTTTTTC  (SEQ ID NO:57)
TTGGGTGGTGTGGAGTGTTGAGAATCTGCTGTTGCT
TCTTCATCACTGGCAAACATATCTTCATG
``` or a complement thereof, or a fragment thereof.

Exemplary nucleic acid sequences suitable for design of primers for amplification of a Target Region III nucleic acid, and suitable for use in the methods of the invention, are indicated by underlined typeface in FIG. 1. Suitable sequences for primers for amplification of Target Region III nucleic acid correspond to nucleotides 280-306 and 355-380 of the nucleotide sequence of SEQ ID NO:03, or a complement thereof.

Probes suitable for use in the invention can be designed from any sequence positioned within the sequence of an amplification product that would be produced using two selected primers. Suitable sequences for use as a probe for detection of Target Region III nucleic acid correspond to nucleotides 330-354 of the nucleotide sequence of SEQ ID NO:03, or a complement thereof.

In one embodiment, detection of target region III nucleic acid involves production of an amplification product of at least 464, at least 425, at least 400, at least 375, at least 350, at least 325, at least 300, at least 275, at least 250, at least 225, at least 200, at least 175, at least 150, at least 125, at least 120, at least 115, at least 110, at least 100, at least 95, at least 90, at least 85, at least 80, at least 75, at least 70, at least 65, at least 60, at least 55, at least 50, at least 45, at least 40, at least 35, at least 30, at least 28, at least 26, at least 24, at least 22, at least 20 consecutive nucleotides of SEQ ID NO:03.

The methods of the invention can involve detection of target region III nucleic acid either alone or in combination with detection of one or more of target regions I-II and IV-V as described herein. For example, the methods of the invention can involve detection of target region III (BK3) and target region IV (BK4); target region III (BK3) and target region V (BK5); target region III (BK3) and target region I (BK1); target region III (BK3) and target region II (BK); target region I (BK1), target region II (BK2), and target region III (BK3); target region III (BK3), target region IV (BK4), and target region V (BK5); or target region III (BK3), target region I (BK1), and target region V (BK5) and the like. It will be understood that detection of all combination of target regions I-V are contemplates by the present methods.

Exemplary primers and probes are discussed in greater detail below.

Target Region IV (BK4)

In another embodiment, the invention provides for detection of BKV in a sample, such as a biological sample, by detection of target nucleic acid sequence region IV (FIG. 1, Target Region IV (also referred to as BK4), alignment position 612-864 based on numbering of GenBank Accession No. AY628224) as follows:

```
ATGGGTGCTGCTCTAGCACTTTTGGGGGACCTAGTT  (SEQ ID NO:04)
GCCAGTGTATCTGAGGCTGCTGCTGCCACAGGATTT
TCAGTGGCTGAAATTGCTGCTGGGGAGGCTGCTGCT
GCTATAGAAGTTCAAATTGCATCCCTTGCTACTGTA
GAGGGCATAACAAGTACCTCAGAGGCTATAGCTGCC
ATAGGCCTAACTCCTCAAACATATGCTGTAATTGCT
GGTGCTCCTGGGGCTATTGCTGGGTTTGCTGCTTTA
A
``` or a complement thereof, or a fragment thereof, wherein the 5' and 3' end of the nucleic acid is contained within SEQ ID NO:04. This conserved sequence in the BKV genome is shown in the alignment of the three genomes in FIG. 1. In one embodiment of particular interest, the target region is a subsequence of Target Region IV, such as:

```
ATGGGTGCTGCTCTAGCACTTTTGGGGGACCTAGTT  (SEQ ID NO:58)
GCCAGTGTATCTGAGGCTGCTGCTGCCACAGGATTT
TCAGTGGCTGAAATTGCTGCTGG
``` or a complement thereof, or a fragment thereof.

Exemplary nucleic acid sequences suitable for design of primers for amplification of a Target Region IV nucleic acid, and suitable for use in the methods of the invention, are indicated by underlined typeface in FIG. 1. Suitable sequences for primers for amplification of Target Region IV nucleic acid correspond to nucleotides 1-19 and 76-95 of the nucleotide sequence of SEQ ID NO:04, or a complement thereof.

Probes suitable for use in the invention can be designed from any sequence positioned within the sequence of an amplification product that would be produced using two selected primers. Suitable sequences for use as a probe for detection of Target Region IV nucleic acid correspond to nucleotides 36-62 of the nucleotide sequence of SEQ ID NO:04, or a complement thereof.

In one embodiment, detection of target region IV nucleic acid involves production of an amplification product of at least 253, at least 250, at least 225, at least 200, at least 175, at least 150, at least 125, at least 120, at least 115, at least 100, at least 95, at least 90, at least 85, at least 80, at least 75, at least 70, at least 65, at least 60, at least 55, at least 50, at least 45, at least 40, at least 35, at least 30, at least 28, at least 26, at least 24, at least 22, at least 20 consecutive nucleotides of SEQ ID NO:04.

The methods of the invention can involve detection of target region IV nucleic acid either alone or in combination with detection of one or more of target regions I-III and V as described herein. For example, the methods of the invention can involve detection of target region IV (BK4) and target region I (BK1); target region IV (BK4) and target region II (BK2); target region IV (BK4) and target region III (BK3); target region IV (BK4) and target region IV (BK5); target region I (BK1), target region II (BK2), and target region IV (BK4); target region III (BK3), target region IV (BK4) and target region V (BK5); or target region I (BK1), target region IV (BK4) and target region V (BK5) and the like. It will be understood that detection of all combination of target regions I-V are contemplates by the present methods.

Exemplary primers and probes are discussed in greater detail below.

Target Region V

In another embodiment, the invention provides for detection of BKV in a sample, such as a biological sample, by detection of target nucleic acid sequence region V (FIG. 1, Target Region V (also refereed to as BK5), alignment position 2810-2895 based on numbering of GenBank Accession No. AY628224) as follows:

GGGGCTGAAGTATCTGAGACTTGGGAAGAGCATTGT (SEQ ID NO:05)
GATTGGGATTCAGTGCTTGATCCATGTCCAGAGTCT
TCAGTTTCTGAATC or complement thereof, or a fragment thereof, wherein the 5' and 3' end of the nucleic acid is contained within SEQ ID NO:05. This conserved sequence in the BKV genome is shown in the alignment of the three genomes in FIG. 1. In one embodiment of particular interest, the target region is a subsequence of Target Region V, such as:

GGGCTGAAGTATCTGAGACTTGGGAAGAGCATTGTG (SEQ ID NO:59)
ATTGGGATTCAGTGCTTGATCCATGTC or complement thereof, or a fragment thereof.

Exemplary nucleic acid sequences suitable for design of primers for amplification of a Target Region V nucleic acid, and suitable for use in the methods of the invention, are indicated by underlined typeface in FIG. 1. Suitable sequences for primers for amplification of Target Region V nucleic acid correspond to nucleotides 2-18 and 47-64 of the nucleotide sequence of SEQ ID NO:05, or a complement thereof.

Probes suitable for use in the invention can be designed from any sequence positioned within the sequence of an amplification product that would be produced using two selected primers. Suitable sequences for use as a probe for detection of Target Region V nucleic acid correspond to nucleotides 19-41 of the nucleotide sequence of SEQ ID NO:05, or a complement thereof.

In one embodiment, detection of target region V nucleic acid involves production of an amplification product of at least 86, at least 80, at least 75, at least 70, at least 65, at least 60, at least 55, at least 50, at least 45, at least 40, at least 35, at least 30, at least 28, at least 26, at least 24, at least 22, at least 20 consecutive nucleotides of SEQ ID NO:05.

The methods of the invention can involve detection of target region V nucleic acid either alone or in combination with detection of one or more of target regions I-IV as described herein. For example, the methods of the invention can involve detection of target region V (BK5) and target region I (BK1); target region V (BK5) and target region II (BK2); target region V (BK5) and target region III (BK3); target region IV (BK4) and target region V (BKV); target region V (BK5), target region II (BK2), and target region III (BK3); target region III (BK3), target region IV (BK4), and target region V (BK5); or target region I (BK1), target region III (BK3), and target region V (BK5) and the like. It will be understood that detection of all combination of target regions I-V are contemplates by the present methods.

Exemplary primers and probes are discussed in greater detail below.

Primers and Probes

As described above, the target nucleic acid sequence regions I-V are conserved nucleic acid regions in different BKV genotypes. Primers and probes for use in these assays are preferably derived from the target nucleic acid sequence regions I-V as described above. In one embodiment of particular interest, primers and probes for use with the present assays are designed from the highly conserved nucleotide sequences of the target nucleic acid sequence regions I-V.

In general, the primers provide for amplification of target nucleic acid to produce as target nucleic acid amplification product (also referred to as an "amplicon"). Primers may be, and preferably are, used in connection with a probe. 5' primers generally bind to a region to provide for amplification of the target nucleic, and preferably bind to a 5' portion of the target sequence, as exemplified in FIG. 1. 3' primers generally bind to a sequence that is complementary to a 3' portion of the nucleic acid generated by extension from the 5' primer, as exemplified in FIG. 1. The 5' and 3' primers may be separated by about 10, 20, 30, or 40 contiguous nucleotides, usually about 30 contiguous nucleotides. In certain embodiments, primers are designed so as to have a sequence complementary to one or more variant nucleotides within a target region sequence and/or to have a 3' end adjacent a variant nucleotide of a sequence of a target region. Probes are generally designed so as to have a sequence complementary to one or more variant nucleotides within a target region sequence. In some embodiments involving amplification-based detection, probes are designed so as to have a sequence complementary to a sequence flanked by the sequence(s) complementary to one or more primers used for amplification.

Primers and probes for use in the assays herein are designed based on the sequence disclosed herein and are readily synthesized by standard techniques, e.g., solid phase synthesis via phosphoramidite chemistry, as disclosed in U.S. Pat. Nos. 4,458,066 and 4,415,732, incorporated herein by reference; Beaucage et al. (1992) Tetrahedron 48:2223-2311; and Applied Biosystems User Bulletin No. 13 (1 Apr. 1987). Other chemical synthesis methods include, for example, the phosphotriester method described by Narang et al., Meth. Enzymol. (1979) 68:90 and the phosphodiester method disclosed by Brown et al., Meth. Enzymol. (1979) 68:109. Poly (A) or poly(C), or other non-complementary nucleotide extensions may be incorporated into probes using these same methods. Hexaethylene oxide extensions may be coupled to probes by methods known in the art. Cload et al. (1991) J. Am. Chem. Soc. 113:6324-6326; U.S. Pat. No. 4,914,210 to Levenson et al.; Durand et al. (1990) Nucleic Acids Res. 18:6353-6359; and Horn et al. (1986) Tet. Lett. 27:4705-4708.

Typically, the primer sequences are in the range of between 10-75 nucleotides in length, such as 10 to 70, 12 to 65, 15 to 60, 20 to 55, 25 to 50, 30 to 45, and the like. More typically, primers are in the range of between 18 to 40, 19 to 35, 20 to 30, 21 to 29, 22 to 28, 23 to 27, 24-25 nucleotides long, and any length between the stated ranges. Primers of about 20 to 22 nucleotides in length are of particular interest.

The typical probe is in the range of between 10-50 nucleotides long, such as such as 10 to 50, 12 to 45, 15 to 40, 20 to 35, 25 to 30 and the like. More typically, probes are in the range of between 18 to 40, 19 to 35, 20 to 30, 21 to 29, 22 to 28, 23 to 27, 24-25 nucleotides long, and any length between the stated ranges. Probes of about 20 to 22 nucleotides in length are of particular interest.

In some embodiments, the subject methods provide for detection of any BKV genotype in a sample, such a biological sample. In such embodiments, the subject methods detect a target nucleic acid region, or fragment thereof, by using primers and probe that correspond to sequences within the target region. Exemplary primers within the Target Regions I-V suitable for use in the methods of the invention are indicated by bold typeface in FIG. 1. Probes suitable for use in the invention can be designed from any sequence positioned within the sequence of an amplification product that would be produced using two selected primers. A probe suitable for use with such an embodiment is selected such that it corresponds to a region that shares a nucleotide sequence between the different BKV genotypes to be detected.

In other embodiments, the subject methods provide for detection and discrimination between different genotypes in a sample, such a biological sample. In such embodiments, the subject methods detect a target nucleic acid region, or fragment thereof, by using primers and probe that correspond to sequences within the target region. Exemplary primers within the Target Regions I-V suitable for use in the methods of the invention are indicated by bold typeface in FIG. 1. Probes suitable for use in the invention can be designed from any sequence positioned within the sequence of an amplification product that would be produced using two selected primers. In such embodiments the sequence of the probe is selected such that it corresponds to a region that differs in sequence by one or more nucleotides between the different BKV genotypes to be detected.

Exemplary nucleic acid sequences of the BKV genotypes that are suitable for use are primers and probes in the assays of the present invention are described in Table 1. The sequence numbering presented in Table 1 is the numbering of GenBank Accession No. AY628224 in FIG. 1.

TABLE 1

Exemplary Primer and Probe Sequences for Detection of Target Regions I-V of BKV Nucleic Acid (Sequence Provided Based on BKV Genome Sequence; Sequence Numbering Based on Numbering of GenBank Accession No. AY628224 of FIG. 1)

| SEQ ID NO.: | | Start | End | Length | Sequence 5' to 3' |
|---|---|---|---|---|---|
| Target Region I (BK1) (corresponding to nucleotides 435-585 of AY628224) | | | | | |
| SEQ ID NO:06 | F | 435 | 460 | 26 | AACAAAAAAAGAGCTCAGAGGATTTT |
| SEQ ID NO:07 | R | 527 | 552 | 26 | AAGTACCACTGCTTTACCTGCTGTAA |
| SEQ ID NO:08 | P | 490 | 524 | 34 | TTTGTAGAGGTGAAGACAGTGTAGACGGGAAAAA |
| Target Region II (BK2) (corresponding to nucleotides 1418-1545 of AY628224) | | | | | |
| SEQ ID NO:09 | F | 1450 | 1467 | 18 | TTGCCCCAGGAGGTGCTA |
| SEQ ID NO:10 | R | 1498 | 1520 | 23 | TTTACTTCTAGGCCTGTACGGGA |
| SEQ ID NO:11 | P | 1469 | 1497 | 29 | TCAAAGAACTGCTCCTCAATGGATGTTGC |
| Target Region III (BK3) (corresponding to nucleotides 4097-4560 of AY628224) | | | | | |

TABLE 1-continued

Exemplary Primer and Probe Sequences for Detection of Target Regions I-V of BKV Nucleic Acid (Sequence Provided Based on BKV Genome Sequence; Sequence Numbering Based on Numbering of GenBank Accession No. AY628224 of FIG. 1)

| SEQ ID NO.: | | Start | End | Length | Sequence 5' to 3' |
|---|---|---|---|---|---|
| SEQ ID NO:12 | F | 4375 | 4404 | 27 | GGAAAGTCTTTAGGGTCTTCTACCTTT |
| SEQ ID NO:13 | R | 4452 | 4478 | 26 | TCATCACTGGCAAACATATCTTCATG |
| SEQ ID NO:14 | P | 4426 | 4450 | 25 | GTGTTGAGAATCTGCTGTTGCTTCT |
| Target Region IV (BK4) (corresponding to nucleotides 612-864 of AY628224) | | | | | |
| SEQ ID NO:15 | F | 612 | 620 | 19 | ATGGGTGCTGCTCTAGCAC |
| SEQ ID NO:16 | R | 677 | 696 | 20 | GTGGCTGAAATTGCTGCTGG |
| SEQ ID NO:17 | P | 646 | 663 | 27 | TGCCAGTGTATCTGAGGCTGCTGCTGC |
| Target Region V (BK5) (corresponding to nucleotides 2810-2895 of AY628224) | | | | | |
| SEQ ID NO:18 | F | 2811 | 2827 | 17 | GGGCTGAAGTATCTGAG |
| SEQ ID NO:19 | R | 2856 | 2873 | 18 | CAGTGCTTGATCCATGTC |
| SEQ ID NO:20 | P | 2828 | 2950 | 23 | CTTGGGAAGAGCATTGTGATTGG |

"F" refers to forward primer, "R" refers to reverse primer, and "P" refers to probe.

The probes may be coupled to labels for detection. There are several methods and compositions known for derivatizing oligonucleotides with reactive functionalities which permit the addition of a label. For example, several approaches are available for biotinylating probes so that radioactive, fluorescent, chemiluminescent, enzymatic, or electron dense labels can be attached via avidin. See, e.g., Broken et al., Nucl. Acids Res. (1978) 5:363-384 which discloses the use of ferritin-avidin-biotin labels; and Chollet et al. Nucl. Acids Res. (1985) 13:1529-1541 which discloses biotinylation of the 5' termini of oligonucleotides via an aminoalkylphosphoramide linker arm. Several methods are also available for synthesizing amino-derivatized oligonucleotides which are readily labeled by fluorescent or other types of compounds derivatized by amino-reactive groups, such as isothiocyanate, N-hydroxysuccinimide, or the like, see, e.g., Connolly (1987) Nucl. Acids Res. 15:3131-3139, Gibson et al. (1987) Nucl. Acids Res. 15:6455-6467 and U.S. Pat. No. 4,605,735 to Miyoshi et al. Methods are also available for synthesizing sulfhydryl-derivatized oligonucleotides which can be reacted with thiol-specific labels, see, e.g., U.S. Pat. No. 4,757,141 to Fung et al., Connolly et al. (1985) Nuc. Acids Res. 13:4485-4502 and Spoat et al. (1987) Nucl. Acids Res. 15:4837-4848. A comprehensive review of methodologies for labeling DNA fragments is provided in Matthews et al., Anal. Biochem. (1988) 169:1-25.

For example, probes may be fluorescently labeled by linking a fluorescent molecule to the non-ligating terminus of the probe. Guidance for selecting appropriate fluorescent labels can be found in Smith et al., Meth. Enzymol. (1987) 155:260-301; Karger et al., Nucl. Acids Res. (1991) 19:4955-4962; Haugland (1989) Handbook of Fluorescent Probes and Research Chemicals (Molecular Probes, Inc., Eugene, Oreg.). Preferred fluorescent labels include fluorescein and derivatives thereof, such as disclosed in U.S. Pat. No. 4,318, 846 and Lee et al., Cytometry (1989) 10:151-164, and 6-FAM, JOE, TAMRA, ROX, HEX-1, HEX-2, ZOE, TET-1 or NAN-2, and the like.

Additionally, probes can be labeled with an acridinium ester (AE). Current technologies allow the AE label to be placed at any location within the probe. See, e.g., Nelson et al. (1995) "Detection of Acridinium Esters by Chemiluminescence" in Nonisotopic Probing, Blotting and Sequencing, Kricka L. J. (ed) Academic Press, San Diego, Calif.; Nelson et al. (1994) "Application of the Hybridization Protection Assay (HPA) to PCR" in The Polymerase Chain Reaction, Mullis et al. (eds.) Birkhauser, Boston, Mass.; Weeks et al., Clin. Chem. (1983) 29:1474-1479; Berry et al., Clin. Chem. (1988) 34:2087-2090. An AE molecule can be directly attached to the probe using non-nucleotide-based linker arm chemistry that allows placement of the label at any location within the probe. See, e.g., U.S. Pat. Nos. 5,585,481 and 5,185,439.

If a solid support is used in the assay (e.g., to capture amplicons of target nucleic acid using a probe), the oligonucleotide probe may be attached to the solid support in a variety of manners. For example, the probe may be attached to the solid support by attachment of the 3' or 5' terminal nucleotide of the probe to the solid support. More preferably, the probe is attached to the solid support by a linker which serves to distance the probe from the solid support. The linker is usually at least 15-30 atoms in length, more preferably at least 15-50 atoms in length. The required length of the linker will depend on the particular solid support used. For example, a six atom linker is generally sufficient when high cross-linked polystyrene is used as the solid support.

A wide variety of linkers are known in the art which may be used to attach the oligonucleotide probe to the solid support. The linker may be formed of any compound which does not significantly interfere with the hybridization of the target sequence to the probe attached to the solid support. The linker may be formed of a homopolymeric oligonucleotide which can be readily added on to the linker by automated synthesis. Alternatively, polymers such as functionalized polyethylene glycol can be used as the linker. Such polymers are preferred over homopolymeric oligonucleotides because they do not significantly interfere with the hybridization of probe to the target oligonucleotide. Polyethylene glycol is particularly preferred.

The linkages between the solid support, the linker and the probe are normally not cleaved during removal of base protecting groups under basic conditions at high temperature. Examples of preferred linkages include carbamate and amide linkages.

Examples of preferred types of solid supports for immobilization of the oligonucleotide probe include controlled pore glass, glass plates, polystyrene, avidin-coated polystyrene beads, cellulose, nylon, acrylamide gel and activated dextran.

In certain embodiments, an internal control (IC) or an internal standard is added to serve as a control to show that any negative result is not due to failure of the assay. The use of the IC permits the control of the separation process, the amplification process, and the detection system, and permits the monitoring of assay performance and quantification for the sample(s). The IC can be included at any suitable point, for example, in the lysis buffer. In one embodiment, the IC comprises phage nucleic acid. Where a solid support is used in the assay, the solid support may additionally include probes specific to the internal standard (IC probe), thereby facilitating capture when using the IC probe. The IC probe can optionally be coupled with a detectable label that is different from the detectable label for the target sequence. In embodiments where the detectable label is a fluorophore, the IC can be quantified spectrophotometrically and by limit of detection studies.

Detection of BKV in a Sample

In one aspect, the assay detects the presence of BKV in a sample. In such an aspect, the assay is an amplification-based assay using degenerate primers and probes, where the primers and probes are designed to provide for amplification of a target nucleic acid sequence region of the BKV genome.

As discussed above, the assay detects the presence of one or more target nucleic acid regions (e.g., Target Regions I-V), or a portion thereof. The target nucleic acid sequence regions I-V are conserved nucleic acid regions in different BKV genotypes. Primers and probes for use in these assays are preferably derived from the target nucleic acid sequence regions I-V as described above. Particularly preferred primers and probes for use with the present assays are designed from the highly conserved nucleotide sequences of the target nucleic acid sequence regions I-V.

As discussed above, in one embodiment, the primers and/or probes are designed for nucleic acid-based detection, particularly an amplification method, of a target nucleic acid having a target nucleic acid sequence described above, e.g., target nucleic acid sequence region I-V. That is, in such an embodiment, the primers are designed to amplify a target sequence having the nucleic acid sequence of a nucleic acid sequence described above, e.g., target nucleic acid sequence region I-V.

In another embodiment, the primers and/or probes are designed for nucleic acid-based detection, particularly an amplification method, of a target nucleic acid having a nucleic acid sequence that is a fragment of a target nucleic acid sequence described above, e.g., target nucleic acid sequence region I-V. That is, in such an embodiment, the primers are designed to amplify a target sequence having the nucleic acid sequence of a portion smaller than the entire nucleic acid sequence described above, e.g., target nucleic acid sequence region I-V.

Specific detection of BKV nucleic acid in a sample is generally accomplished by detection of one or more of the target sequence regions I-V, or a fragment thereof. In one embodiment, BKV target nucleic acid is detected by use of primers and probes designed upon the sequences of target sequence region V.

In an embodiment of particular interest, the target sequence is detected using primers having the sequence ATGGGT-GCTGCTCTAGCAC (5' primer) (SEQ ID NO:15), GTG-GCTGAAATTGCTGCTGG (3' primer) (SEQ ID NO: 16), and a probe having the sequence TGCCAGTGTATCTGAG-GCTGCTGCTGC (SEQ ID NO: 17) is of particular interest.

In another embodiment of particular interest, the target sequence is detected using primers having the sequence GGGCTGAAGTATCTGAG (5' primer) (SEQ ID NO: 18), CAGTGCTTGATCCATGTC (3' primer) (SEQ ID NO: 19), and a probe having the sequence CTTGGGAAGAGCAT-TGTGATTGG (SEQ ID NO:20) is of particular interest.

Of particular interest is the use of these primers and probes in a real-time RT PCR method for detection of BKV in a sample, with use of a dual-labeled TaqMan Probe.

Methods of Detection

The invention provides DNA-based assay for detecting BKV in a sample. Detection may be done using a wide variety of methods, including direct sequencing, hybridization with sequence-specific oligomers, gel electrophoresis and mass spectrometry. These methods can use heterogeneous or homogeneous formats, isotopic or nonisotopic labels, as well as no labels at all.

Preferably, the methods involve amplifying nucleic acids from a sample. If a diagnostic nucleic acid is obtained, the presence of BKV in a sample is indicated. In general, the methods involve amplifying a nucleic acid from a sample using a detection primer and at least one other primer, as described above, and assessing the amplified nucleic acids. The methods are highly sensitive, and may detect as few as 5 copies of BKV per reaction, which is equivalent to 200 copies of DNA per mL of specimen, although detection may be limited by the limit of linear range detection. Thus, the invention generally provides for detection of BKV in a sample, where the BKV is present in at least 200 copies of DNA per mL of specimen.

As is known in the art, an amplified nucleic acid may be assessed by a number of methods, including, for example, determining the presence or absence of the nucleic acid, determining the size of the nucleic acid or determining the abundance of a nucleic acid in relation to another amplified nucleic acid. In most embodiments, an amplified nucleic acid is assessed using gel electrophoresis, nucleic acid hybridization, sequencing, and/or detection of a signal from a label bound to the amplified nucleic acid. Methods of amplifying (e.g., by polymerase chain reaction) nucleic acid, methods of performing primers extension, and methods of assessing nucleic acids are generally well known in the art (e.g., see Ausubel, et al, Short Protocols in Molecular Biology, 3rd ed., Wiley & Sons, 1995 and Sambrook, et al, Molecular Cloning: A Laboratory Manual, Third Edition, (2001) Cold Spring Harbor, N.Y.) and need not be described in any great detail.

For example, primers and probes described above may be used in polymerase chain reaction (PCR)-based techniques to detect BKV in biological samples. PCR is a technique for amplifying a desired target nucleic acid sequence contained in a nucleic acid molecule or mixture of molecules. In PCR, a pair of primers is employed in excess to hybridize to the complementary strands of the target nucleic acid. The primers are each extended by a polymerase using the target nucleic acid as a template. The extension products become target sequences themselves after dissociation from the original target strand. New primers are then hybridized and extended by a polymerase, and the cycle is repeated to geometrically increase the number of target sequence molecules. The PCR method for amplifying target nucleic acid sequences in a sample is well known in the art and has been described in, e.g., Innis et al. (eds.) PCR Protocols (Academic Press, NY 1990); Taylor (1991) Polymerase chain reaction: basic principles and automation, in PCR: A Practical Approach, McPherson et al. (eds.) IRL Press, Oxford; Saiki et al. (1986) Nature 324: 163; as well as in U.S. Pat. Nos. 4,683,195, 4,683,202 and 4,889,818, all incorporated herein by reference in their entireties.

In particular, PCR uses relatively short oligonucleotide primers which flank the target nucleotide sequence to be amplified, oriented such that their 3' ends face each other, each primer extending toward the other. The polynucleotide sample is extracted and denatured, preferably by heat, and hybridized with first and second primers which are present in molar excess. Polymerization is catalyzed in the presence of the four deoxyribonucleotide triphosphates (dNTPs-DATP, dGTP, dCTP and dTTP) using a primer- and template-dependent polynucleotide polymerizing agent, such as any enzyme capable of producing primer extension products, for example, E. coli DNA polymerase I, Klenow fragment of DNA polymerase I, T4 DNA polymerase, thermostable DNA polymerases isolated from Thermus aquaticus (Taq), available from a variety of sources (for example, Perkin Elmer), Thermus thermophilus (United States Biochemicals), Bacillus stereothermophilus (Bio-Rad), or Thermococcus litoralis ("Vent" polymerase, New England Biolabs). This results in two "long products" which contain the respective primers at their 5' ends covalently linked to the newly synthesized complements of the original strands.

The reaction mixture is then returned to polymerizing conditions, e.g., by lowering the temperature, inactivating a denaturing agent, or adding more polymerase, and a second cycle is initiated. The second cycle provides the two original strands, the two long products from the first cycle, two new long products replicated from the original strands, and two "short products" replicated from the long products. The short products have the sequence of the target sequence with a primer at each end. On each additional cycle, an additional two long products are produced, and a number of short products equal to the number of long and short products remaining at the end of the previous cycle. Thus, the number of short products containing the target sequence grow exponentially with each cycle. Preferably, PCR is carried out with a commercially available thermal cycler, e.g., Perkin Elmer.

The fluorogenic 5' nuclease assay, known as the TAQ-MAN™ assay (Perkin-Elmer), is a powerful and versatile PCR-based detection system for nucleic acid targets. For a detailed description of the TAQMAN™ assay, reagents and conditions for use therein, see, e.g., Holland et al., Proc. Natl. Acad. Sci, U.S.A. (1991) 88:7276-7280; U.S. Pat. Nos. 5,538,848, 5,723,591, and 5,876,930, all incorporated herein by reference in their entireties. Hence, primers and probes derived from regions of the BKV genome described herein can be used in TAQMAN™ analyses to detect the presence of infection in a biological sample. Analysis is performed in conjunction with thermal cycling by monitoring the generation of fluorescence signals. The assay system dispenses with the need for gel electrophoretic analysis, and has the capability to generate quantitative data allowing the determination of target copy numbers.

The fluorogenic 5' nuclease assay is conveniently performed using, for example, AMPLITAQ GOLD™ DNA polymerase, which has endogenous 5' nuclease activity, to digest an internal oligonucleotide probe labeled with both a fluorescent reporter dye and a quencher (see, Holland et al., Proc. Natl. Acad. Sci. USA (1991) 88:7276-7280; and Lee et al., Nucl. Acids Res. (1993) 21:3761-3766). Assay results are detected by measuring changes in fluorescence that occur during the amplification cycle as the fluorescent probe is digested, uncoupling the dye and quencher labels and causing an increase in the fluorescent signal that is proportional to the amplification of target nucleic acid.

The amplification products can be detected in solution or using solid supports. In this method, the TAQMAN™ probe is designed to hybridize to a target sequence within the desired PCR product. The 5' end of the TAQMAN™ probe contains a fluorescent reporter dye. The 3' end of the probe is blocked to prevent probe extension and contains a dye that will quench the fluorescence of the 5' fluorophore. During subsequent amplification, the 5' fluorescent label is cleaved off if a polymerase with 5' exonuclease activity is present in the reaction. Excision of the 5' fluorophore results in an increase in fluorescence which can be detected.

In particular, the oligonucleotide probe is constructed such that the probe exists in at least one single-stranded conformation when unhybridized where the quencher molecule is near enough to the reporter molecule to quench the fluorescence of the reporter molecule. The oligonucleotide probe also exists in at least one conformation when hybridized to a target polynucleotide such that the quencher molecule is not positioned close enough to the reporter molecule to quench the fluorescence of the reporter molecule. By adopting these hybridized and unhybridized conformations, the reporter molecule and quencher molecule on the probe exhibit different fluorescence signal intensities when the probe is hybridized and unhybridized. As a result, it is possible to determine whether the probe is hybridized or unhybridized based on a change in the fluorescence intensity of the reporter molecule, the quencher molecule, or a combination thereof. In addition, because the probe can be designed such that the quencher molecule quenches the reporter molecule when the probe is not hybridized, the probe can be designed such that the reporter molecule exhibits limited fluorescence unless the probe is either hybridized or digested.

Accordingly, the present invention relates to methods for amplifying a target BKV nucleotide sequence using a nucleic acid polymerase having 5' to 3' nuclease activity, one or more primers capable of hybridizing to the target BKV sequence or its extension product, and an oligonucleotide probe capable of hybridizing to the target BKV sequence 3' relative to the primer. During amplification, the polymerase digests the oligonucleotide probe when it is hybridized to the target sequence, thereby separating the reporter molecule from the quencher molecule. As the amplification is conducted, the fluorescence of the reporter molecule is monitored, with fluorescence corresponding to the occurrence of nucleic acid amplification. The reporter molecule is preferably a fluorescein dye and the quencher molecule is preferably a rhodamine dye.

Another method of detection involves use of target sequence-specific oligonucleotide probes, which contain a region of complementarity to the target sequence described above. The probes may be used in hybridization protection assays (HPA). In this embodiment, the probes are conveniently labeled with acridinium ester (AE), a highly chemiluminescent molecule. See, e.g., Nelson et al. (1995) "Detection of Acridinium Esters by Chemiluminescence" in Nonisotopic Probing, Blotting and Sequencing, Kricka L. J. (ed) Academic Press, San Diego, Calif.; Nelson et al. (1994) "Application of the Hybridization Protection Assay (HPA) to PCR" in The Polymerase Chain Reaction, Mullis et al. (eds.) Birkhauser, Boston, Mass.; Weeks et al., Clin. Chem. (1983) 29:1474-1479; Berry et al., Clin. Chem. (1988) 34:2087-2090. One AE molecule is directly attached to the probe using a non-nucleotide-based linker arm chemistry that allows placement of the label at any location within the probe. See, e.g., U.S. Pat. Nos. 5,585,481 and 5,185,439. Chemiluminescence is triggered by reaction with alkaline hydrogen peroxide which yields an excited N-methyl acridone that subsequently collapses to ground state with the emission of a photon. Additionally, AE causes ester hydrolysis which yields the nonchemiluminescent-methyl acridinium carboxylic acid.

When the AE molecule is covalently attached to a nucleic acid probe, hydrolysis is rapid under mildly alkaline conditions. When the AE-labeled probe is exactly complementary to the target nucleic acid, the rate of AE hydrolysis is greatly reduced. Thus, hybridized and unhybridized AE-labeled probe can be detected directly in solution, without the need for physical separation.

HPA generally consists of the following steps: (a) the AE-labeled probe is hybridized with the target nucleic acid in solution for about 15 to about 30 minutes. A mild alkaline solution is then added and AE coupled to the unhybridized probe is hydrolyzed. This reaction takes approximately 5 to 10 minutes. The remaining hybrid-associated AE is detected as a measure of the amount of target present. This step takes approximately 2 to 5 seconds. Preferably, the differential hydrolysis step is conducted at the same temperature as the hybridization step, typically at 50 to 70 degrees celsius. Alternatively, a second differential hydrolysis step may be conducted at room temperature. This allows elevated pHs to be used, for example in the range of 10-11, which yields larger differences in the rate of hydrolysis between hybridized and unhybridized AE-labeled probe. HPA is described in detail in, e.g., U.S. Pat. Nos. 6,004,745; 5,948,899; and 5,283,174, the disclosures of which are incorporated by reference herein in their entireties.

The oligonucleotide molecules of the present invention may also be used in nucleic acid sequence-based amplification (NASBA). This method is a promoter-directed, enzymatic process that induces in vitro continuous, homogeneous and isothermal amplification of a specific nucleic acid to provide RNA copies of the nucleic acid. The reagents for conducting NASBA include a first DNA primer with a 5' tail comprising a promoter, a second DNA primer, reverse transcriptase, RNAse-H, T7 RNA polymerase, NTP's and dNTP's. Using NASBA, large amounts of single-stranded RNA are generated from either single-stranded RNA or DNA, or double-stranded DNA. When RNA is to be amplified, the ssRNA serves as a template for the synthesis of a first DNA strand by elongation of a first primer containing an RNA polymerase recognition site. This DNA strand in turn serves as the template for the synthesis of a second, complementary, DNA strand by elongation of a second primer, resulting in a double-stranded active RNA-polymerase promoter site, and the second DNA strand serves as a template for the synthesis of large amounts of the first template, the ssRNA, with the aid of a RNA polymerase. The NASBA technique is known in the art and described in, e.g., European Patent 329,822, International Patent Application No. WO 91/02814, and U.S. Pat. Nos. 6,063,603, 5,554,517 and 5,409,818, all of which are incorporated herein in their entireties.

The BKV sequences described herein are also useful in nucleic acid hybridization and amplification techniques that utilize branched DNA molecules. In a basic nucleic acid hybridization assay, single-stranded analyte nucleic acid is hybridized to a labeled single-stranded nucleic acid probe and resulting labeled duplexes are detected. Variations of this basic scheme have been developed to facilitate separation of the duplexes to be detected from extraneous materials and/or to amplify the signal that is detected. One method for amplifying the signal uses amplification multimers that are polynucleotides with a first segment that hybridizes specifically to the analyte nucleic acid or a strand of nucleic acid bound to the analyte and iterations of a second segment that hybridizes specifically to a labeled probe. The amplification is theoretically proportional to the number of iterations of the second segment. The multimers may be either linear or branched. Two general types of branched multimers are useful in these techniques: forked and combed. Methods for making and using branched nucleic acid molecules are known in the art and described in, e.g., U.S. Pat. No. 5,849,481, incorporated herein by reference in its entirety.

As is readily apparent, design of the assays described herein are subject to a great deal of variation, and many formats are known in the art. The above descriptions are merely provided as guidance and one of skill in the art can readily modify the described protocols, using techniques well known in the art.

Kits

Kits for use in connection with the subject invention are also provided. The above-described assay reagents, including the primers, probes, solid support with bound probes, as well as other detection reagents, can be provided in kits, with suitable instructions and other necessary reagents, in order to conduct the assays as described above. The kit will normally contain in separate containers the combination of primers and probes (either already bound to a solid matrix or separate with reagents for binding them to the matrix), control formulations (positive and/or negative), labeled reagents when the assay format requires same and signal generating reagents (e.g., enzyme substrate) if the label does not generate a signal directly. Instructions (e.g., written, tape, VCR, CD-ROM, etc.) for carrying out the assay usually will be included in the kit. The kit can also contain, depending on the particular assay used, other packaged reagents and materials (i.e. wash buffers and the like). Standard assays, such as those described above, can be conducted using these kits.

The instructions are generally recorded on a suitable recording medium. For example, the instructions may be printed on a substrate, such as paper or plastic, etc. As such, the instructions may be present in the kits as a package insert, in the labeling of the container of the kit or components thereof (e.g., associated with the packaging or subpackaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed from or from where the instructions can be downloaded.

Still further, the kit may be one in which the instructions are obtained are downloaded from a remote source, as in the Internet or world wide web. Some form of access security or identification protocol may be used to limit access to those entitled to use the subject invention. As with the instructions, the means for obtaining the instructions and/or programming is generally recorded on a suitable recording medium.

In general, kits of the invention include at least one primer, usually at least two primers (a 5' and a 3' primer), usually at least two primers and a probe, as described above. Kits may also contain instructions for using the kit to detect BKV in a sample using the methods described above, including the above discussed PCR methods. Also included in the subject kits may be buffers, dNTPs, and controls, (e.g., positive and negative control nucleic acids) for performing the subject methods. Primers in the subject kits may be detectably labeled or unlabeled).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Materials and Methods

The following method and material were used in the Example(s) below.

Specimen Types and Handing. Samples for use in detection of BKV according to the invention can be any suitable biological sample, such as serum, plasma, amniotic fluid, and tissue specimen. Tissue specimens should be stored frozen at $-20\pm10°$ C. in saline or phosphate buffered saline (PBS). Serum, plasma, and amniotic fluid should be stored frozen at $-20\pm10°$ C. All of the above specimen types, as needed, can be shipped on dry ice via overnight express, Primers and Probes. Oligonucleotide primers and probes were designed and analyzed for their suitability for PCR and hybridization by computer analysis using standard program (Primer Express, Applied Biosystems). Oligonucleotide primers and fluorogenic probes were synthesized by qualified vendors. Oligonucleotide primers were desalted and lyophilized. Oligonucleotide primer pair sets for detection of BKV were as follows:

| SEQ ID NO.: | Sequence 5' to 3' |
|---|---|
| Target Region I (BK1) | |
| SEQ ID NO:06 F | AACAAAAAAAGAGCTCAGAGGATTT |
| SEQ ID NO:07 R | AAGTACCACTGCTTTACCTGCTGTAA |
| SEQ ID NO:08 P | TTTGTAGAGGTGAAGACAGTGTAGACGGGAAAAA |
| Target Region II (BK2) | |
| SEQ ID NO:09 F | TTGCCCCAGGAGGTGCTA |
| SEQ ID NO:10 R | TTTACTTCTAGGCCTGTACGGGA |
| SEQ ID NO:11 P | TCAAAGAACTGCTCCTCAATGGATGTTGC |
| Target Region III (BK3) | |
| SEQ ID NO:12 F | GGAAAGTCTTTAGGGTCTTCTACCTTT |
| SEQ ID NO:13 R | TCATCACTGGCAAACATATCTTCATG |
| SEQ ID NO:14 P | GTGTTGAGAATCTGCTGTTGCTTCT |
| Target Region IV (BK4) | |
| SEQ ID NO:15 F | ATGGGTGCTGCTCTAGCAC |
| SEQ ID NO:16 R | GTGGCTGAAATTGCTGCTGG |
| SEQ ID NO:17 P | TGCCAGTGTATCTGAGGCTGCTGCTGC |
| Target Region V (BK5) | |
| SEQ ID NO:18 F | GGGCTGAAGTATCTGAG |
| SEQ ID NO:19 R | CAGTGCTTGATCCATGTC |
| SEQ ID NO:20 P | CTTGGGAAGAGCATTGTGATTGG |

"F" refers to the forward primer "R" to the reverse primer, and "P" refers to probe. Probes are frozen at a 100 µM concentration. The working concentration of the probes is 5 µM and are diluted 1:10 with 10 mM Tris-HCl, pH 8.0, and distributed into 100 µL aliquots.

Probes can be stored at $-20°$ C. or lower and protected from light.

Enzymes. The following enzymes are used: 2×TaqMan® Universal PCR Master Mix Applied Biosystems Cat. #4304437 or 4318157, which includes the AmpliTaq Gold DNA Polymerase of Applied Biosystems Reagents and Buffers. The following were used in the assays: QIAamp DNA Blood Mini Kit (QIAGEN Cat. No. 51106);

Equipment. Equipment used included the ABI PRISM® Sequence Detection System 7500

Amplification. DNA amplification was achieved by widely used PCR method described above (see, for example, Persing et al, 1993, Diagnostic Molecular Microbiology: Principles and Amplifications, American Society for Microbiology, Washing D.C.). Amplified DNA sequence was detected by hybridization and cleavage of dual labeled oligonucleotide probe by the Taqman method. Briefly, the amplification and detection protocols were as follows: extracted DNA from clinical specimens were amplified in 25 µl PCR reaction mixture (PCR Master Mix, Applied Biosystems) containing 500 nM of each primers, 100 nM of dual labeled probed (Taqman probe), 200 uM of each of the four dNTPs. The AmpliTaq Gold polymerase was used in the mix, which is a heat activation (hot start) enzyme to enhance the specificity and sensitivity of the amplification. The PCR reaction was subjected to thermal cycling (10 min at 95 C, followed by 40 cycles of 30 second at 95 C, 30 second at 60 C) by using ABI7500 Real Time PCR System. The amplification and detection was monitored at real time, and was analyzed after completion of PCR cycling by using ABI's Sequence Detection Software (v1.2.2).

Specificity. The specificity of oligonucleotide primers and probes, derived from the sequenced DNA and the sequences available in GenBank, were tested on a panel of clinical BKV positive and negative samples. The primers and probes were also tested on JCV positive and negative samples, as well as a number of controls. The results were compared with the result by PCR assay currently used in clinical laboratories. Some of the amplified nucleic acids were sequenced in order to validate the specificity of the assay. The sequencing of the amplified nucleic acids confirmed that all PCR fragments were indeed BKV sequences. None of these sequences fragments correlated to JCV sequences or sequences from any other species.

Sensitivity. The sensitivity of the assays was analyzed by titration of known concentration series of BKV DNA and converting the concentrations into standard curves. Since there are several primer/probe sets targeting different regions, the sensitivity varied slightly. Overall, the analytical sensitivity reached 5 copy or lower per reaction tube. Based on the sample preparation procedure and volume adjustment protocol, this analytical sensitivity was equivalent to about 200 copies per ml for clinical specimen (e.g., serum, urine, or other form of liquid specimen).

EXAMPLE 1

Complete Sequencing of BKV Whole Genome

In order to understand the genomic diversity of BKV and to identify candidate sequences for its diagnostic applications, whole viral genome sequencing was performed. Urine samples were collected from 13 BKV positive patients. To avoid close clinical relationship, these patients were chosen from geographically diversified resources and were otherwise randomly selected. Samples were extracted for viral DNA by regular method. The extracted DNA was then amplified for its whole 5.1 kb genome by long PCR protocol (Stratagene). The amplified viral DNA was sequenced by four-color, dideoxy termination method with a set of pre-designed sequencing primers, and separated on ABI377 sequencer system. The sequence pieces were assembled into complete 5.1-5.2 kb contigs by Lasergene 6 software for each BKV genome for analysis.

Thirteen assembled BKV contigs were aligned against each other and also aligned against all published BKV sequences. Published sequence information was acquired from public databases (GenBank, EMBL and Swiss-Port). 32 complete BKV genome sequences were compared, including the 13 newly sequenced BKV sequences and the 19 published BKV sequences (GenBank Accession Nos.: AY628224, AY628225, AY628226, AY628227, AY628228, AY628229, AY628230, AY628231, AY628232, AY628233, AY628234, AY628235, AY628236, AY628237, AY628238, M23122, NC001538, V01108, and V01109).

First, all the sequences from the BKV strains were compared to one another. Then, the BKV sequences were then compared to genomes of other closely related species. Of all the species that were screened, of particular interest were the human polyomavirus JC viruses (JCV), another member in the polyomavirus family.

Complete sequence alignment within BKV genome allowed for the selection of several candidate sequence regions for diagnostic detection. These regions share consensus across all 32 BKV genomes, and have minimal variations in their sequences. Sequences outside these regions are either not consensus or are highly polymorphic, which make them very difficult to be used for ubiquity detection in diagnostic applications. A comparative analysis was further performed against sequences from all other species in public databases. Notably, JCV shares a high homology with BKV. Despite the homology, comparison of selected regions of BKV with JCV showed some sequence differences. These sequence differences, though limited, are critical for differential detection of BKV from JCV.

Of the 5100+ base pairs from the complete whole genome, there are a total of 142 previously unpublished nucleotide variations that were identified. Of these nucleotide variations, 105 were nucleotide substitutions (single or multiple base pairs) and 37 were deletions or insertions (multiple base pairs). The newly identified variations distributed throughout the entire BKV genome. A fine map of genetic diversity of BKV was created by combining the newly identified sequence variations with variations from public databases. As shown in FIG. 1, this map illustrates regions which are highly polymorphic and regions which are relatively conservative. Analysis of this fine map allows for selection of candidate sequence regions for diagnostic applications.

EXAMPLE 2

Identification of Target Region I ("BK1")

As shown in FIG. 1, the comparison of sequences across all newly completed nucleic acid sequences and published nucleic acid sequences allowed the selection of more than one sequence regions that are conserved and will provide for specific and sensitive nucleic acid based detection of the presence or absence of BKV in a biological sample. The BK1 region comprising of nucleotides 435 to 585 of GenBank Accession No. AY628224 was selected for PCR primer design. The nucleic acid sequence of the BK1 target sequence is:

```
AACAAAAAAAAGAGCTCAGAGGATTTTTATTTTTAT (SEQ ID NO:01)
TTTAGAGCTTTTGCTGGAATTTTGTAGAGGTGAAGA
CAGTGTAGACGGGAAAAACAAAGGTACCACTGCTTT
ACCTGCTGTAAAAGACTCTGTAAAAGACTCCTAGGT
AAGTAAT
```

The strategy used to design the nucleic acid based amplification primers was based on the analysis of multiple sequences alignment of all BKV genomic sequences and sequences of closely related viruses. This analysis was designed to include all variants of BKV. This analysis was also designed to exclude any closely related, but non BKV sequences, such as sequence of JCV. A careful analysis of these alignments allowed the selection of oligonucleotide sequences which cover sequences of all BKV variants but discriminate sequences from any other closely related genera, thereby permitting the genus-specific amplification and ubiquitous detection and identification of BKV. The sequences of the primers and probe for the BK1 target region are as follows:

| SEQ ID NO.: | | Sequence 5' to 3' |
|---|---|---|
| Target Region I (BK1) | | |
| SEQ ID NO:06 | F | AACAAAAAAAAGAGCTCAGAGGATTT |
| SEQ ID NO:07 | R | AAGTACCACTGCTTTACCTGCTGTAA |
| SEQ ID NO:08 | P | TTTGTAGAGGTGAAGACAGTGTAGACGGGAAAAA |

For confirmation of specific detection of BKV, PCR amplification products from BKV specimens were sequenced and analyzed. The amplification product sequences were aligned well with the sequence of BKV, and none of the amplification product sequences were identified as sequence of JCV or of any other genera. The results of the assay are shown in FIG. 2. Template concentrations ranged from 50 copies per reaction to 50,000 per reaction, and the assay were performed in duplicate. BK1 assay: slope=−3.58, intercept=43.428, and $R^2$=0.997.

EXAMPLE 3

Identification of Target Region II ("BK2")

The comparison of nucleic acid sequences across all newly completed BKV nucleic acid sequences and published BKV nucleic acid sequences allowed the selection of the BK2 target region. The BK2 target region comprises nucleotides 1418 to 1545 of GenBank Accession No. AY628224. The nucleic acid sequence of the BK2 target sequence is:

```
TGTACATTCAGGAGAGTTTATAGAAAAAACTATTGC (SEQ ID NO:02)
CCCAGGAGGTGCTAATCAAAGAACTGCTCCTCAATG
GATGTTGCCTTTACTTCTAGGCCTGTACGGGACTGT
AACACCTGCTCTTGAAGCAT
```

The strategy used to design the nucleic acid based amplification primers and probes was based on the analysis of multiple sequences alignment of all BKV sequences and sequences of closely related viruses. This analysis was designed to include all variants of BKV. This analysis was also designed to exclude any closely related, but non BK sequences, such as sequence of JCV. A careful analysis of these alignments allowed the selection of oligonucleotide sequences which cover sequences of all BKV variants but discriminate sequences from any other closely related genera, thereby permitting the genus-specific amplification and ubiquitous detection and identification of BKV. The sequences of the primers and probe for the BK2 target region are as follows:

| SEQ ID NO.: | | Sequence 5' to 3' |
|---|---|---|
| Target Region II (BK2) | | |
| SEQ ID NO:09 | F | TTGCCCCAGGAGGTGCTA |
| SEQ ID NO:10 | R | TTTACTTCTAGGCCTGTACGGGA |
| SEQ ID NO:11 | P | TCAAAGAACTGCTCCTCAATGGATGTTGC |

For confirmation of specific detection of BKV, PCR amplification products from BKV specimens were sequenced and analyzed. The amplification product sequences were aligned well with the sequence of BKV, and none of the amplification product sequences were identified as sequence of JCV or of any other genera. The results of the assay are shown in FIG. 2. Template concentrations ranged from 50 copies per reaction to 50,000 per reaction, and the assay were performed in duplicate. For the For the BK2 assay: slope=−3.48, intercept=44.053, $R^2$=0.999.

EXAMPLE 4

Identification of Target Region III ("BK3")

The comparison of nucleic acid sequences across all newly completed BKV nucleic acid sequences and published BKV nucleic acid sequences allowed the selection of the BK2 target region. The BK3 target region comprises nucleotides 4097 to 4560 of GenBank Accession No. AY628224. The nucleic acid sequence of the BK3 target sequence is:

```
AGTAAGTATTCCTTATTAACACCCTTACAAATTAAA (SEQ ID NO:03)
AAACTAAAGGTACACAGCTTTTGACAGAAATTATTA
ATTGCAGAAACTCTATGTCTATGTGGAGTTAAAAAG
AATATAATATTATGCCCAGCACACATGTGTCTACTA
ATGAAAGTTACAGAATATTTTTCCATAAGTTTTTTA
TACAGAATTTGAGCTTTTTCTTTAGTAGTATACACA
GCAAAGCAGGCAAGGGTTCTATTACTAAATACAGCT
TGACTAAGAAACTGGTGTAGATCAGAGGGAAAGTCT
TTAGGGTCTTCTACCTTTCTCTTTTTCTTGGGTGGT
GTGGAGTGTTGAGAATCTGCTGTTGCTTCTTCATCA
CTGGCAAACATATCTTCATGGCAAAATAAATCTTCA
TCCCATTTTTCATTAAAGGAGCTCCACCAGGACTCC
CACTCTTCTGTTCCATAGGTTGGCACCTATAA
```

The strategy used to design the nucleic acid based amplification primers and probes was based on the analysis of multiple sequences alignment of all BKV sequences and sequences of closely related viruses. This analysis was designed to include all variants of BKV. This analysis was also designed to exclude any closely related, but non BK sequences, such as sequence of JCV. A careful analysis of these alignments allowed the selection of oligonucleotide sequences which cover sequences of all BKV variants but discriminate sequences from any other closely related genera, thereby permitting the genus-specific amplification and ubiquitous detection and identification of BKV. The sequences of the primers and probe for the BK3 target region are as follows:

| SEQ ID NO.: | | Sequence 5' to 3' |
|---|---|---|
| Target Region III (BK3) | | |
| SEQ ID NO:12 | F | GGAAAGTCTTTAGGGTCTTCTACCTTT |

-continued

| SEQ ID NO.: | | Sequence 5' to 3' |
|---|---|---|
| SEQ ID NO:13 | R | TCATCACTGGCAAACATATCTTCATG |
| SEQ ID NO:14 | P | GTGTTGAGAATCTGCTGTTGCTTCT |

For confirmation of specific detection of BKV, PCR amplification products from BKV specimens were sequenced and analyzed. The amplification product sequences were aligned well with the sequence of BKV, and none of amplification product sequences were identified as sequence of JCV or of any other genera. The results of the assay are shown in FIG. 2. Template concentrations ranged from 50 copies per reaction to 50,000 per reaction, and the assay were performed in duplicate. For the BK3 assay: slope=−3.49, intercept=44.819, $R^2$=0.999.

EXAMPLE 5

Identification of Target Region IV ("BK4")

The comparison of nucleic acid sequences across all newly completed BKV nucleic acid sequences and published BKV nucleic acid sequences allowed the selection of the BK4 target region. The BK4 target region comprises nucleotides 612 to 864 of GenBank Accession No. AY628224. The nucleic acid sequence of the BK4 target sequence is:

```
ATGGGTGCTGCTCTAGCACTTTTGGGGGACCTAGTT (SEQ ID NO:04)
GCCAGTGTATCTGAGGCTGCTGCTGCCACAGGATTT
TCAGTGGCTGAAATTGCTGCTGGGGAGGCTGCTGCT
GCTATAGAAGTTCAAATTGCATCCCTTGCTACTGTA
GAGGGCATAACAAGTACCTCAGAGGCTATAGCTGCC
ATAGGCCTAACTCCTCAAACATATGCTGTAATTGCT
GGTGCTCCTGGGGCTATTGCTGGGTTTGCTGCTTTA
A
```

The strategy used to design the nucleic acid based amplification primers and probes was based on the analysis of multiple sequences alignment of all BKV sequences and sequences of closely related viruses. This analysis was designed to include all variants of BKV. This analysis was also designed to exclude any closely related, but non BK sequences, such as sequence of JCV. A careful analysis of these alignments allowed the selection of oligonucleotide sequences which cover sequences of all BKV variants but discriminate sequences from any other closely related genera, thereby permitting the genus-specific amplification and ubiquitous detection and identification of BKV. The sequences of the primers and probe for the BK4 target region are as follows:

| SEQ ID NO.: | | Sequence 5' to 3' |
|---|---|---|
| Target Region IV (BK4) | | |
| SEQ ID NO:15 | F | ATGGGTGCTGCTCTAGCAC |
| SEQ ID NO:16 | R | GTGGCTGAAATTGCTGCTGG |
| SEQ ID NO:17 | P | TGCCAGTGTATCTGAGGCTGCTGCTGC |

For confirmation of specific detection of BKV, PCR amplification products from BKV specimens were sequenced and analyzed. The amplification product sequences were aligned well with the sequence of BKV, and none of amplification product sequences were identified as sequence of JCV or of any other genera. The results of the assay are shown in FIG. 2. Template concentrations ranged from 50 copies per reaction to 50,000 per reaction, and the assay were performed in duplicate. For the BK4 assay: slope=−3.21, intercept=41.466, $R^2$=0.999.

The analytical sensitivity of the oligonucleotide primer and probe was tested by titration of known concentration series of DNA and calculated by using standard curve analysis. It was demonstrated that the analytical sensitivity of the assay reached 5 copy or lower per reaction tube. Adjusted from the sample preparation procedure and volume adjustment protocol, this analytical sensitivity is equivalent to about 200 copies per ml of liquid clinical specimens.

The primer/probe set was tested on a panel of total 333 previously tested clinical samples. The panel included 47 of known BKV positive (detected), and 286 of known BKV negative (non detected) samples. The oligonucleotide primer/probe set detected all 47 positive samples. Furthermore, out of the 284 negative samples, it detected 34 as BKV positive. To validate those "missed" positive result, 28 were sequenced. All of the 28 sequenced amplification products were identified as BKV. The remaining 6 samples could not be sequenced due to insufficient sample volume. Overall, at least 10% of clinically negative samples was detected as BKV positive by the new primer/probe strategy and were validated by sequencing as true positive. The failure of detecting such percentage of true positive could be caused by primer/probe mismatch on variation sites or poor PCR efficiency or both.

EXAMPLE 6

Identification of Target Region V ("BK5")

The comparison of nucleic acid sequences across all newly completed BKV nucleic acid sequences and published BKV nucleic acid sequences allowed the selection of the BK4 target region. The BK4 target region comprises nucleotides 2810 to 2895 of GenBank Accession No. AY628224. The nucleic acid sequence of the BK5 target sequence is:

```
                                            (SEQ ID NO:05)
GGGGCTGAAGTATCTGAGACTTGGGAAGAGCATTGTGATTGGGATTCAGT

GCTTGATCCATGTCCAGAGTCTTCAGTTTCTGAATC
```

The strategy used to design the nucleic acid based amplification primers and probes was based on the analysis of multiple sequences alignment of all BKV sequences and sequences of closely related viruses. This analysis was designed to include all variants of BKV. This analysis was also designed to exclude any closely related, but non BK sequences, such as sequence of JCV. A careful analysis of these alignments allowed the selection of oligonucleotide sequences which cover sequences of all BKV variants but discriminate sequences from any other closely related genera, thereby permitting the genus-specific amplification and ubiquitous detection and identification of BKV. The sequences of the primers and probe for the BK5 target region are as follows:

| SEQ ID NO.: | | Sequence 5' to 3' |
|---|---|---|
| Target Region V (BK5) | | |
| SEQ ID NO:18 | F | GGGCTGAAGTATCTGAG |
| SEQ ID NO:19 | R | CAGTGCTTGATCCATGTC |
| SEQ ID NO:20 | P | CTTGGGAAGAGCATTGTGATTGG |

For confirmation of specific detection of BKV, PCR amplification products from BKV specimens were sequenced and analyzed. The amplification product sequences were aligned well with the sequence of BKV, and none of amplification product sequences were identified as sequence of JCV or of any other genera. The results of the assay are shown in FIG. 2. Template concentrations ranged from 50 copies per reaction to 50,000 per reaction, and the assay were performed in duplicate. For the BK5 assay: slope=−3.61, intercept=47.324, $R^2$=0.994.

It is evident from the above results and discussion that the subject invention provides an important new means for the detection of BK virus as well as differentiating between different BK virus genotypes or strains. As such, the subject methods and systems find use in a variety of different applications, including research, medical, therapeutic, diagnostic, military and other applications. Accordingly, the present invention represents a significant contribution to the art.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of detecting the presence or absence of BK virus (BKV) nucleic acid in a sample, the method comprising contacting said sample with one or more oligonucleotides designed to hybridize to SEQ ID NO: 1 or a complement thereof but not to JC virus nucleic acid under conditions which discriminate between BKV and JCV nucleic acid and detecting if the hybridization of said one or more oligonucleotides to SEQ ID NO: 1 or a complement thereof has occurred, wherein said hybridization detects the presence or absence of BKV nucleic acid.

2. The method of claim 1, wherein said step of detecting if hybridization has occurred comprises nucleic acid-based amplification.

3. The method of claim 2, wherein said amplification generates a product about 30 nucleotides or less in length.

4. The method of claim 1, further comprising detecting the presence or absence of a second BKV nucleic acid in the sample, wherein said detecting a second BKV nucleic acid is achieved by contacting said sample with one or more oligonucleotides designed to hybridize to SEQ ID NO: 4 or a complement thereof but not to JC virus nucleic acid under conditions which discriminate between BKV and JCV nucleic acid and detecting if the hybridization of said one or more oligonucleotides to SEQ ID NO: 4 or a complement thereof has occurred, wherein said hybridization detects the presence or absence of BKV nucleic acid.

5. A method of detecting the presence or absence of BK virus (BKV) nucleic acid in a sample, the method comprising contacting said sample with one or more oligonucleotides designed to hybridize to SEQ ID NO: 4 or a complement thereof but not to JC virus nucleic acid under conditions which discriminate between BKV and JCV nucleic acid and detecting if the hybridization of said one or more oligonucleotides to SEQ ID NO: 4 or a complement thereof has occurred, wherein said hybridization detects the presence or absence of BKV nucleic acid.

6. The method of claim 5, wherein said step of detecting if hybridization has occurred comprises nucleic acid-based amplification.

7. The method of claim 6, wherein said amplification generates a product about 30 nucleotides or less in length.

8. The method of claim 1, wherein one of said oligonucleotide comprises nucleotides 57-90 of SEQ ID NO: 1 or a complement thereof.

9. The method of claim 2, wherein said nucleic acid amplification is achieved by amplifying a portion of SEQ ID NO: 1 using primer pairs of SEQ ID NO: 6 and SEQ ID NO: 7 or a complement thereof.

10. The method of claim 1, wherein at least one of said oligonucleotides designed to hybridize to SEQ ID NO: 1 or a complement thereof is a degenerate oligonucleotide.

11. The method of claim 1, wherein at least one of said oligonucleotides designed to hybridize to SEQ ID NO: 1 or a complement thereof comprises a detectable label.

12. The method of claim 11, wherein said detectable label is a fluorophore.

13. The method of claim 12, wherein at least one or more of said oligonucleotides designed to hybridize to SEQ ID NO: 1 or a complement thereof comprises a quencher molecule.

14. The method of claim 13, wherein the fluorophore and quencher molecule are attached to same oligonucleotide.

15. The method of claim 1, wherein said step of detecting if hybridization has occurred comprises nucleic acid sequencing.

16. The method of claim 4, wherein said detecting a second BKV nucleic acid is achieved by amplifying a portion of SEQ ID NO: 4 or complement thereof.

17. The method of claim 4, wherein at least one of said oligonucleotides designed to hybridize to SEQ ID NO: 4 or a complement thereof is a degenerate oligonucleotide.

18. The method of claim 4, wherein at least one of said oligonucleotides designed to hybridize to SEQ ID NO: 4 or a complement thereof comprises a detectable label.

19. The method of claim 18, wherein said detectable label is a fluorophore.

20. The method of claim 19, wherein at least one or more of said oligonucleotides designed to hybridize to SEQ ID NO: 4 or a complement thereof comprises a quencher molecule.

21. The method of claim 20, wherein the fluorophore and quencher molecule are attached to same oligonucleotide.

22. The method of claim 4, wherein said step of detecting if hybridization has occurred comprises nucleic acid sequencing.

23. The method of claim 5, wherein one of said oligonucleotides designed to hybridize to SEQ ID NO: 4 or a complement thereof comprises nucleotides 32-62 of SEQ ID NO: 4.

24. The method of claim 5, wherein at least one of said oligonucleotides designed to hybridize to SEQ ID NO: 4 or a complement thereof is a degenerate oligonucleotide.

25. The method of claim 5, wherein at least one of said oligonucleotides designed to hybridize to SEQ ID NO: 4 or a complement thereof comprises a detectable label.

26. The method of claim 25, wherein said detectable label is a fluorophore.

27. The method of claim 26, wherein at least one or more of said oligonucleotides designed to hybridize to SEQ ID NO: 4 or a complement thereof comprises a quencher molecule.

28. The method of claim 27, wherein the fluorophore and quencher molecule are attached to same oligonucleotide.

29. The method of claim 5, wherein said step of detecting if hybridization has occurred comprises nucleic acid sequencing.

30. The method of claim 6, wherein said nucleic acid amplification is achieved by amplifying a portion of SEQ ID NO: 4 or a complement thereof using primer pairs of SEQ ID NO: 15 and SEQ ID NO: 16.

* * * * *

UNITED STATES PATENT AND TRADEMARK OFFICE
CERTIFICATE OF CORRECTION

| | | |
|---|---|---|
| PATENT NO. | : 7,892,795 B2 | Page 1 of 1 |
| APPLICATION NO. | : 11/246904 | |
| DATED | : February 22, 2011 | |
| INVENTOR(S) | : Fan Chen et al. | |

It is certified that error appears in the above-identified patent and that said Letters Patent is hereby corrected as shown below:

Column 3, line 39, delete the word "intemucleotide" and insert --internucleotide--.

Column 3, line 60, delete the word "andN" and insert --and N--.

Column 8, line 53, delete the word "MRNA" and insert --mRNA--.

Column 10, line 2, delete the phrase "25.degree. C." and insert --25°C--.

Column 14, line 4 and 67, delete the word "contemplates" and insert --contemplated--.

Column 16, line 7, delete the word "contemplates" and insert --contemplated--.

Column 17, line 9, delete the word "contemplates" and insert --contemplated--.

Column 18, line 4, delete the word "contemplates" and insert --contemplated--.

Column 23, line 62, delete the word "DATP" and insert --dATP--.

Column 29, line 60, delete the word "method" and insert --methods--.

Column 35, line 8, delete the word "assay" and insert --assays--.

Signed and Sealed this
Twelfth Day of July, 2011

David J. Kappos
*Director of the United States Patent and Trademark Office*

```
                          SEQUENCE LISTING

<160> NUMBER OF SEQ ID NOS: 54

<210> SEQ ID NO 1
<211> LENGTH: 151
<212> TYPE: DNA
<213> ORGANISM: Human polyomavirus type BK virus

<400> SEQUENCE: 1
aacaaaaaaa agagctcaga ggatttttat ttttatttta gagcttttgc tggaattttg      60
tagaggtgaa gacagtgtag acgggaaaaa caaaggtacc actgctttac ctgctgtaaa     120
agactctgta aaagactcct aggtaagtaa t                                    151

<210> SEQ ID NO 2
<211> LENGTH: 128
<212> TYPE: DNA
<213> ORGANISM: Human polyomavirus type BK virus

<400> SEQUENCE: 2
tgtacattca ggagagttta tagaaaaaac tattgcccca ggaggtgcta atcaaagaac      60
tgctcctcaa tggatgttgc ctttacttct aggcctgtac gggactgtaa cacctgctct     120
tgaagcat                                                              128

<210> SEQ ID NO 3
<211> LENGTH: 464
<212> TYPE: DNA
<213> ORGANISM: Human polyomavirus type BK virus

<400> SEQUENCE: 3
agtaagtatt ccttattaac acccttacaa attaaaaaac taaaggtaca cagcttttga      60
cagaaattat taattgcaga aactctatgt ctatgtggag ttaaaaagaa tataatatta     120
tgcccagcac acatgtgtct actaatgaaa gttacagaat attttccat aagtttttta     180 tacagaattt gagcttttc tttagtagta tacacagcaa agcaggcaag ggttctatta     240
ctaaatacag cttgactaag aaactggtgt agatcagagg gaaagtcttt agggtcttct     300
acctttctct ttttcttggg tggtgtggag tgttgagaat ctgctgttgc ttcttcatca     360
ctggcaaaca tatcttcatg gcaaaataaa tcttcatccc attttcatt aaaggagctc     420 caccaggact cccactcttc tgttccatag gttggcacct ataa                     464

<210> SEQ ID NO 4
<211> LENGTH: 253
<212> TYPE: DNA
```

-continued

<213> ORGANISM: Human polyomavirus type BK virus

<400> SEQUENCE: 4

```
atgggtgctg ctctagcact tttgggggac ctagttgcca gtgtatctga ggctgctgct      60
gccacaggat tttcagtggc tgaaattgct gctggggagg ctgctgctgc tatagaagtt     120
caaattgcat cccttgctac tgtagagggc ataacaagta cctcagaggc tatagctgcc     180
ataggcctaa ctcctcaaac atatgctgta attgctggtg ctcctggggc tattgctggg     240
tttgctgctt taa                                                        253
```

<210> SEQ ID NO 5
<211> LENGTH: 86
<212> TYPE: DNA
<213> ORGANISM: Human polyomavirus type BK virus

<400> SEQUENCE: 5

```
ggggctgaag tatctgagac ttgggaagag cattgtgatt gggattcagt gcttgatcca      60
tgtccagagt cttcagtttc tgaatc                                           86
```

<210> SEQ ID NO 6
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 6

```
aacaaaaaaa agagctcaga ggattt                                           26
```

<210> SEQ ID NO 7
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 7

```
aagtaccact gctttacctg ctgtaa                                           26
```

<210> SEQ ID NO 8
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 8

```
tttgtagagg tgaagacagt gtagacggga aaaa                                  34
```

<210> SEQ ID NO 9
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 9

```
ttgccccagg aggtgcta                                                    18
```

<210> SEQ ID NO 10
<211> LENGTH: 23
<212> TYPE: DNA
<213> ORGANISM: Artificial Sequence

```
<220> FEATURE:
<223> OTHER INFORMATION: synthetic oligonucleotide

<400> SEQUENCE: 10
tttacttcta ggcctgtacg gga                                              23

<210> SEQ ID NO 11
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 11
tcaaagaact gctcctcaat ggatgttgc                                        29

<210> SEQ ID NO 12
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 12
ggaaagtctt tagggtcttc taccttt                                          27

<210> SEQ ID NO 13
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 13
tcatcactgg caaacatatc ttcatg                                           26

<210> SEQ ID NO 14
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 14
gtgttgagaa tctgctgttg cttct                                            25

<210> SEQ ID NO 15
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 15
atgggtgctg ctctagcac                                                   19

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 16
gtggctgaaa ttgctgctgg                                                  20
```

-continued

```
<210> SEQ ID NO 17
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 17
tgccagtgta tctgaggctg ctgctgc                                         27

<210> SEQ ID NO 18
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 18
gggctgaagt atctgag                                                    17

<210> SEQ ID NO 19
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 19
cagtgcttga tccatgtc                                                   18

<210> SEQ ID NO 20
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 20
cttgggaaga gcattgtgat tgg                                             23

<210> SEQ ID NO 21
<211> LENGTH: 4012
<212> TYPE: DNA
<213> ORGANISM: Human polyomavirus type BK virus consensus sequenc

<400> SEQUENCE: 21
acagaagaag tgcatgactg cagcacagag aatgagcgat tttgcggcca gaatcttgtg     60
gtttcgccag ctgtcacgac aaaaaaaggc tcagaggatt ttattttat tttagagctt     120 ttgctggaat tttgtagagg taagacagtg tagacgggaa aaacaaagta ccactgcttt    180
acctgctgta aagactctgt aaaagactcc taggtaagta atcttttttt ttgtatttca    240
ggttatgggt gctgctctag cacttttggg ggacctagtt gccagtgtat ctgaggctgc    300
tgctgccaca ggttttcgtg gctgaaattg ctgctgggga ggctgctgct gcatagaagt    360
tcaaattgca tcccttgcta ctgagagggc ataacaatac ctcagaggct atagctgcat    420
aggcctaacc ctcaaacata tgctgtaatt gctggtgctc cggggctatt gctgggtttg    480
ctgctttatt caaactgtta tggtattagt tcttgctcaa gtagggtaag ttttttgatt    540
gggatcacaa agtttccact gtaggcctta tcagcaatca ggcatggctt gaattgttta    600
acccagatga gtactagata ttgtttcctg gtgtaaatac ttttgtaata atattccaata   660 ctgatcctag gcattggggt ccttcttgtt tgctactatt tccaggcttt gtggcatgtt    720
```

-continued

```
attaggatga tatacctcta tactcacaga attgcaagag aacagaagat ttttaggact    780
cttggctaga ttttttggaga aacacctgga cattgtaaat gccctaact tttataatta    840
tattcaatat tattctattt ccctatttag gcctaatggt agcaagtgct gaaagggaag    900
gacccgtaat tttggccatc taagatagat atgctgacag tataaagaag ttaccaaaga    960
atggattaag aaataaatgt acattcagga gagtttatag aaaaactat tgccccagga    1020
ggtgctaatc aaagaactgc tcctcaatgg atgttgcctt tcttctaggc ctgtacggga    1080
ctgtaacacc tgctcttgaa gcattgaaga tggccccaca aaagaaaagg agagtgtcca    1140
ggggcagctc ccaaaaagcc aaggaaccgt gcaagtgcca aaactctaat aaaaggagga    1200
gtagaagttc tagaagttaa aactggtaga tgctatacaa gtagaatgct tctaaaccca    1260
gaaatgggga gatgaaacct tagggcttta gtcctaatgc taaatgcttt agtgatagcc    1320
cagaagaaaa atgcttcctg ttacagacag caagaattcc ctccaataat gaggactaac    1380
ctgtggaatt actatgtggg aggctgtacg taaaacagag gtatggaata actagatgct    1440
aaccttcagc agggtccaaa agtcatgaat ggtggaggaa accttcaggc agaatttcac    1500
tttttgctgt ggtgggaccc ttggaaatgc agggagtcta tgaatacgca agtacccagg    1560
tacttacccc aaaaaccaca gccagtccca gtaatgaata ctgacataag gcctattgga    1620
caaaacaat gctatccagt tgatgctggt cctgaccagt agaaatgaaa atctaggtat    1680
tttggactca caggagggga aaatgttccc cagtacttca tgtaccaaca cagctaccac    1740
agtgttgctg atgaacaggg tgtggggccc ttgtaaagct gatgcctgta tgtttcagct    1800
gctgatattt gtggctgttt actaacagtc tggacacaac agtggagggc cttcaagata    1860
ttttagacgc ctgagaaaaa gatctgtaaa accttaccaa tttcctttgc tagtgaccta    1920
taacagggaa cccaaagtgg atgggcagcc tatgtatggt atggatccag tggaggtagg    1980
gtgtttgatg gcacagaact tccaggggac ccagatatga taagatatat tgaacaggac    2040
aattgcaaac aaaatgttta aacaggtgct ttattgtata tatttaataa atgctgcttt    2100
ttatacatta actttgttat tttggggggtg gtgttttagg cttttaaaac atgaaagcct    2160
ttacacaaat gactcttctt ggggttttct acggggctga agtatctgag acttgggaag    2220
agcattgtga ttgggattca gtgcttgatc catgtccaga gtcttcagtt tctgaatctc    2280
ttctcttgta tacaagaata catttcccat gcatatatta tatttcatcc ttgaaaaagt    2340
atacatactt atctcagaat ccagccttttc ttccattcaa caattctaga tgtatatctg    2400
aaaatcagct acaggcctac caaattagag tagcaaaggt cattccactt tgtaattctt    2460
ttttcaagta aaatcgagtt tgaggatttc ttaaataatt ttggctaaaa tctattgtct    2520
tacaaatcta gctgagtttt ggacaggata ctcattcatt gtaacacctg gtggaaatat    2580
ttggtctttt gtttaatgtt tttttctaaa ttacttacac ttccactaat aatcctaaac    2640
tgtctaaatt gtttattcca tgtcctgaag gcaaatcctt tgattcagcc cgtccttaca    2700
tctcaaaaac aaccatactg atcatagcac accagtcaaa gtagccttcc atgggtatta    2760
catttaagct ttcccacaaa tctaaaccct gcagctagtt gttttccact atcatggacc    2820
tttaataacc agtatcttct tttaggtaca ttaaaacaaa cagtgaaaat caaaatacag    2880
aatccatttt aggtacaaac atgagccagc aaccctgcca tatattgttc atacgcattt    2940
ccatgagccc aaatataaat ccatttatct aatatatgat taatcttctg ttagcatttc    3000
ttcctgtcat atgaggtatc tacctttttt agctaaactg tatcactgct tgctgacaaa    3060
```

-continued

```
tttttttttt actttctgca aaattagcat ttgcaatgct tttcatgata ttaaagtgta    3120
ggtgtctttt ttgacacttt ttcactctct acattgtatg aaattctaaa tacataccaa    3180
tataaacaca tctcacactt tgttctactg catatcagta ttaattccag aacctgcttt    3240
gttcttcagg tctctgggta aatcatgctc ctttagcccc cttgaatctt tctctattat    3300
tatggtccta gttaaggcac ttaagtaagt attccttatt aacaccctta caaattaaaa    3360
aactaaagta cacagctttt gacagaatta ttaattgcag aaactctatg tctatgtgga    3420
gttaaaaaga atataatatt atgccagcaa catgtgtcta ctataaagtt acagatattt    3480
ttccataagt ttttatatca gattagcttt ttctttagtg tatacacagc aaacaggcag    3540
gttctattac taaaacagct tgactaagaa actggtgtag atcaaggaaa gtctttaggg    3600
tcttctacct tctttttttt gggtggtgtg agtgttggaa tctgctgttg ctctcatcac    3660
tggcaaacat atctcatggc aaataatctt catcccattt ttcattaaag gactccacca    3720
gactcccact cttctgttcc ataggttggc acctataaaa aaaaattact tagggttttt    3780
ttaaaataca aacttctagg tcaatagaca ccttcatctc attacaatca tatcgtgcct    3840
tcaactttct taaatttct ttaagattcg cactcaaggc aagttgatgt cctgtatcga    3900
aagcaaatgt ccataggcta cctacactat ttaaaaagtc ctcctttatt tgcaggggat    3960
cttacctaac tctcaaggaa gtcggcagcg gcaaagacct atcctaatac ca    4012
```

<210> SEQ ID NO 22  
<211> LENGTH: 5141  
<212> TYPE: DNA  
<213> ORGANISM: Human polyomavirus type BK virus majority sequence

<400> SEQUENCE: 22

```
ttttgcaaaa attgcaaaag aatagggatt tccccaaata gttttgctag gcctcagaaa      60
aagcctccac acccttacta cttgagagaa agggtggagg cagaggcggc ctcggcctct     120
tatatattat aaaaaaaaag gccacaggga ggagctgctt acccatggaa tgcagccaaa     180
ccatgacctc aggaaggaaa gtgcatgact gggcagccag ccagtggcag ttaatagtga     240
aaccccgccc ctaaaattct caaataaaca caagaggaag tggaaactgg ccaaaggagt     300
ggaaagcagc cagacagaca tgttttgcga gcctaggaat cttggccttg tccccagtta     360
aactggacaa aggccatggt tctgcgccag ctgtcacgac aagcttctgt gaaagttggt     420
aaaacctgga ctggaacaaa aaaaagagct cagaggattt ttatttttat tttagagctt     480
ttgctggaat tttgtagagg tgaagacagt gtagacggga aaaacaaaag taccactgct     540
ttacctgctg taaagactc tgtaaaagac tcctaggtaa gtaatccctt ttttttgta     600 tttccaggtt gatgggtgct gctctagcac ttttggggga cctagttgcc agtgtatctg     660
aggctgctgc tgccacagga ttttcagtgg ctgaaattgc tgctggggag gctgctgctg     720
ctatagaagt tcaaattgca tcccttgcta ctgtagaggg cataacaagt acctcagagg     780
ctatagctgc tataggccta actcctcaaa catatgctgt aattgctggt gctcctgggg     840
ctattgctgg gtttgctgct ttaattcaaa ctgttactgg tattagttcc ttggctcaag     900
tagggtatag gttttttagt gattgggatc acaaagtttc cactgtaggc ctctatcagc     960
aatcaggcat ggctttggaa ttgtttaacc cagatgagta ctatgatatt tgtttcctg    1020 gtgtaaatac ttttgtaaat aatattcaat accttgatcc taggcattgg ggtccttctt    1080
tgtttgctac tatttcccag gctttgtggc atgttattag ggatgatata cctgctataa    1140
cctcacaaga attgcaaaga agaacagaaa gatttttag agactccttg gctagatttt    1200
```

```
tggaggaaac tacctggaca attgtaaatg cccctataaa cttttataat tatattcaag    1260
aatattattc tgatctttcc cctattaggc cctcaatggt tagacaagta gctgaaaggg    1320
aaggtacccg tgtacatttt ggccatactt atagtataga tgatgctgac agtatagaag    1380
aagttacaca aagaatggac ttaagaaatc aacaaactgt acattcagga gagtttatag    1440
aaaaaactat tgccccagga ggtgctaatc aaagaactgc tcctcaatgg atgttgcctt    1500
tacttctagg cctgtacggg actgtaacac ctgctcttga agcatatgaa gatggcccca    1560
accaaaagaa aaggagagtg tccaggggca gctcccaaaa agccaaagga acccgtgcaa    1620
gtgccaaaac tactaataaa aggaggagta gaagttctag aagttaaaac tggggtagat    1680
gctataacag aggtagaatg cttcctaaac ccagaaatgg gggatccaga tgaaaacctt    1740 aggggctttta gtctaaagct aagtgctgaa aatgacttta gcagtgatag cccagaaaga    1800
aaaatgcttc cctgttacag cacagcaaga attcccctcc ccaatttaaa tgaggaccta    1860
acctgtggaa atctactgat gtgggaggct gtaactgtac aaacagaggt cattggaata    1920
actagcatgc ttaaccttca tgcagggtca caaaaagtgc atgagcatgg tggaggtaaa    1980
cctattcaag gcagtaattt ccacttcttt gctgttggtg gagacccctt ggaaatgcag    2040
ggagtgctaa tgaattacag gacaaagtac ccagatggta ctataacccc aaaaaaccca    2100
acagcccagt cccaggtaat gaatactgac cataaggcct atttggacaa aaacaatgct    2160
tatccagttg agtgctgggt tcctgatccc agtagaaatg aaaatactag gtattttggg    2220
actttcacag gaggggaaaa tgttcccccca gtacttcatg tgaccaacac agctaccaca    2280
gtgttgctag atgaacaggg tgtggggcct cttttgtaaag ctgatagcct gtatgtttca    2340
gctgctgata tttgtggcct gtttactaac agctctggaa cacaacagtg gagaggcctt    2400
gcaagatatt ttaagattcg cctgagaaaa agatctgtaa aaaatcctta cccaatttcc    2460
tttttgctaa gtgaccttat aaacaggaga acccagagag tggatgggca gcctatgtat    2520
ggtatggaat cccaggtaga agaggtcagg gtgtttgatg gcacagaaag acttccaggg    2580
gacccagata tgataagata tattgacaaa caaggacaat tgcaaaccaa aatgcttttaa    2640 acaggtgctt ttattgtaca tatacattta ataaatgctg cttttgtata agccactttt    2700
aagcttgtgt tattttgggg gtggtgtttt aggcctttta aaacactgaa agcctttaca    2760
caaatgcaac tcttgactat gggggtctga cctttgggaa tcttcagcag gggctgaagt    2820
atctgagact tgggaagagc attgtgattg ggattcagtg cttgatccat gtccagagtc    2880
ttcagtttct gaatcttctt ctcttgtgat atcaagaata catttccccca tgcatatatt    2940 atatttcatc cttgaaaaag tatacatact tatctcagaa tccagccttt ccttccattc    3000
aacaattcta gattgtatat ctgttgcaaa atcagctaca ggcctaaacc aaattagcag    3060
tagcaacaag gtcattccac tttgtaaaat tcttttttca gtaagaaact ctgagttttg    3120
taaggatttt cttaaatata ttttgggcct aaaatctatc tgtcttacaa atctagcctg    3180
cagggtttta gggacaggat actcattcat tgtaaccagg cctggtggaa atatttgggt    3240
tcttttgttt aaatgtttct tttctaaatt aaccttaaca cttccatcta aataatctct    3300
caaactgtct aaattgttta ttccatgtcc tgaaggcaaa tcctttgatt cagctcctgt    3360
tccttttaca tcttcaaaaa caaccatgta ctgatctata gctacaccta gttcaaaggt    3420
tagcctttcc atgggtaggt ttacatttaa ggctttacct ccacacaaat ctaataaccc    3480
tgcagctagt gttgtttttc cactatcaat gggaccttta aataaccagt atcttctttt    3540
```

-continued

```
aggtacatta aaaacaatac agtgcaaaaa atcaaatata acagaatcca ttttaggtag    3600
caaacagtgc agccaagcaa cacctgccat atattgttct agtacagcat ttccatgagc    3660
tccaaatatt aaatccattt tatctaatat atgattaaat ctttctgtta gcatttcttc    3720
tctggtcata tgaagggtat ctactctttt tttagctaaa actgtatcta ctgcttgctg    3780
acaaatactt ttttgatttt tactttctgc aaaaatagta gcatttgcaa aatgcttttc    3840
atgatactta aagtgataag gttggtcttt tttctgacac ttttacact cctctacatt     3900 gtattgaaat tctaaataca tacctaataa taaaaacaca tcctcacact ttgtctctac    3960
tgcatactca gtaattaatt tccaagacac ctgctttgtt tcttcaggct cttctgggtt    4020
aaaatcatgc tcctttaagc ccccttgaat gctttcttct attgtatggt atggatctct    4080
agttaaggca ctatatagta agtattcctt attaacaccc ttacaaatta aaaaactaaa    4140
ggtacacagc ttttgacaga aattattaat tgcagaaact ctatgtctat gtggagttaa    4200
aaagaatata atattatgcc cagcacacat gtgtctacta ataaaagtta cagaatattt    4260
ttccataagt tttttataca gaatttgagc ttttctttta gtagtataca cagcaaagca    4320
ggcaagggtt ctattactaa atacagcttg actaagaaac tggtgtagat cagaaggaaa    4380
gtctttaggg tcttctacct ttctttttt cttgggtggt gttgagtgtt gagaatctgc     4440
tgttgcttct tcatcactgg caaacatatc ttcatggcaa ataaatctt catcccattt      4500 ttcattaaag gagctccacc aggactccca ctcttctgtt ccataggttg gcacctataa    4560
aaaaaataat tacttagggc ctttaaatat tttattattt atctaaatat aagttagtta    4620
ccttaaagct ttagatctct gaagggagtt tctccaatta tttggaccca ccattgcaga    4680
gtttcttcag ttaggtctaa gccaaaccac tgtgtgaagc agtcaatgca gtagcaatct    4740
atccaaacca agggctcttt tcttaaaaat tttctattta aatgccttaa tctaagctga    4800
catagcatgc aagggcagtg cacagaaggc ttttggaac aaataggcca ttccttgcag     4860
tacagggtat ctgggcaaag aggaaaatca gcacaaacct ctgagctact ccaggttcca    4920
aaatcaggct gatgagctac ctttacatcc tgctccattt ttttatataa agtattcatt    4980
ctcttcattt tatcctcgtc gccccctttg tcagggtgaa attccttaca cttccttaaa    5040
taggcttttc tcattaaggg aaggtttccc caggcagctc tttcaaggcc taaaaggtcc    5100
atgagctcca tggattcttc cctgttaagc actttatcca t                        5141
```

<210> SEQ ID NO 23
<211> LENGTH: 5141
<212> TYPE: DNA
<213> ORGANISM: Human polyomavirus type BK virus

<400> SEQUENCE: 23

```
ttttgcaaaa attgcaaaag aatagggatt tccccaaata tttttgctag gcctcagaaa      60
aagcctccac acccttacta cttgagagaa agggtggagg cagaggcggc ctcggcctct     120
tatatattat aaaaaaaaag gccacaggga ggagctgcta acccatggaa tgtagccaaa     180
ccatgacctc aggaaggaaa gtgcatgact gggcagccag ccagtggcag ttaatagtga    240
aaccccgccc ctaaaattct caaataaaca caagaggaag tggaaactgg ccaaaggagt    300
ggaaagcagc cagacagaca tgttttgcga gcctaggaat cttggccttg tcccagtta     360 aactggacaa aggccatggt tctgcgccag ctgtcacgac aagcttctgt gaaagttagt    420
aaaacctgga ctgaacaaa aaaaagagct cagaggattt ttattttat ttagagctt      480 ttgctggaat tttgtagagg tgaagacagt gtagacggga aaaacaaagg taccactgct    540
```

```
ttacctgctg taaaagactc tgtaaaagac tcctaggtaa gtaatccctt tttttttgta      600
tttccaggtt gatgggtgct gctctagcac ttttggggga cctagttgcc agtgtatctg      660
aggctgctgc tgccacagga ttttcagtgg ctgaaattgc tgctgggggag gctgctgctg     720
ctatagaagt tcaaattgca tcccttgcta ctgtagaggg cataacaagt acctcagagg      780
ctatagctgc cataggccta actcctcaaa catatgctgt aattgctggt gctcctgggg      840
ctattgctgg gtttgctgct ttaattcaaa ctgttactgg tattagttcc ttggctcaag      900
tagggtatag gttttttagt gattgggatc acaaagtttc cactgtaggc ctctatcagc      960
aatcaggcat ggctttggaa ttgtttaacc cagatgagta ctatgatatt ttgtttcctg     1020
gtgtaaatac ttttgtaaat aatattcaat accttgatcc taggcattgg ggtccttcct     1080
tgtttgctac tatttcccag gctttgtggc atgttattag ggatgatata cctgctataa     1140
cctcacaaga attgcaaaga gaacagaaa gattttttag agactccttg gctagatttt      1200
tggaggaaac tacctggaca attgtaaatg cccctataaa cttttataat tatattcaag     1260
aatattattc tgatctttcc cctattaggc cctcaatggt tagacaagtg gctgaaaggg     1320
aaggtacccg tgtacatttt ggccatactt atagtataga tgatgctgac agtatagaag     1380
aagttacaca aagaatggac ttaagaaatc agcaaactgt acattcagga gagtttatag     1440
aaaaaactat tgccccagga ggtgctaatc aaagaactgc tcctcaatgg atgttgcctt     1500
tacttctagg cctgtacggg actgtaacac ctgctcttga agcatatgaa gatggcccca     1560
accaaaagaa aaggagagtg tccaggggca gctcccaaaa agccaaagga acccgtgcaa     1620
gtgccaaaac tactaataaa aggaggagta gaagttctag aagttaaaac tggggtagat     1680
gctataacag aggtagaatg cttcctaaac ccagaaatgg gggatccaga tgaaaacctt     1740
agggctttta gtctaaagct aagtgctgaa aatgacttta gcagtgatag cccagaaaga     1800
aaaatgcttc cctgttacag cacagcaaga attccctcc ccaatttaaa tgaggaccta      1860
acctgtggaa atctactgat gtgggaggct gtaactgtac aaacagaggt cattggaata     1920
actagcatgc ttaaccttca cgcagggtca caaaaagtgc atgagcatgg tggaggtaaa     1980
cctattcaag gcagtaattt ccacttcttt gctgttggtg agaccccctt ggaaatgcag     2040
ggagtgctaa tgaattacag gaccaagtac ccagatggta ctataacccc aaaaaaccca     2100
acagcccagt cccaggtaat gaatactgac cataaggcct atttggacaa aaacaatgct     2160
tatccagttg agtgctgggt tcctgatccc agtagaaatg aaaatactag gtattttgga     2220
actttcacag gaggggaaaa tgttccccca gtacttcatg tgaccaacac agctaccaca     2280
gtgttgctag atgaacaggg tgtggggcct cttgtaaag ctgatagcct gtatgtttca      2340
gctgctgata tttgtggcct gtttactaac agctctggaa cacaacagtg gagaggcctt     2400
gcaagatatt ttaagattcg cctgagaaaa agatctgtaa aaaatcctta cccaatttcc     2460
tttttgctga gtgaccttat aaacaggaga acccagagag tggatgggca gcctatgtat     2520
ggtatggaat cccaggtaga agaggtcagg gtgtttgatg cacagaaag acttccaggg     2580
gacccagata tgataagata tattgataga caaggacaat gcaaaccaa atgctttaa      2640
acaggtgctt ttattgtaca tatacattta ataaatgctg cttttgtata agccacttt     2700
aagcttgtgt tattttgggg gtggtgtttt aggccttta aaacattgaa agcctttaca     2760
caaatgcaac tcttgactat ggggtctga cctttgggaa tcttcagccg ggctgaagt      2820
atctgagact tgggaagagc attgtgattg ggattcagtg cttgatccat gtccagagtc    2880
```

```
ttcagtttct gaatcttctt ctcttgtgat atcaagaata catttcccca tgcatatatt      2940
atatttcatc cttgaaaaag tatacatact tatctcagaa tccagccttt ccttccattc      3000
aacaattcta gattgtatat ctgttgcaaa atcagctaca ggcctaaacc aaattagcag      3060
tagcaacaag gtcattccac tttgtaaaat tcttttttca agtaagaact ctgagttttg      3120
taaggatttt cttaaatata ttttgggtct aaaatctatc tgtcttacaa atctagcctg      3180
cagggtttta ggaacaggat actcattcat tgtaaccagg cctggtggaa atatttgggt      3240
tcttttgttt aaatgtttct tttctaaatt aaccttaaca cttccatcta aataatctct      3300
caaactgtct aaattgttta ttccatgtcc tgaaggcaaa tcctttgatt cagccccgt       3360 tccttttaca tcttcaaaaa caaccatgta ctgatctata gctacaccta gttcaaaggt      3420
tagcctttcc atgggtaggt ttacatttaa ggctttacct ccacacaaat ctaataaccc      3480
tgcagctagt gttgtttttc cactatcaat gggacccttta aataaccagt atcttctttt    3540
aggtacatta aaaacaatac agtgcaaaaa atcaaatata acagaatcca ttttaggtag     3600
caaacagtgc agccaagcaa cacctgccat atattgttcc agtacagcat ttccatgagc     3660
tccaaatatt aaatccattt tatctaatat atgattaaat ctttctgtta gcatttcttc     3720
tctggtcata tgaagggtat ctactctttt tttagctaaa actgtatcta ctgcttgctg     3780
acaaatactt ttttgatttt tacttctgc aaaaatagta gcatttgcaa aatgcttttc      3840
atgatactta aagtgataag gttggtcttt tttctgacac tttttacact cttctacatt     3900
gtattgaaat tctaaataca tacccaataa taaaagcaca tcctcacact ttgtctctac     3960
tgcatactca gtaattaatc tccaagacac ctgctttgtt tcttcaggct cttctgggtt     4020
aaaatcatgc tcctttaagc ccccttgaat gctttcttct attgtatggt atggatctct     4080
agttaaggca ctatatagta agtattcctt attaacaccc ttacaaatta aaaaactaaa     4140
ggtacacagc ttttgacaga aattattaat tgcagaaact ctatgtctat gtggagttaa     4200
aaagaatata atattatgcc cagcacacat gtgtctacta atgaaagtta cagaatattt     4260
ttccataagt ttttatata gaatttgagc ttttttcttta gtagtataca cagcaaagca    4320
ggcaagggtt ctattactaa atacagcttg actaagaaac tggtgtagat cagagggaaa     4380
gtctttaggg tcttctacct ttctcttttt cttgggtggt gtggagtgtt gagaatctgc     4440
tgttgcttct tcatcactgg caaacatatc ttcatggcaa aataaatctt catcccattt     4500
ttcattaaag gagctccacc aggactccca ctcttctgtt ccataggttg gcacctataa     4560
aaaaaataat tacttagggc ctttaaatat tttcttattt atctaaatat aagttagtta     4620
ccttaaagct ttagatctct gaagggagtt tctccaatta tttggaccca ccattgcaga     4680
gtttcttcag ttaggtctaa gccaaaccac tgtgtgaagc agtcaatgca gtagcaatct     4740
atccaaacca agggctcttt tcttaaaaat tttctattta aatgccttaa tctaagctga     4800
catagcatgc aagggcagtg cacagaaggc ttttggaac aaataggcca ttccttgcag      4860
tacagggtat ctgggcaaag aggaaaatca gcacaaacct ctgagctact ccaggttcca     4920
aaatcaggct gatgagctac ctttacatcc tgctccattt ttttatataa agtattcatt     4980
ctcttcattt tatcctcgtc gcccccttg tcagggcgaa attccttaca cttccttaaa      5040
taggcttttc tcattaaggg aaggtttccc caggcagctc tttcaaggcc taaaaggtcc     5100
atgagctcca tggattcttc cctgttaagc actttatcca t                         5141
```

<210> SEQ ID NO 24
<211> LENGTH: 5141

```
<212> TYPE: DNA
<213> ORGANISM: Human polyomavirus type BK virus

<400> SEQUENCE: 24
ttttgcaaaa attgcaaaag aatagggatt tccccaaata ttttgctag gcctcagaaa       60
aagcctccac acccttacta cttgagagaa agggtggagg cagaggcggc ctcggcctct     120
tatatattat aaaaaaaaag gccacaggga ggagctgcta acccatggaa tgtagccaaa     180
ccatgacctc aggaaggaaa gtgcatgact gggcagccag ccagtggcag ttaatagtga     240
aaccccgccc ctaaaattct caaataaaca caagaggaag tggaaactgg ccaaaggagt     300
ggaaagcagc cagacagaca tgttttgcga gcctaggaat cttggccttg tccccagtta     360
aactggacaa aggccatggt tctgcgccag ctgtcacgac aagcttctgt gaaagttagt     420
aaaacctgga ctgaacaaa aaaagagct cagaggattt ttattttat tttagagctt        480
ttgctggaat tttgtagagg tgaagacagt gtagacggga aaaacaaaag taccactgct     540
ttacctgctg taaaagactc tgtaaaagac tcctaggtaa gtaatcccct ttttttgta      600
tttccaggtt gatgggtgct gctctagcac ttttggggga cctagttgcc agtgtatctg     660
aggctgctgc tgccacagga ttttcagtgg ctgaaattgc tgctggggag gctgctgctg     720
ctatagaagt tcaaattgca tcccttgcta ctgtagaggg cataacaagt acctcagagg     780
ctatagctgc tataggccta actcctcaaa catatgctgt aattgctggt gctcctgggg     840
ctattgctgg gtttgctgct taattcaaa ctgttactgg tattagttcc ttggctcaag      900
tagggtatag gttttttagt gattgggatc acaaagtttc cactgtaggc ctctatcagc     960
aatcaggcat ggctttagaa ttgtttaacc cagatgagta ctatgatatt ttgttcctg     1020
gtgtaaaatac ttttgtaaat aatattcaat accttgatcc taggcattgg ggtccttcct  1080
tgtttgctac tatttcccag gctttgtggc atgttattag ggatgatata cctgctataa  1140
cctcacagga attgcaaaga agaacagaaa gatttttag agactccttg gctagatttt   1200
tggaggaaac tacctggaca attgtaaatg ccctatgaa cttttataat tatattcaag   1260
aatattattc tgatctttcc cctattaggc cctcaatggt cagacaagtg gctgaaaggg  1320
aaggtacccg tgtacatttt ggccatactt atagtataga tgatgctgac agtatagaag  1380
aagttacaca aagaatggac ttaagaaatc aacaaactgt acattcagga gagttttatag 1440
aaaaaactat tgccccagga ggtgctaatc aaagaactgc tcctcaatgg atgttgcctt  1500
tacttctagg cctgtacggg actgtaacac ctgctcttga agcatatgaa gatggcccca 1560
accaaaagaa aaggagagtg tccaggggca gctcccaaaa agccaaagga acccgtgcaa 1620
gtgccaaaac tactaataaa aggaggagta gaagttctag aagttaaaac tggggtagat 1680
gctataacac aggtagaatg cttcctaaac ccagaaatgg gggatccaga tgaaaacctt 1740
aggggcttta gtctaaagct aagtgctgaa atgactttta gcagtgatag cccagaaaga 1800
aaaatgcttc cctgttacag cacagcaaga attccctcc ccaatttaaa tgaggaccta    1860
acctgtggaa atctactgat gtgggaggct gtaactgtac aaacagaggt cattggaata 1920
actagcatgc ttaaccttca tgcagggtca caaaagtgc atgagcatgg tggaggtaaa  1980
cctattcgag gcagtaattt ccacttcttt gctgttggtg gagaccccct tggaaatgcag 2040
ggagtgctaa tgaattacag gaccaagtac ccagaaggta ctataacccc aaaaaaccca 2100
acagcccagt cccaggtaat gaatactgac cataaggcct atttggacaa aaacaatgcc 2160
tatccagttg agtgctgggt tcctgatccc agtagaaatg aaaatactag gtattttggg 2220
```

```
actttcacag gaggggaaaa tgttccccca gtacttcatg tgaccaacac agctaccaca    2280
gtgttgctag atgaacaggg tgtggggcct ctttgtaaag ctgatagcct gtatgtttca    2340
gctgctgata tttgtggcct gtttactaac agctctggaa cacaacagtg agaggcctt    2400 gcaagatatt ttaagatccg cctgagaaaa agatctgtaa aaaatcctta cccaatttcc    2460
ttttcgctaa gtgaccttat aaacaggaga acccagagag tggatgggca gcctatgtat    2520
ggtatggaat cccaggtaga agaggtcagg gtgtttgatg gcacagaaag acttccaggg    2580
gacccagata tgataagata tattgataaa caaggacaat tgcaaaccaa aatgctttaa    2640
acaggtgctt ttattgtaca tatacattta ataaatgctg cttttgtata agccactttt    2700
aagcttgtgt tattttgggg gtggtgtttt aggccttta aaacattgaa agcctttaca    2760
caaatgcaac tcttcactat gggggtctga cctttgggaa tcttcagcag gggctgaagt    2820
atctgagact tgggaagagc attgtgattg ggattcagtg cttgatccat gtccagagtc    2880
ttcagtttct gaatcttctt ctcttgtgat atcaagaata catttcccca tgcatatatt    2940
atatttcatc cttgaaaaag tatacatact tatctcagaa tccagccttt ccttccattc    3000
aacaattcta gattgtatat ctgttgcaaa atcagctaca ggcctaaacc aaattagcag    3060
tagcaacaag gtcattccac tttgtaaaat tcttttttca agtaagaact ctgagttttg    3120
taaggatttt cttaaatata ttttgggtct aaaatctatc tgtcttacaa atctagcctg    3180
cagggtttta ggaacaggat actcattcat tgtaaccagg cctggtggaa atatttgggt    3240
tcttttgttt aaatgtttct tttctaaatt aaccttaaca cttccatcta aataatctct    3300
caaactgtct aaattgttta ttccatgtcc tgaaggcaaa tcctttgatt cagcccctgt    3360
tccttttaca tcttcaaaaa caaccatgta ctgatctata gctacaccta gttcaaaggt    3420
tagcctttcc atgggtaggt ttacatttaa ggctttacct ccacacaaat ctagtaaccc    3480
tgcagctagt gttgttttc cactatcaat gggaccttta ataaccagt atcttctttt    3540 aggtacatta aaacaatac agtgcaaaaa atcaaatata acagaatcca ttttaggtag    3600
caaacagtgc agccaggcaa cacctgccat atattgttcc agtacagcat ttccatgagc    3660
tccaaatatt aaatccattt tatctaatat atgattaaat cttttctgtta gcatttcttc    3720 tctggtcata tgaagggtat ctactctttt tttagctaaa actgtatcta ctgcttgctg    3780
acaaatactt ttttgatttt tactttctgc aaaaatagta gcatttgcaa aatgcttttc    3840
atgatactta aagtgataag gttggtcttt tttctgacac tttttacact cttctacatt    3900
gtattgaaat tctaaatata cacccaataa taaaaacaca tcctcacact ttgtctctac    3960
tgcatactca gtaattaatt tccaagacac ctgctttgtt tcttcaggct cttctgggtt    4020
aaaatcatgc tcctttaagc ccccttgaat gctttcttct attgtatggt atggatctct    4080
agttaaggca ctatatagta agtattcctt attaacaccc ttacaaatta aaaaactaaa    4140
ggtacacagc ttttgacaga aattattaat tgcagaaact ctatgtctat gtggagttaa    4200
aaagaatata atattatgcc cagcacacat gtgtctacta ataaaagtta cagaatattt    4260
ttccataagt tttttataca gaatttgagc ttttctttta gtagtataca cagcaaagca    4320
ggcaagggtt ctattactaa atacagcttg actaagaaac tggtgtagat cagaaggaaa    4380
gtctttaggg tcttctacct ttctcttttt cttgggtggt gtggagtgtt gagaatctgc    4440
tgttgcttct tcatcactgg caaacatatc ttcatggcaa aataaatctt catcccattt    4500
ttcattaaag gagctccacc aggactccca ctcttctgtt ccataggttg cacctataa    4560 aaaaaataat tacttagggc ctttaaatat tttcttattt atctaaatat aagttagtta    4620
```

```
ccttaaagct ttagatctct gaagggagtt tctccaatta ttttggaccca ccattgcaga    4680 gtttcttcag ttaggtctaa gccaaaccac tgtgtgaagc agtcaatgca gtagcaatct    4740
atccaaacca agggctcttt tcttaaaaat tttctattta aatgccttaa tctaagctga    4800
catagcatgc aagggcagtg cacagaaggc ttttggaac aaataggcca atccttgcag     4860
tacagggtat ctgggcaaag aggaaaatca gcacaaacct ctgagctact ccaggttcca    4920
aaatcaggct gatgagctac ctttacatcc tgctccattt ttttatataa agtattcatt    4980
ctcttcattt tatcctcgtc gccccctttg tcagggtgaa attccttaca cttccttaaa    5040 taggctttc tcattaaggg aaggtttccc caggcagctc tttcaaggcc taaaaggtcc     5100
atgagctcca tggattcttc cctgttaagc actttatcca t                        5141

<210> SEQ ID NO 25
<211> LENGTH: 5141
<212> TYPE: DNA
<213> ORGANISM: Human polyomavirus type BK virus

<400> SEQUENCE: 25
ttttgcaaaa attgcaaaag aatagggatt tccccaaata ttttgctag gcctcagaaa       60 aagcctccac acccttacta cttgagagaa agggtggagg cagaggcggc ctcggcctct     120
tatatattat aaaaaaaaag gccacaggga ggagctgcta acccatggaa tgtagccaaa     180
ccatgacctc aggaaggaaa gtgcatgact gggcagccag ccagtggcag ttaatagtga    240
aaccccgccc ctaaaattct caaataaaca caagaggaag tggaaactgg ccaaaggagt    300
ggaaagcagc cagacagaca tgttttgcga gcctaggaat cttggccttg tccccagtta    360
aactggacaa aggccatggt tctgcgccag ctgtcacgac aagcttctgt gaaagttagt    420
aaaacctgga ctggaacaaa aaaagagct cagaggattt ttatttttat tttagagctt     480
ttgctggaat tttgtagagg tgaagacagt gtagacggga aaaacaaaag taccactgct    540
ttacctgctg taaaagactc tgtaaaagac tcctaggtaa gtaatccctt ttttttgta     600 tttccaggtt gatgggtgct gctctagcac tttgggggga cctagttgcc agtgtatctg    660
aggctgctgc tgccacagga ttttcagtgg ctgaaattgc tgctggggag ctgctgctg    720 ctatagaagt tcaaattgca tcccttgcta ctgtagaggg cataacaagt acctcagagg    780
ctatagctgc tataggccta actcctcaaa catatgctgt aattgctggt gctcctgggg    840
ctattgctgg gtttgctgct ttaattcaaa ctgttactgg tattagttcc ttggctcaag    900
tagggtatag gtttttagt gattgggatc acaaagtttc cactgtaggc ctctatcagc     960
aatcaggcat ggctttggaa ttgtttaacc cagatgagta ctatgatatt tgtttcctg    1020 gtgtaaatac ttttgtaaat aatattcaat accttgatcc taggcattgg ggtccttcct   1080
tgtttgctac tatttcccag gctttgtggc atgttattag ggatgatata cctgctataa   1140
cctcacaaga attgcaaaga agaacagaaa gatttttag agactccttg gctagatttt   1200
tggaggaaac tacctggaca attgtaaatg cccctatgaa cttttataat tatattcaag   1260
aatattattc tgatctttcc cctattaggc cctcaatggt tagacaagtg gctgaaaggg   1320
aaggtacccg tgtacatttt ggccatactt atagtataga tgatgctgac agtatagaag   1380
aagttacaca aagaatggac ttaagaaatc aacaaactgt acattcagga gagtttatag   1440
aaaaaactat tgccccagga ggtgctaatc aaagaactgc tcctcaatgg atgttgcctt   1500
tacttctagg cctgtacggg actgtaacac ctgctcttga agcatatgaa gatggcccca   1560
```

```
gccaaaagaa aaggagagtg tccaggggca gctcccaaaa agccaaagga acccgtgcaa    1620
gtgccaaaac tactaataaa aggaggagta gaagttctag aagttaaaac tggggtagat    1680
gctataacag aggtagaatg cttcctaaac ccagaaatgg gggatccaga tgaaaacctt    1740
aggggcttta gtctaaagct aagtgctgaa aatgacttta gcagtgatag cccagaaaga    1800
aaaatgcttc cctgttacag cacagcaaga attcccctcc ccaatttaaa tgaggaccta    1860
acctgtggaa atctactgat gtgggaggct gtaactgtac aaacagaggt cattggaata    1920
actagcatgc ttaaccttca tgcagggtca caaaaagtgc atgagcatgg tggaggtaaa    1980
cctattcaag gcagtaattt ccacttcttt gctgttggtg gagaccccct ggaaatgcag    2040
ggagtgctaa tgaattacag gaccaagtac ccagatggta ctataacccc aaaaaaccca    2100
acagcccagt cccaggtaat gaatactgac cataaggcct atttggacaa aaacaatgct    2160
tatccagttg agtgctgggt tcctgatccc agtagaaatg aaaatactag gtattttgga    2220
actttcacag gaggggaaaa tgttccccca gtacttcatg tgaccaacac agctaccaca    2280
gtgttgctag atgaacaggg tgtggggcct cttttgtaaag ctgatagcct gtatgtttca    2340
```

```
tgcatactca gtaattaatt tccaagacac ctgctttgtt tcttcaggct cttctgggtt    4020
aaaatcatgc tcctttaagc ccccttgaat gctttcttct attgtatggt atggatctct    4080
agttaaggca ctatatagta agtattcctt attaacaccc ttacaaatta aaaaactaaa    4140
ggtacacagc ttttgacaga aattattaat tgcagaaact ctatgtctat gtggagttaa    4200
aaagaatata atattatgcc cagcacacat gtgtctacta ataaaagtta cagaatattt    4260
ttccataagt ttttatacag aatttgagc ttttttcttta gtagtataca cagcaaagca    4320
ggcaagggtt ctattactaa atacagcttg actaagaaac tggtgtagat cagaaggaaa    4380
gtctttaggg tcttctacct ttctcttttt cttgggtggt gtggagtgtt gagaatctgc    4440
tgttgcttct tcatcactgg caaacatatc ttcatggcaa ataaatcttt catcccattt    4500
ttcattaaag gagctccacc aggactccca ctcttctgtt ccataggttg gcacctataa    4560
aaaaaataat tacttagggc ctttaaatat tttcttattt atctaaatat aagttagtta    4620
ccttaaagct ttagatctct gaagggagtt tctccaatta tttggaccca ccattgcaga    4680
gtttcttcag ttaggtctaa gccaaaccac tgtgtgaagc agtcaatgca gtagcaatct    4740
atccaaacca agggctcttt tcttaaaaat tttctattta aatgccttaa tctaagctga    4800
catagcatgc aagggcagtg cacagaaggc ttttttgaac aaataggcca atccttgcag    4860
tacagggtat ctgggcaaag aggaaaatca gcacaaacct ctgagctact ccaggttcca    4920
aaatcaggct gatgagctac ctttacatcc tgctccattt ttttatataa agtattcatt    4980
ctcttcattt tatcctcgtc gcccccttg tcagggtgaa attccttaca cttccttaaa    5040
taggcttttc tcattagggg aaggtttccc caggcagctc tttcaaggcc taaaaggtcc    5100
atgagctcca tggattcttc cctgttaagc actttatcca t                       5141
```

<210> SEQ ID NO 26
<211> LENGTH: 5141
<212> TYPE: DNA
<213> ORGANISM: Human polyomavirus type BK virus

<400> SEQUENCE: 26

```
ttttgcaaaa attgcaaaag aatagggatt tccccaaata tttttgctag gcctcagaaa      60
aagcctccac acccttacta cttgagagaa agggtggagg cagaggcggc ctcggcctct     120
tatatattat aaaaaaaaag gccacaggga ggagctgcta acccatggaa tgtagccaaa     180
ccatgacctc aggaaggaaa gtgcatgact gggcagccag ccagtggcag ttaatagtga     240
aaccccgccc ctaaaattct caaataaaca caagaggaag tggaaactgg ccaaaggagt     300
ggaaagcagc cagacagaca tgttttgcga gcctaggaat cttggccttg tccccagtta     360
aactggacaa aggccatggt tctgcgccag ctgtcacgac aagcttctgt gaaagttagt     420
aaaacctgga ctgaacaaa aaaagagct cagaggattt ttattttat tttagagctt     480 ttgctggaat tttgtagagg tgaagacagt gtagacggga aaaacaaaag taccactgct     540
ttacctgctg taaagactc tgtaaaagac tcctaggtaa gtaatccctt ttttttttgta     600 tttccaggtt gatgggtgct gctctagcac ttttgggga cctagttgcc agtgtatctg     660
aggctgctgc tgccacagga ttttcagtgg ctgaaattgc tgctggggag ctgctgctg     720 ctatagaagt tcaaattgca tcccttgcta ctgtagaggg cataacaagt acctcagagg     780
ctatagctgc tataggccta actcctcaaa catatgctgt aattgctggt gctcctgggg     840
ctattgctgg gtttgctgct taattcaaa ctgttactgg tattagttcc ttggctcaag     900
```

```
tagggtatag gttttttagt gattgggatc acaaagtttc cactgtaggc ctctatcagc       960
aatcaggcat ggctttggaa ttgtttaacc cagatgagta ctatgatatt ttgtttcctg      1020
gtgtaaatac ttttgtaaat aatattcaat accttgatcc taggcattgg ggtccttcct      1080
tgtttgctac tatttcccag gctttgtggc atgttattag ggatgatata cctgctataa      1140
cctcacaaga attgcaaaga agaacagaaa gattttttag agactccttg gctagatttt      1200
tggaggaaac tacctggaca attgtaaatg cccctatgaa cttttataat tatattcaag      1260
aatattattc tgatctttcc cctattaggc cctcaatggt tagacaagtg gctgaaaggg      1320
aaggtacccg tgtacatttt ggccatactt atagtataga tgatgctgac agtatagaag      1380
aagttacaca aagaatggac ttaagaaatc aacaaactgt acattcagga gagtttatag      1440
aaaaaactat tgccccagga ggtgctaatc aaagaactgc tcctcaatgg atgttgcctt      1500
tacttctagg cctgtacggg actgtaacac ctgctcttga agcatatgaa gatggcccca      1560
accaaaagaa aaggagagtg tccaggggca gctcccaaaa agccaaagga acccgtgcaa      1620
gtgccaaaac tactaataaa aggaggagta aagttctag aagttaaaac tggggtagat       1680
gctataacag aggtagaatg cttcctaaac ccagaaatgg gggatccaga tgaaaacctt      1740
aggggcttta gtctaaagct aagtgctgaa atgactttta gcagtgatag cccagaaaga      1800
aaaatgcttc cctgttacag cacagcaaga attcccctcc ccaatttaaa tgaggaccta      1860
acctgtggaa atctactgat gtgggaggct gtaactgtac aaacagaggt cattggaata      1920
actagcatgc ttaaccttca tgcagggtca caaaaagtgc atgagcatgg tggaggtaaa      1980
cctattcaag gcagtaattt ccacttctt gctgttggtg gagacccctt ggaaatgcag       2040
ggagtgctaa tgaattacag gaccaagtac ccagatggta ctataacccc aaaaaaccca      2100
acagcccagt cccaggtaat gaatactgac cataaggcct atttggacaa aaacaatgct      2160
tatccagttg agtgctgggt tcctgatccc agtagaaatg aaaatactag gtattttgga      2220
actttcacag gagggaaaa tgttcccccca gtacttcatg tgaccaacac agctaccaca      2280
gtgttgctag atgaacaggg tgtgggggcct ctttgtaaag ctgatagcct gtatgtttca      2340
gctgctgata tttgtggcct gtttactaac agctctggaa cacaacagtg gagaggcctt      2400
gcaagatatt ttaagattcg cctgagaaaa agatctgtaa aaaatcctta cccaatttcc      2460 ttttttgctga gtgaccttat aaacaggaga acccagagag tggatgggca gcctatgtat      2520
ggtatggaat cccaggtaga agaggtcagg gtgtttgatg gcacagaaag acttccaggg      2580
gacccagata tgataagata tattgataaa caaggacaat gcaaaccaa atgctttaa        2640 acaggtgctt ttattgtaca tatacattta ataaatgctg cttttgtata agccacttt       2700 aagcttgtgt tattttgggg gtggtgtttt aggccttta aaacattgaa agcctttaca       2760
caaatgcaac tcttgactat gggggtctga ccttgggaa tcttcagcag gggctgaagt       2820
atctgagact gggaagagc attgtgattg ggattcagtg cttgatccat gtccagagtc       2880
ttcagtttct gaatcttctt ctcttgtgat atcaagaata catttcccca tgcatatatt      2940
atatttcatc cttgaaaaag tatacatact tatctcagaa tccagccttt ccttccattc      3000
aacaattcta gattgtatat ctgttgcaaa atcagctaca ggcctagacc aaattagcag     3060
tagcaacaag gtcattccac tttgtaaaat tctttttca agtaagaact ctgagttttg      3120
taaggatttt cttaaatata ttttgggtct aaaatctatc tgtcttacaa atctagcctg     3180
cagggtttta ggaacaggat actcattcat tgtaaccagg cctggtggaa atatttgggt    3240
tcttttgttt aaatgtttct tttctaaatt aaccttaaca cttccatcta aataatctct   3300
```

```
caaactgtct aaattgttta ttccatgtcc tgaaggcaaa tcctttgatt cagccccagt      3360
tccttttaca tcttcaaaaa caaccatgta ctgatctata gctacaccta gttcaaaggt      3420 tagccttttcc atgggtaggt ttacatttaa ggctttacct ccacacaaat ctaataaccc     3480
tgcagctagt gttgtttttc cactatcaat gggacccttta aataaccagt atcttctttt    3540
aggtacatta aaaacaatac agtgcaaaaa atcaaatata acagaatcca ttttaggtag      3600
caaacagtgc agccaagcaa cacctgccat atattgttcc agtacagcat ttccatgagc      3660
tccaaatatt aaatccatt tatctaatat atgattaaat ctttctgtta gcatttcttc       3720
tctggtcata tgaagggtat ctactctttt tttagctaaa actgtatcta ctgcttgctg     3780
acaaatactt ttttgatttt tactttctgc aaaaatagta gcatttgcaa aatgcttttc     3840
atgatactta aagtgataag gttggtcttt tttctgacac tttttacact cttctacatt     3900
gtattgaaat ctaaataca tacccaataa taaaaacaca tcctcacact ttgtctctac      3960
tgcatactca gtaattaatt tccaagacac ctgctttgtt tcttcaggct cttctgggtt     4020
aaaatcatgc tcctttaagc cccttgaat gctttcttct attgtatggt atggatctct      4080
agttaaggca ctatatagta agtattcctt attaacaccc ttacaaatta aaaaactaaa     4140
ggtacacagc ttttgacaga aattattaat tgcagaaact ctatgtctat gtggagttaa     4200
aaagaatata atattatgcc cagcacacat gtgtctacta ataaaagtta cagaatattt     4260
ttccataagt tttttataca gaatttgagc tttttcttta gtagtataca cagcaaagca    4320
ggcaagggtt ctattactaa atacagcttg actaagaaac tggtgtagat cagaaggaaa    4380
gtctttaggg tcttctacct ttctctttt cttgggtggt gtggagtgtt gagaatctgc     4440
tgttgcttct tcatcactgg caaacatatc ttcatggcaa aataaatctt catcccattt    4500
ttcattaaag gagctccacc aggactccca ctcttctgtt ccataggttg gcacctataa    4560
aaaaaataat tacttagggc cttaaatat tttcttattt atctaaatat aagttagtta     4620
ccttaaagct ttagatctct gaagggagtt tctccaatta tttggaccca ccattgcaga    4680
gtttcttcag ttaggtctaa gccaaaccac tgtgtgaagc agtcaatgca gtagcaatct    4740
atccaaacca agggctcttt tcttaaaaat tttctattta aatgccttaa tctaagctga    4800
catagcatgc aagggcagtg cacagaaggc ttttggaac aaataggcca atccttgcag     4860
tacagggtat ctgggcaaag aggaaaatca gcacaaacct ctgagctact ccaggttcca    4920
aaatcaggct gatgagctac ctttacatcc tgccccattt ttttatataa agtattcatt    4980
ctcttcattt tatcctcgtc gccccctttg tcagggtgaa attccttaca cttccttaaa    5040
taggcttttc tcattaaggg aaggtttccc caggcagctc tttcaaggcc taaaaggtcc    5100
atgagctcca tggattcttc cctgttaagc actttatcca t                        5141

<210> SEQ ID NO 27
<211> LENGTH: 5141
<212> TYPE: DNA
<213> ORGANISM: Human polyomavirus type BK virus

<400> SEQUENCE: 27
ttttgcaaaa attgcaaaag aatagggatt tccccaaata ttttttgctag gcctcagaaa     60 aagcctccac acccttacta cttgagagaa agggtggagg cagaggcggc ctcggcctct    120
tatatattat aaaaaaaaag gccacaggga ggagctgcta acccatggaa tgtagccaaa    180
ccatgaccct aggaaggaaa gtgcatgact gggcagccag ccagtggcag ttaatagtga    240
```

```
aaccccgccc ctaaaattct caaataaaca caagaggaag tggaaactgg ccaaaggagt    300
ggaaagcagc cagacagaca tgttttgcga gcctaggaat cttggccttg tccccagtta    360
aactggacaa aggccatggt tctgcgccag ctgtcacgac atgcttctgt gaaagttagt    420
aaaacctgga ctgaacaaa aaaagagct cagaggattt ttatttttat tttagagctt    480
ttgctggaat tttgtagagg tgaagacagt gtagacggga aaaacaaaag taccactgct    540
ttacctgctg taaaagactc tgtaaaagac tcctaggtaa gtaatcccttt tttttttgta    600
tttccaggtt gatgggtgct gctctagcac ttttgggga cctagttgcc agtgtatctg    660
aggctgctgc tgccacagga ttttcagtgg ctgaaattgc tgctggggag ctgctgctg    720
ctatagaagt tcaaattgca tcccttgcta ctgtagaggg cataacaagt acctcagagg    780
ctatagctgc tataggccta actcctcaaa catatgctgt aattgctggt gctcctgggg    840
ctattgctgg gtttgctgct ttaattcaaa ctgttactgg tattagttcc ttggctcaag    900
tagggtatag gttttttagt gattgggatc acaaagtttc cactgtaggc ctctatcagc    960
aatcaggcat ggctttggaa ttgtttaacc cagatgagta ctatgatatt ttgtttcctg    1020
gtgtaaatac ttttgtaaat aatattcaat accttgatcc taggcattgg ggtccttcct    1080
tgtttgctac tatttcccag gctttgtggc atgttattag ggatgatata cctgctataa    1140
cctcacaaga attgcaaaga gaacagaaa gattttttag agactccttg gctagatttt    1200
tggaggaaac tacctggaca attgtaaatg cccctatgaa cttttataat tatattcaag    1260
aatattattc tgatctttcc cctattaggc cctcaatggt tagacaagtg gctgaaaggg    1320
aaggtacccg tgtacatttt ggccatactt atagtataga tgatgctgac agtatagaag    1380
aagttacaca aagaatggac ttaagaaatc aacaaactgt acattcagga gagtttatag    1440
aaaaaactat tgccccagga ggtgctaatc aaagaactgc tcctcaatgg atgttgcctt    1500
tacttctagg cctgtacggg actgtaacac ctgctcttga agcatatgaa gatggcccca    1560
accaaaagaa aaggagagtg tccaggggca gctcccaaaa agccaaagga acccgtgcaa    1620
gtgccaaaac tactaataaa aggaggagta gaagttctag aagttaaaac tggggtagat    1680
gctataacag aggtagaatg cttcctaaac ccagaaatgg gggatccaga tgaaaaccttt    1740
aggggcttta gtctaaagct aagtgctgaa atgacttta gcagtgatag cccagaaaga    1800
aaaatgcttc cctgttacag cacagcaaga attcccctcc ccaatttaaa tgaggaccta    1860
acctgtggga atctactgat gtgggaggct gtaactgtac aaacagaggt cattggaata    1920
actagcatgc ttaaccttca tgcagggtca caaaaagtgc atgagcatgg tggaggtaaa    1980
cctattcaag gcagtaattt ccacttcttt gctgttggtg agacccctt ggaaatgcag    2040
ggagtgctaa tgaattacag gaccaagtac ccagatggta ctataacccc aaaaaaccca    2100
acagcccagt cccaggtaat gaatactgac cataaggcct atttggacaa aaacaatgct    2160
tatccagttg agtgctgggt tcctgatccc agtagaaatg aaaatactag gtattttgga    2220
actttcacag gaggggaaaa tgttcccccca gtacttcatg tgaccaacac agctaccaca    2280
gtgttgctag atgaacaggg tgtggggcct ctttgtaaag ctgatagcct gtatgtttca    2340
gctgctgata tttgtggcct gtttactaac agctctggaa cacaacagtg gagaggcctt    2400
gcaagatatt ttaagattcg cctgagaaaa agatctgtaa aaaatccttta cccaatttcc    2460
tttttgctga gtgaccttat aaacaggaga acccagagag tggatgggca gcctatgtat    2520
ggtatggaat cccaggtaga agaggtcagg gtgtttgatg gcacagaaag acttccaggg    2580
gacccagata tgataagata tattgataaa caaggacaat tgcaaaccaa aatgctttaa    2640
```

```
acaggtgctt ttattgtaca tatgcattta ataaatgctg cttttgtata agccactttt    2700
aagcttgtgt tattttgggg gtggtgtttt aggccttttta aaacattgaa agcctttaca    2760
caaatgcaac tcttgactat gggggtctga cctttgggaa tcttcagcag gggctgaagt    2820
atctgagact tgggaagagc attgtgattg ggattcagtg cttgatccat gtccagagtc    2880
ttcagtttct gaatcttctt ctcttgtgat atcaagaata catttcccca tgcatatatt    2940
atatttcatc cttgaaaaag tatacatact tatctcagaa tccagccttt ccttccattc    3000
aacaattcta gattgtatat ctgttgcaaa atcagctaca ggcctaaacc aaattagcag    3060
tagcaacaag gtcattccac tttgtaaaat tctttttta agtaagaact ctgagttttg    3120
taaggatttt cttaaatata ttttgggtct aaaatctatc tgtcttacaa atctagcctg    3180
cagggtttta ggaacaggat actcattcat tgtaaccagg cctggtggaa atatttgggt    3240
tcttttgttt aaatgtttct tttctaaatt aaccttaaca cttccatcta ataatctct    3300 caaactgtct aaattgttta ttccatgtcc tgaaggcaaa tcctttgatt cagccccagt    3360 tcctttaca tcttcaaaaa caaccatgta ctgatctata gctacaccta gttcaaaggt    3420
tagcctttcc atgggtaggt ttacatttaa ggctttacct ccacacaaat ctaataaccc    3480
tgcagctagt gttgttttc cactatcaat gggaccttta aataaccagt atcttctttt    3540
aggtacatta aaaacaatac agtgcaaaaa atcaaatata acagaatcca ttttaggtag    3600
caaacagtgc agccaagcaa cacctgccat atattgttcc agtacggcat tccatgagc    3660 tccaaatatt aaatccattt tatctaatat atgattaaat cttctgtta gcatttcttc    3720 tctggtcata tgaagggtat ctactctttt tttagctaaa actgtatcta ctgcttgctg    3780
acaaatactt ttttgatttt tactttctgc aaaaatagta gcatttgcaa aatgcttttc    3840
atgatactta aagtgataag gttggtcttt tttctgacac ttttttacact cttctacatt    3900 gtattgaaat tctaaataca tacccaataa taaaacaca tcctcacact ttgtctctac    3960
tgcatactca gtaattaatt tccaagacac ctgctttgtt tcttcaggct cttctgggtt    4020
aaaatcatgc tcctttaagc ccccttgaat gctttcttct attgtatggt atggatctct    4080
agttaaggca ctatatagta agtattcctt attaacaccc ttacaaatta aaaaactaaa    4140
ggtacacagc ttttgacaga aattattaat tgcagaaact ctatgtctat gtggagttaa    4200
aaagaatata atattatgcc cagcacacat gtgtctacta ataaagtta cagaatattt    4260 ttccataagt ttttataca gaatttgagc ttttctttta gtagtataca cagcaaagca    4320
ggcaagggtt ctattactaa atacagcttg actaagaaac tggtgtagat cagaaggaaa    4380
gtctttaggg tcttctacct ttctcttttt cttgggtggt gtggagtgtt gagaatctgc    4440
tgttgcttct tcatcactgg caaacatatc ttcatggcaa aataaatctt catcccattt    4500
ttcattaaag gagctccacc aggactccca ctcttctgtt ccataggttg gcacctataa    4560
aaaaaataat tacttagggc ctttaaatat tttcttattt atctaaatat aagttagtta    4620
ccttaaagct ttagatctct gaagggagtt tctccaatta tttggaccca ccattgcaga    4680
gtttcttcag ttaggtctaa gccaaaccac tgtgtgaagc agtcaatgca gtagcaatct    4740
atccaaacca agggctcttt tcttaaaaat tttctattta aatgccttaa tctaagctga    4800
catagcatgc aagggcagtg cacagaaggc ttttttggaac aaataggcca atccttgcag    4860
tacagggtat ctgggcaaag aggaaaatca gcacaaacct ctgagctact ccaggttcca    4920
aaatcaggct gatgagctac ctttacatcc tgctccattt ttttatataa agtattcatt    4980
```

```
ctcttcattt tatcctcgtc gcccccttg tcagggtgaa attccttaca cttccttaaa    5040 taggctttc tcattaaggg aaggtttccc caggcagctc tttcaaggcc taaaaggtcc    5100
atgagctcca tggattcttc cctgttaagc actttatcca t                       5141
```

<210> SEQ ID NO 28
<211> LENGTH: 5141
<212> TYPE: DNA
<213> ORGANISM: Human polyomavirus type BK virus

<400> SEQUENCE: 28

```
ttttgcaaaa attgcaaaag aatagggatt tccccaaata ttttgctag gcctcagaaa      60 aagcctccac acccttacta cttgagagaa agggtggagg cagaggcggc ctcggcctct   120
tatatattat aaaaaaaaag gccacaggga ggagctgcta acccatggaa tgtagccaaa   180
ccatgacctc aggaaggaaa gtgcatgact gggcagccag ccagtggcag ttaatagtga   240
aaccccgccc ctaaaattct caaataaaca caagaggaag tggaaactgg ccaaaggagt   300
ggaaagcagc cagacagaca tgttttgcga gcctaggaat cttggccttg tccccagtta   360
aactggacaa aggccatggt tctgcgccag ctgtcacgac aagcttctgt gaaagttagt   420
aaaacctgga ctgaacaaa aaaagagct cagaggattt ttatttttat tttagagctt   480
ttgctggaat tttgtagagg tgaagacagt gtagacggga aaaacaaaag taccactgct   540
ttacctgctg taaaagactc tgtaaaagac tcctaggtaa gtaatcccttt tttttttgta   600 tttccaggtt gatgggtgct gctctagcac tttgggggga cctagttgcc agtgtatctg   660
aggctgctgc tgccacagga ttttcagtgg ctgaaattgc tgctggggag gctgctgctg   720
ctatagaagt tcaaattgca tcccttgcta ctgtagaggg cataacaagt acctcagagg   780
ctatagctgc tataggccta actcctcaaa catatgctgt aattgctggt gctcctgggg   840
ctattgctgg gtttgctgct ttaattcaaa ctgttactgg tattagttcc ttggctcaag   900
tagggtatag gttttttagt gattgggatc acaaagttc cactgtaggc ctctatcagc   960
aatcaggcat ggctttggaa ttgtttaacc cagatgagta ctatgatatt ttgtttcctg  1020
gtgtaaatac ttttgtaaat aatattcaat accttgatcc taggcattgg ggtccttcct  1080
tgtttgctac tatttcccag gctttgtggc atgttattag ggatgatata cctgctataa  1140
cctcacaaga attgcaaaga gaacagaaa gatttttag agactccttg gctagatttt  1200
tggaggaaac tacctggaca attgtaaatg cccctatgaa cttttataat tatattcaag  1260
aatattattc tgatctttcc cctattaggc cctcaatggt tagacaagtg gctgaaaggg  1320
aaggtacccg tgtacattt ggccatactt atagtataga tgatgctgac agtatagaag  1380
aagttacaca aagaatggac ttaagaaatc aacaaactgt acattcagga gagtttatag  1440
aaaaaactat tgccccagga ggtgctaatc aaagaactgc tcctcaatgg atgttgcctt  1500
tacttctagg cctgtacggg actgtaacac ctgctcttga agcatatgaa gatggcccca  1560
accaaaagaa aaggagagtg tccagggca gctcccaaaa agccaaagga acccgtgcaa  1620
gtgccaaaac tactaataaa aggaggagta gaagttctag aagttaaaac tggggtagat  1680
gctataacag aggtagaatg cttcctaaac ccagaaatgg gggatccaga tgaaaaccctt  1740 agggctttta gtctaaagct aagtgctgaa atgactttta gcagtgatag cccagaaaga  1800
aaaatgcttc cctgttacag cacagcaaga attcccctcc ccaatttaaa tgaggaccta  1860
acctgtggaa atctactgat gtgggaggct gtaactgtac aaacagaggt cattggaata  1920
actagcatgc ttaaccttca tgcagggtca caaaaagtgc atgagcatgg tggaggtaaa  1980
```

```
cctattcaag gcagtaattt ccacttcttt gctgttggtg gagacccctt ggaaatgcag   2040
ggagtgctaa tgaattacag gaccaagtac ccagatggta ctataacccc aaaaaaccca   2100
acagcccagt cccaggtaat gaatactgac cataaggcct atttggacaa aaacaatgct   2160
tatccagttg agtgctgggt tcctgatccc agtagaaatg aaaatactag gtattttgga   2220
actttcacag gaggggaaaa tgttccccca gtacttcatg tgaccaacac agctaccaca   2280
gtgttgctag atgaacaggg tgtggggcct ctttgtaaag ctgatagcct gtatgtttca   2340
gctgctgata tttgtggcct gtttactaac agctctggaa cacaacagtg gagaggcctt   2400
gcaagatatt ttaagattcg cctgagaaaa agatctgtaa aaaatcctta cccaatttcc   2460
tttttgctga gtgaccttat aaccaggaga acccagagag tggatgggca gcctatgtat   2520
ggtatggaat cccaggtaga agaggtcagg gtgtttgatg gcacagaaag acttccaggg   2580
gacccagata tgataagata tattgataaa caaggacaat tgcaaaccaa aatgctttaa   2640
acaggtgctt ttattgtaca tatacattta ataaatgctg cttttgtata agccacttt    2700 aagcttgtgt tattttgggg gtggtgtttt aggccttta aaacattgaa agcctttaca    2760
caaatgcaac tcttgactat ggggctctga cctttgggaa tcttcagcag gggctgaagt   2820
atctgagact tgggaagagc attgtgattg ggattcagtg cttgatccat gtccagagtc   2880
ttcagtttct gaatcttctt ctcttgtgat atcaagaata catttcccca tgcatatatt   2940
atatttcatc cttgaaaaag tatacatact tatctcagaa ccagcctttt ccttccattc   3000
aacaattcta gattgtatat ctgttgcaaa atcagctaca ggcctaaacc aaattagcag   3060
tagcaacaag gtcattccac tttgtaaaat tctttttttca agtaagaact ctgagttttg   3120
taaggatttt cttaaatata ttttgggtct aaaatctatc tgtcttacaa atctagcctg   3180
cagggtttta ggaacaggat actcattcat tgtaaccagg cctggtggaa atatttgggt   3240 tctttgttt aaatgtttct tttctaaatt aaccttaaca cttccatcta aataatctct    3300
caaactgtct aaattgttta ttccatgtcc tgaaggcaaa tcctttgatt cagccccagt   3360 tcctttaca tcttcaaaaa caaccatgta ctgatctata gctacaccta gttcaaaggt    3420 tagccttttcc atgggtaggt ttacatttaa ggctttacct ccacacaaat ctaataaccc   3480
tgcagctagt gttgttttc cactatcaat gggacccttta ataaccagt atcttctttt    3540 aggtacatta aaaacaatac agtgcaaaaa atcaaatata acagaatcca ttttaggtag   3600
caaacagtgc agccaagcaa cacctgccat atattgttcc agtacagcat ttccatgagc   3660
tccaaatatt aaatccattt tatctaatat atgattaaat cttctgtta gcatttcttc     3720 tctggtcata tgaagggtat ctactctttt tttagctaaa actgtatcta ctgcttgctg   3780
acaaatactt ttttgatctt tacttctgc aaaaatagta gcatttgcaa aatgcttttc     3840
atgatactta aagtgataag gttggtctttt tttctgacac tttttacact cttctacatt   3900
gtattgaaat tctaaataca tacccaataa taaaaacaca tcctcacact ttgtctctac   3960
tgcatactca gtaattaatt tccaagacac ctgctttgtt tcttcaggct cttctgggtt   4020
aaaatcatgc tcctttaagc ccccttgaat gctttcttct attgtatggt atggatctct   4080
agttaaggca ctatatagta agtattcctt attaacaccc ttacaaatta aaaaactaaa   4140
ggtacacagc ttttgacaga aattattaat tgcagaaact ctatgtctat gtggagttaa   4200
aaagaatata atattatgcc cagcacacat gtgtctacta ataaaagtta cagaatattt   4260
ttccataagt ttttttataca gaatttgagc ttttctttta gtagtataca cagcaaagca   4320
```

```
ggcaagggtt ctattactaa acacagcttg actaagaaac tggtgtagat cagaaggaaa      4380
gtctttaggg tcttctacct ttctcttttt cttgggtggt gtggagtgtt gagaatctgc      4440
tgttgcttct tcatcactgg caaacatatc ttcatggcaa ataaatctt catcccattt       4500 ttcattaaag gagctccacc aggactccca ctcttctgtt ccataggttg cacctataa       4560 aaaaaataat tacttagggc ctttaaatat tttcttattt atctaaatat aagttagtta      4620
ccttaaagct ttagatctct gaagggagtt tctccaatta tttggaccca ccattgcaga     4680
gtttcttcag ttaggtctaa gccaaaccac tgtgtgaagc agtcaatgca gtagcaatct      4740
atccaaacca agggctcttt tcttaaaaat tttctattta aatgccttaa tctaagctga     4800
catagcatgc aagggcagtg cacagaaggc ttttggaac aaataggcca atccttgcag      4860
tacagggtat ctgggcaaag aggaaaatca gcacaaacct ctgagctact ccaggttcca    4920
aaatcaggct gatgagctac ctttacatcc tgctccattt ttttatataa agtattcatt    4980
ctcttcattt tatcctcgtc gcccctttg tcagggtgaa attccttaca cttccttaaa     5040
taggcttttc tcattaaggg aaggtttccc caggcagctc tttcaaggcc taaaaggtcc    5100
atgagctcca tggattcttc cctgttaagc actttatcca t                        5141
```

<210> SEQ ID NO 29
<211> LENGTH: 5141
<212> TYPE: DNA
<213> ORGANISM: Human polyomavirus type BK virus

<400> SEQUENCE: 29

```
ttttgcaaaa attgcaaaag aatagggatt ccccaaaata ttttcgctag gcctcagaaa      60
aagcctccac acccttacta cttgagagaa agggtggagg cagaggcggc ctcggcctct     120
tatatattat aaaaaaaaag gccacaggga ggagctgcta acccatggaa tgtagccaaa     180
ccatgacctc aggaaggaaa gtgcatgact gggcagccag ccagtggcag ttaatagtga    240
aaccccgccc ctaaaattct caaataaaca caagaggaag tggaaactgg ccaaaggagt    300
ggaaagcagc cagacagaca tgttttgcga gcctaggaat cttggccttg tccccagtta    360
aactggacaa aggccatggt tctgcgccag ctgtcacgac aagcttctgt gaaagttagt    420
aaaacctgga ctggaacaaa aaaagagct cagaggattt ttattttat tttagagctt      480 ttgctggaat tttgtagagg tgaagacagt gtagacggga aaaacaaaag taccactgct   540
ttacctgctg taaaagactc tgtaaaagac tcctaggtaa gtaatccctt ttttttgta    600 tttccaggtt gatgggtgct gctctagcac tttgggga cctagttgcc agtgtatctg      660
aggctgctgc tgccacaggg ttttcagtgg ctgaaattgc tgctggggag gctgctgctg    720
ctatagaagt tcaaattgca tcccttgcta ctgtagaggg cataacaagt acctcagagg    780
ctatagctgc tataggccta actcctcaaa catatgctgt aattgctggt gctcctgggg    840
ctattgctgg gtttgctgct ttaattcaaa ctgttactgg tattagttcc ttggctcaag    900
tagggtatag gttttttagt gattgggatc acaaagtttc cactgtaggc ctctatcagc    960
aatcaggcat ggctttggaa ttgtttaacc cagatgagta ctatgatatt ttgtttcctg   1020
gtgtaaatac ttttgtaaat aatattcaat accttgatcc taggcattgg ggtccttcct   1080
tgtttgctac tatttcccag gctttgtggc atgttattag ggatgatata cctgctataa   1140
cctcacaaga attgcaaaga gaacagaaa gatttttag agactccttg gctagatttt    1200
tggaggaaac tacctggaca attgtaaatg ccccctatgaa cttttataat tatattcaag   1260
aatattattc tgatctttcc cctattaggc cctcaatggt tagacaagtg gctgaaaggg   1320
```

```
aaggtacccg tgtacatttt ggccatactt atagtataga tgatgctgac agtatagaag    1380
aagttacaca aagaatggac ttaagaaatc aacaaactgt acattcagga gagtttatag    1440
aaaaaactat tgccccagga ggtgctaatc aaagaactgc tcctcaatgg atgttgcctt    1500
tacttctagg cctgtacggg actgtaacac ctgctcttga agcatatgaa gatggcccca    1560
accaaaagaa aaggagagtg tccaggggca gctcccaaaa agccaaagga acccgtgcaa    1620
gtgccaaaac tactaataaa aggaggagta gaagttctag aagttaaaac tggggtagat    1680
gctataacag aggtagaatg cttcctaaac ccagaaatgg gggatccaga tgaaaacctt    1740
aggggcttta gtctaaagct aagtgctgaa aatgacttta gcagtgatag cccagaaaga    1800
aaaatgcttc cctgttacag cacagcaaga attcccctcc ccaatttaaa tgaggaccta    1860
acctgtggaa atctactgat gtgggaggct gtaactgtac aaacagaggt cattggaata    1920
actagcatgc ctaaccttca tgcagggtca caaaaagtgc atgagcatgg tggaggtaaa    1980
cctattcaag gcagtaattt ccacttcttt gctgttggtg gagacccctt ggaaatgcag    2040
ggagtgctaa tgaattacag gaccaagtac ccagatggta ctataacccc aaaaaaccca    2100
acagcccagt cccaggtaat gaatactgac cataaggcct atttggacaa aaacaatgct    2160
tatccagttg agtgctgggt tcctgatccc agtagaaatg aaaatactag gtattttgga    2220
actttcacag gaggggaaaa tgttcccccca gtacttcatg tgaccaacac agctaccaca    2280
gtgttgctag atgaacaggg tgtggggcct ctttgtaaag ctgatagcct gtatgtttca    2340
gctgctgata tttgtggcct gtttactaac agctctggaa cacaacagtg gagaggcctt    2400
gcaagatatt ttaagattcg cctgagaaaa agatctgtaa aaaatcctta cccaatttcc    2460 ttttgctga gtgaccttat aaacaggaga acccagagag tggatgggca gcctatgtat    2520
ggtatggaat cccaggtaga agaggtcagg gtgtttgatg gcacagaaag acttccaggg    2580
gacccagata tgataagata tattgataag caaggacaat tgcaaaccaa aatgctttaa    2640
acaggtgctt ttattgtaca tatacattta ataaatgctg cttttgtata agccactttt    2700
aagcttgtgt tattttgggg gtggtgtttt aggcctttta aaacattgaa agcctttaca    2760
caaatgcagc tcttgactat gggggtctga cctttgggaa tcttcagcag gggctgaagt    2820
atctgagact tgggaagagc attgtgattg ggattcagtg cttgatccat gtccagagtc    2880
ttcagtttct gaatcttctt ctcttgtgat atcaagaata catttcccca tgcatatatt    2940
atatttcatc cttgaaaaag tatacatact tatctcagaa tccagccttt ccttccattc    3000
aacaattcta gattgtatat ctgttgcaaa atcagctaca ggcctaaacc aaattagcag    3060
tagcaacaag gtcattccac tttgtaaaat tcttttttca gtaagaaact ctgagttttg    3120
taaggatttt cttaaatata ttttgggtct aaaatctatc tgtcttacaa atctagcctg    3180
cagggtttta ggaacaggat actcattcat tgtaaccagg cctggtggaa atatttgggt    3240
tcttttgttt aaatgtttct tttctaaatt aaccttaaca cttccatcta aataatctct    3300
caaactgtct aaattgttta ttccatgtcc tgaaggcaaa tcctttgatt cagccccagt    3360
tccttttaca tctccaaaaa caaccatgta ctgatctata gctacaccta gttcaaaggt    3420 tagccttttcc atgggtaggt ttacatttaa ggctttacct ccacacaaat ctaataaccc    3480
tgcagctagt gttgttttc cactatcaat gggaccctta aataaccagt atcttctttt    3540
aggtacatta aaaacaatac agtgcaaaaa atcaaatata acagaatcca ttttaggtag    3600
caaacagtgc agccaagcaa cacctgccat atattgttcc agtacagcat ttccatgagc    3660
```

```
tccaaatatt aaatccattt tatctaatat atgattaaat ctttctgtta gcatttcttc   3720
tctggtcata tgaagggtat ctactctttt tttagctaaa actgtatcta ctgcttgctg   3780
acaaatactt ttttgatttt tactttctgc aaaaatagta gcatttgcaa aatgcttttc   3840
atgatactta aagtgataag gttggtcctt tttctgacac tttttacact cttctacatt   3900
gtattgaaat tctaaataca tacccaataa taaaaacaca tcctcacact ttgtctctac   3960
tgcatactca gtaattaatt tccaagacac ctgctttgtt tcttcaggct cttctgggtt   4020
aaaatcatgc tcctttaagc ccccttgaat gctttcttct attgtatggt atggatctct   4080
agttaaggca ctatatagta agtattcctt attaacaccc ttacaaatta aaaaactaaa   4140
ggtacacagc ttttgacaga aattattaat tgcagaaact ctatgtctat gtggagttaa   4200
aaagaatata atattatgcc cagcacacat gtgtctacta ataaaagtta cagaatattt   4260
ttccataagt tttttataca ggatttgagc ttttctttta gtagtataca cagcaaagca   4320
ggcaagggtt ctattactaa atacagcttg actaagaaac tggtgtagat cagaaggaaa   4380
gtctttaggg tcttctacct ttctctttttt cttgggtggt gtggagtgtt gagaatctgc   4440
tgttgcttct tcatcactgg caaacatatc ttcatggcaa aataaatctt catcccattt   4500
ttcattaaag gagctccacc aggactccca ctcttctgtt ccataggttg gcacctataa   4560
aaaaaataat tacttagggc ctttaaatat tttcttattt atctaaatat aagttagtta   4620
ccctaaagct ttagatctct gaagggagtt tctccaatta tttggaccca ccattgcaga   4680
gtttcttcag ttaggtctaa gccaaaccac tgtgtgaagc agtcaatgca gtagcaatct   4740
atccaaacca agggctcttt tcttaaaaat tttctattta aatgccttaa tctaagctga   4800
catagcatgc aagggcagtg cacagaaggc ttttggaac aaataggcca atccttgcag   4860
tacagggtat ctgggcaaag aggaaaatca gcacaaacct ctgagctact ccaggttcca   4920
aaatcaggct gatgagctac ctttacatcc tgctccattt ttttatataa agtattcatt   4980
ctcttcattt tatcctcgtc gccccctttg tcagggtgaa attccttaca cctccttaaa   5040
taggcttttc tcattaaggg aaggtttccc caggcagctc tttcaaggcc taaaaggtcc   5100
atgagctcca tggattcttc cctgttaagc actttatcca t                      5141

<210> SEQ ID NO 30
<211> LENGTH: 5141
<212> TYPE: DNA
<213> ORGANISM: Human polyomavirus type BK virus

<400> SEQUENCE: 30
ttttgcaaaa attgcaaaag aatagggatt tccccaaata ttttttgctag gcctcagaaa     60 aagcctccac acccttacta cttgagagaa agggtggagg cagaggcggc ctcggcctct    120
tatatattat aaaaaaaaag gccacaggga ggagctgcta acccatggaa tgtagccaaa    180
ccatgacctc aggaaggaaa gtgcatgact gggcagccag ccagtggcag ttaatagtga    240
aaccccgccc ctaaaattct caaataaaca caagaggaag tggaaactgg ccaaaggagt    300
ggaaagcagc cagacagaca tgttttgcga gcctaggaat cttggccttg tcccagtta    360 aactggacaa aggccatggt tctgcgccag ctgtcacgac aagcttctgt gaaagttagt    420
aaaacctgga ctgaacaaa aaaagagct cagaggattt ttattttttat tttagagctt    480 ttgctggaat tttgtagagg tgaagacagt gtagacggga aaaacaaaag taccactgct    540
ttacctgctg taaagactc tgtaaaagac tcctaggtaa gtaatccctt tttttttgta    600
tttccaggtt gatgggtgct gctctagcac ttttgggga cctagttgcc agtgtatctg    660
```

```
aggctgctgc tgccacagga ttttcagtgg ctgaaattgc tgctggggag gctgctgctg     720
ctatagaagt tcaaattgca tcccttgcta ctgcagaggg cataacaagt acctcagagg     780
ctatagctgt tataggccta actcctcaaa catatgctgt aattgctggt gctcctgggg     840
ctattgctgg gtttgctgct ttaattcaaa ctgttactgg tattagttcc ttggctcaag     900
tagggtatag gttttttagt gattgggatc acaaagtttc cactgtaggc ctctatcagc     960
aatcaggcat ggctttggaa ttgtttaacc cagatgagta ctatgatatt ttgtttcctg    1020
gtgtaaatac ttttgtaaat aatattcaat accttgatcc taggcattgg ggtccttcct    1080
tgtttgctac tatttcccag gctttgtggc atgttattag ggatgatata cctgctataa    1140
cctcacaaga attgcaaaga agaacagaaa gatttttttag agactccttg gctagatttt    1200
tggaggaaac tacctggaca attgtaaatg ccctatgaa cttttataat tatattcaag    1260
aatattattc tgatctttcc cctattaggc cctcaatggt tagacaagtg gctgaaaggg    1320
aaggtacccg tgtacatttt ggccatactt atagtataga tgatgctgac agtatagaag    1380
aagttacaca aagaatggac ttaagaaatc aacaaactgt acattcagga gagtttatag    1440
aaaaaactat tgccccagga ggtgctaatc aaagaactgc tcctcaatgg atgttgcctt    1500
tacttctagg cctgtacggg actgtaacac ctgctcttga agcatatgaa gatgccccca    1560
accaaaagaa aaggagagtg tccaggggca gctcccaaaa agccagagga acccgtgcaa    1620
gtgccaaaac tactaataaa aggaggagta gaagttctag aagttaaaac tggggtagat    1680
gctataacag aggtagaatg cttcctaaac ccagaaatgg gggatccaga tgaaaacctt    1740
agggggcttta gtctaaagct aagtgctgaa aatgacttta gcagtgatag cccagaaaga    1800
aaaatgcttc cctgttacag cacagcaaga attcccctcc ccaatttaaa tgaggaccta    1860
acctgtggaa atctactgat gtgggaggct gtaactgtac aaacagaggt cattggaata    1920
actagcatgc ttaaccttca tgcagggtca caaaaagtgc atgagcatgg tggaggtaaa    1980
cctattcaag gcagtaattt ccacttctttt gctgttggtg gagacccctt ggaaatgcag    2040
ggagtgctaa tgaattacag gaccaagtac ccagatggta ctataacccc aaaaaaccca    2100
acagcccagt cccaggtaat gaatactgac cataaggcct atttggacaa aaacaatgct    2160
tatccagttg agtgctgggt tcctgatccc agtagaaatg aaaatactag gtattttgga    2220
actttcacag gaggggaaaa tgttcccca gtacttcatg tgaccaacac agctaccaca    2280
gtgttgctag atgaacaggg tgtgggggcct cttttgtaaag ctgatagcct gtatgtttca    2340
gctgctgata tttgtggcct gtttactaac agctctggaa cacaacagtg gagaggcctt    2400
gcaagatatt ttaagattcg cctgagaaaa agatctgtaa aaaatcctta cccaatttcc    2460
tttttgctga gtgaccttat aaacaggaga acccagagag tggatgggca gcctatgtat    2520
ggtatggaat cccaggtaga agaggtcagg gtgtttgatg gcacagaaag acttccaggg    2580
gacccagata tgataagata tattgataaa caaggacaat tgcaaaccaa aatgctttaa    2640
acaggtgctt ttattgtaca tatacatttta ataaatgctg cttttgtata agccactttt    2700
aagcttgtgt tattttgggg gtggtgtttt aggccttttta aaacattgaa agcctttaca    2760
caaatgcaac tcttgactat gggggtctga cctttgggaa tcttcagcag gggctgaagt    2820
atctgagact tgggaagagc attgtgattg ggattcagtg cttgatccat gtccagagtc    2880
ttcagttct gaatcttctt ctcttgtgat atcaagaata catttcccca tgcatatatt    2940
atatttcatc cttgaaaaag tatacatact tatctcagaa tccagccttt ccttccattc    3000
```

```
aacaattcta gattgtatat ctgttgcaaa atcagctaca ggcctaaacc aaattagcag    3060
tagcaacaag gtcattccac tttgtaaaat tcttttttca agtaagaact ctgagttttg    3120
taaggatttt cttaaatata ttttgggtct aaaatctatc tgtcttacaa atctagcctg    3180
cagggtttta ggaacaggat actcattcat tgtaaccagg cctggtggaa atatttgggt    3240
ccttttgttt aaatgtttct tttctaaatt aaccttaaca cttccatcta ataatctct    3300 caaactgtct aaattgttta ttccatgtcc tgaaggcaaa tcctttgatt cagcccagt    3360 tccttttaca tcttcaaaaa caaccatgta ctgatctata gctacaccta gttcaaaggt    3420 tagccttttcc atgggtaggt ttacatttaa ggctttacct ccacacaaat ctaataaccc    3480
tgcagctagt gttgtttttc cactatcaat gggacctta aataaccagt atcttctttt    3540
aggtacatta aaaacaatac agtgcaaaaa atcaaatata acagaatcca ttttaggtag    3600
caaacagtgc agccaagcaa cacctgccat atattgttcc agtacagcat tccatgagc    3660 tccaaatatt aaatccattc tatctaatat atgattaaat ctttctgtta gcatttcttc    3720
tctggtcata tgaagggtat ctactctttt tttagctaaa actgtatcta ctgcttgctg    3780
acaaatactt ttttgatttt tacttctgc aaaaatagta gcatttgcaa aatgcttttc    3840
atgatactta aagtgataag gttggtcttt tttctgacac ttttacact cttctacatt    3900 gtattgaaat ctaaataca tacccaataa taaaacaca tcctcacact ttgtctctac    3960
tgcatactca gtaattaatt ccaagacac ctgctttgtt tcttcaggct cttctgggtt    4020
aaaatcatgc tcctttaagc ccccttgaat gctttcttct attgtatggt atggatctct    4080
agttaaggca ctatatagta agtattcctt attaacaccc ttacaaatta aaaaactaaa    4140
ggtacacagc ttttgacaga aattattaat tgcagaaact ctatgtctat gtggagttaa    4200
aaagaatata atattatgcc cagcacacat gtgtctacta ataaaagtta caggatattt    4260
ttccataagt ttttatatca gaatttgagc ttttctttta gtagtataca cagcaaagca    4320
ggcaagggtt ctattactaa atacagcttg actaagaaac tggtgtagat cagaaggaaa    4380
gtctttaggg tcttctacct ttctctttttt cttgggtggt gtggagtgtt gagaatctgc    4440
tgttgcttct tcatcactgg caaacatatc ttcatggcaa aataaatctt catcccattt    4500
ttcattaaag gagctccacc aggactccca ctcttctgtt ccataggttg gcacctataa    4560
aaaaaaaaat tacttagggc ctttaaatat tttcttattt atctaaatat aagttagtta    4620
ccttaaagct ttagatctct gaagggagtt tctccaatta tttggaccca ccattgcaga    4680
gtttcttcag ttaggtctaa gccaaaccac tgtgtgaagc agtcaatgca gtagcaatct    4740
atccaaacca agggctcttt tcttaaaaat tttctattta aatgccttaa tctaagctga    4800
catagcatgc aagggcagtg gacagaaggc ttttggaac aaataggcca atccttgcag    4860 tacgggtat ctgggcaaag aggcaaatca gcacaaacct ctgagctact ccaggttcca    4920
aaatcaggct gatgagctac ctttacatcc tgctccattt ttttatataa agtattcatt    4980
ctcttcattt tatcctcgtc gccccctttg tcagggtgaa attccttaca cttccttaaa    5040
taggcttttc tcattaaggg aaggtttccc caggcagctc tttcaaggcc taaaaggtcc    5100
atgagctcca tggattcttc cctgttaagc actttatcca t                        5141
```

<210> SEQ ID NO 31
<211> LENGTH: 5141
<212> TYPE: DNA
<213> ORGANISM: Human polyomavirus type BK virus

<400> SEQUENCE: 31

-continued

| | |
|---|---|
| ttttgcaaaa attgcaaaag aataggGatt tccccaaata ttttTgctag gcctcagaaa | 60 |
| aagcctccac acccttacta cttgagagaa agggtggagg cagaggcggc ctcggcctct | 120 |
| tatatattat aaaaaaaaag gccacaggga ggagctgcta acccatggaa tgtagccaaa | 180 |
| ccatgacctc aggaaggaaa gtgcatgact gggcagccag ccagtggcag ttaatagtga | 240 |
| aaccccgccc ctaaaattct caaataaaca caagagggga tggaaactgg ccaaggagt | 300 |
| ggaaagcagc cagacagaca tgttttgcga gcctaggaat cttggccttg tccccagtta | 360 |
| aactggacaa aggccatggt tctgcgccag ctgtcacgac aagcttctgt gaaagttagt | 420 |
| aaaacctgga ctgaacaaa aaaagagct cagaggattt ttatttttat tttagagctt | 480 |
| ttgctggaat tttgtagagg tgaagacagt gtagacggga aaacaaaag taccactgct | 540 |
| ttacctgctg taaaagactc tgtaaaagac tcctaggtaa gtaatccctt ttttttgta | 600 |
| tttccaggtt gatgggtgct gctctagcac ttttggggga cctagttgcc agtgtatctg | 660 |
| aggctgctgc tgccacagga ttttcagtgg ctgaaattgc tgctgggag gctgctgctg | 720 |
| ctatagaagt tcaaattgca tcccttgcta ctgtagaggg cataacaagt acctcagagg | 780 |
| ctatagctgc tataggccta actcctcaaa catatgctgt aattgctggt gctcctgggg | 840 |
| ctattgctgg gtttgctgct ttaattcaaa ctgttactgg tattagttcc ttggctcaag | 900 |
| tagggtatag gttttttagt gattgggatc acaaagtttc cactgtaggc ctctatcagc | 960 |
| aatcaggcat ggctttggaa ttgtttaacc cagatgagta ctatgatatt ttgtttcctg | 1020 |
| gtgtaaatac ttttgtaaat aatattcaat accttgatcc taggcattgg ggtccttcct | 1080 |
| tgtttgctac tatttcccag gctttgtggc atgttattag ggatgatata cctgctataa | 1140 |
| cctcacaaga attgcaaaga gaacagaaa gatttttag agactccttg gctagattt | 1200 |
| tggaggaaac tacctggaca attgtaaatg cccctatgaa cttttataat tatattcaag | 1260 |
| aatattattc tgatctttcc cctattaggc cctcaatggt tagacaagtg gctgaaaggg | 1320 |
| aaggtacccg tgtacatttt ggccatactt atagtataga tgatgctgac agtatagaag | 1380 |
| aagttacaca aagaatggac ttaagaaatc aacaaactgt acattcagga gagtttatag | 1440 |
| aaaaaactat tgccccagga ggtgctaatc aaagaactgc tcctcaatgg atgttgcctt | 1500 |
| tacttctagg cctgtacggg actgtaacac ctgctcttga agcatatgaa gatggccca | 1560 |
| accaaaagaa aaggagagtg tccaggggca gctcccaaaa agccaaagga acccgtgcaa | 1620 |
| gtgccaaaac tactaataaa aggaggagta aagttctag aagttaaaac tggggtagat | 1680 |
| gctataacag aggtagaatg cttcctaaac ccagaaatgg gggatccaga tgaaaaccttt | 1740 |
| agggGcttta gtctaaagct aagtgctgaa atgactttta gcagtgatag cccagaaaga | 1800 |
| aaaatgcttc cctgttacag cacagcaaga attcccctcc ccaatttaaa tgaggaccta | 1860 |
| acctgtggaa atctactgat gtgggaggct gtaactgtac aaacagaggt cattggaata | 1920 |
| actagcatgc ttaaccttca tgcagggtca caaaagtgc atgagcatgg tggaggtaaa | 1980 |
| cctattcaag gcagtaattt ccacttcttt gctgttggtg gagaccccctt ggaaatgcag | 2040 |
| ggagtgctaa tgaattacag gaccaagtac ccagatggta ctataaccccc aaaaaaccca | 2100 |
| acagcccagt cccaggtaat gaatactgac cataaggcct attttggacaa aaacaatgct | 2160 |
| tatccagttg agtgctgggt tcctgatccc agtagaaatg aaaatactag gtattttgga | 2220 |
| actttcacag gaggggaaaa tgttccccca gtacttcatg tgaccaacac agctaccaca | 2280 |
| gtgttgctag atgaacaggg tgtggggcct ctttgtaaag ctgatagcct gtatgtttca | 2340 |

```
gctgctgata tttgtggcct gtttactaac agctctggaa cacaacagtg gagaggcctt     2400
gcaagatatt ttaagattcg cctgagaaaa agatctgtaa aaaatcctta cccaatttcc     2460
tttttgctga gtgaccttat aaacaggaga acccagagag tggatgggca gcctatgtat     2520
ggtatggaat cccaggtaga agaggtcagg gtgtttgatg gcacagaaag acttccaggg     2580
gacccagata tgataagata tattgataaa caaggacaat tgcaaaccaa aatgctttaa     2640
acaggtgctt ttattgtaca tatacattta ataaatgctg cttttgtata agccacttt      2700 aagcttgtgt tattttgggg gtggtgtttt aggcctttta aaacattgaa agcctttaca     2760
caaatgcaac tcttgactat gggggtctga cctttgggaa tcttcagcag gggctgaagt     2820
atctgagact tgggaagagc attgtgattg ggattcagtg cttgatccat gtccagagtc     2880
ttcagtttct gaatcttctt ctcttgtgat accaagaata catttcccca tgcatatatt     2940
atatttcatc cttgaaaaag tatacatact tatctcagaa tccagccttt ccttccattc     3000
aacaattcta gattgtatat ctgttgcaaa atcagctaca ggcctaaacc aaattagcag     3060
tagcaacaag gtcattccac tttgtagaat tctttttca agtaagaact ctgagttttg      3120
taaggatttt cttaaatata ttttgggtct aaaatctatc tgtcttacaa atctagcctg     3180
cagggtttta ggaacaggat actcattcat tgtaaccagg cctggtggaa atatttgggt     3240
tcttttgttt aaatgtttct tttctaaatt aaccttaaca cttccatcta aataatctct     3300
caaactgtct aaattgttta ttccatgtcc tgaaggcaaa tcctttgatt cagccccagt     3360
tccttttaca tcttcaaaaa caaccatgta ctgatctata gctacaccta gttcaaaggt     3420
tagcctttcc atgggtaggt ttacatttaa ggctttacct ccacacaaat ctaataaccc     3480
tgcagctagt gttgtttttc cactatcaat gggaccttta ataaccagt atcttctttt      3540 aggtacatta aaaacaatac agtgcaaaaa atcaaatata acagaatcca ttttaggtag     3600
caaacagtgc agccaagcaa cacctgccat atattgttcc agtacagcat ttccatgagc     3660
tccaaatatc aaatccattt tatctaatat atgattaaat cttctgttta gcatttcttc     3720
tctggtcata tgaagggtat ctactctttt tttagctaaa actgtatcta ctgcttgctg     3780
acaaatactt ttttgatttt tactttctgc aaaaatagta gcatttgcaa aatgcttttc     3840
atgatactta aagtgataag gttggtcttt tttctgacac tttttacact cttctacatt     3900
gtattgaaat tctaaataca tacccaataa taaaaacaca tcctcacact ttgtctctac     3960
tgcatactca gtaattaatt tccaagacac ctgctttgtt tcttcaggct cttctgggtt     4020
aaaatcatgc tcctttaagc ccccttgaat gctttcttct attgtatggt atggatctct     4080
agttaaggca ctatatagta agtattcctt attaacaccc ttacaaatta aaaaactaaa     4140
ggtacacagc ttttgacaga aattattaat tgcagaaact ctatgtctat gtggagttaa     4200
aaagaatata atattatgcc cagcacacat gtgtctacta ataaaagtta cagaatattt     4260
ttccataagt ttttatcaa gaatttgagc ttttcttta gtgtataca cagcaaagca       4320 ggcaagggtt ctattactaa atacagcttg actaagaaac tggtgtagat cagagggaaa     4380
gtctttaggg tcttctacct ttctcttttt cttgggtggt gtggagtgtt gagaatctgc     4440
tgttgcttct tcatcactgg caaacatatc ttcatggcaa ataaatctt catcccattt      4500 ttcattaaag gagctccacc aggactccca ctcttctgtt ccataggttg cacctataa      4560 aaaaaataat tacttagggc ctttaaatat tttcttattt atctaaatat aagttagtta     4620
ccttaaagct ttagatctct gaagggagtt tctccaatta tttggaccca ccattgcaga     4680
gtttcttcag ttaggtctaa gccaaaccac tgtgtgaagc agtcaatgca gtagcaatct     4740
```

```
atccaaacca agggctcttt tcttaaaaat tttctattta aatgccttaa tctaagctga    4800
catagcatgc aagggcagtg cacagaaggc ttttggaac aaataggcca atccttgcag     4860
tacagggtat ctgggcaaag aggaaaatca gcacaaacct ctgagctact ccaggttcca    4920
aaatcaggct gatgagctac ctttacatcc tgctccattt ttttatataa agtattcatt    4980
ctcttcattt tatcctcgtc gcccctttg tcagggtgaa attccttaca cttccttaaa     5040
taggcttttc tcattaaggg aaggtttccc caggcagctc tttcaaggcc taaaaggtcc    5100
atgagctcca tggattcttc cctgttaagc actttatcca t                       5141

<210> SEQ ID NO 32
<211> LENGTH: 5140
<212> TYPE: DNA
<213> ORGANISM: Human polyomavirus type BK virus

<400> SEQUENCE: 32
ttttgcaaaa attgcaaaag aatagggatt tccccaaata ttttgctag gcctcagaaa      60 aagcctccac acccttacta cttgagagaa agggtggagg cagaggcggc ctcggcctct    120
tatatattat aaaaaaaaag gccacaggga ggagctgcta acccatggaa tgtagccaaa    180
ccatgacctc aggaaggaaa gtgcatgact gggcagccag ccagtggcag ttaatagtga    240
aaccccgccc taaaattctc aaataaacac aagaggaagt ggaaactggc caaaggagtg    300
gaaagcagcc agacagacat gttttgcgag cctaggaatc ttggccttgt ccccagttaa    360
actggacaaa ggccatggtt ctgcgccagc tgtcacgaca agcttctgtg aaagttagta    420
aaacctggac tggaacaaaa aaaagagctc agaggatttt tatttttatt ttagagcttt    480
tgctggaatt ttgtagaggt gaagacagtg tagacggaa aaacaaaagt accactgctt     540
tacctgctgt aaaagactct gtaaagact cctaggtaag taatccctt ttttttgtat      600 ttccaggttg atgggtgctg ctctagcact tttgggggac ctagttgcca gtgtatctga    660
ggctgctgct gccacaggat tttcagtggc tgaaattgct gctggggagg ctgctgctgc    720
tatagaagtt caaattgcat cccttgctac tgtagagggc ataacaagta cctcagaggc    780
tatagctgct ataggcctaa ctcctcaaac atatgctgta attgctggtg ctcctgggc     840 tattgctggg tttgctgctt taattcaaac tgttactggt attagttcct ggctcaagt     900 agggtatagg ttttttagtg attgggatca caaagtttcc actgtaggcc tctatcagca    960
atcaggcatg cttttggaat tgtttaaccc agatgagtac tatgatattt tgtttcctgg    1020
tgtaaatact tttgtaaata atattcaata ccttgatcct aggcattggg gtccttcctt    1080
gtttgctact atttcccagg cttttgtggca tgttattagg gatgatatac ctgctatgac    1140
ctcacaagaa ttgcaaagaa gaacagaaag attttttaga gactccttgg ctagattttt    1200
ggaggaaact acctgacaa ttgtaaatgc ccctatgaac tttataatt atattcaaga     1260 atattattct gatctttccc ctattaggcc ctcaatggtt agacaagtgg ctgaaaggga    1320
aggtacccgt gtacattttg gccatactta tagtatagat gatgctgaca gtatagaaga    1380
agttacacaa agaatggact taagaaatca acaaactgta cattcaggag agtttataga    1440
aaaaactatt gccccaggag gtgctaatca agaactgct cctcaatgga tgttgccttt      1500
acttctaggc ctgtacggga ctgtaacacc tgctcttgaa gcatatgaag atggccccaa    1560
ccaaaagaaa aggagagtgt ccagggggcag ctcccaaaaa gccaaaggaa cccgtgcaag    1620
tgccaaaact actaataaaa ggaggagtag aagttctaga agttaaaact ggggtagatg    1680
```

```
ctataacaga ggtagaatgc ttcctaaacc cagaaatggg ggatccagat gaaaacctta    1740
ggggctttag tctaaagcta agtgctgaaa atgactttag cagtgatagc ccagaaagaa    1800
aaatgcttcc ctgttacagc acagcaagaa ttcccctccc caatttaaat gaggacctaa    1860
cctgtggaaa tctactgatg tgggaggctg taactgtaca aacagaggtt actgaataa     1920 ctagcatgct taaccttcat gcagggtcac aaaaagtgca tgagcatggt ggaggtaaac    1980
ctattcaagg cagtaatttc cacttctttg ctgttggtgg agacccttg gaaatgcagg     2040 gagtgctaat gaattacagg accaagtacc cagatggtac tataacccca aaaaacccaa    2100
cagcccagtc ccaggtaatg aatactgacc ataaggccta tttggacaaa acaatgctt    2160 atccagttga gtgctgggtt cctgatccca gtagaaatga aaatactagg tattttggaa    2220 cttcacagg aggggaaaat gttcccccag tacttcatgt gaccaacaca gctaccacag     2280
tgttgctaga tgaacagggt gtggggcctc tttgtaaagc tgatggcctg tatgtttcag    2340
ctgctgatat ttgtggcctg tttactaaca gctctggaac acaacagtgg agaggccttg    2400
caagatattt taagactcgc ctgagaaaaa gatctgtaaa aaatccttac ccaatttcct    2460
ctttgctgag tgaccttata aacaggagaa cccagagagt ggatgggcag cctatgtatg    2520
gtatggaatc ccaggtagaa gaggtcaggg tgtttgatgg cacagaaaga cttccagggg    2580
acccagatat gataagatat attgataaac aaggacaatt gcaaaccaaa atgctttaaa    2640
caggtgcttt tattgtacat atacatttaa taaatgctgc ttttgtataa gccactttta    2700
agcttgtgtt attttggggg tggtgtttta ggccttttaa aacattgaaa gcctttacac    2760
aaatgcaact cttgactatg ggggtctgac cttttgggaat cttcagcagg ggctgaagta    2820
tctgagactt gggaagagca ttgtgattgg gattcagtgc ttgatccatg tccagagtct    2880
tcagtttctg aatcttcttc tcttgtgata tcaagaatac atttccccat gcatatatta    2940
tatttcatcc ttgaaaaagt atacatactt atctcagaat ccagccttt cttccattca    3000 acaattctag attgtatatc tgttgcaaaa tcagctacag gcctaaacca aattagcagt    3060
agcaacaagg tcattccact ttgtaaaatt cttttttcaa gtaagaactc tgagttttgt    3120
aaggattttc ttaaatatat tttgggtcta aaatctatct gtcttacaaa tctagcctgc    3180
agggttttag gaacaggata ctcattcatt gtaaccaggc ctggtggaaa tatttgggtt    3240
cttttgttta aatgtttctt ttctaaatta accttaacac ttccacctaa ataatctctc    3300
aaactgtcta aattgtttat tccatgtcct gaaggcaaat cctttgattc agccccagtt    3360
ccttttacat cttcaaaaac aaccacgtac tgatctatag ctacacctag ttcaaaggtt    3420
agcctttcca tgggtaggtt tacatttaag gctttacctc cacacaaatc taataaccct    3480
gcagctagtg ttgtttttcc actatcagtg ggacctttaa ataaccagta tcttcttta    3540 ggtacattaa aaacaataca gtgcaaaaaa tcaaatataa cagaatccat tttaggtagc    3600
aaacagtgca gccaagcaac acctgccata tattgttcca gtacagcatt tccatgagct    3660
ccaaatatta aatccatttt atctaatata tgattaaatc tttctgttag catttcttct    3720
ctggtcatat gaagggtatc tactcttttt ttagctaaaa ctgtatctac tgcttgctga    3780
caaatacttt tttgattttt acttctgca aaaatagtag catttgcaaa atgctttca     3840 tgatacttaa agtgataagg ttggtctttt ttctgacact ttttgcactc ttctacattg    3900
tattgaaatt ctaaatacat acccaataat aaaaacacat cctcacactt tgtctctact    3960
gcatactcag taattaattt ccaagacacc tgctttgttt cttcaggctc ttctgggtta    4020
aaatcatgct cctttaagcc cccttgaatg ctttcttcta ttgtatggta tggatctcta    4080
```

```
gttaaggcac tatatagtaa gtattcctta ttaacaccct tacaaattaa aaaactaaag    4140
gtacacagct tttgacagaa attattaatt gcagaaactc tatgtctatg tggagttaaa    4200
aagaatataa tattatgccc agcacacatg tgtctactaa taaaagttac agaatatttt    4260
tccataagtt ttttatacag aatttgagct ttttctttag tagtatacac agcaaagcag    4320
gcaagggttc tattactaaa tacagcttga ctaagaaact ggtgtagatc agaaggaaag    4380
tctttagggt cttctacctc tctctttttc ttgggtggtg tggagtgttg agaatctgct    4440
gttgcttctt catcactggc aaacatatct tcatggcaaa ataaatcttc atcccatttt    4500
tcattaaagg agctccacca ggactcccac tcttctgttc cataggttgg cacctataaa    4560
aaaaataatt acttagggcc tttaaatatt ttcttattta tctaaatata agttagttac    4620
cttaaagctt tagatctctg aagggagttt ctccaattat ttggacccac cattgcagag    4680
tttcttcagc taggtctaag ccaaaccact gtgtgaagca gtcaatgcag tagcaatcta    4740
tccaaaccaa gggctctttt cttaaaaatt ttctatttaa atgccttaat ctaagctgac    4800
atagcatgca agggcagtgc acagaaggct ttttggaaca aataggccat tccttgcagt    4860
acagggtatc tgggcaaaga ggaaaatcag cacaaacctc tgagctactc caggttccaa    4920
aatcaggctg atgagctacc tttacatcct gctccatttt tttatataaa gtattcattc    4980
tcttcatttt atcctcgtcg ccccctttgt cagggtgaaa ttccttacac ttccttaaat    5040
aggcttttct cattaaggga aggtttcccc aggcagctct ttcaaggcct aaaaggtcca    5100
tgagctccat ggattcttcc ctgttaagca ctttatccat                         5140

<210> SEQ ID NO 33
<211> LENGTH: 5092
<212> TYPE: DNA
<213> ORGANISM: Human polyomavirus type BK virus

<400> SEQUENCE: 33
ttttgcaaaa attgcaaaag aatagggatt tccccaaata gttttgctag gcctcagaaa      60
aagcctccac acccttacta cttgaaagaa agggtggagg cagaggcggc ctcggcctct     120
tatatattat aaaaaaaaag gccacaggga ggagctgctt acccatggaa tgcagccaaa     180
ccatgaccct caggaaggaa agtgcatgact gggcagccag ccaagaggaa gtggaaactg     240
gccaaaggag tggaaagcag ccagacagac atgttttgcg ggcctaggaa tcttggcctt     300
gtccccagtt aaactggaca aaggccatgg ttctgcgcca gctgtcacga caagcttctg     360
tgaaacttgg taaaacctgg actggaacaa aaaaagagc tcagaggatt tttatttttta     420 ttttagagct tttgctggaa ttttgtagag gtgaagacag tgtagacggg aaaaacaaaa     480
gtaccactgc tttacctgct gtaaaagact ctgtaaaaga ctcctaggta agtaatccct     540
ttttttttgt atttccaggt tgatgggtgc tgctctagca ctttttgggg acctagttgc     600
cagtgtatct gaggctgctg ctgccacagg attttcagtg gctgaaattg ctgctgggga     660
ggctgctgct gctatagaag ttcaaattgc atcccttgct actgtagagg cataacaag      720 tacctcagag gctatagctg ctataggcct aactcctcaa acatatgctg taattgctgg     780
tgctcctggg gctattgctg ggtttgctgc tttaattcaa actgttactg gtattagttc     840
cttggctcaa gtagggtata ggtttttag tgattgggat cacaaagttt ccactgtagg     900
cctctatcag caatcaggca tggctttgga attgttttaac ccagatgagt actatgatat     960
attgtttcct ggtgtaaata cttttgtaaa taatattcaa taccttgatc ctaggcattg    1020
```

```
gggtccttct tgtttgcta ctatttctca ggctttgtgg catgttatta gggatgatat    1080
acctgctata acctcacaag aattgcaaag aagaacagaa agattttta gagactcctt    1140 ggctagattt ttggaggaaa ctacctggac aattgtaaat gccctatga acttttataa    1200 ttatattcaa gaatattatt ctgatctttc ccctattagg cccttaatgg ttagacaagt    1260
agctgaaagg gaaggtaccc gtgtacattt tggccatact tatagtatag atgatgctga    1320
cagtatagaa gaagttacac aaagaatgga cttaagaaat caacaaactg tacattcagg    1380
agagtttata gaaaaaacta ttgccccagg aggtgctaat caaagaactg ctcctcaatg    1440
gatgttgcct ttacttctag gcctgtacgg gactgtaaca cctgctcttg aagcatatga    1500
agatggcccc aacaaaaaga aaaggagagt gtccaggggc agctcccaaa agccaaagg    1560 aacccgtgca agtgccaaaa ctactaataa aaggaggagt agaagttcta gaagttaaaa    1620
ctgggctaga tgctataaca gaggtagaat gcttcctaaa cccagaaatg ggggatccag    1680
atgaaaacct tagggctttt agtctaaagc taagtgctga aaatgacttt agcagtgata    1740
gcccagaaag aaaaatgctt ccctgttaca gcacagcaag aattcccctc cccaatttaa    1800
atgaggacct aacctgtgga aatctactga tgtgggaggc tgtaacagta caaacagagg    1860
tcattggaat aactagcatg cttaaccttc atgcagggtc acaaaaagtg catgagcatg    1920
gtggaggtaa acctattcaa ggcagtaatt ccactttttt tgctgttggt ggagacccct    1980
tggaaatgca gggagtgcta atgaattaca ggacaaagta cccagaaggt actataaccc    2040 caaaaaccc aacagcccag tcccaagtaa tgaatactga ccataaggcc tatttggaca    2100
aaaacaatgc ttatccagtt gagtgctgga ttcctgatcc cagtagaaat gaaaatacta    2160
ggtattttgg gactttcaca ggaggggaaa atgttcccc agtacttcat gtgaccaaca    2220
cagctaccac agtgttgcta gatgaacagg gtgtggggcc tctttgtaaa gctgatagcc    2280
tgtatgtttc agctgctgat atttgtggcc tgtttactaa cagctctgga acacaacagt    2340
ggagaggcct tgcaagatat tttaagattc gcctgagaaa aagatctgta aaaaatcctt    2400
acccaatttc cttttgcta agtgaccta taaacagggg aacccagaga gtggatgggc    2460
agcctatgta tggtatggaa tcccaggtag aagaggtcag ggtgtttgat ggcacagaaa    2520
gacttccagg ggacccagat atgataagat atattgacaa acaaggacaa ttgcaaacta    2580
aaatggttta aacaggtgct tttattgtac atatacattt aataaatgct gcttttgtat    2640
aagccagttc taagcttgtg ttattttggg ggtggtgttt taggcctttt aaaacactga    2700
aagcctttac acaaatgcaa ctcttgacta tgggggtctg acctttggga atcttcagca    2760
ggggctgaag tatctgagac ttgggaagag cattgtgatt gggattcagt gcttgatcca    2820
tgtccagagt cttcagtttc tgaatcttct tctcttgtga tatcaagaat acatttcccc    2880
atgcatatat tatatttcat ccttgaaaaa gtatacatac ttatctcaga atccagcctt    2940
tccttccatt caacaattct agattgtata tctgttgcaa aatcagctac aggcctaaac    3000
caaattagca gtagcaacaa ggtcattcca ctttgtaaaa ttcttttttc aagtaagaac    3060
tctgagtttt gtaaggattt tcttaaatat attttgggcc taaatctat ctgtcttaca    3120 aatctagcct gcagggtttt agggacagga tactcattca ttgtaaccag gcctggtgga    3180
aatatttggg ttcttttgtt taatgtttc ttttctaaat taaccttaac acttccatct    3240
aaataatctc tcaaactgtc taaattgttt attccatgtc ctgaaggcaa atcctttgat    3300
tcagctcctg ttcctttac atcttcaaaa acaaccatgt actgatctat agctacacct    3360
agttcaaagg tcagcctttc catgggtagg tttacattta aagctttacc tccacacaaa    3420
```

-continued

```
tctaataacc ctgcagctag tgttgttttt ccactatcaa tgggaccttt aaataaccag    3480
tatcttcttt taggtacatt aaaaacaata cagtgcaaaa atcaaatat aacagaatcc     3540 attttaggta acaaacagtg cagccaagca acacctgcca tatattgttc taatacagca    3600
tttccatgag ccccaaatat taaatccatt ttatctaata tatgattaaa tctttctgtt    3660
agcatttctt ctctagtcat atggaggcta tctactcttt ttttagctaa aactgtatct    3720
actgcttgct gacaaatact ttttgattt ttactttctg caaagatagt agcatttgca     3780
aaatgctttt catgatactt aaagtgataa ggttggtctt ttttctgaca cttttttacac   3840 tcctctacat tgtattgaaa ttctaaatac atacctaata ataaaaacac atcctcacac    3900
tttgttccta ctgcatactc agtaattaat ttccaagaga cctgctttgt ttcttcaggc    3960
tcttctgggt taaaatcatg ctcctttaag cccccttgaa tgctttcttc tattgtatgg    4020
tatggatctc tagttaaggc actatatagt aagtattcct tattaacacc cttacaaatt    4080
aaaaaactaa aggtacacag cttttgacag aaattattaa ttgcagaaac tctatgtcta    4140
tgtggagtta aaaagaatat aatattatgc ccagcacaca tgtgtctact aataaaagtt    4200
acagaatatt tttccataag ttttttatac agaatttgag cttttcttt agtagtatac     4260 acagcaaagc aggcaagggt tctattacta aatacagctt gactaagaaa ctggtgtaga    4320
tcacaaggaa agtctttagg gtcttctacc tttcttttt tcttgggtgg tgttgagtgt     4380
tgagaatctg ctgttgcttc ttcatcactg gcaaacatat cttcatggca aaataaatct    4440
tcatcccatt tttcattaaa ggagctccac caggactccc actcttctgt tccataggtt    4500
ggcacctata aaacaaataa ttacttaggg cctttaaata ttttattatt tatttaaata    4560
taaggtagtt accttaaagc tttagatctc tgaagggagt ttctccaatt atttggaccc    4620
accattgcag agtttcttca gttaggtcta agccaaacca ctgtgtgaag cagtcaatgc    4680
agtagcaatc tatccaaacc aagggctctt ttcttaaaaa ttttctattt aaatgcctta    4740
atctaagctg acatagcatg caaggacagt gcacagaagg cttttggaa caaataggcc     4800 attccttgca gtacaggtc tctgggcaaa gaggaaaatc agcacaaacc tctgagctac     4860
tccaggttcc aaaatcaggc tgatgagcta cctttacatc ttgctccatt tttttatata    4920
aagtattcat tctcttcatt ttatcctcgt cgcccccttt gtcagggtga aattccttac    4980
acttccttaa ataggctttt ctcattaagg aaaggtttcc ccaggcagct ctttcaaggc    5040
ccaaaaggtc catgagctcc atggattctt ccctgttaag cactttatcc at            5092
```

<210> SEQ ID NO 34
<211> LENGTH: 5141
<212> TYPE: DNA
<213> ORGANISM: Human polyomavirus type BK virus

<400> SEQUENCE: 34

```
ttttgcaaaa attgcaaaag aatagggatt tccccaaata gttttgctag gcctcagaaa      60
aagcctccac acccttacta cttgaaagaa agggtggagg cagaggcggc ctcggcctct     120
tatatattat aaaaaaaaag gccacaggga ggagctgctt acccatggaa tgcagccaaa    180 ccatgaccctc aggaaggaaa gtgcatgact gggcagccag ccagtggcag ttaatagtga   240
aaccccgccc ctgaaattct caaataaaca caagaggaag tggaaactgg ccaaaggagt    300
ggaaagcagc cagacagaca tgttttgcgg gcctaggaat cttggccttg tcccagtta    360 aactggacaa aggccatggt tctgcgccag ctgtcacgac aagcttctgt gaaacttggt   420
```

```
aaaacctgga ctggaacaaa aaaaagagct cagaggattt ttattttat tttagagctt      480 ttgctggaat tttgtagagg tgaagacagt gtagacggga aaaacaaaag taccactgct      540
ttacctgctg taaaagactc tgtaaaagac tcctaggtaa gtaatcectt ttttttgta      600 tttccaggtt gatgggtgct gctctagcac ttttggggga cctagttgcc agtgtatctg      660
aggctgctgc tgccacagga ttttcagtgg ctgaaattgc tgctggggag gctgctgctg      720
ctatagaagt tcaaattgca tccecttgcta ctgtagaggg cataacaagt acctcagagg      780
ctatagctgc tataggccta actcctcaaa catatgctgt aattgctggt gctcctgggg      840
ctattgctgg gtttgctgct ttaattcaaa ctgttactgg tattagttcc ttggctcaag      900
tagggtatag gttttttagt gattgggatc acaaagtttc cactgtaggc ctctatcagc      960
aatcaggcat ggctttggaa ttgtttaacc cagatgagta ctatgatata ttgtttcctg     1020
gtgtaaatac ttttgtaaat aatattcaat accttgatcc taggcattgg ggtccttctt     1080
tgtttgctac tatttctcag gctttgtggc atgttattag ggatgatata cctgctataa     1140
cctcacaaga attgcaaaga agaacagaaa gattttttag agactccttg gctagatttt     1200
tggaggaaac tacctggaca attgtaaatg cccctatgaa cttttataat tatattcaag     1260
aatattattc tgatctttcc cctattaggc cctcaatggt tagacaagta gctgaaaggg     1320
aaggtacccg tgtacatttt ggccatactt atagtataga ttatgctgac agtatagaag     1380
aagttacaca aagaatggac ttaagaaatc aacaaactgt acattcagga gagtttatag     1440
aaaaaactat tgccccagga ggtgctaatc aaagaactgc tcctcaatgg atgttgcctt     1500
tacttctagg cctgtacggg actgtaacac ctgctcttga agcatatgaa gatggcccca     1560
acaaaaagaa aaggagagtg tccaggggca gctcccaaaa agccaaagga acccgtgcaa     1620
gtgccaaaac tactaataaa aggaggagta gaagttctag aagttaaaac tgggctagat     1680
gctataacag aggtagaatg cttcctaaac ccagaaatgg gggatccaga tgaaaacctt     1740
aggggcttta gtctaaagct aagtgctgaa aatgacttta gcagtgatag cccagaaaga     1800
aaaatgcttc cctgttacag cacagcaaga attcccctcc ccaatttaaa tgaggaccta     1860
acctgtggaa atctactgat gtgggaggct gtaacagtac aaacagaggt cattggaata     1920
actagcatgc ttaaccttca tgcagggtca caaaaagtgc atgagcatgg tggaggtaaa     1980
cctattcaag gcagtaattt ccactttttt gctgttggtg gagaccccctt ggaaatgcag     2040 ggagtgctaa tgaattacag gacaaagtac ccagaaggta ctataacccc aaaaaaccca     2100
acagcccagt cccaagtaat gaatactgac cataaggcct atttggacaa aaacaatgct     2160
tatccagttg agtgctggat tcctgatccc agtagaaatg aaaatactag gtattttggg     2220
actttcacag gaggggaaaa tgttcccca gtacttcatg tgaccaacac agctaccaca     2280
gtgttgctag atgaacaggg tgtggggcct cttgtaaag ctgatagcct gtatgtttca     2340
gctgctgata tttgtggcct gtttactaac agctctggaa cacaacagtg gagaggcctt     2400
gcaagatatt ttaagattcg cctgagaaaa agatctgtaa aaaatcctta cccaatttcc     2460
tttttgctaa gtgaccttat aaacaggaga acccagagag tggatgggca gcctatgtat     2520
ggtatggaat cccaggtaga agaggtcagg gtgtttgatg gcacagaaag acttccaggg     2580
gacccagata tgataagata tattgacaaa caaggacaat tgcaaactaa aatggtttaa     2640
acaggtgctt ttattgtaca tatacattta ataaatgctg cttttgtata agccagttct     2700
aagcttgtgt tattttgggg gtggtgtttt aggcctttta aaacactgaa agcctttaca     2760
caaatgcaac tcttgactat gggggtctga cctttgggaa tcttcagcag gggctgaagt     2820
```

```
atctgagact tgggaagagc attgtgattg ggattcagtg cttgatccat gtccagagtc    2880
ttcagtttct gaatcttctt ctcttgtgat atcaagaata catttcccca tgcatatatt    2940
atatttcatc cttgaaaaag tatacatact tatctcagaa tccagccttt ccttccattc    3000
aacaattcta gattgtatat ctgttgcaaa atcagctaca ggcctaaacc aaattagcag    3060
tagcaacaag gtcattccac tttgtaaaat tcttttttca agtaagaact ctgagttttg    3120
taaggatttt cttaaatata ttttgggcct aaaatctatc tgtcttacaa atctagcctg    3180
cagggtttta gggacaggat actcattcat tgtaaccagg cctggtggaa atatttgggt    3240
tcttttgttt aaatgtttct tttctaaatt aaccttaaca cttccatcta ataatctct    3300 caaactgtct aaattgttta ttccatgtcc tgaaggcaaa tcctttgatt cagctcctgt    3360
tccttttaca tcttcaaaaa caaccatgta ctgatctata gctacaccta gttcaaaggt    3420
cagcctttcc atgggtaggt ttacatttaa agctttacct ccacacaaat ctaataaccc    3480
tgcagctagt gttgtttttc cactatcaat gggaccttta aataaccagt atcttctttt    3540
aggtacatta aaaacaatac agtgcaaaaa atcaaatata acagaatcca ttttaggtaa    3600
caaacagtgc agccaagcaa cacctgccat atattgttct aatacagcat ttccatgagc    3660
cccaaatatt aaatccattt tatctaatat atgattaaat cttctgttta gcatttcttc    3720
tctagtcata tgaaggctat ctactctttt tttagctaaa actgtatcta ctgcttgctg    3780
acaaatactt ttttgatttt tactttctgc aaagatagta gcatttgcaa aatgcttttc    3840
atgatactta aagtgataag gttggtcttt tttctgacac ttttacact cctctacatt    3900 gtattgaaat tctaaataca tacctaataa taaaaacaca tcctcacact tgtttctac    3960 tgcatactca gtaattaatt tccaagagac ctgctttgtt tcttcaggct cttctgggtt    4020
aaaatcatgc tcctttaagc ccccttgaat gctttcttct attgtatggt atggatctct    4080
agttaaggca ctatatagta agtattcctt attaacaccc ttacaaatta aaaaactaaa    4140
ggtacacagc ttttgacaga aattattaat tgcagaaact ctatgtctat gtggagttaa    4200
aaagaatata atattatgcc cagcacacat gtgtctacta ataaaagtta cagaatattt    4260
ttccataagt ttttatacag aatttgagc ttttttcttt a gtagtataca cagcaaagca    4320
ggcaagggtt ctattactaa atacagcttg actaagaaac tggtgtagat cacaaggaaa    4380
gtctttaggg tcttctacct ttcttttttt cttgggtggt gttgagtgtt gagaatctgc    4440
tgttgcttct tcatcactgg caaacatatc ttcatggcaa aataaatctt catcccattt    4500
ttcattaaag gagctccacc aggactccca ctcttctgtt ccataggttg gcacctataa    4560
aacaaataat tacttagggc ctttaaatat tttattattt atttaaatat aaggtagtta    4620
ccttaaagct ttagatctct gaagggagtt tctccaatta tttggaccca ccattgcaga    4680
gtttcttcag ttaggtctaa gccaaaccac tgtgtgaagc agtcaatgca gtagcaatct    4740
atccaaacca agggctcttt tcttaaaaat tttctattta aatgccttaa tctaagctga    4800
catagcatgc aagggcagtg cacagaaggc ttttggaac aaataggcca ttccttgcag    4860
tacagggtat ctgggcaaag aggaaaatca gcacaaacct ctgagctact ccaggttcca    4920
aaatcaggct gatgagctac ctttacatct tgctccattt ttttatataa agtattcatt    4980
ctcttcattt tatcctcgtc gccccctttg tcagggtgaa attccttaca cttccttaaa    5040
taggcttttc tcattaagga aaggtttccc caggcagctc tttcaaggcc caaaaggtcc    5100
atgagctcca tggattcttc cctgttaagc actttatcca t                        5141
```

<210> SEQ ID NO 35
<211> LENGTH: 5141
<212> TYPE: DNA
<213> ORGANISM: Human polyomavirus type BK virus

<400> SEQUENCE: 35

```
ttttgcaaaa attgcaaaag aataggatt tccccaaata gttttgctag gcctcagaaa        60
aagcctccac acccttacta cttgaaagaa agggtggagg cagaggcggc ctcggcctct       120
tatatattat aaaaaaaaag gccacaggga ggagctgctt acccatggaa tgcagccaaa       180
ccatgacctc aggaaggaaa gtgcatgact gggcagccag ccagtggcag ttaatagtga       240
aaccccgccc ctgaaattct caaataaaca caagaggaag tggaaactgg ccaaaggagt       300
ggaaagcagc cagacagaca tgttttgcgg gcctaggaat cttggccttg tccccagtta       360
aactggacaa aggccatggt tctgcgccag ctgtcacgac aggcttctgt gaaacttggt       420
aaaacctgga ctggaacaaa aaaaagagct cagaggattt ttatttttat tttagagctt       480
ttgctggaat tttgtagagg tgaagacagt gtagacggga aaaacaaaag taccactgct       540
ttacctgctg taaagactc tgtaaaagac tcctaggtaa gtaatccctt ttttttgta         600
tttccaggtt gatgggtgct gctctagcac ttttggggga cctagttgcc agtgtatctg       660
aggctgctgc tgccacagga ttttcagtgg ctgaaattgc tgctgggag gctgctgctg         720
ctatagaagt tcaaattgca tcccttgcta ctgtagaggg cataacaagt acctcagagg       780
ctatagctgc tataggccta actcctcaaa catatgctgt aattgctggt gctcctgggg       840
ctattgctgg gtttgctgct ttaattcaaa ctgttactgg tattagttcc ttggctcaag       900
tagggtatag gtttttagt gattgggatc acaaagtttc cactgtaggc ctctatcagc        960
aatcaggcat ggcttttggaa ttgtttaacc cagatgagta ctatgatata tgtttcctg      1020
gtgtaaatac ttttgtaaat aatattcaat accttgatcc taggcattgg ggtccttctt      1080
tgtttgctac tatttctcag gctttgtggc atgttattag ggatgatata cctgctataa      1140
cctcacaaga attgcaaaga agaacagaaa gattttttag agactccttg gctagatttt      1200
tggaggaaac tacctggaca attgtaaatg cccctatgaa cttttataat tatattcaag      1260
aatattattc tgatctttcc cctattaggc ccttaatggt tagacaagta gctgaaaggg      1320
aaggtacccg tgtacatttt ggccatgctt atagtataga tgatgctgac agtatagaag      1380
aagttacaca aagaatggac ttaagaaatc aacaaactgt acattcagga gagtttataag     1440
aaaaaactat tgccccagga ggtgctaatc aaagaactgc tcctcaatgg atgttgcctt      1500
tacttctagg cctgtacggg actgtaacac ctgctcttga agcatatgaa gatggcccca      1560
acaaaaagaa aaggagagtg tccaggggca gctcccaaaa agccaaagga acccgtgcaa      1620
gtgccaaaac tactaataaa aggaggagta gaagttctag aagttaaaac tgggctagat      1680
gctataacag aggtagaatg cttcctaaac ccagaaatgg gggatccaga tgaaaacctt      1740
agggggcttta gtctaaagct aagtgctgaa atgacttta gcagtgatag cccagaaaga      1800
aaaatgcttc cctgttacag cacagcaaga attccctcc ccaatttaaa tgaggaccta      1860
acctgtggaa atctactgat gtgggaggct gtaacagtac aaacagaggt cattggaata      1920
actagcatgc ttaaccttca tgcagggtca caaaaagtgc atgagcatgg tggaggtaaa      1980
cctattcaag gcagtaattt ccactttttt gctgttggtg gagacccctt ggaaatgcag      2040
ggagtgctaa tgaattacag gacaaagtac ccagaaggta ctataccccc aaaaaaccca      2100
acagcccagt cccaagtaat gaatactgac cataaggcct atttggacaa aaacaatgct      2160
```

```
tatccagttg agtgctggat tcctgatccc agtagaaatg aaaatactag gtattttggg    2220
actttcacag gagggaaaa tgttccccca gtacttcatg tgaccaacac agctaccaca    2280
gtgttgctag atgaacaggg tgtggggcct ctttgtaaag ctgatagcct gtatgtttca    2340
gctgctgata tttgtggcct gtttactaac agctctggaa cacaacagtg gagaggcctt    2400
gcaagatatt ttaagattcg cctgagaaaa agatctgtaa aaaatcctta cccaatttcc    2460
tttttgctaa gtgaccttat aaacaggaga acccagagag tggatgggca gcctatgtat    2520
ggtatggaat cccaggtaga agaggtcagg gtgtttgatg gcacagaaag acttccaggg    2580
gacccagata tgataagata tattgacaaa caaggacaat tgcaaactaa aatggtttaa    2640
acaggtgctt ttattgtaca tatacattta ataaatgctg cttttgtata agccagttct    2700
aagcttgtgt tattttgggg gtggtgtttt aggccttta aaacactgaa agcctttaca    2760
caaatgcaac tcttgactat gggggtctga cctttgggaa tcttcagcag gggctgaagt    2820
atctgagact tgggaagagc attgtgattg ggattcagtg cttgatccat gtccagagtc    2880
ttcagtttct gaatcttctt ctcttgtgat atcaagaata catttcccca tgcatatatt    2940
atatttcatc cttgaaaaag tatacatact tatctcagaa tccagccttt ccttccattc    3000
aacaattcta gattgtatat ctgttgcaaa atcagctaca ggcctaaacc aaattagcag    3060
tagcaacaag gtcattccac tttgtaaaat tcttttttca gtaagaact ctgagttttg    3120 taaggatttt cttaaatata ttttgggcct aaaatctatc tgtcttacaa atctagcctg    3180
cagggtttta gggacaggat actcattcat tgtaaccagg cctggtggaa atatttgggt    3240
tcttttgttt aaatgtttct tttctaaatt aaccttaaca cttccatcta ataatctct    3300 caaactgtct aaattgttta ttccatgtcc tgaaggcaaa tcctttgatt cagctcctgt    3360
tccttttaca tcttcaaaaa caaccatgta ctgatctata gctacaccta gttcaaaggt    3420
cagcctttcc atgggtaggt ttacatttaa agctttacct ccacacaaat ctaataaccc    3480
tgcagctagt gttgtttttc cactatcaat gggacccttta aataaccagt atcttctttt    3540
aggtacatta aaaacaatac agtgcaaaaa atcaaatata acagaatcca ttttaggtaa    3600
caaacagtgc agccaagcaa cacctgccat atattgttct aatacagcat tccatgagc    3660 cccaaatatt aaatccattt tatctaatat atgattaaat ctttctgtta gcatttcttc    3720
tctagtcata tgaaggctat ctactctttt tttagctaaa actgtatcta ctgcttgctg    3780
acaaatgctt ttttgatttt tactttctgc aaagatagta gcatttgcac aatgcttttc    3840
atgatactta aagtgataag gttggtcttt tttctgacac ttttttacact cctctacatt    3900 gtattgaaat tctaaataca tacctaataa taaaaacaca tcctcacact ttgtttctac    3960
tgcatactca gtaattaatt tccaagagac ctgctttgct tcttcaggct cttctgggtt    4020
aaaatcatgc tccttaagc ccccttgaat gctttcttct attgtatggt atggatctct    4080
agttaaggca ctatatagta agtattcctt attaacaccc ttacaaatta aaaaactaaa    4140
ggtacacagc ttttgacaga aattattaat tgcagaaact ctatgtctat gtggagttaa    4200
aaagaatata atattatgcc cagcacacat gtgtctacta ataaaagtta cagaatattt    4260
ttccataagt tttttataca gaatttgagc ttttttcttta gtagtataca cagcaaagca    4320
ggcaagggtt ctattactaa atacagcttg actaagaaac tggtgtagat cacaaggaaa    4380
gtctttaggg tcttctacct ttcttttttt cttgggtggt gttgagtgtt gagaatctgc    4440
tgttgcttct tcatcactgg caaacatatc ttcatggcaa aataaatctt catcccattt    4500
```

-continued

```
ttcattaaag gagctccacc aggactccca ctcttctgtt ccataggttg gcacctataa    4560
aacaaataat tacttagggc ctttaaatat tttattattt atttaaatat aaggtagtta    4620
ccttaaagct ttagatctct gaagggagtt tctccaatta tttggaccca ccattgcaga    4680
gtttcttcag ttaggtctaa gccaaaccac tgtgtgaagc agtcaatgca gtagcaatct    4740
atccaaacca agggctcttt tcttaaaaat tttctattta aatgccttaa tctaagctga    4800
catagcatgc aagggcagtg cacagaaggc ttttggaac aaataggcca ttccttgcag     4860
tacagggtat ctgggcaaag aggaaaatca gcacaaacct ctgagctact ccaggttcca    4920
aaatcaggct gatgagctac ctttacatct tgctccattt ttttatataa agtattcatt    4980
ctcttcattt tatcctcgtc gccccctttg tcagggtgaa attccttaca cttccttaaa    5040
taggcttttc tcattaagga aaggtttccc caggcagctc tttcaaggcc caaaaggtcc    5100
atgagctcca tggattcttc cctgttaagc actttatcca t                       5141
```

<210> SEQ ID NO 36
<211> LENGTH: 5129
<212> TYPE: DNA
<213> ORGANISM: Human polyomavirus type BK virus

<400> SEQUENCE: 36

```
ttttgcaaaa attgcaaaag aatagggatt tccccaaata ttttttgctag gcctcagaaa     60 aagcctccac acccttacta cttgagagaa agggtggagg cagaggcggc ctcggcctct    120
tatatattat aaaaaaaaag gccacaggga ggagctgcta acccatggaa tgtagccaaa    180
ccatgacctc aggaaggaaa gtgcatgact gggcagccag ccagtggcag ttaatagtga    240
aaccccgccc ctaaaattct caaataaaca caagagggga tggaaactgg ccaaaggagt    300
ggaaagcagc cagacagaca tgttttgcga gcctaggaat cttggccttg tccccagtta    360
aactggacaa aggccatggt tctgcgccag ctgtcacgga aagttagtaa aacctggact    420
ggaacaaaaa aaagagctca gaggattttt attttttattt tagagctttt gctggaattt    480
tgtagaggtg aagacagtgt agacgggaaa acaaaaagta ccactgcttt acctgctgta    540
aaagactctg taaaagactc ctaggtaagt aatccctttt ttttgtatt tccaggttga     600 tgggtgctgc tctagcactt tgggggacc tagttgccag tgtatctgag gctgctgctg     660
ccacaggatt tcagtggct gaaattgctg ctggggaggc tgctgctgct atagaagttc      720
aaattgcatc ccttgctact gtagagggca taacaagtac ctcagaggct atagctgcta    780
taggcctaac tcctcaaaca tatgctgtaa ttgctggtgc cctgggggct attgctgggt    840
ttgctgcttt aattcaaact gttactggta ttagttcctt ggctcaagta gggtataggt    900
tttttagtga ttgggatcac aaagtttcca ctgtaggcct ctatcagcaa tcaggcatgg    960
ctttggaatt gtttaaccca gatgagtact acgatatttt gtttcctggt gtaaatactt   1020
ttgtaaataa tattcaatac cttgatccta ggcattgggg tccttccttg tttgctacta   1080
tttcccaggc tttgtggcat gttattaggg atgatatacc tgctataacc tcacaggaat   1140
tgcaaagaag aacagaaaga ttttttagag actccttggc tagattttg gaggaaacta    1200 cctggacaat tgtaaatgcc cctatgaact tttataatta tattcaagaa tattattctg    1260
atcttccccc tattaggccc tcaatggtca gacaagtggc tgaaagggaa ggtacccgtg    1320 tacatttgg ccatacttat agtatagatg atgctgacag tatagaagaa gttacacaaa    1380
gaatggactt aagaaatcaa caaactgtac attcaggaga gttatagaa aaaactattg     1440 ccccaggagg tgctaatcaa agaactgctc ctcaatggat gttgccttta cttctaggcc    1500
```

-continued

```
tgtacgggac tgtaacacct gctcttgaag catatgaaga tggccccaac caaaagaaaa    1560
ggagagtgtc caggggcagc tcccaaaaag ccaaggaac ccgtgcaagt gccaaaacta     1620
ctaataaaag gaggagtaga agttctagaa gttaaaactg gggtagatgc tataacagag    1680
gtagaatgct tcctaaaccc agaaatgggg gatccagatg aaaaccttag gggctttagt    1740
ctaaagctaa gtgctcaaaa tgactttagc agtgatagcc cagaaagaaa aatgcttccc    1800
tgttacagca cagcaagaat tcccctcccc aatttaaatg aggacctaac ctgtggaaat    1860
ctactgatgt gggaggctgt aactgtacaa acagaggtca ttggaataac tagcatgctt    1920
aaccttcatg cagggtcaca aaagtgcat gagcatggtg gaggtaaacc tattcaaggc     1980
agtaatttcc acttctttgc tgttggtgga gatcccttgg aaatgcaggg agtgctaatg    2040
aattacagga ccaagtaccc agaaggtact ataaccccaa aaacccaac agcccagtcc     2100 caggtaatga atactgacca taaggcctat ttggacaaaa acaatgccta tccagttgag    2160
tgctgggttc ctgatcccag tagaaatgaa aatactaggt attttgggac tttcacagga    2220
ggggaaaatg ttcccccagt acttcatgtg accaacacag ctaccacagt gttgctagat    2280
gaacagggtg tggggcctct ttgtaaagct gatagcctgt atgtttcagc tgctgatatt    2340
tgtggcctgt ttactaacag ctctggaaca caacagtgga gaggccttgc aagatatttt    2400
aagatccgcc tgagaaaaag atctgtaaaa aatccttacc caatttcctt tttgctaagt    2460
gaccttataa acaggagaac ccagagagtg gatgggcagc ctatgtatgg tatggaatcc    2520
caggtagaag aggtcagggt gtttgatggc acagaaagac ttccagggga cccagatatg    2580
ataagatata ttgataaaca aggacaattg caaaccaaaa tgctttaaac aggtgctttt    2640
attgtacata tacattaat aaatgctgct tttgtataag ccacttttaa gcttgtgtta     2700
ttttgggggt ggtgttttag gccttttaaa acattgaaag cctttacaca aatgcaactc    2760
ttcactatgg gggtctgacc tttgggaatc ttcagcaggg gctgaagtat ctgagacttg    2820
ggaagagcat tgtgattggg attcagtgct tgatccatgt ccagagtctt cagtttctga    2880
atcttcttct cttgtgatat caagaataca tttccccatg catatattat atttcatcct    2940 tgaaaagta tacatactta tctcagaatc cagccttcc ttccattcaa caattctaga      3000
ttgtatatct gttgcaaaat cagctacagg cctaaaccaa attagcagta gcaacaaggt    3060
cattccactt tgtaaaattc ttttttcaag taagaactct gagttttgta aggattttct    3120
taaatatatt tgggtctaa aatctatctg tcttacaaat ctagcctgca gggttttagg     3180
aacaggatac tcattcattg taaccaggcc tggtggaaat atttgggttc ttttgtttaa    3240
atgtttcttt tctaaattaa ccttaacact tccatctaaa taatctctca aactgtctaa    3300
attgtttatt ccatgtcctg aaggcaaatc ctttgattca gcccctgttc cttttacatc    3360
ttcaaaaaca accatgtact gatctatagc tacacctagt tcaaaggtta gccttttccat   3420 gggtaggttt acatttaagg ctttacctcc acacaaatct agtaaccctg cagctagtgt    3480 tgttttttcca ctatcaatgg gacctttaaa taaccagtat cttcttttag gtacattaaa   3540
aacaatacag tgcaaaaaat caaatataac agaatccatt ttaggtagca acagtgcag    3600 ccaggcaaca cctgccatat attgttccag tacagcattt ccatgagctc caaatattaa    3660
atccatttta tctaatatat gattaaatct ttctgttagc atttcttctc tggtcatatg    3720
aagggtatct actctttttt tagctaaaac tgtatctact gcttgctgac aaatactttt    3780 ttgatttta ctttctgcaa aaatagtagc atttgcaaaa tgcttttcat gatacttaaa     3840
```

```
gtgataaggt tggtcttttt tctgacactt tttacactct tctacattgt attgaaattc    3900
taaatacata cccaataata aaaacacatc ctcacacttt gtctctactg catactcagt    3960
aattaatttc caagacacct gctttgtttc ttcaggctct tctgggttaa aatcatgctc    4020 cttttaagccc ccttgaatgc tttcttctat tgtatggtat ggatctctag ttaaggcact   4080
atatagtaag tattccttat taacacccct acaaattaaa aaactaaagg tacacagctt    4140
ttgacagaaa ttattaattg cagaaactct atgtctatgt ggagttaaaa agaatataat    4200
attatgccca gcacacatgt gtctactaat aaaagttaca gaatatttttt ccataagttt   4260 tttatacaga atttgagctt tttctttagt agtatacaca gcaaagcagg caagggttct    4320
attactaaat acagcttgac taagaaactg gtgtagatca aaggaaagt ctttagggtc     4380 ttctacccttt ctcttttttct tgggtggtgt ggagtgttga aatctgctg ttgcttcttc   4440 atcactggca acatatctt catggcaaaa taaatcttca tcccattttt cattaaagga    4500
gctccaccag gactcccact cttctgttcc ataggttggc acctataaaa aaataatta    4560 cttagggcct ttaaatattt tcttatttat ctaaatataa gttagttacc ttaaagcttt    4620
agatctctga agggagtttc tccaattatt tggacccacc attgcagagt ttcttcagtt    4680
aggtctaagc caaaccactg tgtgaagcag tcaatgcagt agcaatctat ccaaaccaag    4740
ggctcttttc ttaaaaattt tctatttaaa tgccttaatc taagctgaca tagcatgcaa    4800
gggcagtgca cagaaggctt tttggaacaa ataggccaat ccttgcagta cagggtatct    4860
gggcaaagag gaaaatcagc acaaacctct gagctactcc aggttccaaa atcaggctga    4920
tgagctacct ttacatcctg ctccattttt ttatataaag tattcattct cttcatttta    4980
tcctcgtcgc cccctttgtc agggtgaaat tccttacact tccttaaata ggcttttctc    5040
attaagggaa ggtttcccca ggcagctctt ccaaggccta aaggtccat gagctccatg     5100 gattcttccc tgttaagcac tttatccat                                     5129

<210> SEQ ID NO 37
<211> LENGTH: 5132
<212> TYPE: DNA
<213> ORGANISM: Human polyomavirus type BK virus

<400> SEQUENCE: 37
ttttgcaaaa attgcaaaag aatagggatt tccccaaata ttttttgctag gcctcagaaa    60 aagcctccac acccttacta cttgagagaa agggtggagg cagaggcggc ctcggcctct   120
tatatattat aaaaaaaaag gccacaggga ggagctgcta acccatggaa tgtagccaaa   180
caggaaggaa agtgcatgac tgggcagcca gccagtggca gttaatagtg aaaccccgcc   240
cctaaaattc tcaaataaac acaagaggga gtggaaactg gccaaggag tggaaagcag    300 ccagacagac atgttttgcg agcctaggaa tcttggcctt gtccccagtt aaactggaca   360
aaggccatgg ttctgcgcca gctgtcacga caagcttctg tgaaagttag taaaacctgg    420
actggaacaa aaaaagagc tcagaggatt tttattttta ttttagagct tttgctggaa    480
ttttgtagag gtgaagacag tgtagacggg aaaaacaaaa gtaccactgc tttacctgct    540
gtaaaagact ctgtaaaaga ctcctaggta agtaatccct ttttttttgt atttccaggt    600
tgatgggtgc tgctctagca cttttggggg acctagttgc cagtgtatct gaggctgctg    660
ctgccacagg attttcggtg gctgaaattg ctgctgggga ggctgctgct gctatagaag    720
ttcaaattgc atcccttgct actgtagagg gcataacaag tacctcagag gctatagctg    780
ctataggcct aactcctcaa acatatgctg taattgctgg tgctcctggg gctattgctg    840
```

```
ggtttgctgc tttaattcaa actgttactg gtattagttc cttggctcaa gtagggtaca    900
ggttttttag tgattgggat cacaaagttt ccactgtagg cctctatcag caatcaggca    960
tggctttgga attgtttaac ccagatgagt actatgatat tttgtttcct ggtgtaaata   1020
cttttgtaaa taatattcaa taccttgatc ctaggcattg gggtccttcc ttgtttgcta   1080
ctatttccca ggctttgtgg catgttatta gggatgatat acctgctata acctcacagg   1140
aattgcaaag aagaacagaa agatttttta gagactcctt ggctagattt ttggaggaaa   1200
ctacctggac aattgtaaat gcccctatga acttttataa ttatattcaa gaatattatt   1260
ctgatctttc ccctattagg ccctcaatgg tcagacaagt ggctgaaagg gaaggtaccc   1320
gtgtacattt tggccatact tatagtatag atgatgctga cagtatagaa gaagttacac   1380
aaagaatgga cttaagaaat caacaaactg tacattcagg agagtttata gaaaaaacta   1440
ttgccccagg aggtgctaat caagaactg ctcctcaatg gatgttgcct ttacttctag    1500
gcctgtacgg gactgtaaca cctgctcttg aagcatatga agatggcccc aaccaaaaga   1560
aaggagagt gtccaggggc agctcccaaa aagccaaagg aacccgtgca agtgccaaaa    1620
ctactaataa aaggaggagt agaagttcta gaagttaaaa ctggggtaga tgctataaca   1680
gaggtagaat gcttcctaaa cccagaaatg ggggatccag atgaaaacct tagggcttt    1740
agtctaaagc taagtgctca aaatgacttt agcagtgata gcccagaaag aaaaatgctt   1800
ccctgttaca gcacagcaag aattcccctc cccaatttaa atgaggacct aacctgtgga   1860
aatctactga tgtgggaggc tgtaactgta caaacagagg tcattggaat aactagcatg   1920
cttaaccttc atgcagggtc acaaaaagtg catgagcatg gtggaggtaa acctattcaa   1980
ggcagtaatt tccacttctt tgctgttggt ggagacccct tggaaatgca gggagtgcta   2040
atgaattact ggaccaagta cccagaaggt actataaccc caaaaaaccc aacagcccag   2100
tcccaggtaa tgaatactga ccataaggcc tatttggaca aaaacaatgc ctatccagtt   2160
gagtgctggg ttcctgatcc cagtagaaat gaaaatacta ggtattttgg gactttcaca   2220
ggaggggaaa atgttccccc agtacttcat gtgaccaaca cagctaccac agtgttgcta   2280
gatgaacagg gtgtggggcc tctttgtaaa gctgatagcc tgtatgtttc agctgctgat   2340
atttgtggcc tgtttactaa cagctctgga acacaacagt ggagaggcct tgcaagatat   2400
tttaagatcc gcctgagaaa aagatctgta aaaaatcctt acccaatttc cttttttgcta  2460
agtgaccta taaacaggag aacccagaga gtggatgggc agcctatgta tggtatggaa   2520
tcccaggtag aagaggtcag ggtgtttgat ggcacagaaa gacttccagg ggacccagat   2580
atgataagat atattgataa acaaggacaa ttgcaaacca aaatgcttta acaggtgct    2640
tttattgtac atatacattt aataaatgct gcttttgtat aagccacttt taagcttgtg   2700
ttattttggg ggtggtgttt taggcctttt aaaacattga aagcctttac acaaatgcaa   2760
ctcttcacta tggggtctg accttgggaa atcttcagca ggggctgaag tatctgagac    2820
ttgggaagag cattgtgatt gggattcagt gcttgatcca tgtccagagt cttcagtttc   2880
tgaatcttct tctcttgtga tatcaagaat acatttcccc atgcatatat tatatttcat   2940
ccttgaaaaa gtatacatac ttatctcaga atccagcctt tccttccatt caacaattct   3000
agattgtata tctgttgcaa atcagctac aggcctaaac caaattagca gtagcaacaa    3060
ggtcattcca ctttgtaaaa ttcttttttc aagtaagaac tctgagtttt gtaaggattt   3120
tcttaaatat attttgggtc taaatctat ctgtcttaca aatctagcct gcagggtttt    3180
```

| | |
|---|---|
| aggaacagga tactcattca ttgtaaccag gcctggtgga aatatttggg ttcttttgtt | 3240 |
| taaatgtttc ttttctaaat taaccttaac acttccatct aaataatctc tcaaactgtc | 3300 |
| taaattgttt attccatgtc ctgaaggcaa atcctttgat tcagcccctg ttccttttac | 3360 |
| atcttcaaaa acaaccatgt actgatctat agctacacct agttcaaagg ttagcctttc | 3420 |
| catgggtagg tttacattta aggctttacc tccacacaaa tctagtaacc ctgcagctag | 3480 |
| tgttgttttt ccactatcaa tgggaccttt aaataaccag tatcttcttt taggtacatt | 3540 |
| aaaaacaata cagtgcaaaa atcaaatat aacagaatcc attttaggta gcaaacagtg | 3600 |
| cagccaggca acacctgcca tatattgttc cagtacagca tttccatgag ctccaaatat | 3660 |
| taaatccatt ttatctaata tatgattaaa tctttctgtt agcatttctt ctctggtcat | 3720 |
| atgaagggta tctactcttt ttttagctaa aactgtatct actgcttgct gacaaatact | 3780 |
| tttttgattt ttactttctg caaaaatagt agcatttgca aaatgctttt catgatactt | 3840 |
| aaagtgataa ggttggtctt ttttctgaca cttttttacac tcttctacat tgtattgaaa | 3900 |
| ttctaaatac atacccaata ataaaaacac atcctcacac tttgtctcta ctgcatactc | 3960 |
| agtaattaat ttccaagaca cctgctttgt ttcttcaggc tcttctgggt taaaatcatg | 4020 |
| ctcctttaag cccccttgaa tgcttcttc tattgtatgg tatggatctc tagttaaggc | 4080 |
| actatatagt aagtattcct tattaacacc cttacaaatt aaaaaactaa aggtacacag | 4140 |
| cttttgacag aaattattaa ttgcagaaac tctatgtcta tgtggagtta aaaagaatat | 4200 |
| aatattatgc ccagcacaca tgtgtctact aataaaaagtt acagaatatt tttccataag | 4260 |
| tttttttatac agaatttgag ctttttcttt agtagtatac acagcaaagc aggcaagggt | 4320 |
| tctattacta aatacagctt gactaagaaa ctggtgtaga tcagaaggaa agtctttagg | 4380 |
| gtcttctacc tttctctttt tcttgggtgg tgtggagtgt tgagaatctg ctgttgcttc | 4440 |
| ttcatcactg gcaaacatat cttcatggca aaataaatct tcatcccatt tttcattaaa | 4500 |
| ggagctccac caggactccc actcttctgt tccataggtt ggcacctata aaaaaaataa | 4560 |
| ttacttaggg cctttaaata ttttcttatt tatctaaata taagttagtt accttaaagc | 4620 |
| tttagatctc tgaagggagt ttctccaatt atttggaccc accattgcag agtttcttca | 4680 |
| gttaggtcta agccaaacca ctgtgtgaag cagtcaatgc agtagcaatc tatccaaacc | 4740 |
| aagggctctt ttcttaaaaa ttttctattt aaatgcctta atctaagctg acatagcatg | 4800 |
| caagggcagt gcacagaagg ctttttggaa caaataggcc aatccttgca gtacagggta | 4860 |
| tctgggcaaa gaggaaaatc agcacaaacc tctgagctac tccaggttcc aaaatcaggc | 4920 |
| tgatgagcta cctttacatc ctgctccatt ttttatata agtattcat tctcttcatt | 4980 |
| ttatcctcgt cgcccccttt gtcagggtga aattccttac acttccttaa ataggctttt | 5040 |
| ctcattaagg gaaggtttcc ccaggcagct cttcaaggc ctaaaaggtc catgagctcc | 5100 |
| atggattctt ccctgttaag cactttatcc at | 5132 |

<210> SEQ ID NO 38
<211> LENGTH: 5098
<212> TYPE: DNA
<213> ORGANISM: Human polyomavirus type BK virus

<400> SEQUENCE: 38

| | |
|---|---|
| ttttgcaaaa aattgcaaaa gaatagggat ttccccaaat agtttgcta ggcctcagaa | 60 |
| aaagcctcca cacccttact acttcagaga aagggtggag gcagaggcgg cctcggcctc | 120 |
| ttatatatta taaaaaaaaa ggccacaggg aggagctgct tacccatgga atgcagccaa | 180 |

```
accatgacct caagaagcaa gtgcatgact gggcagccag ccagtggcag ttaatagtga      240
aaccccgccc ctaacattct caaataaaca caagaggaag tggaaactgt ccaaaggagt      300
ggaaagcagc cagacagaca tgttttgcga gcctaagaat cttgtggttt tgcgccagct      360
gtcacgacaa gcttcagtga aagttggtaa aacctggact ggaactaaaa aaagagctca      420
gaggattttt atttttattt tagagctttt gctggaattt tgtagaggtg aagacagtgt      480
agacgggaaa acaaaagta ccactgcttt acctgctgta aaagactctg taaaagactc       540
ctaggtaagt aatgcttttt ttttgtattt tcaggttgat gggtgctgct ctagcacttt      600
tgggggacct agttgccagt gtatctgagg ctgctgctgc acaggatttt tcagtggctg      660
aaattgctgc tggggaggct gctgctgcca tagaagttca aattgcatcc cttgctactg      720
tagagggcat aacaactacc tcagaggcta tagctgctat aggcctaaca cctcaaacat      780
atgctgtaat tgctggtgct ccaggggcta ttgctgggtt tgctgcttta attcaaactg      840
ttactggtat tagttctttg gctcaagtag ggtataggtt ttttagtgat tgggatcaca      900
aagtttccac tgtaggcctt tatcagcaat caggcatggc tttggaattg tttaacccag      960
atgagtacta tgatattttg tttcctggtg taaatacttt tgttaataat attcaatatc     1020
tagatcctag gcattggggt ccttctttgt ttgctactat ttcccaggct ttgtggcatg     1080
ttattagaga tgatatacct gctataactt cacaagaatt gcaaaggaga acagagagat     1140
tttttaggga ctcttggct agattttgg aagaaaccac ctggacaatt gtaaatgccc        1200
ccataaactt ttataattat attcaggatt attattctaa tttgtcccct attaggcctt     1260
caatggttag gcaagtagct gaaagggaag gtacccatgt aaattttggc catacctaca     1320
gcatagataa tgctgacagt atagaagaag ttacccaaaa aatggattta agaaataagg     1380
aaagtgtaca ttcaggagag tttatagaaa aaactattgc cccaggaggt gctaatcaaa     1440
gaactgctcc tcaatggatg ttgccttttgc ttctaggcct gtacgggact gtaacacctg    1500
ctcttgaagc atatgaagat ggccccaacc aaaagaaaag gagagtgtcc aggggcagct     1560
cccaaaaagc caaggaacc cgtgcaagtg ccaaaactac taataaaagg aggagtagaa       1620
gttctagaag ttaaaactgg ggtagatgct ataacagagg tagaatgctt tctaaaccca     1680
gaaatggggg atccagatga taaccttagg ggctatagtc agcacctaag tgctgaaaat     1740
gcctttgaga gtgatagccc agacagaaaa atgcttcctt gttacagtac agcaagaatt     1800
ccactgccca acctaaatga ggacctaacc tgtggaaatc tactaatgtg ggaggctgta     1860
actgtaaaaa cagaggttat tggaataact agcatgctta accttcatgc agggtcccaa     1920
aaagttcatg agaatggtgg aagtaaacct gtccaaggca gtaatttcca ctttttttgct   1980 gtgggtggag accccttgga aatgcaggga gtgctaatga attacagaac aaagtaccca     2040
caaggtacta taacccctaa aaaccctaca gctcagtccc aggtaatgaa tactgatcat     2100
aaggcctatt tggacaaaaa caatgcttat ccagttgagt gctggattcc tgatcctagt     2160
agaaatgaaa atactaggta ttttggaact tacacaggag gggaaaatgt tcctccagta     2220
cttcatgtta ccaacacagc taccacagtg ttgctggatg aacagggtgt ggggcctctg     2280
tgtaaagctg atagcctgta tgtttcagct gctgatattt gtgggctgtt tactaacagc    2340
tctgggacac aacagtggag aggccttgca agatatttta agattcgcct gagaaaaaga     2400
tctgtgaaga atccttaccc aatttccttt ttgctaagtg accttataaa caggagaacc     2460
caaaaagtgg atgggcagcc tatgtatggt atggaatctc aggttgagga ggtaagggtg     2520
```

-continued

```
tttgatggca cagaacagct tccaggggac ccagatatga taagatatat tgacagacaa   2580
ggacaattgc aaacaaaaat ggtttaaaca ggtgctttat tgtacatata tatgcttaat   2640
aaatgctgct tttgtataac acagttgaag cttctgttat tttggggggtg gtgttttagg   2700
ccttttaaaa cactgaaagc ctttacacaa atgtaactct tggctgtgag ggttttctga   2760
atcaggggct gaagtatctg agacttggga gagcattgt gattgggatt cagtgcttga   2820
tccatgtcca gagtcttcag tttctgaatc ttcttctctt gtaatatcaa gaatacattt   2880
tcccatgcat atattatatt tcatccttga aaaagtatac atacttatct cagaatccag   2940
cctttccttc cattcaacaa ttctagactg tatatctttt gaaaaatcag ctacaggcct   3000
aaaccaaatt agtagtagca aaagggtcat tccactttgt aatattcttt tttcaagtaa   3060
aaactcagag ttttgcaggg actttcttaa atatattttg ggtctaaaat ctatctgtct   3120
tacaaatcta gcctgaagag ttttagggac aggatactca ttcattgtaa ctaaccctgg   3180
tggaaatatt tgtgttcttt tgtttaaatg tttcttttct aaattaacct taacacttcc   3240
atctagataa tccctcaaac tgtctaaatt gtttattcca tgtcctgaag gcaaatcctt   3300
tgattcagct cctgtccctt ttacatcttc aaaaacaacc atgtactgat caatagccac   3360
acccagttca aaagttagcc tttccatggg taaatttaca tttaaagctt tacctccaca   3420
taagtctaat aaccctgcag ctaaggttgt tttgccacta tcaattggac ctttaaataa   3480
ccagtatctt cttttaggta cattaaaaac aacacagtga agaaaatcaa aaataacaga   3540
atccattttta ggtagcaaac aatgtagcca agcaacccct gccatatatt gttctagtac   3600
agcatttcca tgagctccaa atattaaatc cattttatct aatatatgat taaatctttc   3660
tgttagcatt tcttccctgg tcatatgaag ggtatctact cttttttag ctaatactgt   3720
atctactgct tgctgacaaa actttttttg attttttactt tctgcaaaaa taatagcatt   3780
tgcaaaatgc ttttcatgat acttaaagtg gtaaggttga tctttttttt gacactttt   3840
acactcctct acattgtatt gaaattctaa atacataccc aataataaaa acacatcctc   3900
acactttgtt tctactgcat attcagtaat taatttccaa gacacctgct tgtttcttc   3960
aggctcctct gggttaaagt catgctcctt taagcccccct tgaatgcttt cctctattat   4020
atggtatgga tccctagtta aggcactgta tagtaagtat tccttattaa cacccttaca   4080
aattaaaaaa ctaaaagtac acagcttttg acagaaatta ttaattgcag aaactctatg   4140
tctatgtgga gttaaaaaga atataatatt atgaccagca cacatgtgtc tactgataaa   4200
agttacagaa tattttttcca taagttttttt atacagaatt tgagcttttt ctttagtggt   4260
atacacagca aaacaggcaa gtgttctatt actaaaataca gcttgactaa gaaactggtg   4320
tagatcagag ggaaagtctt tagggtcttc tacctttctt tttttttggg gtggtgttga   4380
gtgttgggaa tctgctgttg cttcttcatc actggcaaac atatcctcat ggcagaataa   4440
atcttcatcc catttttcat taaaggagct ccaccaggac tcccactctt ctgttccata   4500
ggttggcacc tataaaaaaa aaataattac ttagggtctt cttttaattt actactttc   4560
taaatataaa ttagttacct taaagcttta gatctctgaa gggagtttct ccaattattt   4620
ggacccacca ttgcagggtt tcttcagtga ggtctaagcc aaaccactgt gtgaagcaat   4680
caatgcagta gcaatctatc caaaccaatg gctcttttct taaaaatttt ctattttaaat   4740
gccttaatct tagctgacat agcatgcaag ggcaatgcac tgaaggcttt ttggaacaaa   4800
taggccattc cttgcagtac aaagtatctg ggcaaagagg aaaatcagca caaacctctg   4860
agctattcca ggttccaaaa tcaggctgat gagctaccttt tacatcctgc tccatttttt   4920
```

-continued

```
tatataaagt attcattctc ttcattttat cctcgtcgcc cccttttgtca gggtgaaatt    4980 ccttacactt ttttaaatag gcttttctca ttaagggaag gtttccccag gcagctcttt    5040
caaggcctaa aaggtccatg agctccatgg attcttccct gtttaagact ttatccat     5098

<210> SEQ ID NO 39
<211> LENGTH: 5153
<212> TYPE: DNA
<213> ORGANISM: Human polyomavirus type BK virus

<400> SEQUENCE: 39
ttttgcaaaa attgcaaaag aatagggatt tccccaaata gttttgctag gcctcagaaa      60
aagcctccac acccttacta cttgagagaa agggtggagg cagaggcggc ctcggcctct    120
tatatattat aaaaaaaaag gccacaggga ggagctgctt acccatggaa tgcagccaaa    180
ccatgacctc aggaaggaaa gtgcatgact cacaggggaa tgcagccaaa ccatgacctc    240
aggaaggaaa gtgcatgact cacagggagg agctgcttac ccatggaatg cagccaaacc    300
atgacctcag gaaggaaagt gcatgacaga catgttttgc gagcctagga atcttggcct    360
tgtccccagt taaactggac aaaggccatg gttctgcgcc agctgtcacg acaagcttca    420
gtgaaagttg gtaaaacctg gactggaaca aaaaaaagag ctcagaggat ttttattttt    480
attttagagc ttttgctgga attttgtaga ggtgaagaca gtgtagacgg gaaaaacaaa    540
agtaccactg ctttacctgc tgtaaaagac tctgtaaaag actcctaggt aagtaatccc    600 ttttttttg tatttccagg ttcatgggtg ctgctctagc acttttgggg gacctagttg    660
ccagtgtatc tgaggctgct gctgccacag gattttcagt ggctgaaatt gctgctgggg    720
aggctgctgc tgctatagaa gttcaaattg catcccttgc tactgtagag ggcataacaa    780
gtacctcaga ggctatagct gctataggcc taactcctca aacatatgct gtaattgctg    840
gtgctcctgg ggctattgct gggtttgctg ctttaattca aactgttagt ggtattagtt    900
ccttagctca gtagggtat aagttctttg atgattggga tcacaaagtt ccactgtag     960 gcctctatca gcaatcaggc atggcttttgg aattgtttaa cccagatgag tactatgata   1020
ttctgtttcc tggtgtaaat acttttgtta ataatattca ataccttgat cctaggcatt   1080
ggggtccttc tttgtttgct actatttccc aggcttgtg gcatgttatt agggatgata   1140
taccttctat aacctcacag gaattgcaga gaagaacaga agattttttt agagactcct   1200
tggctagatt tttggaggaa actacctgga caattgtaaa tgccctata aactttata    1260 attatattca acaatattat tctgatcttt cccctattag gccctcaatg gttagacaag   1320
tagctgaaag ggaaggtacc cgtgtacatt ttggccatac ttatagtata gatgatgctg   1380
acagtataga agaagttaca caaagaatgg acttaagaaa tcaacaaagt gtacattcag   1440
gagagtttat agaaaaaact attgccccag gaggtgctaa tcaaagaact gctcctcaat   1500
ggatgttgcc tttacttcta ggcctgtacg ggactgtaac acctgctctt gaagcatatg   1560
aagatggccc caaccaaaag aaaaggagag tgtccagggg cagctcccaa aaagccaaag   1620
gaacccgtgc aagtgccaaa actactaata aaaggaggag tagaagttct agaagttaaa   1680
actggggtag atgctattac agaggtagaa tgcttcctaa acccagaaat ggggggatcca  1740 gatgaaaacc ttaggggctt tagtctaaag ctaagtgctg aaaatgactt tagcagtgat   1800
agcccagaga gaaaaatgct tccctgttac agcacagcaa gaattcccct cccccaattta   1860 aatgaggacc taacctgtgg aaatctactg atgtgggagg ctgtaactgt acaaacagag   1920
```

```
gttattggaa taactagcat gcttaacctt catgcagggt cacaaaaagt gcatgagcat   1980
ggtggaggaa aacctattca aggcagtaat ttccacttct ttgctgtagg tggagaaccc   2040
ttggaaatgc agggagtgct aatgaattac aggtcaaagt accctgatgg tactataacc   2100
cctaaaaacc caacagccca gtcccaggta atgaatactg accataaggc ctatttggac   2160
aaaaacaatg cttatccagt tgagtgctgg gtacctgatc ccagtagaaa tgaaaatgct   2220
aggtattttg ggactttcac aggaggggaa aatgttcccc cagtacttca tgtgaccaac   2280
acagctacca cagtgttgct agatgaacag ggtgtggggc ctctttgtaa agctgatagc   2340
ctgtatgttt cagctgctga tatttgtggc ctgtttacta acagctctgg aacacaacag   2400
tggagaggcc ttgcaagata ttttaagatc cgcctgagaa aaagatctgt aaagaatcct   2460
tacccaattt cctttttgct aagtgacctt ataaacagga gaacccagag agtggatggg   2520
cagcctatgt atggtatgga atcccaggta gaagaggtta gggtgtttga tggcacagaa   2580
agacttccag gggacccaga tatgataaga tatattgaca acagggacaa attgcaaacc   2640
aaaatgcttt aaacaggtgc ttttattgta catatacatt taataaatgc tgcttttgta   2700
taagccactt ttaagcttgt gttattttgg gggtggtgtt ttaggccttt taaaacactg   2760 aaagcccttta cacaaatgca actcttgact atgggggtct gacctttggg aatcttcagc   2820
aggggctgaa gtatctgaga cttgggaaga gcattgtgat tgggattcag tgcttgatcc   2880
atgtccagag tcttcagttt ctgaatcctc ttctcttgta atatcaagaa tacatttccc   2940
catgcatata ttatatttca tccttgaaaa agtatacata cttatctcag aatccagcct   3000
ttccttccat tcaacaattc tagattgtat atcagttgca aaatcagcta caggcctaaa   3060
ccaaattagc agtagcaaca aggtcattcc actttgtaaa attctttttt caagtaagaa   3120
ctctgagttt tgtaaggatt ttcttaaata tattttgggc ctaaaatcta tttgtcttac   3180
aaatctagct tgcagggttt tagggacagg atactcattc attgtaacca agcctggtgg   3240
aaatatttgg gttcttttgt ttaaatgttt cttttctaaa tttaccttaa cacttccatc   3300
taaataatct ctcaaactgt ctaaattgtt tattccatgt cctgaaggca aatcctttga   3360
ttcagctcct gtccctttta catcttcaaa aacaaccatg tactgatcta tagctacacc   3420
tagctcaaag gttagccttt ccatgggtag gtttacattt aaggcttac caccacacaa   3480 atctaataac cctgcagcta gtgttgtttt tccactatca atgggacctt taaataacca   3540
gtatcttctt ttaggtacat tgaaaacaat acagtgcaaa aaatcaaata ttacagaatc   3600
cattttaggt agcaaacagt gcagccaagc aacacctgcc atatattgtt ctagtacagc   3660
atttccatga gctccaaata ttaaatccat tttatctaat atatgattga atctttctgt   3720
tagcatttct tccctggtca tatgaagggt atctactctt tttttagcta aaactgtatc   3780
tactgcttgc tgacaaatac tttttttgatt tttacttttct gcaaaaataa tagcatttgc   3840
aaagtgcttt tcatgatact taaagtgata aggctggtct tttttctgac acttttttaca   3900 ctcctctaca ttgtattgaa attctaaata catacctaat aataaaaaca catcctcaca   3960
ctttgtctct actgcatact cagtaattaa tttccaagac acctgctttg tttcttcagg   4020
ctcttctggg ctaaaatcat gctccttttaa gccccctttga atgctttctt ctatagtatg   4080
gtatggatct ctagttaagg cactatatag taagtattcc ttattaacac ccttacaaat   4140
taaaaaacta aggtacaca gcttttgaca gaaattatta attgcagaaa ctctatgtct   4200
atgtggagtt aaaaagaata taatattatg cccagcacac atgtgtctac taataaaagt   4260
tacagaatat ttttccataa gttttttata cagaatttga gcttttttctt tagtagtata   4320
```

| | | |
|---|---|---|
| cacagcaaag caggcaaggg ttctattact aaatacagct tgactaagaa actggtgtag | 4380 |
| atcagaggga aagtctttag ggtcttctac ctttctttt tttttgggtg gtgttgagtg | 4440 |
| ttgagaatct gctgttgctt cttcatcact ggcaaacata tcttcatggc aaaataaatc | 4500 |
| ttcatcccat ttttcattaa aggaactcca ccaggactcc cactcttctg ttccataggt | 4560 |
| tggcacctat aaaaaaaata attacttagg gccttttaat attttattat ttatctaaat | 4620 |
| ataagttagt taccttaaag ctttagatct ctgaagggag tttctccaat tatttggacc | 4680 |
| caccattgca gagtttcttc agttaggtct aagccaaacc actgtgtgaa gcagtcaatg | 4740 |
| cagtagcaat ctatccaaac caagggctct tttcttaaaa attttctatt taaatgcctt | 4800 |
| aatctaagct gacatagcat gcaagggcag tgcacagaag cttttttgga acaaataggc | 4860 |
| cattccttgc agtacagggt atctgggcaa agaggaaaat cagcacaaac ctctgagcta | 4920 |
| ctccaggttc caaatcagg ctgatgagct acctttacat cctgctccat tttttttatac | 4980 |
| aaagtattca ttctcttcat tttatcctcg tcgccccctt tgtcagggtg aaattcctta | 5040 |
| cacttcctta aataagcttt tctcattaag ggaagatttc cccaggcagc tctttcaagg | 5100 |
| cctaaaaggt ccatgagctc catggattct tccctgttaa gaactttatc cat | 5153 |

<210> SEQ ID NO 40
<211> LENGTH: 5153
<212> TYPE: DNA
<213> ORGANISM: Human polyomavirus type BK virus

<400> SEQUENCE: 40

| | | |
|---|---|---|
| ttttgcaaaa attgcaaaag aatagggatt tccccaaata gttttgctag gcctcagaaa | 60 |
| aagcctccac acccttacta cttgagagaa agggtggagg cagaggcggc ctcggcctct | 120 |
| tatatattat aaaaaaaaag gccacaggga ggagctgctt acccatggaa tgcagccaaa | 180 |
| ccatgaccct caggaaggaaa gtgcatgact cacaggggga tgcagccaaa ccatgaccct | 240 |
| aggaaggaaa gtgcatgact cacagggagg agctgcttac ccatggaatg cagccaaacc | 300 |
| atgacctcag gaaggaaagt gcatgacaga catgttttgc gagcctagga atcttggcct | 360 |
| tgtccccagt taaactggac aaaggccatg ttctgcgcc agctgtcacg acaagcttca | 420 |
| gtgaaagttg gtaaaacctg gactggaaca aaaaaagag ctcagaggat tttatttt | 480 |
| attttagagc ttttgctgga attttgtaga ggtgaagaca gtgtagacgg gaaaaacaaa | 540 |
| agtaccactg ctttacctgc tgtaaaagac tctgtaaaag actcctaggt aagtaatccc | 600 |
| ttttttttg tatttccagg ttcatgggtg ctgctctagc acttttgggg gacctagttg | 660 |
| ccagtgtatc tgaggctgct gctgccacag gattttcagt ggctgaaatt gctgctgggg | 720 |
| aggctgctgc tgctatagaa gttcaaattg catcccttgc tactgtagag ggcataacaa | 780 |
| gtacctcaga ggctatagct gctataggcc taactcctca aacatatgct gtaattgctg | 840 |
| gtgctcctgg ggctattgct gggtttgctg ctttaattca aactgttagt ggtattagtt | 900 |
| ccttagctca gtagggtat aagttctttg atgattggga tcacaaagtt tccactgtag | 960 |
| gcctctatca gcaatcaggc atggctttgg aattgtttaa cccagatgag tactatgata | 1020 |
| ttctgtttcc tggtgtaaat actttttgtta ataatattca ataccttgat cctaggcatt | 1080 |
| ggggtccttc tttgtttgct actatttccc aggctttgtg gcatgttatt agggatgata | 1140 |
| taccttctat aacctcacag gaattgcaga gaagaacaga aagattttt agagactcct | 1200 |
| tggctagatt tttggaggaa actacctgga caattgtaaa tgcccctata aacttttata | 1260 |

```
attatattca acaatattat tctgatcttt cccctattag gccctcaatg gttagacaag    1320
tagctgaaag ggaaggtacc cgtgtacatt ttggccatac ttatagtata gatgatgctg    1380
acagtataga agaagttaca caaagaatgg acttaagaaa tcaacaaagt gtacattcag    1440
gagagtttat agaaaaaact attgccccag gaggtgctaa tcaaagaact gctcctcaat    1500
ggatgttgcc tttacttcta ggcctgtacg ggactgtaac acctgctctt gaagcatatg    1560
aagatggccc caaccaaaag aaaaggagag tgtccagggg cagctcccaa aaagccaaag    1620
gaacccgtgc aagtgccaaa actactaata aaggaggag tagaagttct agaagttaaa     1680
actggggtag atgctattac agaggtagaa tgcttcctaa acccagaaat ggggatcca     1740 gatgaaaacc ttaggggctt tagtctaaag ctaagtgctg aaaatgactt tagcagtgat    1800
agcccagaga gaaaaatgct tccctgttac agcacagcaa gaattcccct ccccaattta    1860
aatgaggacc taacctgtgg aaatctactg atgtgggagg ctgtaactgt acaaacagag    1920
gttattggaa taactagcat gcttaacctt catgcagggt cacaaaaagt gcatgagcat    1980
ggtggaggaa aacctattca aggcagtaat ttccacttct ttgctgtagg tggagaaccc    2040
ttggaaatgc agggagtgct aatgaattac aggtcaaagt accctgatgg tactataacc    2100
cctaaaaacc caacagccca gtcccaggta atgaatactg accataaggc ctatttggac    2160
aaaaacaatg cttatccagt tgagtgctgg gtacctgatc ccagtagaaa tgaaaatgct    2220
aggtattttg ggactttcac aggaggggaa aatgttcccc cagtacttca tgtgaccaac    2280
acagctacca cagtgttgct agatgaacag ggtgtgtggg ctctttgtaa agctgatagc    2340
ctgtatgttt cagctgctga tatttgtggc ctgtttacta acagctctgg aacacaacag    2400
tggagaggcc ttgcaagata ttttaagatc cgcctgagaa aaagatctgt aaagaatcct    2460
tacccaattt ccttttttgct aagtgaccct ataaacagga gaacccagag agtggatggg    2520
cagcctatgt atggtatgga atcccaggta gaagaggtta gggtgtttga tggcacagaa    2580
agacttccag gggacccaga tatgataaga tatattgaca acagggaca attgcaaacc     2640 aaaatgcttt aaacaggtgc ttttattgta catatacatt taataaatgc tgcttttgta    2700
taagccactt ttaagcttgt gttattttgg gggtggtgtt ttaggccttt taaaacactg    2760
aaagccttta cacaaatgca actcttgact atgggggtct gacctttggg aatcttcagc    2820
aggggctgaa gtatctgaga cttgggaaga gcattgtgat tgggattcag tgcttgatcc    2880
atgtccagag tcttcagttt ctgaatcctc ttctcttgta atatcaagaa tacatttccc    2940
catgcatata ttatatttca tccttgaaaa agtatacata cttatctcag aatccagcct    3000
ttccttccat tcaacaattc tagattgtat atcagttgca aaatcagcta caggcctaaa    3060
ccaaattagc agtagcaaca aggtcattcc actttgtaaa attctttttt caagtaagaa    3120
ctctgagttt tgtaaggatt ttcttaaata tattttgggc ctaaaatcta tttgtcttac    3180
aaatctagct tgcagggttt tagggacagg atactcattc attgtaacca agcctggtgg    3240
aaatatttgg gttcttttgt ttaaatgttt cttttctaaa tttaccttaa cacttccatc    3300
taaataatct ctcaaactgt ctaaattgtt tattccatgt cctgaaggca aatcctttga    3360
ttcagctcct gtccctttta catcttcaaa acaaccatg tactgatcta gctacacc      3420 tagctcaaag gttagccttt ccatgggtag gtttacattt aaggctttac caccacacaa    3480
atctaataac cctgcagcta gtgttgtttt tccactatca atgggacctt taaataacca    3540
gtatcttctt ttaggtacat tgaaaacaat acagtgcaaa aaatcaaata ttacagaatc    3600
cattttaggt agcaaacagt gcagccaagc aacacctgcc atatattgtt ctagtacagc    3660
```

```
atttccatga gctccaaata ttaaatccat tttatctaat atatgattga atctttctgt    3720
tagcatttct tccctggtca tatgaagggt atctactctt tttttagcta aaactgtatc    3780
tactgcttgc tgacaaatac ttttttgatt tttactttct gcaaaaataa tagcatttgc    3840
aaagtgcttt tcatgatact taaagtgata aggctggtct tttttctgac acttttttaca   3900 ctcctctaca ttgtattgaa attctaaata catacctaat aataaaaaca catcctcaca    3960
ctttgtctct actgcatact cagtaattaa tttccaagac acctgctttg tttcttcagg    4020
ctcttctggg ctaaaatcat gctcctttaa gccccttga atgctttctt ctatagtatg     4080
gtatggatct ctagttaagg cactatatag taagtattcc ttattaacac ccttacaaat    4140
taaaaaacta aaggtacaca gcttttgaca gaaattatta attgcagaaa ctctatgtct    4200
atgtggagtt aaaaagaata taatattatg cccagcacac atgtgtctac taataaaagt    4260 tacagaaatat ttttccataa gttttttata cagaatttga gcttttctt tagtagtata    4320 cacagcaaag caggcaaggg ttctattact aaatacagct tgactaagaa actggtgtag    4380
atcagaggga aagtctttag ggtcttctac cttttctttt ttttgggtg gtgttgagtg     4440 ttgagaatct gctgttgctt cttcatcact ggcaaacata tcttcatggc aaaataaatc    4500
ttcatcccat ttttcattaa aggaactcca ccaggactcc cactcttctg ttccataggt    4560
tggcacctat aaaaaaaata attcttagg gccttttaat attttattat ttatctaaat     4620
ataagttagt taccttaaag ctttagatct ctgaagggag tttctccaat tatttggacc    4680
caccattgca gagtttcttc agttaggtct aagccaaacc actgtgtgaa gcagtcaatg    4740
cagtagcaat ctatccaaac caagggctct tttcttaaaa attttctatt taaatgcctt    4800
aatctaagct gacatagcat gcaagggcag tgcacagaag gcttttgga acaaataggc     4860 cattccttgc agtacagggt atctgggcaa agaggaaaat cagcacaaac ctctgagcta    4920
ctccaggttc caaaatcagg ctgatgagct accttttacat cctgctccat ttttttatac   4980
aaagtattca ttctcttcat tttatcctcg tcgccccctt tgtcagggtg aaattcctta    5040
cacttcctta aataagcttt tctcattaag ggaagatttc cccaggcagc tctttcaagg    5100
cctaaaaggt ccatgagctc catggattct tccctgttaa gaactttatc cat           5153
```

<210> SEQ ID NO 41
<211> LENGTH: 4963
<212> TYPE: DNA
<213> ORGANISM: Human polyomavirus type BK virus

<400> SEQUENCE: 41

```
accatgacct caggaaggaa agtgcatgac tgggcagcca gccagtggca gttaatagtg     60
aaaccatgcc aaaccatgac ctcaggaagg aaagtgcatg actgggcagc cagccagtgg    120
cagttaattt gcgagcctag gaatcttggc cttgtcccca gttaaactgg acaaaggcca    180
tggttctgcg ccagctgtca cgacaagctt cagtgaaagt tggtaaaacc tggactggaa    240
caaaaaaaag agctcagagg attttattt ttatttaga gcttttgctg gaattttgta     300
gaggtgaaga cagtgtagac gggaaaaaca aaagtaccac tgctttacct gctgtaaaag    360
actctgtaaa agactcctag gtaagtaatc ccttttttttt tgtatttcca ggttcatggg   420
tgctgctcta gcacttttgg gggacctagt tgccagtgta tctgaggctg ctgctgccac    480
aggattttca gtggctgaaa ttgctgctgg ggaggctgct gctgctatag aagttcaaat    540
tgcatccctt gctactgtag agggcataac aagtacctca gaggctatag ctgctatagg    600
```

```
cctaactcct caaacatatg ctgtaattgc tggtgctcct ggggctattg ctgggtttgc    660
tgctttaatt caaactgtta gtggtattag ttccttggct caagtagggt ataggttctt    720
tagtgattgg gatcacaaag tttccactgt aggcctctat cagcaatcag gcatggcttt    780
ggaattgttt aacccagatg agtactatga tattctgttt cctggtgtaa atacttttgt    840
taataatatt caataccttg atcctaggca ttggggtcct tctttgtttg ctactatttc    900
ccaggctttg tggcatgtta ttagggatga atacctttct ataacctcac aggaattgca    960
gagaagaaca gaaagatttt ttagagactc cttggctaga ttttttggagg aaactacctg   1020 gacaattgta aatgccccta taaacttttta taattatatt caacaatatt attctgatct   1080
ttcccctatt aggccctcaa tggttagaca gtagctgaa agggaaggta cccgtgtaca    1140
ttttggccat acttatagta tagatgatgc tgacagtata aagaagtta cacaaagaat    1200 ggacttaaga aatcaacaaa gtgtacattc aggagagttt atagaaaaaa ctattgcccc    1260
aggaggtgct aatcaaagaa ctgctcctca atggatgttg cctttacttc taggcctgta    1320
cgggactgta acacctgctc ttgaagcatg tgaagatggc cccaaccaaa agaaaaggag    1380
agtgtccagg ggcagctccc aaaaagccaa aggaacccgt gcaagtgcca aaactactaa    1440 taaaggagg agtagaagtt ctagaagtta aaactggggt agatgctatt acagaggtag    1500
aatgcttcct aaacccagaa atgggggatc cagatgaaaa ccttagggc tttagtctaa    1560 agctaagtgc tgaaaatgac tttagcagtg atagcccaga gagaaaatg cttccctgtt    1620 acagcacagc aagaattccc ctccccaatt taaatgagga cctaacctgt ggaaatctac    1680
tgatgtggga ggctgtaact gtacaaacag aggttattgg aataactagc atgcttaacc    1740
ttcatgcagg gtcacaaaaa gtgcatgagc atggtggagg aaaacctatt caaggcagta    1800
atttccactt cttttgctgtt ggtggagacc ccttggaaat gcagggagtg ctaatgaatt    1860
acaggacaaa gtacccagat ggtactataa cccctaaaaa cccaacagcc cagtcccagg    1920
taatgaatac tgaccataag gcctatttgg acaaaaacaa tgcttatcca gttgagtgct    1980
gggttcctga tcctagtaga aatgaaaata ctaggtatt tgggactttc acaggagggg    2040
aaaatgttcc cccagtactt catgtgacca acacagctac cacagtgttg ctagatgaac    2100
agggtgtggg gcctctttgt aaagctgata gcctgtatgt ttcagctgct gatatttgtg    2160
gcctgtttac taacagctct ggaacacaac agtggagagg ccttgcaaga tattttaaga    2220
tccgcctgag aaaagatctgt gtaaagaatc cttacctaat ttcctttttg ctaagtgacc    2280
ttataaacag gagaacccag agagtggatg ggcagcctat gtatgtatg gaatcccagg    2340 tagaagaggt tagggtgttt gatggcacag aaagacttcc aggggaccca gatatgataa    2400
gatatattga caaacaggga caattgcaaa ccaaaatgct ttaaacaggt gcttttattg    2460
tacatataca tttaataaat gctgcttttg tataagccac ttttaagctt gtgttatttt    2520
gggggtggtg tttaggcct tttaaaaacac tgaaagcctt tacacaaatg caactcttga    2580 ctatggggt ctgacctttg ggaatcttca gcagggctg aagtatctga gacttgggaa    2640
gagcattgtg attgggattc agtgcttgat ccatgtccag agtcttcagt ttctgaatcc    2700
tcttctcttg taatatcaag aatacatttc cccatgcata tattatattt catccttgaa    2760
aaagtataca tacttatctc agaatccagc ctttccttcc attcaacaat tctagattgt    2820
atatcagttg caaatcagc tacaggccta aaccaaatta gcagtagcaa caaggtcatt    2880
ccactttgta aaattctttt ttcaagtaag aactctgagt tttgtaagga ttttcttaaa    2940
tatattttgg gcctaaaatc tatttgtctt acaaatctag cttgcagggt tttagggaca    3000
```

```
ggatactcat tcattgtaac caagcctggt ggaaatattt gggttctttt gtttaaatgt   3060
ttcttttcta aatttacctt aacacttcca tctaaataat ctctcaaact gtctaaattg   3120
tttattccat gtcctgaagg caaatccttt gattcagctc ctgtcccttt tacatcttca   3180
aaaacaacca tgtactgatc tatagctaca cctagctcaa aggttagcct ttccatgggt   3240
aggtttacat ttaaggcttt acctctacac aaatctaaca accctgcagc tagtgttgtt   3300
tttccactat caatgggacc tttaaataac cagtatcttc ttttaggtac attgaaaaca   3360
atacagtgca aaaatcaaa tattacagaa tccattttag gtagcaaaca gtgcagccaa    3420
gcaacacctg ccatatattg ttctagtaca gcatttccat gagctccaaa tattaaatcc   3480
attttatcta atatatgatt gaatctttct gttagcattt cttccctggt catatgaagg   3540
gtatctactc tttttttagc taaaactgta tctactgctt gctgacaaat aacttttttg   3600
tttttacttt ctgcaaaaat aatagcattt gcaaagtgct tttcatgata cttaaagtga   3660
taaggctggt ctttttttctg acactttta cactcctcta cattgtattg aaattctaaa   3720
tacataccta ataataaaaa cacatcctca cactttgtct ctactgcata ctcagtaatt   3780
aatttccaag acacctgctt tgtttcttca ggctcttctg ggttaaaatc atgctccttt   3840
aagccccctt gaatgctttc ttctatagta tggtatggat ctctagttaa ggcactatat   3900
agtaagtatt ccttattaac acccttacaa attaaaaaac taaaggtaca cagcttttga   3960
cagaaattat taattgcaga aactctatgt ctatgtggag ttaaaaagaa tataatatta   4020
tgcccagcac acatgtgtct actaataaaa gttacagaat atttttccat aagttttta   4080 tacagaattt gagcttttc tttagtagta tacacagcaa agcaggcaag ggttctatta   4140
ctaaatacag cttgactaag aaactggtgt agatcagagg gaaagtcttt agggtcttct   4200 accttttcttt ttttttggg tggtgttgag tgttgagaat ctgctgttgc ttcttcatca   4260
ctggcaaaca tatcttcatg gcaaaataaa tcttcatccc attttcatt aaaggaactc   4320 caccaggact cccactcttc tgttccatag gttggcacct ataaaaaaaa taattactta   4380
gggcataggc cattccttgc agtacagggt atctgggcaa agaggaaaat cagcacaaac   4440
ctctgagcta ctccaggttc caaaatcagg ctgatgagct acctttacat cctgctccat   4500 tttttatac aaagtattca ttctcttcat tttatcctcg tcgccccctt tgtcagggtg   4560
aaattcctta cacttcctta aagcttttct cattaaggga agatttcccc aggcagctct   4620
ttcaaggcct aaaaggtcca tgagctccat ggattcttcc ctgttaagaa ctttatccat   4680
ttttgcaaaa attgcaaaag aatagggatt tccccaaata gttttgctag gcctcagaaa   4740
aagcctccac acccttacta cttgagagaa agggtggagg cagaggcggc ctcggcctct   4800
tatatattat aaaaaaaaag gccacaggga ggagctgctt acccatggaa tgcagccaaa   4860
ccatgacctc aggaaggaaa gtgcatgact gggcagccag ccagtggcag ttaatagtga   4920
aaccccgccc ctaaaatctc tcttacccat ggaatgcagc caa                    4963

<210> SEQ ID NO 42
<211> LENGTH: 5147
<212> TYPE: DNA
<213> ORGANISM: Human polyomavirus type BK virus

<400> SEQUENCE: 42
ttttgcaaaa attgcaaaag aatagggatt tccccaaata gttttgctag gcctcagaaa    60
aagcctccac acccttacta cttgagagaa agggtggagg cagaggcggc ctcggcctct   120
```

```
tatatattat aaaaaaaaag gccacaggga ggagctgctt acccatgaa tgcagccaaa      180
ccatgacctc aggaaggaaa gtgcatgact gggcagccag ccagtggcag ttaatagtga      240
aaccccgccc ctaaaattct caaataaaca caagaggaag tggaaactgg ccaaaggagt      300
ggaaagcagc cagacagaca tgttttgcga gcctaggaat cttggccttg tccccagtta      360
aactggacaa aggccatggt tctgcgccag ctgtcacgac aagcttctgt gaaagttggt      420
aaaacctgga ctgaacaaa aaaagagct cagaggattt ttatttttat tttagagctt       480
ttgctggaat tttgtagagg tgaagacagt gtagacggga aaaacaaaag taccactgct     540
ttacctgcta taaagactc tgtaaaagac tcctaggtaa gtaatccctt ttttttgta       600
tttccaggtt catgggtgct gctctagcac ttttggggga cctagttgcc agtgtatctg     660
aggctgctgc tgccacagga ttttcagtgg ctgaaattgc tgctggggag ctgctgctg     720
ctatagaagt tcaaattgca tcccttgcta ctgtagaggg cataacaagt acctcagagg     780
ctatagctgc tataggccta actcctcaaa catatgctgt aattgctggt gctcctgggg     840
ctattgctgg gtttgctgct ttaattcaaa ctgttagtgg tattagttcc ttggctcaag     900
tagggtatag gttctttagt gattgggatc acaaagtttc cactgtaggc ctctatcagc     960
aatcaggcat ggctttggaa ttgtttaacc cagatgagta ctatgatatt ctgtttcctg    1020
gtgtaaatac ttttgttaat aatattcaat accttgatcc taggcattgg ggtccttctt    1080
tgtttgctac tatttcccag gctttgtggc atgttattag ggatgatata ccttctataa    1140
cctcacagga attgcagaga agaacagaaa gattttttag agactccttg gctagatttt    1200
tggaggaaac tacctggacc attgtaaatg cccctataaa cttttataat tatattcaac    1260
aatattattc tgatctgtcc cctattaggc cctcaatggt tagacaagta gctgaaaggg    1320
aaggtacccg tgtacatttt ggccatactt atagtataga tgatgctgac agtatagaag    1380
aagttacaca aagaatggat ttaagaaatc aacaaagtgt acattcagga gagtttatag    1440
aaaaaactat tgccccagga ggtgctaatc aaagaactgc tcctcaatgg atgttgcctt    1500
tacttctagg cctgtacggg actgtaacac ctgctcttga agcatatgaa gatggcccca    1560
accaaaagaa aaggagagtg tccaggggca gctcccaaaa agccaaagga acccgtgcaa    1620
gtgccaaaac tactaataaa aggaggagta gaagttctag aagttaaaac tggggtagat    1680
gctattacag aggtagaatg cttcctaaac ccagaaatgg gggatccgga tccagatgaa    1740
aaccttaggg gctttagtct aaagctaagt gctgaaaatg actttagcag tgatagccca    1800
gagagaaaaa tgcttccctg ttacagcaca gcaagaattc ccctccccaa tttaaatgag    1860
gacctaaccct gtggaaatct actgatgtgg gaggctgtaa ctgtacaaac agaggttatt    1920
ggaataacta gcatgcttaa ccttcatgca gggtcacaaa aagtgcatga gcatggtgga    1980
ggaaaaccta ttcaaggcag taatttccac ttctttgctg ttggtggaga cccccttgga    2040
atgcagggag tgctaatgaa ttacaggaca agtacccag atggtactat aacccctaaa    2100
aacccaacag cccagtccca ggtaatgaat actgaccata aggcctattt ggacaaaaac    2160
aatgcttatc cagttgagtg ctgggttcct gatcccagta gaaatgaaaa tactaggtat    2220
tttgggactt tcacaggagg ggaaaatgtt cccccagtac ttcatgtgac caacacagct    2280
accacagtgt tgctagatga acagggtgtg gggcctcttt gtaaagctga tagcctgtat    2340
gtttcagctg ctgatatttg tggcctgttt actaacagct ctggaacaca acagtggaga    2400
ggccttgcaa gatattttaa gatccgcctg agaaaaagat ctgtaaagaa tccttaccca    2460
atttcctttt tgctaagtga cctcataaac aggagaaccc agagagtgga tgggcagcct    2520
```

```
atgtatggta tggaatccca ggtagaagag gttagggtgt ttgatggcac agaaagactt    2580 ccagggacc cagatatgat aagatatatt gacaaacagg gacaattgca aaccaaaatg     2640
ctttaaacag gtgctttat tgtacatata catttaataa atgctgcttt tgtataagcc     2700
acttttaacc ttgtgttatt ttgggggtgg tgttttaggc cttttaaaac actgaaagcc    2760
tttacacaaa tgtaactctt gactatgggg gtctgacctt tgggaatctt cagcaggggc    2820
tgaagtatct gagacttggg aagagcattg tgattgggat tcagtgcttg atccatgtcc    2880
agagtcttca gtttctgaat cctcttctct tgtgatatca agaatacatt tccccatgca    2940
tatattatat ttcatccttg aaaagtata catacttatc tcagaatcca gcctttcctt    3000
ccattcaaca attctagatt gtatatctgt tgcaaaatca gctacaggcc taaaccaaat    3060
tagcagtagc aacaaggtca ttccactttg taaaattctt ttttcaagta agaactctga   3120
gttttgtaag gattttctta aatatatttt gggcctaaaa tctatttgtc ttacaaatct   3180
agcttgcagg gttttaggga caggatactc attcattgta accaagcctg gtggaaatat   3240
ttgggttctt ttgttttaaat gttttttttc taaatttacc ttaacacttc catctaaata  3300
atctcttaaa ctgtctaaat tgtttattcc atgtcctgaa ggcaaatcct ttgattcagc   3360
ccctgtccct tttacatctt caaaaacaac catgtactga tctatagcta cacctagctc   3420
aaaggttagc ctttccatgg gtaggtttac atttaaggct ttacctccac acaaatctaa   3480
taaccctgca gctagtgttg tttttccact atcaatggga cctttaaata accagtatct   3540
tcttttaggt acattgaaaa caatacagtg caaaaaatca aatataacag aatccatttt   3600
aggtagcaaa cagtgcagcc aagcaacacc tgccatatat tgttctagta cagcatttcc   3660
atgagctcca aatattaaat ccattttatc taatatatga ttgaatcttt ctgttagcat   3720
ttcttccctg gtcatatgaa gggtatctac tcttttttta gctaaaactg tatctactgc   3780
ttgctgacaa atacttttt gattttact ttctgcaaag ataatagcat ttgcaaagtg     3840
cttttcatga tacttaaagt gataaggttg gtcttttttc tgacactttt tacactcctc   3900
tacattgtat tgaaattcta aatacatacc taataataaa aacacatcct cacactttgt   3960
ctctactgca tactcagtaa ttaatttcca agacacctgc tttgtttctt caggctcttc   4020
tgggttaaaa tcatgctcct ttaagccccc ttgaatgctt tcttctatag tatggtatgg   4080
ctctctagtt aaggcactat atagtaagta ttccttatta acacccttac aaattaaaaa    4140
actaaaggta cacagctttt gacagaagtt attaattgca gaaactctat gtctatgtgg    4200
agttaaaaag aatataatat tatgcccagc acacatgtgt ctactaataa aagttacaga    4260
atatttttcc ataagttttt tatacagaat ttgagctttt tctttagtag tatacacagc    4320
aaagcaggca agggttctat tactaaatac agcttgacta agaaactggt gtagatcaga    4380
gggaaagtct ttagggtctt ctacctttct ttttttcttg ggtggtgttg agtgttgaga    4440
atctgctgtt gcttcttcat cactggcaaa catatcttca tggcaaaata agtcttcatc    4500 ccattttca ttaaaggaac tccaccagga ctcccactct tctgttccat aggttggcac     4560
ctataaaaaa aataattact tagggccttt taatatttta ttatttatct aaatataagt    4620
tagttacctt aaagctttag atctctgaag ggagtttctc caattatttg gacccaccat    4680
tgcagagttt cttcagttag gtctaagcca aaccactgtg tgaagcagtc aatgcagtag    4740
caatctatcc aaaccaaggg ctcttttctt aaaaatttc tatttaaatg ccttaatcta    4800
agctgacata gcatgcaagg gcagtgcaca gaaggctttt tggaacaaat aggccattcc    4860
```

-continued

| | |
|---|---|
| ttgcagtaca gggtatctgg gcaaagagga aaatcagcac aaacctctga gctactccag | 4920 |
| gttccaaaat caggctgatg agctacccttt acatcctgct ccattttttt atataaagta | 4980 |
| ttcattctct tcattttatc ctcgtcgccc cctttgtcag ggtgaaattc cttacacttc | 5040 |
| cttaaataag cttttctcat taagggaaga tttccccagg cagctctttc aaggcctaaa | 5100 |
| aggtccatga gctccatgga ttcttccctg ttaagcactt tatccat | 5147 |

<210> SEQ ID NO 43
<211> LENGTH: 5147
<212> TYPE: DNA
<213> ORGANISM: Human polyomavirus type BK virus

<400> SEQUENCE: 43

| | |
|---|---|
| ttttgcaaaa attgcaaaag aatagggatt tccccaaata gttttgctag gcctcagaaa | 60 |
| aagcctccac acccttacta cttgagagaa agggtggagg cagaggcggc ctcggcctct | 120 |
| tatatattat aaaaaaaaag gccacaggga ggagctgctt acccatggaa tgcagccaaa | 180 |
| ccatgaccct aggaaggaaa gtgcatgact gggcagccag ccagtggcag ttaatagtga | 240 |
| aaccccgccc ctgaaattct caaataaaca caagaggaag tggaaactgg ccaaaggagt | 300 |
| ggaaagcagc cagacagaca tgttttgcgg gcctaggaat cttggccttg tccccagtta | 360 |
| aactggacaa aggccatggt tctgcgccag ctgtcacgac aagcttctgt gaaacttggt | 420 |
| aaaacctgga ctggaacaaa aaaagagct cagaggattt ttattttat tttagagctt | 480 |
| ttgctggaat tttgtagagg tgaagacagt gtagacggga aaaacaaaag taccactgct | 540 |
| ttacctgctg taaaagactc tgtaaaagac tcctaggtaa gtaatcccctt tttttttgta | 600 |
| tttccaggtt gatgggtgct gctctagcac ttttggggga cctagttgcc agtgtatctg | 660 |
| aggctgctgc tgccacagga ttttcagtgg ctgaaattgc tgctggggag ctgctgctg | 720 |
| ctatagaagt tcaaattgca tcccttgcta ctgtagaggg cataacaagt acctcagagg | 780 |
| ctatagctgc tataggccta actcctcaaa catatgctgt aattgctggt gctcctgggg | 840 |
| ctattgctgg gtttgctgct ttaattcaaa ctgttactgg tattagttcc ttggctcaag | 900 |
| tagggtatag gttttttagt gattgggatc acaaagtttc cactgtaggc ctctatcagc | 960 |
| aatcaggcat ggctttggaa ttgtttaacc cagatgagta ctatgatata ttgtttcctg | 1020 |
| gtgtaaatac ttttgtaaat aatattcaat accttgatcc taggcattgg ggtccttctt | 1080 |
| tgtttgctac tatttctcag gctttgtggc atgttattag ggatgatata cctgctataa | 1140 |
| cctcacaaga attgcaaaga agaacagaaa gattttttag agactccttg gctagatttt | 1200 |
| tggaggaaac tacctggaca attgtaaatg cccctataaa cttttataat tatattcaag | 1260 |
| aatattattc tgatctttcc cctattaggc cctcaatggt tagacaagta gctgaaaggg | 1320 |
| aaggtacccg tgtacatttt ggccatactt atagtataga tgatgctgac agtatagaag | 1380 |
| aagttacaca aagaatggac ttaagaaatc aacaaactgt acattcagga gagtttatag | 1440 |
| aaaaaactat tgccccagga ggtgctaatc aaagaactgc tcctcaatgg atgttgcctt | 1500 |
| tacttctagg cctgtacggg actgtaacac ctgctcttga agcatatgaa gatggcccca | 1560 |
| acaaaaagaa aaggagagtg tccagggca gctcccaaaa agccaaagga acccgtgcaa | 1620 |
| gtgccaaaac tactaataaa aggaggagta gaagttctag aagttaaaac tgggctagat | 1680 |
| gctataacag aggtagaatg cttcctaaac ccagaaatgg gggatccgga tccagatgaa | 1740 |
| aaccttaggg gctttagtct aaagctaagt gctgaaaatg actttagcag tgatagccca | 1800 |
| gaaagaaaaa tgcttcccctg ttacagcaca gcaagaattc ccctcccccaa tttaaatgag | 1860 |

```
gacctaacct gtggaaatct actgatgtgg gaggctgtaa cagtacaaac agaggtcatt    1920
ggaataacta gcatgcttaa ccttcatgca gggtcacaaa aagtgcatga gcatggtgga    1980
ggtaaaccta ttcaaggcag taatttccac ttttttgctg ttggtggaga ccccttggaa    2040
atgcagggag tgctaatgaa ttacaggaca aagtacccag aaggtactat aaccccaaaa    2100
aacccaacag cccagtccca agtaatgaat actgaccata aggcctattt ggacaaaaac    2160
aatgcttatc cagttgagtg ctggattcct gatcccagta gaaatgaaaa tactaggtat    2220
tttgggactt tcacaggagg ggaaaatgtt cccccagtac ttcatgtgac caacacagct    2280
accacagtgt tgctagatga acagggtgtg gggcctcttt gtaaagctga tagcctgtat    2340
gtttcagctg ctgatatttg tggcctgttt actaacagct ctggaacaca acagtggaga    2400
ggccttgcaa gatattttaa gattcgcctg agaaaaagat ctgtaaaaaa tccttaccca    2460 atttccttt tgctaagtga ccttataaac aggagaaccc agagagtgga tgggcagcct    2520
atgtatggta tggaatccca ggtagaagag gttagggtgt ttgatggcac agaaagactt    2580
ccaggggacc cagatatgat aagatatatt gacaaacaag gacaattgca aactaaaatg    2640
gtttaaacag gtgcttttat tgttgatata catttaataa atgctgcttt tgtataagcc    2700
agttttaagc ttgtgttatt ttgggggtgg tgttttaggc cttttaaaac actgaaagcc    2760
tttacacaaa tgcaactctt gactatgggg gtctgacctt tgggaatctt cagcagggc    2820 tgaagtatct gagacttggg aagagcattg tgattgggat tcagtgcttg atccatgtcc    2880
agagtcttca gtttctgaat cttcttctct tgtgatatca agaatacatt ttcccatgca    2940
tatattatat ttcatccttg aaaaagtata catacttatc tcagaatcca gcctttcctt    3000
ccattcaaca attctagatt gtatatctgt tgcaaaatca gctacaggcc taaaccaaat    3060
tagcagtagc aacaaggtca ttccactttg tagaattctt ttttcaagta agaactctga    3120
gttttgtaag gattttctta aatatatttt gggcctaaaa tctatctgtc ttacaaatct    3180
agcctgcagg gttttaggga caggatactc attcattgta accaggcctg gtggaaatat    3240
ttgggttctt ttgtttaaat gtttcttttc taaattaacc ttaacacttc catctaaata    3300
atctctcaaa ctgtctaaat tgtttattcc atgtcctgaa ggcaaatcct ttgattcagc    3360
tcctgttcct tttacatctt caaaaacaac catgtactga tctatagcta cacctagttc    3420
aaaggtcagc cttccatgg gtaggtttac atttaaagct ttacctccac acaaatctaa    3480
taaccctgca gctagtgttg ttttccact atcaatggga cctttaaata accagtatct    3540
tcttttaggt acattaaaaa caatacagtg caaaaaatca aatataacag aatccatttt    3600
aggtaacaaa cagtgcagcc aagcaacacc tgccatatat tgttctaata cagcatttcc    3660
atgagcccca atattaaat ccattttatc taatatatga ttaaatcttt ctgttagcat    3720
ttcttctcta gtcatatgaa ggctatctac tcttttttta gctaaaactg tatctactgc    3780
ttgctgacaa atactttttt gattttact ttctgcaaag atagtagcat ttgcaaaatg    3840
cttttcatga tacttaaagt gataaggttg gtctttttc tgacactttt tacactcctc    3900
tacattgtat tgaaattcta aatacatacc taataataaa aacacatcct cacactttgt    3960
ttctactgca tactcagtaa ttaatttcca agagacctgc tttgtttctt caggctcttc    4020
tgggttaaaa tcatgctcct ttaagccccc ttgaatgctt tcttctattg tatggtatgg    4080
atctctagtt aaggcactat atagtaagta ttccttatta acaccttac aaattaaaaa    4140 actaaaggta cacagctttt gacagaaatt attaattgca gaaactctat gtctatgtgg    4200
```

```
agttaaaaag aatataatat tatgcccagc atacatgtgt ctactaataa aagttacaga      4260
atatttttcc ataagttttt tatacagaat ttgagctttt tctttagtag tatacacagc      4320
aaagcaggca agggttctat tactaaatac agcttgacta agaaactggt gtagatcaga      4380
aggaaagtct ttagggtctt ctacctttct ttttttcttg ggtggtgttg agtgttgaga      4440
atctgctgtt gcttcttcat cactggcaaa catatcttca tggcaaaata aatcttcatc      4500
ccatttttca ttaaaggaac tccaccagga ctcccactct tctgttccat aggttggcac      4560
ctataaaaca aataattact tagggccttt aaatatttta ttatttatct aaatataagg      4620
tagttacctt aaagctttag atctctgaag ggagtttctc caattatttg gacccaccat      4680
tgcagagttt cttcagttag gtctaagcca aaccactgtg tgaagcagtc aatgcagtag      4740
caatctatcc aaaccaaggg ctcttttctt aaaaattttc tatttaaatg ccttaatcta      4800
agctgacata gcatgcaagg gcagtgcaca gaaggctttt tggaacaaat aggccattcc      4860
ttgcagtaca gggtatctgg gcaaagagga aaatcagcac aaacctctga gctactccag      4920
gttccaaaat caggctgatg agctaccttt acatcttgct ccatttttt atataaagta       4980 ttcattctct tcatttttatc ctcgtcgccc cctttgtcag ggtgaaattc cttcacttc       5040 cttaaatagg ctttttctcat taagggaagg ttttccccagg cagctctttc aaggcccaaa    5100
aggtccatga gctccatgga ttcttccctg ttaagcactt tatccat                   5147

<210> SEQ ID NO 44
<211> LENGTH: 5196
<212> TYPE: DNA
<213> ORGANISM: Human polyomavirus type BK virus

<400> SEQUENCE: 44
ttttgcaaaa attgcaaaag aatagggatt tccccaaata gttttgctag gcctcagaaa        60
aagcctccac acccttacta cttgagagaa agggtggagg ccgaggcggc ctcggcctct      120
tatatattat aaaaaaaaag gccacaggga ggagctgctt acccatggaa tgcagccaaa      180 ccatgaccctc aggaaggaaa gtgcatgact cacaggggaa tgcagccaaa ccatgacctc    240
aggaaggaaa gtgcatgact gggcagccag ccagtggcag ttaatagtga accccgccc       300 ctgaaattct caaataaaca caagaggaag tggaaactgg ccaaaggagt ggaaagcgcc      360
agacagacat gttttgcggg cctaggaatc ttggccttgt ccccagttaa actgacaaa      420 ggccatggtt ctgcgccagc tgtcacgaca agcttctgtg aaacttggta aaacctggac     480
tggaacaaaa aaaagagctc agaggatttt tattttatt ttagagcttt tgctggaatt      540
ttgtagaggt gaagacagtg tagacgggaa aaacaaaagt accactgctt tacctgctgt     600
aaaagactct gtaaaagact cctaggtaag taatcccttt tttttgtat ttccaggttg      660 atgggtgctg ctctagcact tttgggggac ctagttgcca gtgtatctga ggctgctgct     720
gccacaggat tttcagtggc tgaaattgct gctgggggagg ctgctgctgc tatagaagtt   780
caaattgcat cccttgctac tgtagagggc ataacaagta cctcagaggc tatagctgct   840
ataggcctaa ctcctcaaac atatgctgta attgctggtg ctcctgggc tattgctggg     900 tttgctgctt taattcaaac tgttactggt attagttcct tggctcaagt agggtatagg   960 tttttagtg attgggatca caaagtttcc actgtaggcc tctatcagca atcaggcatg    1020
gctttggaat tgtttaaccc agatgagtac tatgatatat tgtttcctgg tgtaaatact     1080
tttgtaaata atattcaata ccttgatcct aggcattggg gtcctctttt gtttgctact    1140
atttctcagg ctttgtggca tgttattagg gatgatatac ctgctataac ctcacaagaa   1200
```

```
ttgcaaagaa gaacagaaag attttttaga gactccttgg ctagattttt ggaggaaact    1260
acctggacaa ttgtaaatgc ccctataaac ttttataatt atattcaaga atattattct    1320
gatctttccc ctattaggcc ctcaatggtt agacaagtag ctgaaaggga aggtacccgt    1380
gtacattttg gccatactta tagtatagat gatgctgaca gtatagaaga agttacacaa    1440
agaatggact taagaaatca acaaactgta cattcaggag agtttataga aaaaactatt    1500
gccccaggag gtgctaatca aagaactgct cctcaatgga tgttgccttt acttctaggc    1560
ctgtacggga ctgtaacacc tgctcttgaa gcatatgaag atggcccaa caaaagaaa     1620 aggagagtgt ccaggggcag ctcccaaaaa gccaaggaa cccgtgcaag tgccaaaact    1680
actaataaaa ggaggagtag aagttctaga agttaaaact ggggtagatg ctattacaga    1740
ggtagaatgc ttcctaaacc cagaaatggg ggatccggat ccagatgaaa accttagggg    1800
ctttagtcta aagctaagtg ctgaaaatga ctttagcagt gatagcccag acagaaaaat    1860
gcttccctgt tacagcacag caagaattcc cctccccaat ttaaatgagg acctaacctg    1920
tggaaatcta ctgatgtggg aggctgtaac agtacaaaca gaggtcattg gaataactag    1980
catgcttaac cttcatgcag ggtcacaaaa agtgcatgag catggtggag gtaaacctat    2040
tcaaggcagt aatttccact tttttgctgt tggtggagac cccttggaaa tgcagggagt    2100
gctaatgaat tacaggacaa agtacccaga aggtactata accccaaaaa acccaacagc    2160
ccagtcccaa gtaatgaata ctgaccataa ggcctatttg gacaaaaaca atgcttatcc    2220
agttgagtgc tggattcctg atcccagtag aaatgaaaat actaggtatt ttgggacttt    2280
cacaggaggg gaaaatgttc ccccagtact tcatgtgacc aacacagcta ccacagtgtt    2340
gctagatgaa cagggtgtgg ggcctctttg taaagctgat agcctgtatg tttcagctgc    2400
tgatatttgt ggcctgtttta ctaacagctc tggaacacaa cagtggagag gccttgcaag    2460
atattttaag attcgcctga gaaaaagatc tgtaaaaaat ccttacccaa tttcctttttt    2520 gctaagtgac cttataaaca ggagaaccca gagagtggat gggcagccta tgtatggtat    2580
ggaatcccag gtagaagagg ttagggtgtt tgatggcaca gaaagacttc caggggaccc    2640
agatatgata agatatattg acaaacaagg acaattgcaa accaaaatgc tttaaacagg    2700
tgcttttatt gttgatatac atttaataaa tgctgctttt gtataagcca gttttaagct    2760
tgtgttattt tgggggtggt gttttaggcc ttttaaaaca ctgaaagcct ttacacaaat    2820
gcaactcttg actatggggg tctgacccttt gggaatcttc agcagggggct gaagtatctg    2880 agacttggga agagcattgt gattgggatt cagtgcttga tccatgtcca gagtcttcag    2940
tttctgaatc ttcttctctt gtaatatcaa gaatacattt tcccatgcat atattatatt    3000
tcatccttga aaaagtatac atacttatct cagaatccag cctttccttc cattcaacaa    3060
ttctagattg tatatctgtt gcaaaatcag ctacaggcct aaaccaaatt agcagtagca    3120
acaaggtcat tccactttgt agaattcttt tttcaagtaa gaactctgag tttggtaagg    3180 atttttcttaa atatattttg ggcctaaaat ctatctgtct tacaaatcta gcctgcaggg    3240
ttttagggac aggatactca ttcattgtaa ccaggcctgg tggaaatatt tgggttcttt    3300
tgtttaaatg tttctttttct aaattaacct taacacttcc atctaaataa tctctcaaac    3360
tgtctaaatt gtttattcca tgtcctgaag gcaaatcctt tgattcagct cctgttcctt    3420
ttacatcttc aaaacaaacc atgtactgat ctatagctac acctagttca aaggttagcc    3480
tttccatggg taggtttaca tttaaagctt tacctccaca caaatctaat aaccctgcag    3540
```

-continued

```
ctagtgttgt ttttccacta tcaatgggac cttaaataa ccagtatctt cttttaggta    3600
cattaaaaac aatacagtgc aaaaaatcaa atataacaga atccattta ggtagcaaac    3660
agtgcagcca agcaacacct gccatatatt gttctaatac agcatttcca tgagccccaa    3720
atattaaatc cattttatct aatatatgat taaatctttc tgttagcatt tcttctctag    3780
tcatatgaag gctatctact cttttttag ctaaaactgt atctactgct tgctgacaaa    3840
tactttttg attttactt tctgcaaata tagtagcatt tgcaaaatgc ttttcatgat    3900
acttaaagtg ataaggttgg tcttttttct gacactttt acactcctct acattgtatt    3960
gaaattctaa atacatacct aataataaaa acacatcctc acactttgtt tctactgcat    4020
actcagtaat taatttccaa gagacctgct ttgtttcttc aggctcttct gggttaaaat    4080
catgctcctt taagccccct tgaatgcttt cttctattgt atggtatgga tctctagtta    4140
aggcactata tagtaagtat tccttattaa caccccttaca aattaaaaaa ctaaaggtac    4200
acagcttttg acagaaatta ttaattgcag aaactctatg tctatgtgga gttaaaaaga    4260
atataatatt atgcccagca cacatgtgtc tactaataaa agttacagaa tattttccca    4320
taagttttt atacagaatt tgagcttttt ctttagtagt atacacagca aagcaggcaa    4380
gggttctatt actaaataca gcttgactaa gaaactggtg tagatcagaa ggaaagtctt    4440
tagggtcttc tacctttctt ttttttcttgg gtggtgttga gtgttgagaa tctgctgttg    4500
cttcttcatc actggcaaac atatcttcat ggcaaaataa atcttcatcc cattttcat    4560
taaaggaact ccaccaggac tcccactctt ctgttccata ggttggcacc tataaaacaa    4620
ataattactt agggccttta aatattttat tatttatcta aatataaggt agttaccta    4680
aagctttaga tctctgaagg gagtttctcc aattatttgg acccaccatt gcagagtttc    4740
ttcagttagg tctaagccaa accactgtgt gaagcagtca atgcagtagc aatctatcca    4800
aaccaagggc tctttctta aaatttct atttaaatgc cttaatctaa gctgacatag    4860
catgcaaggg cagtgcacag aaggcttttt ggaacaaata ggccattcct tgcagtacag    4920
ggtatctggg caaagaggaa aatcagcaca aacctctgag ctactccagg ttccaaaatc    4980
aggctgatga gctacccttta catcttgctc cattttttta tataaagtat tcattctctt    5040
cattttatcc tcgtcgcccc ctttgtcagg gtgaaattcc ttacacttcc ttaaataggc    5100
ttttctcatt aagggaaggt ttccccaggc agctctttct aggcccaaaa ggtccatgag    5160
ctccatggat tcttccctgt taagcacttt atccat                               5196
```

<210> SEQ ID NO 45
<211> LENGTH: 5154
<212> TYPE: DNA
<213> ORGANISM: Human polyomavirus type BK virus

<400> SEQUENCE: 45

```
ttttgcaaaa aattgcaaaa gaatagggat ttccccaaat agttttgcta ggcctcagaa      60
aaagcctcca caccctttact acttgagaga aagggtggag gcagaggcgg cctcggcctc     120
ttatatatta taaaaaaaaa ggccacaggg aggagctgct ttcccatgga atgcagccaa     180
accatgacct caggaaggaa agtgcatgac tgggcagcca gccagtggca gttaatagtg     240
aaaccccgcc cctagaatgc tcaaataaac acaagaggaa gtggaaagta gccaaaggag     300
tggaaagcag ccagacagac atgttttgcg agccgaggaa tcttggcctt gtccccagtt     360
aatactggac aaaggccatg gttctgcgcc agctgtcacg acaagcttct gtgaaagtta     420
gtaaaacctg gactggaact aaaaaaagag ctcagaggat tcttattttt atttagagc     480
```

```
ttttgctgga attttgtaga ggtgaagaca gtgtagacgg gaaaaacaaa agtaccactg    540
ctttacctgc tgtaaaagac tctgtaaaag actcctaggt aagtaatccc tttttttttg    600
tatttccagg ttcatgggtg ctgctctagc acttttgggg gacctagttg ccagtgtatc    660
tgaggctgct gctgccacag gattttcagt ggctgaaatt gctgctgggg aggctgctgc    720
tgctatagaa gttcaaattg catcccttgc tactgtagag gcataacaa gtacctcaga    780 ggctatagct gctataggcc taactcctca acatatgct gtaattgctg gtgctccagg    840
ggctattgct gggtttgctg ctttaattca aactgttact ggtattagtt ctttggctca    900
agtagggtat aggttttta gtgattggga tcacaaagtt tccactgtag gcctttatca    960
gcaatcaggc atggcattgg aattgtttaa cccagatgag tactatgata ttttgtttcc   1020
tggtgtaaat acttttgtaa ataatattca atacctagat cctaggcatt ggggtccttc   1080
tttgtttgct actatttccc aggctttgtg gcatgttatt agggatgata tacctgctat   1140
aacttcacaa gaattgcaaa gaagaacaga gagattcttt agagactcct ggctagatt    1200 tttggaagaa actacctgga caattgtaaa tgcccctgta aacttttata attatattca   1260
ggattattat tctaatttgt cccctattag gccttcaatg gttaggcaag ttgctgaaag   1320
ggaaggaacc caggtaaatt ttggccatac ctacagaata gatgatgctg acagtataca   1380
agaagttacc caaagaatgg agttaagaaa taaagagaat gtacattcag gagagtttat   1440
agaaaaaact attgccccag gaggtgctaa tcaaagaact gctcctcaat ggatgttgcc   1500
tttgcttcta ggcctgtacg ggactgtaac acctgctctt gaagcatatg aagatggccc   1560
caaccaaaag aaaaggagag tgtccagggg cagctcccaa aaagccaaag gaacccgtgc   1620
aagtgccaaa actactaata aaaggaggag tagaagttct agaagttaaa actggggtag   1680
atgctataac agaagtagaa tgcttcctaa acccagaaat gggggatccg gatccagatg   1740
aaaaccttag gggctttagt ctaagactaa ctgctgaaac tgcctttgac agtgatagcc   1800
cagacagaaa aatgcttccc tgttacagca cagcaagaat tccactacct aatttgaatg   1860
aggatctaac ctgtggaaat ctactaatgt gggaggctgt gactgtaaaa acagaggtta   1920
ttggaataac tagtatgctt aaccttcatg cagggtcaca gaaagtacat gaaaatggtg   1980
gaggcaaacc tattcaaggc agcaattttc acttttttgc tgtgggtggg gaccccttgg   2040
aaatgcaggg agtacttatg aactacagaa caaagtaccc agaaggtact gtcaccccaa   2100
aaaatcccac agctcagtcc caggtaatga atactgacca taaggcctac ttggacaaaa   2160
acaatgctta tccagttgaa tgctggattc ctgaccctag tagaaatgaa aatactaggt   2220
attttggaac atacacagga ggggaaaatg ttcccccagt acttcatgta accaacacag   2280
ctaccacagt gttgctggat gaacagggtg tggggcctct gtgtaaagct gatagcctgt   2340
atgtttcagc tgctgatatt tgtggactgt ttactaacag gtctggaaca caacagtgga   2400
ggggccttcc aagatatttt aagattcgcc tgagaaaaag atctgtaaag aacccttacc   2460
caatttcctt tttgcttagt gaccttataa acaggagaac ccagagagtg atgggcagc   2520 ctatgtatgg tatggagtct caggtggagg aggtcagggt gtttgatggc acagaacagc   2580
ttccagggga cccagatatg ataagatata ttgacagaca gggacaattg caaacaaaaa   2640
tggtttaaac aaggtgcttt tattgtacat atacatgctt aataaatgct gcttttatat   2700
tacacacttt taatcttgtg ttattttggg ggtggtgttt taggcctttt aaaacactga   2760
aagcctttac acaaatgtaa ctcttcacta tggggtcta gcctttggga atcttcagca   2820
```

```
ggggctgaag tatctgagac ttgggaagag cattgtgatt gggattcagt gcttgatcca   2880
tgtccagagt cttcagtttc tgaatcttct tctcttgtta tatcaagaat acatttcccc   2940
atgcatatat tatatttcat ccttgaaaaa gtatacatac ttatctcaga atccagcctt   3000
tccttccatt caacaattct agactgtata tcttgtgcaa aatcagctac aggcctgaac   3060
caaattagca gtagcaacaa ggtcattcca ctttgtaata ttcttttttc aagtaaaaat   3120
tctgagtttt gcagggattt tcttaaataa attttaggtc taaaatctat ctgtcttaca   3180
aatctagcct gcaaggtttt ggggacagga tactcattca ttgtaactaa acctggtgga   3240
aatatttggg ttcttttgtt taagtgtttc ttttctaaat taactttgac acttccatct   3300
aaataatccc ttaaactgtc taaattgttt attccatgtc ctgaaggcaa atcctttgat   3360
tcagctcctg ttcccttcac atcttcaaaa acaaccatat actgatctat agccacaccc   3420
agttcaaaag taagcctctc catgggtaaa ttcacattta aagctttgcc tccacataaa   3480
tctaataacc ctgcagctag tgttgttttt ccactatcaa ttggaccttt gaataaccag   3540
tatcttcttt taggtacatt aaaaacaata cagtgcagga aatcaaatat aacagaatcc   3600
attttaggta gcaaacagtg cagccaggca actcctgcca tatattgttc tagtacagca   3660
tttccatgag ctccaaatat taaatccatt ttatctaata tatgattaaa tctgtctgtt   3720
agcatttctt ctctggtcat atggagggta tctacccttt ttttagctaa cactgtatcc   3780
actgcttgct gacaaatact tttttgattt ttactttctg caaaaatggt agcatttgca   3840
aaatgctttt catgatattt aaagtggtag ggttggtctt ttttttgaca cttttttacac   3900 tcctctacat tgtactgaaa ttctaaatac atacccaata gtagaaacac atcttcacac   3960 tttgttttcta ctgcatattc agttattaat ttccaggaca cctgctttgt ttcttcaggt   4020
tcctctgggt taaaatcatg ctcctttagg ccccccttgaa tactttcctc tattatataa   4080
tatggatctc tagttaaggc actgtatagt aagtattcct tattaacacc cttacaaatt   4140
aaaaaactaa aagtacacag cttttgacag aaattattaa ttgcagaaac tctatgtcta   4200
tgtggagtta aaaagaatat aatattatga ccagcacaca tgtgtctact aataaaagtt   4260
acagaatatt tttccataag tttttttatac agaattaaag cttttttcttt agtagtatac   4320 acagcaaagc aggcaagagt tctattacta aatacagctt gactaagaaa ctggtgtaga   4380
tcagaaggaa agtctttagg gtcttctacc tttctttttt ttttgggtgg tgttgagtgt   4440
tgagaatctg ctgttgcctc ctcatcactg gcaaacatat cttcatggca aaataaatct   4500
tcatcccatt tttcattaaa ggacctccac caggactccc actcttctgt tccataggtt   4560
ggcacctata aaaaaaacat aattacttag ggccttccta taatttacta tttatctaaa   4620
gataaattag ttaccttaaa gctttagatc tctgaaggga gtctctccaa ttatttggac   4680
ccaccattgc agagtttctt cagttaggtc taagccaaac cactgtgtga agcagtcaat   4740
gcagtagcaa tctatcccaaa ccaagggctc ttttcttaaa aattttctat ttaaatgtct   4800
taatcttagc tgacacagca tgcaagggca gtgcactgaa ggcttttttgg aacaaatagg   4860 ccattccttg cagtacaggg tatctgggca aagaggaaaa tcagcacaaa cctctgagct   4920
actccaggtt ccaaaatcag gctggtgagc taccttttaca tcctgctcca ttttttttata   4980 taaagtattc attctcttca ttttatcctc gtcgcccct ttgtcagggt gaaattcctt   5040
acactttctt aaataggctt tcctcattaa gggaaggttt ccccaggcag ctctttcaag   5100
gcctaaaagg tccatgagct ccatggattc ctccctgttt agaactttat ccat         5154
```

<210> SEQ ID NO 46
<211> LENGTH: 5149
<212> TYPE: DNA
<213> ORGANISM: Human polyomavirus type BK virus

<400> SEQUENCE: 46

```
ttttgcaaaa attgcaaaag aatagggatt tcccccaaat agttttgcta ggcctcagaa      60
aaagcctcca cacccttact acttgagaga aagggtggag gcagaggcgg cctcggcctc     120
ttatatatta taaaaaaaaa ggccacaggg aggagctgct tacccatgga atgcagccaa     180
accatgacct caggaaggaa agtgcatgac tgggcagcca gccagtggca gttaatagtg     240
aaaccccgcc cctgaaattc tcaaataaac acaagaggaa gtggaaactg ccaaaggag      300
tggaaagcag ccagacagac atgttttgcg ggcctaggaa tcttggcctt gtccccagtt     360
aaactggaca aaggccatgg ttctgcgcca gctgtcacga caagcttctg tgaaacttgg     420
taaaacctgg actggaacaa aaaaagagc tcagaggatt tttattttta ttttagagct      480
tttgctggaa ttttgtagag gtgaagacag tgtagacggg aaaaacaaaa gtaccactgc     540
tttacctgct gtaaaagact ctgtaaaaga ctcctaggta agtaatccct ttttttttgt     600
atttccaggt tgatgggtgc tgctctagca cttttggggg acctagttgc cagtgtatct     660
gaggctgctg ctgccacagg attttcagtg gctgaaattg ctgctgggga gctgctgct      720
gctatagaag ttcaaattgc atcccttgct actgtagagg gcataacaag tacctcagag     780
gctatagctg ctataggcct aactcctcaa acatatgctg taattgctgg tgctcctggg     840
gctattgctg ggtttgctgc tttaattcaa actgttactg gtattagttc cttggctcaa     900
gtagggtata ggttttttag tgattgggat cacaaagttt ccactgtagg cctctatcag     960
caatcaggca tggctttgga attgtttaac ccagatgagt actatgatat attgtttcct    1020
ggtgtaaata cttttgtaaa taatattcaa taccttgatc ctaggcattg gggtccttct    1080
ttgtttgcta ctatttctca ggctttgtgg catgttatta gggatgatat acctgctata    1140
acctcacaag aattgcaaag aagaacagaa agatttttta gagactcctt ggctagattt    1200
ttggaggaaa ctacctggac aattgtaaat gcccctataa actttataa ttatattcaa     1260
gaatattatt ctgatctttc ccctattagg ccctcaatgg ttagacaagt agctgaaagg    1320
gaaggtaccc gtgtacattt tggccatact tatagtatag atgatgctga cagtatagaa    1380
gaagttacac aaagaatgga cttaagaaat caacaaactg tacattcagg agagtttata    1440
gaaaaaacta ttgccccagg aggtgctaat caaagaactg ctcctcaatg gatgttgcct    1500
ttacttctag gcctgtacgg gactgtaaca cctgctcttg aagcatatga agatggcccc    1560
aacaaaaaga aaaggagagt gtccaggggc agctcccaaa aagccaaagg aacccgtgca    1620
agtgccaaaa ctgctaataa aaggaggagt agaagttcta gaagttaaaa ctgggctaga    1680
tgctataaca gaggtagaat gcttcctaaa cccagaaatg ggggatccag gatccagatg    1740
aaaaccttag gggctttagt ctaaagctaa gtgctgaaaa tgactttagc agtgatagcc    1800
cagaaagaaa aatgcttccc tgttacagca cagcaagaat tcccctcccc aatttaaatg    1860
aggacctaac ctgtggaaat ctactgatgt gggaggctgt aacagtacaa acagaggtca    1920
ttggaataac tagcatgctt aaccttcatg cagggtcaca aaaagtgcat gagcatggtg    1980
gaggtaaacc tattcaaggc agtaatttcc acttttttgc tgttggtgga gaccccttgg    2040
aaatgcaggg agtgctaatg aattacagga caaagtaccc agaaggtact ataaccccaa    2100
aaaacccaac agcccagtcc caagtaatga atactgacca taaggcctat ttggacaaaa    2160
```

```
acaatgctta tccagttgag tgctggattc ctgatcccag tagaaatgaa aatactaggt   2220
attttgggac tttcacagga ggggaaaatg ttcccccagt acttcatgtg accaacacag   2280
ctaccacagt gttgctagat gaacagggtg tggggcctct ttgtaaagct gatagcctgt   2340
atgtttcagc tgctgatatt tgtggcctgt ttactaacag ctctggaaca caacagtgga   2400
gaggccttgc aagatatttt aagattcgcc tgagaaaaag atctgtaaaa atccttacc    2460 caatttcctt tttgctaagt gaccttataa acaggagaac ccagagagtg gatgggcagc   2520
ctatgtatgg tatggaatcc caggtagaag aggttagggt gtttgatggc acagaaaaac   2580 ttccaggggga cccagatatg ataagatata ttgacaaaca aggacaattg caaaccaaaa  2640 tgcttaaac aggtgctttt attgttgata tacatttaat aaatgctgct tttgtataag    2700
ccagttttaa gcttgtgtta ttttgggggt ggtgttttag gccttttaaa acactgaaag   2760
cctttacaca aatgcaactc ttgactatgg gggtctgacc tttgggaatc ttcagcaggg   2820
gctgaagtat ctgagacttg ggaagagcat tgtgattggg attcagtgct tgatccatgt   2880
ccagagtctt cagtttctga atcttcttct cttgtgatat caagaataca ttttcccatg   2940
catatattat atttcatcct tgaaaaagta tacatactta tctcagaatc cagccttcc    3000 ttccattcaa caattctaga ttgtatatct gttgcaaaat cagctacagg cctaaaccaa   3060
attagcagta gcaacaaggt cattccactt tgtaaaattc ttttttcaag taagaactct   3120
gagttttgta aggattttct taaatatatt ttgggcctaa aatctatctg tcttacaaat   3180
ctagcctgca gggttttagg gacaggatac tcattcattg taaccaggcc tggtggaaat   3240
atttgggttc ttttgtttaa atgtttcttt tctaaattaa ccttaacact tccatctaaa   3300
taatctctca aactgtctaa attgtttatt ccatgtcctg aaggcaaatc ctttgattca   3360
gctcctgttc cttttacatc ttcaaaaaca accatgtact gatctatagc tacacctagt   3420
tcaaaggtta gcctttccat gggtaggttt acatttaaag ctttacctcc acacaaatct   3480
aataaccctg cagctagtgt tgttttcca ctatcaatgg gacctttaaa taaccagtat    3540 cttctttag gtacattaaa aacaatacag tgcaaaaaat caaatataac agaatccatt    3600
ttaggtagca aacagtgcag ccaagcaaca cctgccatat attgttctaa tacagcattt   3660
ccatgagccc caaatattaa atccatttta tctaatatat gattaaatct ttctgttagc   3720
atttcttctc tagtcatatg aaggctatct actctttttt tagctaaaac tgtatctact   3780
gcttgctgac aaatacttttt ttgattttta ctttctgcaa agatagtagc atttgcaaaa  3840
tgcttttcat gatacttaaa gtgataaggt tggtcttttt tctgacactt tttacactcc   3900
tctacattgt attgaaattc taaatacata cctaataata aaaacacatc ctcacacttt   3960
gtttctactg catactcagt aattaatttc caagagacct gctttgtttc ttcaggctct   4020
tctgggttaa aatcatgctc ctttaagccc ccttgaatgc tttcttctat tgtatggtat   4080
ggatctctag ttaaggcact atatagtaag tattccttat taacacccctt acaaattaaa   4140 aaactaaagg tacacagctt ttgacagaaa ttattaattg cagaaactct atgtctatgt   4200
ggagttaaaa agaatataat attatgccca gcacacatgt gtctactaat aaaagttaca   4260 gaatatttttt ccataagttt tttatacaga atttgagctt tttctttagt agtatacaca  4320
gcaaagcagg cgagggttct attactaaat acagcttgac taagaaactg gtgtagatca   4380
gaaggaaagt ctttagggtc ttctacctttt cttttttttct tgggtggtgt tgagtgttga  4440
gaatctgctg ttgcttcttc atcactggca aacatatctt catggcaaaa taatcttca    4500 tcccattttt cattaaagga actccaccaa gactcccact cttctgttcc ataggttggc   4560
```

| | |
|---|---:|
| acctataaaa caaataatta cttagggcct ttaaatattt tattatttat ctaaatataa | 4620 |
| ggtagttacc ttaaagcttt agatctctga agggagtttc tccaattatt tggacccacc | 4680 |
| attgcagagt ttcttcagtt aggtctaagc caaaccactg tgtgaagcag tcaatgcagt | 4740 |
| agcaatctat ccaaaccaag ggctcttttc ttaaaaattt tctatttaaa tgccttaatc | 4800 |
| taagctgaca tagcatgcaa gggcagtgca cagaaggctt tttggaacaa ataggccatt | 4860 |
| ccttgcagta cagggtatct gggcaaagag gaaaatcagc acaaacctct gagctactcc | 4920 |
| aggttccaaa atcaggctga tgagctacct ttacatcttg ctccattttt ttatataaag | 4980 |
| tattcattct cttcatttta tcctcgtcgc cccctttgtc agggtgaaat tccttacact | 5040 |
| tccttaaata ggcttttctc attaagggaa ggtttcccca ggcagctctt tcaaggccca | 5100 |
| aaaggtccat gagctccatg gattcttccc tgttaagcac tttatccat | 5149 |

<210> SEQ ID NO 47
<211> LENGTH: 5146
<212> TYPE: DNA
<213> ORGANISM: Human polyomavirus type BK virus

<400> SEQUENCE: 47

| | |
|---|---:|
| ttttgcaaaa attgcaaaag aatagggatt tccccaaata gttttgctag gcctcagaaa | 60 |
| aagcctccac acccttacta cttgagagaa agggtggagg cagaggcggc ctcggcctct | 120 |
| tatatattat aaaaaaaaag gccacaggga ggagctgctt acccatggaa tgcagccaaa | 180 |
| ccatgaccct caggaaggaaa gtgcatgact gggcagccag ccagtggcag ttaatagtga | 240 |
| aaccccgccc ctgaaattct caaataaaca caagaggaag tggaaactgg ccaaaggagt | 300 |
| ggaaagcagc cagacagaca tgttttgcgg gcctaggaat cttggccttg tccccagtta | 360 |
| aactggacaa aggccatggt tctgcgccag ctgtcacgac aagcttctgt gaaacttggt | 420 |
| aaaacctgga ctggaacaaa aaaaagagct cagaggattt ttatttttat tttagagctt | 480 |
| ttgctggaat tttgtagagg tgaagacagt gtagacggga aaaacaaaag taccactgct | 540 |
| ttacctgctg taaaagactc tgtaaaagac tcctaggtaa gtaatccctt ttttttttgta | 600 |
| tttccaggtt gatgggtgct gctctagcac ttttggggga cctagttgcc agtgtatctg | 660 |
| aggctgctgc tgccacagga ttttcagtgg ctgaaattgc tgctggggag gctgctgctg | 720 |
| ctatagaagt tcaaattgca tcccttgcta ctgtagaggg cataacaagt acctcagagg | 780 |
| ctatagctgc tataggccta actcctcaaa catatgctgt aattgctggt gctcctgggg | 840 |
| ctattgctgg gtttgctgct ttattcaaac tgttactggt attagttcct tggctcaagt | 900 |
| agggtatagg tttttagtg attgggatca caaagtttcc actgtaggcc tctatcagca | 960 |
| atcaggcatg gctttggaat tgtttaaccc agatgagtac tatgatatat gtttcctgg | 1020 |
| tgtaaatact tttgtaaata atattcaata ccttgatcct aggcattggg gtccttcttt | 1080 |
| gtttgctact atttctcagg ctttgtggca tgttattagg gatgatatac ctgctataac | 1140 |
| ctcacaagaa ttgcaagaa gaacagaaag attttttaga gactccttgg ctagattttt | 1200 |
| ggaggaaact acctggacaa ttgtaaatgc ccctataaac ttttataatt atattcaaga | 1260 |
| atattattct gatctttccc ctattaggcc ctcaatggtt agacaagtag ctgaaaggga | 1320 |
| aggtacccgt gtacattttg gccatactta tgtatagat gatgctgaca gtatagaaga | 1380 |
| agttacacaa agaatggact taagaaatca acaaactgta cattcaggag agtttataga | 1440 |
| aaaaactatt gccccaggag gtgctaatca aagaactgct cctcaatgga tgttgccttt | 1500 |

```
acttctaggc ctgtacggga ctgtaacacc tgctcttgaa gcatatgaag atggccccaa    1560
caaaaagaaa aggagagtgt ccaggggcag ctcccaaaaa gccaaaggaa cccgtgcaag    1620
tgccaaaact actaataaaa ggaggagtag aagttctaga agttaaaact gggctagatg    1680
ctataacaga ggtagaatgc ttcctaaacc cagaaatggg ggatccggat ccagatgaaa    1740
accttagggg ctttagtcta aagctaagtg ctgaaaatga cttttagcagt gatagcccag    1800 aaagaaaaat gcttccctgt tacagcacag caagaattcc cctccccaat ttaaatgagg    1860
acctaacctg tggaaatcta ctgatgtggg aggctgtaac agtacaaaca gaggtcattg    1920
gaataactag catgcttaac cttcatgcag ggtcacaaaa agtgcatgag catggtggag    1980
gtaaacctat tcaaggcagt aatttccact tttttgctgt tggtggagac cccttggaaa    2040
tgcagggagt gctaatgaat tacaggacaa agtacccaga aggtactata accccaaaaa    2100
acccaacagc ccagtcccaa gtaatgaata ctgaccataa ggcctatttg gacaaaaaca    2160
atgcttatcc agttgagtgc tggattcctg atcccagtag aaatgaaaat actaggtatt    2220
ttgggacttt cacaggaggg gaaaatgttc ccccagtact tcatgtgacc aacacagcta    2280
ccacagtgtt gctagatgaa cagggtgtgg ggcctctttg taaagctgat agcctgtatg    2340
tttcagctgc tgatatttgt ggcctgttta ctaacagctc tggaacacaa cagtggagag    2400
gccttgcaag atattttaag attcgcctga gaaaagatc tgtaaaaaat ccttacccaa    2460
tttccttttt gctaagtgac cttataaaca ggagaaccca gagagtggat gggcagccta    2520
tgtatggtat ggaatcccag gtagaagagg ttagggtgtt tgatggcaca gaaagacttc    2580
caggggaccc agatatgata agatatattg acaaacaagg acaattgcaa actaaaatgg    2640
tttaaacagg tgcttttatt gttgatatac atttaataaa tgctgctttt gtataagcca    2700
gttttaagct tgtgttattt tggggtggt gttttaggcc ttttaaaaca ctgaaagcct    2760
ttacacaaat gcaactcttg actatggggg tctgaccttt gggaatcttc agcaggggct    2820
gaagtatctg agacttggga agagcattgt gattgggatt cagtgcttga tccatgtcca    2880
gagtcttcag tttctgaatc ttcttctctt gtgatatcaa gaatacattt tcccatgcat    2940
atattatatt tcatccttga aaaagtatac atacttatct cagaatccag cctttccttc    3000
cattcaacaa ttctagattg tatatctgtt gcaaaatcag ctacaggcct aaaccaaatt    3060
agcagtagca acaaggtcat tccactttgt agaattcttt tttcaagtaa gaactctgag    3120
ttttgtaagg attttcttaa atatattttg ggcctaaaat ctatctgtct tacaaatcta    3180
gcctgcaggg ttttagggac aggatactca ttcattgtaa ccaggcctgg tggaaatatt    3240
tgggttcttt tgtttaaatg tttcttttct aaattaacct taacacttcc atctaaataa    3300
tctctcaaac tgtctaaatt gtttattcca tgtcctgaag gcaaatcctt tgattcagct    3360
cctgttcctt ttacatcttc aaaaacaacc atgtactgat ctatagctac acctagttca    3420
aaggtcagcc tttccatggg taggtttaca tttaaagctt tacctccaca caaatctaat    3480
aaccctgcag ctagtgttgt ttttccacta tcaatgggac ctttaaataa ccagtatctt    3540
cttttaggta cattaaaaac aatacagtgc aaaaaatcaa atataacaga atccatttta    3600
ggtaacaaac agtgcagcca agcaacacct gccatatatt gttctaatac agcatttcca    3660
tgagccccaa atattaaatc catttatctc aatatatgat taaatctttc tgttagcatt    3720
tcttctctag tcatatgaag gctatctact cttttttag ctaaaactgt atctactgct    3780
tgctgacaaa tactttttg attttttactt tctgcaaaga tagtagcatt tgcaaaatgc    3840
ttttcatgat acttaaagtg ataaggttgg tcttttttct gacactttt acactcctct     3900
```

```
acattgtatt gaaattctaa atacatacct aataataaaa acacatcctc acactttgtt    3960
tctactgcat actcagtaat taatttccaa gagacctgct tgtttcttc aggctcttct     4020 gggttaaaat catgctcctt taagcccccct tgaatgcttt cttctattgt atggtatgga   4080
tctctagtta aggcactata tagtaagtat tccttattaa caccettaca aattaaaaaa   4140 ctaaaggtac acagcttttg acagaaatta ttaattgcag aaactctatg tctatgtgga   4200
gttaaaaaga atataatatt atgcccagca cacatgtgtc tactaataaa agttacagaa   4260
tatttttcca taagttttt atacagaatt tgagcttttt ctttagtagt atacacagca    4320
aagcaggcaa gggttctatt actaaataca gcttgactaa gaaactggtg tagatcagaa   4380
ggaaagtctt tagggtcttc tacctttctt tttttcttgg gtggtgttga gtgttgagaa   4440
tctgctgttg cttcttcatc actggcaaac atatcttcat ggcaaaataa atcttcatcc   4500 cattttcat taaggaact ccaccaggac tcccactctt ctgttccata ggttggcacc      4560
tataaaacaa ataattactt agggccttta atatttat tatttatcta aatataaggt     4620
agttacctta aagctttaga tctctgaagg gagtttctcc aattatttgg acccaccatt   4680
gcagagtttc ttcagttagg tctaagccaa accactgtgt gaagcagtca atgcagtagc   4740
aatctatcca aaccagggc tcttttctta aaaattttct atttaaatgc cttaatctaa    4800
gctgacatag catgcaaggg cagtgcacag aaggcttttt ggaacaaata ggccattcct   4860
tgcagtacag ggtatctggg caaagaggaa atcagcaca aacctctgag ctactccagg    4920
ttccaaaatc aggctgatga gctacccttta catcttgctc catttttta tataaagtat   4980 tcattctctt catttatcc tcgtcgcccc ctttgtcagg gtgaaattcc ttacacttcc    5040
ttaaataggc ttttctcatt aagggaaggt tccccaggc agctctttca aggcccaaaa    5100
ggtccatgag ctccatggat tcttccctgt taagcacttt atccat                  5146

<210> SEQ ID NO 48
<211> LENGTH: 5153
<212> TYPE: DNA
<213> ORGANISM: Human polyomavirus type BK virus

<400> SEQUENCE: 48
ttttgcaaaa aattgcaaaa gaatagggat ttccccaaat agttttgcta ggcctcagaa      60
aaagcctcca caccettact acttgagaga aagggtggag gcagaggcgg cctcggcctc     120
ttatatatta taaaaaaaaa ggccacaggg aggagctgct ttcccatgga atgcagccaa     180
accatgacct caggaaggaa agtgcatgac tgggcagcca gccagtggca gttaatagtg     240 aaacccccgcc cctagaattc tcaaataaac acaagaggaa gtggaaagta gccaaggag     300 tggaaagcag ccagacagac atgttttgcg agccgaggaa tcttggcctt gtccccagtt     360
aatactggac aaaggccatg gttctacgcc agctgtcacg acaagcttct gtgaaagtta     420
gtaaaacctg gactggaact aaaaaaagag ctcagaggat tcttattttt attttagagc     480
ttttgctgga attttgtaga ggtgaagaca gtgtagacgg gaaaaacaaa agtaccactg     540
ctttacctgc tgtaaaagac tctgtaaaag actcctaggt aagtaatccc tttttttttg    600
tatttccagg ttcatgggtg ctgctctagc acttttgggg gacctagttg ccagtgtatc    660
tgaggctgct gctgccacag gattttcagt ggctgaaatt gctgctgggg aggctgctgc    720
tgctatagaa gttcaaattg catccccttgc tactgtagag gcataacaa gtacctcaga    780 ggctatagct gctataggcc taactcctca aacatatgct gtaattgctg gtgctccagg    840
```

```
ggctattgct gggtttgctg ctttaattca aactgttact ggtattagtt ctttggctca    900
agtagggtat aggttttta gtgattggga tcacaaagtt tccactgtag gcctttatca    960
gcaatcaggc atggcattgg aattgtttaa cccagatgag tactatgata ttttgtttcc   1020
tggtgtaaat acttttgtaa ataatattca atacctagat cctaggcatt ggggtccttc   1080
tttgtttgct actatttccc aggctttgtg gcatgttatt agggatgata tacctgctat   1140
aacttcacaa gaattgcaaa gaagaacaga gagattcttt agagactcct tggctagatt   1200
tttggaagaa actacctgga caattgtaaa tgcccctgta aacttttata attatattca   1260
ggattattat tctaatttgt cccctattag gccttcaatg gttaggcaag ttgctgaaag   1320
ggaaggaacc caggtaaatt ttggccatac ctacagaata gatgatgctg acagtataca   1380
agaagttacc caaagaatgg agttaagaaa taaagagaat gtacattcag gagagtttat   1440
agaaaaaact attgccccag gaggtgctaa tcaaagaact gctcctcaat ggatgttgcc   1500
tttgcttcta ggcctgtacg ggactgtaac acctgctctt gaagcatatg aagatggccc   1560
caaccaaaag aaaaggagag tgtccagggg cagctcccaa aaagccaaag gaatccgtgc   1620
aagtgccaaa actactaata aaaggaggag tagaagttct agaagttaaa acttgggtag   1680
atgctataac agaggtagaa tgcttcctaa acccagaaat gggggatccg gatccagatg   1740
aaaaccttag gggctttagt ctaagactaa ctgctgaaac tgcctttgac agtgatagcc   1800
cagacagaaa aatgcttccc tgttacagca cagcaagaat tccactacct aatttgaatg   1860
aggatctaac ctgtggaaat ctactaatgt gggaggctgt gactgtaaaa acagaggtta   1920
ttggaataac tagtatgctt aaccttcatg cagggtcaca gaaagtacat gaaaatggtg   1980
gaggcaaacc tattcaaggc agcaattttc acttttttgc tgtgggtggg gaccccttgg   2040
aaatgcaggg agtacttatg aactacagaa caaagtaccc agaaggtact gtcaccccaa   2100
aaaatcccac agctcagtcc caggtaatga atactgacca taaggcctac ttggacaaaa   2160
acaatgctta tccagttgaa tgctggattc ctgaccctag tagaaatgaa aatactaggt   2220
attttggaac atacacagga ggggaaaatg ttccccagt acttcatgta accaacacag   2280
ctaccacagt gttgctggat gaacagggtg tggggcctct gtgtaaagct gatagcctgt   2340
atgtttcagc tgctgatatt tgtgactgt ttactaacag ctctggaaca caacagtgga   2400
ggggccttcc aagatatttt aagattcgcc tgagaaaaag atctgtaaag aacccttacc   2460
caatttcctt tttgcttagt gaccttataa acaggagaac ccagagagtg gatgggcagc   2520
ctatgtatgg tatggagtct cacgtggagg aggtcagggt gtttgatggc acagaaacag   2580
cttccagggg acccagatat gataagatat attgacagac agggacaatt gcaaacaaaa   2640
atggtttaaa caaggtgctt ttattgtaca tatacatgct taataaatgc tgcttttata   2700
ttacacactt ttaatcttgt gttattttgg gggtggtgtt ttaggccttt taaaacactg   2760
aaagccttta cacaaatgta actcttcact atgggggtct gacctttggg aatcttcagc   2820
aggggctgaa gtatctgaga cttgggaaga gcattgtgat tgggattcag tgcttgatcc   2880
atgtccagag tcttcagttt ctgaatcttc ttctcttgtt atatcaagaa tacatttccc   2940
catgcatata ttatatttca tccttgaaaa agtatacata cttatctcag aatccagcct   3000
ttccttccat tcaacaattc tagattgtat atcagttgca aaatcagcta caggcctaaa   3060
ccaaattagc agtagcaaca aggtcattcc actttgtaaa attcttttt caagtaagaa   3120
ctctgagttt tgtaaggatt ttcttaaata aattttaggt ctaaaatcta tctgtcttac   3180
aaatctagcc tgcaaggttt tggggacagg atactcattc attgtaacta aacctggtgg   3240
```

-continued

```
aaatatttgg gttcttttgt ttaaatgttt cttttctaaa tttaccttga cacttccatc    3300
taaataatcc cttaaactgt ctaaattgtt tattccatgt cctgaaggca aatcctttga    3360
ttcagctcct gttcccttca catcttcaaa aacaaccata tactgatcta tagccacacc    3420
cagttcaaaa gtaagccttt ccatgggtaa attcacattt aaagctttgc ctccacataa    3480
atctaataac cctgcagcta gtgttgtttt tccactatca attggacctt tgaataacca    3540
gtatcttctt ttaggtacat taaaaacaat acagtgcagg aaatcaaata taacagaatc    3600
cattttaggt agcaaacagt gcagccaggc aactcctgcc atatattgtt ctagtacagc    3660
atttccatga gctccaaata ttaaatccat tttatctaat atatgattaa atctgtctgt    3720 tagcattttct tctctggtca tatggagggt atctacccctt ttttagcta acactgtatc    3780 cactgcttgc tgacaaatac ttttttgatt tttactttct gcaaaaatgg tagcatttgc    3840
aaaatgcttt tcatgatatt taaagtggta gggttggtct ttttttttgac acttttttaca   3900 ctcctctaca ttgtactgaa attctaaata catcccaat agtagaaaca catcttcaca    3960
ctttgtttct actgcatatt cagttattaa tttccaggac acctgctttg tttcttcagg    4020
ttcctctggg ttaaaatcat gctcctttag gccccctga atactttcct ctattatata    4080
atatggatct ctagttaagg cactgtatag taagtattcc ttattaacac ccttacaaat    4140
taaaaaacta aagtacaca gcttttgaca gaaattatta attgcagaaa ctctatgtct    4200
atgtggagtt aaaaagaata taatattatg accagcacac atgtgtctac taataaaagt    4260
tacagaatat ttttccataa gttttttata cagaattaaa gctttttctt tagtagtata    4320
cacagcaaag caggcaagag ttctattact aaatacagct tgactaagaa actggtgtag    4380
atcagaagga aagtctttag ggtcttctac cttttctttt tttttgggtg tgttgagtg     4440 ttgggaatct gctgttgcct cctcatcact ggcaaacata tcttcatggc aaaataaatc    4500
ttcatcccat ttttcattaa aggacctcca ccaggactcc cactcttctg ttccataggt    4560
tggcacctat aaaaaaaata attacttagg gcctttttaat aatttactat ttatctaaag    4620
ataaattagt taccttaaag ctttagatct ctgaagggag tctctccaat tatttggacc    4680
caccattgca gagtttcttc agttaggtct aagccaaacc actgtgtgaa gcagtcaatg    4740
cagtagcaat ctatccaaac caagggctct tttcttaaaa atttttctatt taaatgtctt    4800 aatcttagct gacacagcat gcaagggcag tgcactgaag gcttttttgga acaaataggc    4860 cattccttgc agtacagggt atctgggcaa agaggaaaat cagcacaaac ctctgagcta    4920
ctccaggttc caaaatcagg ctggtgagct acctttacat cctgctccat ttttttatat    4980
aaagtattca ttctcttcat tttatcctcg tcgccccctt tgtcagggtg aaattcctta    5040
cactttctta aataggcttt cctcattaag ggaaggtttc cccaggcagc tcttttcaagg    5100 cctaaaaggt ccatgagctc catggattcc tccctgttta gcactttatc cat           5153
```

<210> SEQ ID NO 49
<211> LENGTH: 5147
<212> TYPE: DNA
<213> ORGANISM: Human polyomavirus type BK virus

<400> SEQUENCE: 49

```
ttttgcaaaa attgcaaaag aatagggatt tccccaaata ttttttgctag gcctcagaaa    60 aagcctccac acccttacta cttgagagaa agggtggagg cagaggcggc ctcggcctct    120
tatatattat aaaaaaaaag gccacaggga ggagctgcta acccatggaa tgtagccaaa    180
```

```
ccatgacctc aggaaggaaa gtgcatgact gggcagccag ccagtggcag ttaatagtga    240
aaccccgccc ctaaaattct caaataaaca caagaggaag tggaaactgg ccaaaggagt    300
ggaaagcagc cagacagaca tgttttgcga gcctaggaat cttggccttg tccccagtta    360
aactggacaa aggccatggt tctgcgccag ctgtcacgac aagcttctgt gaaagttagt    420
aaaacctgga ctggaacaaa aaaaagggct cagaggattt ttattttat tttagagctt    480 ttgctggaat tttgtagagg tgaagacagt gtagacggga aaaacaaaag taccactgct    540
ttacctgctg taaaagactc tgtaaaagac tcctaggtaa gtaatccctt ttttttgta    600 tttccaggtt gatgggtgct gctctagcac ttttggggga cctagttgcc agtgtatctg    660
aggctgctgc tgccacagga ttttcagtgg ctgaaattgc tgctggggag gctgctgctg    720
ctatagaagt tcaaattgca tcccttgcta ctgtagaggg cataacaagt acctcagagg    780
ctatagctgc tataggccta actcctcaaa catatgctgt aattgctggt gctcctgggg    840
ctattgctgg gtttgctgct ttaattcaaa ctgttactgg tattagttcc ttggctcaag    900
tagggtatag gttttttagt gattgggatc acaaagtttc cactgtaggc ctctatcagc    960
aatcaggcat ggctttggaa ttgtttaacc cagatgagta ctatgatatt ttgtttcctg   1020
gtgtaaatac ttttgtaaat aatattcaat accttgatcc taggcattgg ggtccttcct   1080
tgtttgctac tatttcccag gctttgtggc atgttattag ggatgatata cctgctataa   1140
cctcacaaga attgcaaaga agaacagaaa gatttttag agactccttg gctagatttt   1200
tggaggaaac tacctggaca attgtaaatg cccctataaa cttttataat tatattcaag   1260
aatattattc tgatctttcc cctattaggc cctcaatggt tagacaagtg gctgaaaggg   1320
aaggtacccg tgtacatttt ggccatactt atagtataga tgatgctgac agtatagaag   1380
aagttacaca aagaatggac ttaagaaatc aacaaactgt acattcagga gagtttatag   1440
aaaaaactat tgccccagga ggtgctaatc aaagaactgc tcctcaatgg atgttgcctt   1500
tacttctagg cctgtacggg actgtaacac ctgctcttga agcatatgaa gatggcccca   1560
accaaaagaa aaggagagtg tccaggggca gctcccaaaa agccaaagga acccgtgcaa   1620
gtgccaaaac tactaataaa aggaggagta gaagttctag aagttaaaac tggggtagat   1680
gctataacag aggtagaatg cttcctaaac ccagaaatgg gggatccgga tccagatgaa   1740
aaccttaggg gctttagtct aaagctaagt gctgaaaatg actttagcag tgatagccca   1800
gaaagaaaaa tgcttcctg ttacagcaca gcaagaattc ccctcccaa tttaaatgag   1860 gacctaacct gtgaaaatct actgatgtgg gaggctgtaa ctgtacaaac agaggtcatt   1920
ggaataacta gcatgcttaa ccttcatgca gggtcacaaa aagtgcatga gcatggtgga   1980
ggtaaaccta ttcaaggcag taatttccac ttctttgctg ttggtggaga ccccttggaa   2040
atgcagggag tgctaatgaa ttacaggacc aagtacccag atggtactat aaccccaaaa   2100
aacccaacag cccagtccca ggtaatgaat actgaccata aggcctattt ggacaaaaac   2160
aatgcttatc cagttgagtg ctgggttcct gatcctagta gaaatgaaaa tactaggtat   2220
tttgggactt tcacaggagg ggaaaatgtt cccccagtac ttcatgtgac caacacagct   2280
accacagtgt tgctagatga acagggtgtg gggcctcttt gtaaagctga tagcctgtat   2340
gtttcagctg ctgatatttg tggcctgttt actaacagct ctggaacaca acagtggaga   2400
ggccttgcaa gatatttaa gattcgcctg agaaaaagat ctgtaaaaaa tccttaccca   2460
atttcctttt tgctaagtga ccttataaac aggagaaccc agagagtgga tgggcagcct   2520
atgtatggta tggaatccca ggtagaagag gttagggtgt ttgatggcac agaaagactt   2580
```

```
ccagggggacc cagatatgat aagatatatt gataaacaag gacaattgca aaccaaaatg    2640
ctttaaacag gtgcttttat tgtacatata catttaataa atgctgcttt tgtataagcc    2700
acttttaagc ttgtgttatt ttggggtgg tgttttaggc cttttaaaac attgaaagcc     2760
tttacacaaa tgcaactctt gactatgggg gtctaacctt tgggaatctt cagcaggggc    2820
tgaagtatct gagacttggg aagagcattg tgattgggat tcagtgcttg atccatgtcc    2880
agagtcttca gtttctgaat cttcttctct tgtgatatca agaatacatt tccccatgca    2940
tatattatat ttcatccttg aaaaagtata catacttatc tcagaatcca gcctttcctt    3000
ccattcaaca attctagatt gtatatctgt tgcaaaatca gctacaggcc taaaccaaat    3060
tagcagtagc aacaaggtca ttccactttg taaaattctt ttttcaagta agaactctga    3120
gttttgtaag gattttctta aatatatttt gggcctaaaa tctatttgtc ttacaaatct    3180
agcttgcagg gttttaggaa caggatactc attcattgta accaggcctg gtggaaatat    3240
ttgggttctt ttgtttaaat gtttcttttc taaattaacc ttaacacttc catctaaata    3300
atctctcaaa ctgtctaaat tgtttattcc atgtcctgaa ggcaaatcct ttgattcagc    3360
ccctgttcct tttacatctt caaaaacaac catgtactga tctatagcta cacctagttc    3420
aaaggttagc ctttccatgg gtaggtttac atttaaggct ttacctccac acaaatctaa    3480
taaccctgca gctagtgttg tttttccact atcaatggga cctttaaata accagtatct    3540
tcttttaggt acattaaaaa caatacagtg caaaaaatca aatataacag aatccatttt    3600
aggtagcaaa cagtgcagcc aagcaacacc tgccatatat tgttccagta cagcatttcc    3660
atgagctcca aatattaaat ccatttatc taatatatga ttaaatcttt ctgttagcat    3720
ttcttctctg gtcatatgaa gggtatctac tcttttttta gctaaaactg tatctactgc    3780
ttgctgacaa atactttttt gatttttact ttctgcaaaa atagtagcat ttgcaaaatg    3840
cttttcatga tacttaaagt gataaggttg gtcttttttc tgacactttt tacactcttc    3900
tacattgtat tgaaattcta aatacatacc caataataaa aacacatcct cacactttgt    3960
ctctactgca tactcagtaa ttaatttcca agacacctgc tttgtttctt caggctcttc    4020
tgggttaaaa tcatgctcct ttaagccccc ttgaatgctt tcttctattg tatggtatgg    4080
atctctagtt aaggcactat atagtaagta ttccttatta acacccttac aaattaaaaa    4140
actaaaggta cacagctttt gacagaaatt attaattgca gaaactctat gtctatgtgg    4200
agttaaaaag aatataatat tatgcccagc acacatgtgt ctactaataa agttacaga    4260 atatttttcc ataagttttt tatacagaat ttgagctttt tctttagtag tatacacagc    4320
aaagcaggca agggttctat tactaaatac agcttgacta agaaactggt gtagatcaga    4380
aggaaagtct ttagggtctt ctacctttct ctttttcttg ggtggtgtgg agtgttgaga    4440
atctgctgtt gcttcttcat cactggcaaa catatcttca tggcaaaata atcttcatc    4500 ccatttttca ttaaaggagc tccaccagga ctcccactct tctgttccat aggttggcac    4560
ctataaaaaa aataattact tagggccttt aaatattttc ttatttatct aaatataagt    4620
tagttaccct aaagctttag atctctgaag ggagtttctc caattatttg gacccaccat    4680
tgcagagttt cttcagttag gtctaagcca aaccactgtg tgaagcagtc aatgcagtag    4740
caatctatcc aaaccaaggg ctcttttctt aaaaattttc tatttaaatg ccttaatcta    4800
agctgacata gcatgcaagg gcagtgcaca gaaggctttt tggaacaaat aggccaatcc    4860
ttgcagtaca gggtatctgg gcaaagagga aaatcagcac aaacctctga gctactccag    4920
```

```
gttccaaaat caggctgatg agctaccttt acatcctgct ccatttttt atataaagta    4980 ttcattctct tcattttatc ctcgtcgccc cctttgtcag ggtgaaattc cttacacttc    5040
cttaaatagg cttttctcat taagggaagg tttccccagg cagctctttc aaggcctaaa    5100
aggtccatga gctccatgga ttcttccctg ttaagcactt tatccat                  5147

<210> SEQ ID NO 50
<211> LENGTH: 5147
<212> TYPE: DNA
<213> ORGANISM: Human polyomavirus type BK virus

<400> SEQUENCE: 50
ttttgcaaaa attgcaaaag aatagggatt tccccaaata gttttgctag gcctcagaaa      60
aagcctccac acccttacta cttgagagaa agggtggagg cagaggcggc ctcggcctct     120
tatatattat aaaaaaaaag gccacaggga ggagctgctt acccatggaa tgcagccaaa     180
ccatgacctc aggaaggaaa gtgcatgact gggcagccag ccagtggcag ttaatagtga     240
aaccccgccc ctaaaattct caaataaaca caagaggaag tggaaactgg ccaaaggagt     300
ggaaagcagc cagacagaca tgttttgcga gcctaggaat cttggccttg tccccagtta     360
aactggacaa aggccatggt tctgcgccag ctgtcacgac aagcttctgt gaaagttggt     420
aaaacctgga ctggaacaaa aaaaagagct cagaggattt ttattttat tttagagctt     480 ttgctggaat tttgtagagg tgaagacagt gtagacggga aaaacaaaag taccactgct     540
ttacctgctg taaaagactc tgtaaaagac tcctaggtaa gtaatccctt ttttttgta     600 tttccaggtt catgggtgct gctctagcac ttttggggga cctagttgcc agtgtatctg     660
aggctgctgc tgccacagga ttttcagtgg ctgaaattgc tgctggggag gctgctgctg     720
ctatagaagt tcaaattgca tcccttgcta ctgtagaggg cataacaagt acctcagagg     780
ctatagctgc tataggccta actcctcaaa catatgctgt aattgctggt gctcctgggg     840
ctattgctgg gtttgctgct taattcaaa ctgttagtgg tattagttcc ttggctcaag     900
tagggtatag gttctttagt gattgggatc acaaagtttc cactgtaggc ctctatcagc     960
aatcaggcat ggctttggaa ttgtttaacc cagatgagta ctatgatatt ctgtttcctg    1020
gtgtaaatac ttttgttaat aatattcaat accttgatcc taggcattgg ggtccttctt    1080
tgtttgctac tatttcccag gctttgtggc atgttattag ggatgatata ccttctataa    1140
cctcacagga attgcagaga agaacagaaa gatttttag agactccttg gctagatttt    1200
tggaggaaac tacctggacc attgtaaatg ccctataaa cttttataat tatattcaac    1260
aatattattc tgatctgtcc cctattaggc cctcaatggt tagacaagta gctgaaaggg    1320
aaggtacccg tgtacatttt ggccatactt atagtataga tgatgctgac agtatagaag    1380
aagttacaca aagaatggat ttaagaaatc aacaaagtgt acattcagga gagtttatag    1440
aaaaaactat tgccccagga ggtgctaatc aaagaactgc tcctcaatgg atgttgcctt    1500
tacttctagg cctgtacggg actgtaacac ctgctcttga agcatatgaa gatggcccca    1560
accaaaagaa aagagagtg tccaggggca gctcccaaaa agccaaagga acccgtgcaa    1620
gtgccaaaac tactaataaa aggaggagta gaagttctag aagttaaaac tggggtagat    1680
gctattacag aggtagaatg cttcctaaac ccagaaatgg gggatccgga tccagatgaa    1740
aaccttaggg gctttagtct aaagctaagt gctgaaaatg actttagcag tgatagccca    1800
gagagaaaaa tgcttccctg ttacagcaca gcaagaattc cctcccccaa tttaaatgag    1860
gacctaacct gtggaaatct actgatgtgg gaggctgtaa ctgtacaaac agaggttatt    1920
```

-continued

```
ggaataacta gcatgcttaa ccttcatgca gggtcacaaa aagtgcatga gcatggtgga    1980
ggaaaaccta ttcaaggcag taatttccac ttctttgctg ttggtggaga ccccttggaa    2040
atgcagggag tgctaatgaa ttacaggaca aagtacccag atggtactat aaccccctaaa   2100 aacccaacag cccagtccca ggtaatgaat actgaccata aggcctattt ggacaaaaac    2160
aatgcttatc cagttgagtg ctgggttcct gatcccagta gaaatgaaaa tactaggtat    2220
tttgggactt tcacaggagg ggaaaatgtt cccccagtac ttcatgtgac caacacagct    2280
accacagtgt tgctagatga acagggtgtg gggcctcttt gtaaagctga tagcctgtat    2340
gtttcagctg ctgatatttg tggcctgttt actaacagct ctggaacaca acagtggaga    2400
ggccttgcaa gatattttaa gatccgcctg agaaaaagat ctgtaaagaa tccttaccca    2460
atttcctttt tgctaagtga cctcataaac aggagaaccc agagagtgga tgggcagcct    2520
atgtatggta tggaatccca ggtagaagag gttagggtgt ttgatggcac agaaagactt    2580
ccaggggacc cagatatgat aagatatatt gacaaacagg acaattgca aaccaaaatg     2640 ctttaaacag gtgcttttat tgtacatata catttaataa atgctgcttt tgtataagcc    2700 actttttaacc ttgtgttatt tgggggtgg tgttttaggc cttttaaaac actgaaagcc    2760
tttacacaaa tgtaactctt gactatgggg gtctgacctt tgggaatctt cagcaggggc    2820
tgaagtatct gagacttggg aagagcattg tgattgggat tcagtgcttg atccatgtcc    2880
agagtcttca gtttctgaat cctcttctct tgtgatatca agaatacatt tccccatgca    2940
tatattatat ttcatccttg aaaaagtata catacttatc tcagaatcca gcctttcctt    3000
ccattcaaca attctagatt gtatatctgt tgcaaaatca gctacaggcc taaaccaaat    3060
tagcagtagc aacaaggtca ttccactttg tagaattctt ttttcaagta agaactctga    3120
gttttgtaag gatttctta aatatatttt gggcctaaaa tctatttgtc ttacaaatct     3180
agcttgcagg gttttaggga caggatactc attcattgta accaagcctg gtggaaatat    3240
ttgggttctt ttgtttaaat gtttttttc taaatttacc ttaacacttc catctaaata    3300
atctcttaaa ctgtctaaat tgtttattcc atgtcctgaa ggcaaatcct ttgattcagc    3360
ccctgtccct tttacatctt caaaaacaac catgtactga tctatagcca cacctagctc    3420
aaaggttagc ctttccatgg gtaggtttac atttaaggct ttacctccac acaaatctaa    3480
taaccctgca gctagtgttg ttttttccact atcaatggga cctttaaata accagtatct    3540
tcttttaggt acattgaaaa caatacagtg caaaaaatca aatataacag aatccatttt    3600
aggtagcaaa cagtgcagcc aagcaacacc tgccatatat tgttctagta cagcatttcc    3660
atgagctcca aatattaaat ccatttttatc taatatatga ttgaatcttt ctgttagcat    3720
ttcttccctg gtcatatgaa gggtatctac tcttttttta gctaaaactg tatctactgc    3780
ttgctgacaa atacttttt gatttttact ttctgcaaag ataatagcat ttgcaaagtg    3840
cttttcatga tacttaaagt gataaggttg gtctttttc tgacactttt tacactcctc     3900
tacattgtat tgaaattcta aatacatacc taataataaa aacacatcct cacactttgt    3960
ctctactgca tactcagtaa ttaatttcca agacacctgc tttgtttctt caggctcttc    4020
tgggttaaaa tcatgctcct ttaagccccc ttgaatgctt tcttctatag tatggtatgg    4080
ctctctagtt aaggcactat acagtaagta ttccttatta cacccttac aaattaaaaa    4140 actaaaggta cacagctttt gacagaagtt attaattgca gaaactctat gtctatgtgg    4200
agttaaaaag aatataatat tatgcccagc acacatgtgt ctactaataa aagttacaga    4260
```

```
atattttttcc ataagttttt tatacaggat ttgagctttt tctttagtag tatacacagc    4320
aaagcaggca agggttctat tactaaatac agcttgacta agaaactggt gtagatcaga    4380
gggaaagtct ttagggtctt ctacctttct ttttttcttg ggtggtgttg agtgttgaga    4440
atctgctgtt gcttcttcat cactggcaaa catatcttca tggcaaaata agtcttcatc    4500 ccattttttca ttaaaggaac tccaccagga ctcccactct tctgttccat aggttggcac    4560
ctataaaaaa aataattact tagggccttt taatatttta ttatttatct aaatataagt    4620
tagttacctt aaagctttag atctctgaag ggagtttctc caattatttg gacccaccat    4680
tgcagagttt cttcagttag gtctaagcca aaccactgtc tgaagcagtc aatgcagtag    4740
caatctatcc aaaccaaggg ctcttttctt aaaaatttc tatttaaatg ccttaatcta    4800
agctgacata gcatgcaagg gcagtgcaca gaaggctttt tggaacaaat aggccattcc    4860
ttgcagtaca gggtatctgg gcaaagagga aaatcagcac aaacctctga gctactccag    4920
gttccaaaat caggctgatg agctaccttt acatcctgct ccattttttt atataaagta    4980
ttcattctct tcatttttatc ctcgtcgccc cctttgtcag ggtgaaattc cttacacttc    5040
cttaaataag cttttctcat taagggaaga tttccccagg cagctctttc aaggcctaaa    5100
aggtccatga gctccatgga ttcttccctg ttaagcactt tatccat                 5147

<210> SEQ ID NO 51
<211> LENGTH: 5148
<212> TYPE: DNA
<213> ORGANISM: Human polyomavirus type BK virus

<400> SEQUENCE: 51
ttttgcaaaa attgcaaaag aatagggatt tcccccaaat agttttgcta ggcctcagaa      60
aaagcctcca caccttact acttgagaga aagggtggag gcagaggcgg cctcggcctc     120
ttatatatta taaaaaaaaa ggccacaggg aggagctgct tacccatgga atgcagccaa     180
accatgacct caggaaggaa agtgcatgac tgggcagcca gccagtggca gttaatagtg     240 aaacccccgcc cctgaaattc tcaaataaac acaagaggaa gtggaaactg ccaaaggag     300 tggaaagcag ccagacagac atgttttgcg ggcctaggaa tcttggcctt gtccccagtt     360
aaactggaca aaggccatgg ttctgcgcca gctgtcacga caagcttctg tgaaacttgg     420
taaaacctgg actggaacaa aaaaagagc tcagaggatt tttatttta ttttagagct     480 tttgctggaa ttttgtagag gtgaagacag tgtagacggg aaaaacaaaa gtaccactgc     540
tttacctgct gtaagagact ctgtaaaaga ctcctaggta agtaatccct tttttttgt     600 atttccaggt tgatgggtgc tgctctagca cttttggggg acctagttgc cagtgtatct     660
gaggctgctg ctgccacagg attttcagtg gctgaaattg ctgctgggga gctgctgct     720 gctatagaag ttcaaattgc atcccttgct actgtagagg gcataacaag tacctcagag     780
gctatagctg ctataggcct aactcctcaa acatatgctg taattgctgg tgctcctggg     840
gctattgctg ggtttgctgc tttaattcaa actgttactg gtattagttc cttggctcaa     900
gtagggtata ggtttttag tgattgggat cacaaagttt ccactgtagg cctctatcag     960
caatcaggca tggctttgga attgtttaac ccagatgagt actatgatat attgtttcct    1020
ggtgtaaata cttttgtaaa taatattcaa taccttgatc ctaggcattg ggtccttct    1080 ttgtttgcta ctatttctca ggctttgtgg catgttatta ggggatgatat acctgctata    1140 acctcacaag aattgcaaag aagaacagaa agatttttta gagactccctt ggctagattt    1200 ttggaggaaa ctacctggac aattgtaaat gcccctataa acttttataa ttatattcaa    1260
```

```
gaatattatt ctgatctttc ccctattagg ccctcaatgg ttagacaagt agctgaaagg   1320
gaaggtaccc gtgtacattt tggccatact tatagtatag atgatgctga cagtatagaa   1380
gaagttacac aaagaatgga cttaagaaat caacaaactg tacattcagg agagtttata   1440
gaaaaaacta ttgccccagg aggtgctaat caaagaactg ctcctcaatg gatgttgcct   1500
ttacttctag gcctgtacgg gactgtaaca cctgctcttg aagcatatga agatggcccc   1560
aacaaaaaga aaggagagt gtccaggggc agctcccaaa aagccaaagg aacccgtgca   1620
agtgccaaaa ctactaataa aaggaggagt agaagttcta gaagttaaaa ctgggctaga   1680
tgctataaca gaggtagaat gcttcctaaa cccagaaatg ggggatccgg atccagatga   1740
aaaccttagg ggctttagtc taaagctaag tgctgaaaat gactttagca gtgatagccc   1800
agaaagaaaa atgcttccct gttacagcac agcaagaatt cccctcccca atttaaatga   1860
ggacctaacc tgtggaaatc tactgatgtg ggaggctgta acagtacaaa cagaggtcat   1920
tggaataact agcatgctta accttcatgc agggtcacaa aaagtgcatg agcatggtgg   1980
aggtaaacct attcaaggca gtaatttcca cttttttgct gttggtggag accccttgga   2040
aatgcaggga gtgctaatga attacaggac aaagtaccca gaaggtacta taaccccaaa   2100
aaacccaaca gcccagtccc aagtaatgaa tactgaccat aaggcctatt tggacaaaaa   2160
caatgcttat ccagttgagt gctggattcc tgatcccagt agaaatgaaa atactaggta   2220
ttttgggact ttcacaggag gggaaaatgt tcccccagta cttcatgtga ccaacacagc   2280
taccacagtg ttgctagatg aacagggtgt ggggcctctt tgtaaagctg atagcctgta   2340
tgtttcagct gctgatattt gtggcctgtt tactaacagc tctggaacac aacagtggag   2400
aggccttgca agatatttta agattcgcct gagaaaaaga tctgtaaaaa atccttaccc   2460
aatttccttt ttgctaagtg accttataaa caggagaacc cagagagtgg atgggcagcc   2520
tatgtatggt atggaatccc aggtagaaga ggttagggtg tttgatggca cagaaaaact   2580
tccaggggac ccagatatga taagatatat tgacaaacaa ggacaattgc aaaccaaaat   2640
gctttaaaca ggtgctttta ttgttgatat acatttaata aatgctgctt ttgtataagc   2700
cagttttaag cttgtgttat tttgggggtg gtgttttagg ccttttaaaa cactgaaagc   2760
ctttacacaa atgcaactct tgactatggg ggtctgacct ttgggaatct tcagcagggg   2820
ctgaagtatc tgagacttgg gaagagcatt gtgattggga ttcagtgctt gatccatgtc   2880
cagagtcttc agtttctgaa tcttcttctc ttgtgatatc aagaatacat tttcccatgc   2940
atatattata tttcatcctt gaaaagtat acatacttat ctcagaatcc agcctttcct   3000
tccattcaac aattctagat tgtatatctg ttgcaaaatc agctacaggc ctaaaccaaa   3060
ttagcagtag caacaaggtc attccacttt gtagaattct tttttcaagt aagaactctg   3120
agttttgtaa ggattttctt aaatatattt tgggcctaaa atctatctgt cttacaaatc   3180
tagcctgcag ggttttaggg acaggatact cattcattgt aaccaggcct ggtggaaata   3240
tttgggttct tttgtttaaa tgtttctttt ctaaattaac cttaacactt ccatctaaat   3300
aatctctcaa actgtctaaa ttgtttattc catgtcctga aggcaaatcc tttgattcag   3360
ctcctgttcc ttttacatct tcaaaaacaa ccatgtactg atctatagct acacctagtt   3420
caaaggttag cctttccatg ggtaggttta catttaaagc tttacctcca cacaaatcta   3480
ataaccctgc agctagtgtt gttttccac tatcaatggg acctttaaat aaccagtatc   3540
ttcttttagg tacattaaaa acaatacagt gcaaaaaatc aaatataaca gaatccattt   3600
```

```
taggtagcaa acagtgcagc caagcaacac ctgccatata ttgttctaat acagcatttc   3660
catgagcccc aaatattaaa tccatttat ctaatatatg attaaatctt tctgttagca   3720
tttcttctct agtcatatga aggctatcta ctctttttt agctaaaact gtatctactg   3780
cttgctgaca aatacttttt tgattttac tttctgcaaa gatagtagca tttgcaaaat   3840
gcttttcatg atacttaaag tgataaggtt ggtcttttt ctgacacttt ttacactcct   3900
ctacattgta ttgaaattct aaatacatac ctaataataa aaacacatcc tcacactttg   3960
tttctactgc atactcagta attaatttcc aagagacctg ctttgtttct tcaggctctt   4020
ctgggttaaa atcatgctcc tttaagcccc cttgaatgct ttcttctatt gtatggtatg   4080
gatctctagt taaggcacta tatagtaagt attccttatt aacacccta caaattaaaa   4140 aactaaaggt acacagcttt tgacagaaat tattaattgc agaaactcta tgtctatgtg   4200
gagttaaaaa gaatataata ttatgcccag cacacatgtg tctactaata aaagttacag   4260
aatatttttc cataagtttt ttatacagaa tttgagcttt ttctttagta gtatacacag   4320
caaagcaggc gagggttcta ttactaaata cagcttgact aagaaactgg tgtagatcag   4380
aaggaaagtc tttagggtct tctaccttc tttttttctt gggtggtgtt gagtgttgag   4440
aatctgctgt tgcttcttca tcactggcaa acatatcttc atggcaaaat aaatcttcat   4500
cccatttttc attaaaggaa ctccaccagg actcccactc ttctgttcca taggttggca   4560
cctataaaac aaataattac ttagggcctt taaatatttt attatttatc taaatataag   4620
gtagttacct taaagcttta gatctctgaa gggagtttct ccaattattt ggacccacca   4680
ttgcagagtt tcttcagtta ggtctaagcc aaaccactgt gtgaagcagt caatgcagta   4740
gcaatctatc caaccaagg gctcttttct taaaaatttt ctatttaaat gccttaatct   4800
aagctgacat agcatgcaag ggcagtgcac agaaggcttt ttggaacaaa taggccattc   4860
cttgcagtac agggtatctg ggcaaagagg aaaatcagca caaacctctg agctactcca   4920
ggttccaaaa tcaggctgat gagctacctt tacatcttgc tccatttttt tatataaagt   4980
attcattctc ttcatttat cctcgtcgcc ccctttgtca gggtgaaatt ccttacactt   5040
ccttaaatag gcttttctca ttaagggaag gtttccccag gcagctcttt caaggcccaa   5100
aaggtccatg agctccatgg attcttccct gttaagcact ttatccat           5148
```

<210> SEQ ID NO 52
<211> LENGTH: 5147
<212> TYPE: DNA
<213> ORGANISM: Human polyomavirus type BK virus

<400> SEQUENCE: 52

```
ttttgcaaaa attgcaaaag aatagggatt tccccaaata gttttgctag gcctcagaaa    60
aagcctccac acccttacta cttgagagaa agggtggagg cagaggcggc ctcggcctct   120
tatatattat aaaaaaaaag gccacaggga ggagctgctg acccatggaa tgcagccaaa   180 ccatgaccctc aggaaggaaa gtgcatgact gggcagccag ccagtggcag ttaatagtga   240
aaccccgccc ctgaaattct caaataaaca caagaggaag tggaaactgg ccaaaggagt   300
ggaaagcagc cagacagaca tgttttgcgg gcctaggaat cttggccttg tccccagtta   360
aactggacaa aggccatggt tctgcgccag ctgtcacgac aagcttctgt gaacttggt   420 aaacctgga ctggaacaaa aaaagagct cagaggattt ttattttat tttagagctt   480 ttgctggaat tttgtagagg tgaagacagt gtagacggga aaaacaaaag taccactgct   540
ttacctgctg taaaagactc tgtaaaagac tcctaggtaa gtaatcccctt tttttttgta   600
```

-continued

```
tttccaggtt gatgggtgct gctctagcac ttttggggga cctagttgcc agtgtatctg    660
aggctgctgc tgccacagga ttttcagtgg ctgaaattgc tgctggggag gctgctgctg    720
ctatagaagt tcaaattgca tcccttgcta ctgtagaggg cataacaagt acctcagagg    780
ctatagctgc tataggccta actcctcaaa catatgctgt aattgctggt gctcctgggg    840
ctattgctgg gtttgctgct ttaattcaaa ctgttactgg tattagttcc ttggctcaag    900
tagggtatag gttttttagt gattgggatc acaaagtttc cactgtaggc ctctatcagc    960
aatcaggcat ggctttggaa ttgtttaacc cagatgagta ctatgatata ttgtttcctg   1020
gtgtaaatac ttttgtaaat aatattcaat accttgatcc taggcattgg ggtccttctt   1080
tgtttgctac tatttctcag gctttgtggc atgttattag ggatgatata cctgctataa   1140
cctcacaaga attgcaaaga agaacagaaa gattttttag agactccttg gctagatttt   1200
tggaggaaac tacctggaca attgtaaatg cccctataaa cttttataat tatattcaag   1260
aatattattc tgatctttcc cctattaggc cctcaatggt tagacaagta gctgaaaggg   1320
aaggtacccg tgtacatttt ggccatactt atagtataga tgatgctgac agtatagaag   1380
aagttacaca agaatggac ttaagaaatc aacaaactgt acattcagga gagtttatag    1440
aaaaaactat tgccccagga ggtgctaatc aaagaactgc tcctcaatgg atgttgcctt   1500
tacttctagg cctgtacggg actgtaacac ctgctcttga agcatatgaa gatggcccca   1560
acaaaaagaa aaggagagtg tccagggca gctcccaaaa agccaaagga acccgtgcaa    1620
gtgccaaaac tactaataaa aggaggagta gaagttctag aagttaaaac tgggctagat   1680
gctataacag aggtagaatg cttcctaaac ccagaaatgg gggatccgga tccagatgaa   1740
aaccttaggg gctttagtct aaagctaagt gctgaaaatg actttagcag tgatagccca   1800
gaaagaaaaa tgcttccctg ttacagcaca gcaagaattc ccctcccaa tttaaatgag    1860 gacctaacct gtggaaatct actgatgtgg gaggctgtaa cagtacaaac agaggtcatt   1920
ggaataacta gcatgcttaa ccttcatgca gggtcacaaa agtgcatga gcatggtgga    1980 ggtaaaccta ttcaaggcag taatttccac ttttttgctg ttggtggaga ccccttggaa   2040
atgcagggag tgctaatgaa ttacaggaca agtacccag aaggtactat aaccccaaaa    2100
aacccaacag cccagtccca agtaatgaat actgaccata aggcctattt ggacaaaaac   2160
aatgcttatc cagttgagtg ctggattcct gatcccagta gaaatgaaaa tactaggtat   2220
tttgggactt tcacaggagg ggaaaatgtt cccccagtac ttcatgtgac caacacagct   2280
accacagtgt tgctagatga acagggtgtg gggcctcttt gtaaagctga tagcctgtat   2340
gtttcagctg ctgatatttg tggcctgttt actaacagct ctggaacaca acagtggaga   2400
ggccttgcaa gatattttaa gattcgcctg agaaaaagat ctgtaaaaaa tccttaccca   2460
atttcctttt tgctaagtga ccttataaac aggagaaccc agagagtgga tgggcagcct   2520
atgtatggta tggaatccca ggtagaagag gttagggtgt tgatggcac agaaagactt    2580 ccagggacc cagatatgat aagatatatt gacaaacaag gacaattgca aactaaaatg    2640
gtttaaacag gtgcttttat tgttgatata catttaataa atgctgcttt tgtataagcc   2700
agttttaagc ttgtgttatt ttgggggtgg tgttttaggc cttttaaaac actgaaagcc   2760
tttacacaaa tgcaactctt gactatgggg gtctgacctt tgggaatctt cagcagggc    2820 tgaagtatct gagacttggg aagagcattg tgattgggat tcagtgcttg atccatgtcc   2880
agagtcttca gtttctgaat cttcttctct tgtgatatca agaatacatt ttcccatgca   2940
```

```
tatattatat ttcatccttg aaaaagtata catacttatc tcagaatcca gcctttcctt     3000
ccattcaaca attctagatt gtatatctgt tgcaaaatca gctacaggcc taaaccaaat     3060
tagcagtagc aacaaggtca ttccactttg tagaattctt tttcaagta agaactctga      3120 gttttgtaag gattttctta aatatatttt gggcctaaaa tctatctgtc ttacaaatct    3180
agcctgcagg gttttaggga caggatactc attcattgta accaggcctg gtggaaatat    3240
ttgggttctt ttgtttaaat gtttcttttc taaattaacc ttaacacttc catctaaata    3300
atctctcaaa ctgtctaaat tgtttattcc atgtcctgaa ggcaaatcct ttgattcagc    3360
tcctgttcct tttacatctt caaaacaac catgtactga tctatagcta cacctagttc     3420
aaaggtcagc ctttccatgg gtaggtttac atttaaagct ttacctccac acaaatctaa    3480
taaccctgca gctagtgttg ttttccact atcaatggga cctttaaata accagtatct     3540
tcttttaggt acattaaaaa caatacagtg caaaaatca aatataacag aatccatttt     3600
aggtaacaaa cagtgcagcc aagcaacacc tgccatatat tgttctaata cagcatttcc    3660
atgagcccca aatattaaat ccattttatc taatatatga ttaaatctttt ctgttagcat   3720 ttcttctcta gtcatatgaa ggctatctac ttttttta gctaaaactg tatctactgc      3780
ttgctgacaa atactttttt gatttttact ttctgcaaag atagtagcat ttgcaaaatg    3840
cttttcatga tacttaaagt gataaggttg gtcttttttc tgacactttt tacactcctc    3900
tacattgtat tgaaattcta aatacatacc taataataaa aacacatcct cacactttgt    3960
ttctactgca tactcagtaa ttaatttcca agagacctgc tttgtttctt caggctcttc    4020
tgggttaaaa tcatgctcct ttaagccccc ttgaatgctt tcttctattg tatggtatgg    4080
atctctagtt aaggcactat atagtaagta ttccttatta acacccttac aaattaaaaa    4140
actaaaggta cacagctttt gacagaaatt attaattgca gaaactctat gtctatgtgg    4200
agttaaaaag aatataatat tatgcccagc acacatgtgt ctactaataa agttacaga    4260 atattttcc ataagttttt tatacagaat ttgagctttt tctttagtag tatacacagc     4320
aaagcaggca agggttctat tactaaatac agcttgacta agaaactggt gtagatcaga    4380
aggaaagtct ttagggtctt ctacctttct ttttttcttg ggtggtgttg agtgttgaga    4440
atctgctgtt gcttcttcat cactggcaaa catatcttca tggcaaaata aatcttcatc    4500
ccatttttca ttaaaggaac tccaccagga ctcccactct tctgttccat aggttggcac    4560
ctataaaaca ataattact tagggccttt aaatatttta ttatttatct aaatataagg     4620
tagttacctt aaagctttag atctctgaag ggagtttctc caattatttg gacccaccat    4680
tgcagagttt cttcagttag gtctaagcca accactgtg tgaagcagtc aatgcagtag     4740
caatctatcc aaaccaaggg ctcttttctt aaaaattttc tatttaaatg ccttaatcta    4800
agctgacata gcatgcaagg gcagtgcaca gaaggctttt tggaacaaat aggccattcc    4860
ttgcagtaca gggtatctgg gcaaagagga aaatcagcac aaacctctga gctactccag    4920
gttccaaaat caggctgatg agctaccttt acatcttgct ccattttttt atataaagta    4980
ttcattctct tcatttatc ctcgtcgccc cctttgtcag ggtgaaattc cttacacttc     5040
cttaaatagg cttttctcat taagggaagg tttccccagg cagctctttc aaggcccaaa    5100
aggtccatga gctccatgga ttcttccctg ttaagcactt tatccat                  5147
```

<210> SEQ ID NO 53
<211> LENGTH: 5148
<212> TYPE: DNA
<213> ORGANISM: Human polyomavirus type BK virus

<400> SEQUENCE: 53

```
ttttgcaaaa attgcaaaag aatagggatt tcccccaaat agttttgcta ggcctcagaa      60
aaagcctcca caccettact acttgagaga aaggtggag gcagaggcgg cctcggcctc      120
ttatatatta taaaaaaaaa ggccacaggg aggagctgct tacccatgga atgcagccaa     180
accatgacct caggaaggaa agtgcatgac tgggcagcca gccagtggca gttaatagtg     240
aaaccccgcc cctgaaattc tcaaataaac acaagaggaa gtggaaactg ccaaaggag      300
tggaaagcag ccagacagac atgttttgcg ggcctaggaa tcttggcctt gtccccagtt     360
aaactggaca aaggccatgg ttctgcgcca gctgtcacga caagcttctg tgaaacttgg     420
taaaacctgg actggaacaa aaaaaagagc tcagaggatt tttatttta ttttagagct      480
tttgctggaa ttttgtagag gtgaagacag tgtagacggg aaaaacaaaa gtaccactgc     540
tttacctgct gtaagagact ctgtaaaaga ctcctaggta agtaatccct ttttttttgt     600
atttccaggt tgatgggtgc tgctctagca cttttggggg acctagttgc cagtgtatct     660
gaggctgctg ctgccacagg attttcagtg gctgaaattg ctgctgggga ggctgctgct     720
gctatagaag ttcaaattgc atcccttgct actgtagagg gcataacaag tacctcagag     780
gctatagctg ctataggcct aactcctcaa acatatgctg taattgctgg tgctcctggg     840
gctattgctg ggtttgctgc tttaattcaa actgttactg gtattagttc cttggctcaa     900
gtagggtata ggttttttag tgattgggat cacaaagttt ccactgtagg cctctatcag     960
caatcaggca tggctttgga attgtttaac ccagatgagt actatgatat attgtttcct    1020
ggtgtaaata cttttgtaaa taatattcaa taccttgatc ctaggcattg ggtccttct     1080
ttgtttgcta ctatttctca ggctttgtgg catgttatta gggatgatat acctgctata    1140
acctcacaag aattgcaaag aagaacagaa agatttttta gagactcctt ggctagattt    1200
ttggaggaaa ctacctggac aattgtaaat gccectataa acttttataa ttatattcaa    1260
gaatattatt ctgatctttc ccctattagg ccctcaatgg ttagacaagt agctgaaagg    1320
gaaggtaccc gtgtacattt tggccatact tatagtatag atgatgctga cagtatagaa    1380
gaagttacac aaagaatgga cttaagaaat caacaaactg tacattcagg agagtttata    1440
gaaaaaacta ttgccccagg aggtgctaat caaagaactc tcctcaatg gatgttgcct     1500
ttacttctag gcctgtacgg gactgtaaca cctgctcttg aagcatatga agatggcccc    1560
aacaaaaaga aaaggagagt gtccagggc agctcccaaa aagccaaagg aacccgtgca    1620
agtgccaaaa ctactaataa aaggaggagt agaagttcta gaagttaaaa ctgggctaga    1680
tgctataaca gaggtagaat gcttcctaaa cccagaaatg ggggatccgg atccagatga    1740
aaaccttagg ggctttagtc taaagctaag tgctgaaaat gactttagca gtgatagccc    1800
agaaagaaaa atgcttccct gttacagcac agcaagaatt ccctcccca atttaaatga     1860
ggacctaacc tgtggaaatc tactgatgtg ggaggctgta acagtacaaa cagaggtcat    1920
tggaataact agcatgctta accttcatgc agggtcacaa aaagtgcatg agcatggtgg    1980
aggtaaacct attcaaggca gtaatttcca ctttttgct gttggtggag accccttgga    2040
aatgcaggga gtgctaatga attacaggac aaagtaccca gaaggtacta taaccccaaa    2100
aaacccaaca gcccagtccc aagtaatgaa tactgaccat aaggcctatt tggacaaaaa    2160
caatgcttat ccagttgagt gctggattcc tgatcccagt agaaatgaaa atactaggta    2220
ttttgggact tcacaggag gggaaaatgt tcccccagta cttcatgtga ccaacacagc    2280
```

```
taccacagtg ttgctagatg aacagggtgt ggggcctctt tgtaaagctg atagcctgta   2340
tgtttcagct gctgatattt gtggcctgtt tactaacagc tctggaacac aacagtggag   2400
aggccttgca agatatttta agattcgcct gagaaaaaga tctgtaaaaa atccttaccc   2460
aatttccttt ttgctaagtg accttataaa caggagaacc cagagagtgg atgggcagcc   2520
tatgtatggt atggaatccc aggtagaaga ggttagggtg tttgatggca cagaaaaact   2580 tccagggac ccagatatga taagatatat tgacaaacaa ggacaattgc aaaccaaaat    2640
gctttaaaca ggtgctttta ttgttgatat acatttaata aatgctgctt ttgtataagc   2700
cagttttaag cttgtgttat tttggggtg tgtgtttagg cctttttaaaa cactgaaagc   2760 ctttacacaa atgcaactct tgactatggg ggtctgacct ttgggaatct tcagcagggg   2820
ctgaagtatc tgagacttgg gaagagcatt gtgattggga ttcagtgctt gatccatgtc   2880
cagagtcttc agtttctgaa tcttcttctc ttgtgatatc aagaatacat tttcccatgc   2940
atatattata tttcatcctt gaaaagtat acatacttat ctcagaatcc agcctttcct    3000
tccattcaac aattctagat tgtatatctg ttgcaaaatc agctacaggc ctaaaccaaa   3060
ttagcagtag caacaaggtc attccacttt gtagaattct ttttcaagt aagaactctg    3120 agttttgtaa ggattttctt aaatatattt tgggcctaaa atctatctgt cttacaaatc   3180
tagcttgcag ggttttaggg acaggatact cattcattgt aaccaggcct ggtgaaata    3240 tttgggttct tttgtttaaa tgtttctttt ctaaattaac cttaacactt ccatctaaat   3300
aatctctcaa actgtctaaa ttgtttattc catgtcctga aggcaaatcc tttgattcag   3360
ctcctgttcc ttttacatct tcaaaaacaa ccatgtactg atctatagct acacctagtt   3420
caaaggttag cctttccatg ggtaggttta catttaaagc tttacctcca cacaaatcta   3480
ataaccctgc agctagtgtt gttttttccac tatcaatggg acctttaaat aaccagtatc  3540
ttcttttagg tacattaaaa acaatacagt gcaaaaaatc aaatataaca gaatccattt   3600
taggtagcaa acagtgcagc caagcaacac ctgccatata ttgttctaat acagcatttc   3660
catgagcccc aaatattaaa tccatttat ctaatatatg attaaatctt tctgttagca    3720
tttcttctct agtcatatga aggctatcta ctcttttttt agctaaaact gtatctactg   3780
cttgctgaca aatactttttt tgatttttac tttctgcaaa gatagtagca tttgcaaaat  3840
gcttttcatg atacttaaag tgataaggtt ggtcttttttt ctgacacttt ttacactcct  3900
ctacattgta ttgaaattct aaatacatac ctaataataa aaacacatcc tcacactttg   3960
tttctactgc atactcagta attaatttcc aagagacctg ctttgtttct tcaggctctt   4020
ctgggtaaaa atcatgctcc tttaagcccc cttgaatgct ttcttctatt gtatggtatg   4080
gatctctagt taaggcacta tatagtaagt attccttatt aacaccctta caaattaaaa   4140
aactaaaggt acacagcttt tgacagaaat tattaattgc agaaactcta tgtctatgtg   4200
gagttaaaaa gaatataata ttatgcccag cacacatgtg tctactaata aaagttacag   4260 aatattttc cataagtttt ttatacagaa tttgagcttt ttctttagta gtatacacag    4320
caaagcaggc gagggttcta ttactaaata cagcttgact aagaaactgg tgtagatcag   4380
aaggaaagtc tttagggtct tctaccttc tttttttctt gggtggtgtt gagtgttgag    4440
aatctgctgt tgcttcttca tcactggcaa acatatcttc atggcaaaat aaatcttcat   4500
cccatttttc attaaaggaa ctccaccagg actcccactc ttctgttcca taggttggca   4560
cctataaaac aaataattac ttagggcctt taaatatttt attatttatc taaatataag   4620
gtagttacct taaagcttta gatctctgaa gggagtttct ccaattattt ggacccacca   4680
```

```
ttgcagagtt tcttcagtta ggtctaagcc aaaccactgt gtgaagcagt caatgcagta    4740
gcaatctatc caaaccaagg gctcttttct taaaaatttt ctatttaaat gccttaatct    4800
aagctgacat agcatgcaag ggcagtgcac agaaggcttt ttggaacaaa taggccattc    4860
cttgcagtac agggtatctg gcaaagagg aaaatcagca caaacctctg agctactcca    4920
ggttccaaaa tcaggctgat gagctacctt tacatcttgc tccatttttt tatataaagt    4980
attcattctc ttcattttat cctcgtcgcc cctttgtca gggtgaaatt ccttacactt    5040
ccttaaatag gcttttctca ttaagggaag gtttcccag gcagctcttt caaggcccaa    5100
aaggtccatg agctccatgg attcttccct gttaagcact ttatccat                5148

<210> SEQ ID NO 54
<211> LENGTH: 5111
<212> TYPE: DNA
<213> ORGANISM: Human polyomavirus type BK virus

<400> SEQUENCE: 54

ttttgcaaaa attgcaaaag aataggga tt tccccaaata gttttgctag gcctcagaaa      60
aagcctccac acccttacta cttgagagaa agggtggagg cagaggcggc ctcggcctct     120
tatatattat aaaaaaaaag gccacaggga ggagctgctt acccatggaa tgcagccaaa     180
ccatgacctc aggaaggaaa gtgcatgact gggcaggcag ccagtggcag ttaatagtga     240
aaccccgccc ctaaaattct caaataaaca caagaggaag tggaaactgg ccaaaggagt     300
ggaaagcagc cagacagaca tgttttgcga gcctaggaat cttggccttg tccccagtta     360
aactggacaa aggccatggt tctgcgccag ctgtcacgaa caaaaaaag agctcagagg     420 attttatttt ttatttaga gctttgctg aattttgta gaggtaaaga cagtgtagac      480
gggaaaaaca aagtaccac tgctttacct gctgtaaaag actctgtaaa agactcctag     540
gtaagtaatc cctttttttt tgtatttcca ggttcatggg tgctgctcta gcacttttgg     600
gggacctagt tgccagtgta tctgaggctg ctgctgccac aggattttca gtggctgaaa     660

tgctgctgg ggaggctgct gctgctatag aagttcaaat tgcatccctt gctactgtag     720
agggcataac aagtacctca gaggctatag ctgctatagg cctaactcct caaacatatg     780
ctgtaattgc tggtgctcct ggggctattg ctgggtttgc tgctttaatt caaactgtta     840
gtggtattag ttccttggct caagtagggt ataggttctt tagtgattgg gatcacaaag     900

tttccactgt aggcctctat cagcaatcag gcatggcttt ggaattgttt aacccagatg     960
agtactatga taттcтgтттт cctggtgtaa atacttttgt taataatatt cataccttg    1020 atcctaggca ttggggtcct tctttgtttg ctactatttc ccaggctttg tggcatgtta    1080

ttagggatga taccttct ataacctcac aggaattgca gagaagaaca gaaagaттттт    1140

ttagagactc cttggctaga tttttggagg aaactacctg gaccattgta aatgccccta   1200

taaactttta taattatatt caacaatatt attctgattt gtccctatt aggccctcaa    1260

tggttagaca gtagctgaa agggaaggta cccgtgtaca тттттggccaт acttatagta    1320

tagatgatgc tgacagtata aagaagtta cacaagaatt ggatttaaga aatcaacaaa    1380
gtgtacattc aggagagttt atagaaaaaa ctattgcccc aggaggtgct aatcaaagaa    1440
ctgctcctca aтggaтgтг cctttacttc taggcctgta cggactgta acacctgctc     1500

ttgaagcata tgaagatggc cccaaccaaa agaaaaggag agtgtccagg ggcagctccc    1560
aaaaagccaa aggaacccgt gcaagtgcca aaactactaa taaaagagga gtagaagtt    1620
```

```
ctagaagtta aaactggggt agatgctatt acagaggtag aatgcttcct aaacccagaa   1680
atgggggatc cggatccaga tgaaaacctt aggggcttta gtctaaagct aagtgctgaa   1740
aatgacttta gtagtgatag cccagagaga aaaatgcttc cctgttacag cacagcaaga   1800
attcccctgc ccaatttaaa tgaggaccta acctgtggaa atttactgat gtgggaggct   1860
gtaactgtac aaacagaggt tattggaata actagcatgc ttaaccttca tgcagggtca   1920
caaaaagtgc atgagcatgg tggaggaaaa cctattcaag gcagtaattt ccacttcttt   1980
gctgttggtg gagacccctt ggaaatgcag ggagtgctaa tgaattacag gacaaagtac   2040
ccagatggta ctataacccc taaaaaccca acagcccagt cccaggtaat gaatactgac   2100
cataaggcct atttggacaa aaacaatgct tatccagttg agtgctgggt tcctgatccc   2160
agtagaaatg aaaatactag gtattttggg actttcacag gaggggaaaa tgttccccca   2220
gtacttcatg tgaccaacac agctaccaca gtgttgctag atgaacaggg tgtggggccc   2280
ctttgtaaag ctgatagcct gtatgtttca gctgctgata tttgtggcct gtttactaac   2340
agctctggaa cacaacagtg gagaggcctt gcaagatatt ttaagatccg cctgagaaaa   2400
agatctgtaa agaatcctta cccaatttcc tttttgctaa gtgaccttat aaacaggaga   2460
acccagagag tggatgggca gcctatgtat ggtatggaat cccaggtaga ggaggttagg   2520
gtgtttgatg gcacagaaag acttccaggg gacccagata tgataagata tattgacaaa   2580
cagggacaat tgcaaaccaa aatgctttaa acaggtgctt ttattgtaca tatacattta   2640
ataaatgctg cttttgtata agccactttt aagcttgtgt tattttgggg gtggtgtttt   2700
aggtctttta aaacactgaa agcctttaca caaatgtaac tcttgactat ggggtctga   2760 cctttgggaa tcttcagcag gggctgaagt atctgagact tgggaagagc attgtgattg   2820
ggattcagtg cttgatccat gtccagagtc ttcagtttct gaatcctctt ctcttgtgat   2880
atcaagaata catttcccca tgcatatatt atatttcatc cttgaaaaag tatacatact   2940
tatctcagaa tccagccttt ccttccattc aacaattcta gattgtatat ctgttgcaaa   3000
atcagctaca ggcctaaacc aaattagcag tagcaacaag gtcattccac tttgtagaat   3060
tcttttttca agtaaaaact ctgagttttg taaggatttt cttaaatata ttttgggcct   3120
aaaatctatt tgtcttacaa atctagcttg cagggtttta gggacaggat actcattcat   3180
tgtaaccaag cctggtggaa atatttgggt tcttttgttt aaatgtttct tttctaaatt   3240
tactttaaca cttccatcta aataatctct caaactgtct aaattgttta ttccatgtcc   3300
tgaaggcaaa tcctttgatt cagcccctgt cccttttaca tcttcaaaaa caaccatgta   3360
ctgatctata gctacaccta gctcaaaggt tagcctttcc atgggtaggt ttacatttaa   3420
ggctttacct ccacacaaat ctaataaccc tgcagctagt gttgttttt cactatcaat   3480 gggacccttta aataaccagt atcttctttt aggtacattg aaaacaatac agtgcaaaaa   3540
atcaaatata acagaatcca ttttaggtag caaacagtgc agccaagcaa cacctgccat   3600
atattgttct agtacagcat ttccatgagc tccaaatatt aaatccattt tatctaatat   3660
atgattgaat cttctgtta gcatttcttc cctggtcata tgaagggtat ctactctttt   3720
cttagctaaa actgtatcta ctgcttgctg acaaatactt ttttgatttt tactttctgc   3780
aaagataata gcatttgcaa agtgcttttc atgatactta aagtgataag gttggtcttt   3840
tttctgacac ttttacact cctctacatt gtattgaaat tctaaataca tacctaataa   3900
taaaaacaca tcctcacact ttgtctctac tgcatactca gtaattaatt tccaagacac   3960
ctgctttgtt tcttcaggct cttctgggtt aaaatcatgc tcctttaagc cccccttgaat   4020
```

```
gctttcttct atagtatggt atggctctct agttaaggca ctatatagta agtattcctt    4080
attaacaccc ttacaaatta aaaaactaaa ggtacacagc ttttgacaga agttattaat    4140
tgcagaaact ctatgtctat gtggagttaa aaagaatata atattatgcc cagcacacat    4200
gtgtctacta ataaaagtta cagaatattt ttccataagt tttttataca gaatttgagc    4260
tttttcttta gtagtataca cagcaaagca ggcaagggtt ctattactaa atacagcttg    4320
actaagaaac tggtgtagat cagagggaaa gtctttaggg tcttctacct ttcttttttt    4380
cttgggtggt gttgagtgtt gagaatctgc tgttgcttct tcatcactgg caaacatatc    4440
ttcatggcaa aataagtctt catcccattt ttcattaaag gaactccacc aggactccca    4500
ctcttctgtt ccataggttg gcacctataa aaaaaataat tacttagggc cttttaatat    4560
tttattattt atctaaatat aagttagtta ccttaaagct ttagatctct gaagggagtt    4620
tctccaatta tttggaccca ccattgcaga gtttcttcag ttaggtctaa gccaaaccac    4680
tgtgtgaagc agtcaatgca gtagcaatct atccaaacca agggctcttt tcttaaaaat    4740
tttctattta aatgccttaa tctaagctga catagcatgc aagggcagtg cacagaaggc    4800
tttttggaac aaataggcca ttccttgcag tacagggtat ctgggcaaag aggaaaatca    4860
gcacaaacct ctgagctact ccaggttcca aaatcaggct gatgagctac ctttacatcc    4920
tgctccattt ttttatataa agtattcatt ctcttcattt tatcctcgtc gcccctttg    4980 tcagggtgaa attccttaca cttccttaaa taagcttttc tcattaaggg aagatttccc    5040
caggcagctc tttcaaggcc taaaaggtcc atgagctcca tggattcttc cctgttaagc    5100
actttatcca t                                                          5111
```